United States Patent
Peters et al.

(10) Patent No.: US 11,597,724 B2
(45) Date of Patent: Mar. 7, 2023

(54) HERBICIDALLY ACTIVE 3-PHENYLISOXAZOLINE-5-CARBOXAMIDES OF TETRAHYDRO AND DIHYDROFURAN CARBOXYLIC ACIDS AND ESTERS

(71) Applicants: Bayer Aktiengesellschaft, Leverkusen (DE); Bayer CropScience Aktiengesellschaft, Monheim am Rhein (DE)

(72) Inventors: Olaf Peters, Tabarz (DE); Klaus Bernhard Haaf, Kelkheim (DE); Stephen David Lindell, Eppstein (DE); Guido Bojack, Wiesbaden-Naurod (DE); Katherine Rose Law, Bad Soden (DE); Anu Bheemaiah Machettira, Frankfurt am Main (DE); Hansjoerg Dietrich, Liederbach am Taunus (DE); Elmar Gatzweiler, Bad Nauheim (DE); Christopher Hugh Rosinger, Hofheim (DE)

(73) Assignees: Bayer Aktiengesellschaft, Leverkusen (DE); Bayer CropScience Aktiengesellschaft, Monheim am Rhein (DE)

( * ) Notice: Subject to any disclaimer, the term of this patent is extended or adjusted under 35 U.S.C. 154(b) by 310 days.

(21) Appl. No.: 16/621,303

(22) PCT Filed: Jun. 11, 2018

(86) PCT No.: PCT/EP2018/065333
§ 371 (c)(1),
(2) Date: Dec. 11, 2019

(87) PCT Pub. No.: WO2018/228985
PCT Pub. Date: Dec. 20, 2018

(65) Prior Publication Data
US 2021/0292312 A1 Sep. 23, 2021

(30) Foreign Application Priority Data
Jun. 13, 2017 (EP) .................................. 17175777

(51) Int. Cl.
*C07D 413/12* (2006.01)
*A01N 25/32* (2006.01)
*A01N 43/80* (2006.01)

(52) U.S. Cl.
CPC ........... *C07D 413/12* (2013.01); *A01N 25/32* (2013.01); *A01N 43/80* (2013.01)

(58) Field of Classification Search
None
See application file for complete search history.

(56) References Cited

U.S. PATENT DOCUMENTS

| | | |
|---|---|---|
| 5,332,715 A | 7/1994 | Loeher et al. |
| 8,536,097 B2 | 9/2013 | Ahrens et al. |
| 9,078,442 B2 | 7/2015 | Willms et al. |
| 9,510,598 B2 | 12/2016 | Willms et al. |
| 9,516,880 B2 | 12/2016 | Haaf et al. |
| 9,585,392 B2 | 3/2017 | Kuhn et al. |
| 9,776,993 B2 | 10/2017 | Willms et al. |
| 10,104,892 B2 | 10/2018 | Frenzel et al. |
| 2020/0216403 A1* | 7/2020 | Peters .................... A01N 43/80 |

FOREIGN PATENT DOCUMENTS

| | | |
|---|---|---|
| DE | 4017665 A1 | 12/1991 |
| DE | 4026018 A1 | 2/1992 |
| EP | 0 520 371 A2 | 12/1992 |
| WO | 1995/014680 A1 | 6/1995 |
| WO | 1995/014681 A1 | 6/1995 |
| WO | 1998/057937 A2 | 12/1998 |
| WO | 2005/021515 A2 | 3/2005 |
| WO | 2005/021516 A1 | 3/2005 |
| WO | 2005/051931 A2 | 6/2005 |
| WO | 2006/016237 A2 | 2/2006 |
| WO | 2008/035315 A2 | 3/2008 |
| WO | 2012010573 A1 | 1/2012 |
| WO | 2012/130798 A1 | 10/2012 |
| WO | 2014/048827 A1 | 4/2014 |
| WO | 2014/048853 A1 | 4/2014 |
| WO | 2014/048882 A1 | 4/2014 |
| WO | 2014/048940 A2 | 4/2014 |
| WO | WO-2018228986 A1 * | 12/2018 ............. A01N 43/80 |

OTHER PUBLICATIONS

Patani et al. "Bioisosterism: A rational approach . . . " Chem. Rev. 1996, 96,. 3147-3176 (Year: 1996).*
PCT International Search Report for PCT/EP2018/065333, dated Aug. 6, 2018.

* cited by examiner

*Primary Examiner* — Erin E Hirt
(74) *Attorney, Agent, or Firm* — McBee Moore & Vanik IP, LLC

(57) ABSTRACT

The invention relates to 3-phenylisoxazoline-5-carboxamides of tetrahydro- and dihydrofurancarboxylic acids and esters of the general formula (I)

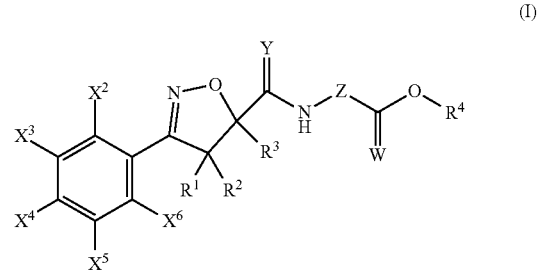

and their agrochemically acceptable salts and to their use in the crop protection sector.

22 Claims, No Drawings

HERBICIDALLY ACTIVE 3-PHENYLISOXAZOLINE-5-CARBOXAMIDES OF TETRAHYDRO AND DIHYDROFURAN CARBOXYLIC ACIDS AND ESTERS

CROSS-REFERENCE TO RELATED APPLICATIONS

This application is the National Stage entry of International Application No. PCT/EP2018/065333, filed 11 Jun. 2018, which claims priority to European Patent Application No. 17175777.6, filed 13 Jun. 2017.

BACKGROUND

Field

The invention relates to the technical field of the herbicides, especially that of the herbicides for selective control of weeds and weed grasses in crops of useful plants.

Specifically, it relates to substituted 3-phenylisoxazoline-5-carboxamides and -5-thioamides of tetrahydro- and dihydrofurancarboxylic acids and esters, to processes for their preparation and to their use as herbicides.

Description of Related Art

WO1995/014681 A1, WO1995/014680 A1, WO 2008/035315 A1, WO2005/051931 A1 and WO2005/021515 A1 each describe, inter alia, 3-phenylisoxazoline-5-carboxamides which are substituted at the phenyl ring in the 3- and 4-positions by alkoxy radicals. WO1998/057937 A1 describes, inter alia, compounds which are substituted at the phenyl ring in the 4-position by an alkoxy radical. WO2006/016237 A1 describes, inter alia, compounds which are substituted at the phenyl ring by an amido radical. The compounds described in the documents mentioned above are disclosed in these documents as being pharmacologically active.

WO2005/021516 A1 discloses 3-(([3-(3-tert-butylphenyl)-5-ethyl-4,5-dihydro-1,2-oxazol-5-yl]carbonyl)amino)-5-fluoro-4-oxopentanoic acid and 3-(([3-(3-tert-butylphenyl)-5-isopropyl-4,5-dihydro-1,2-oxazol-5-yl]carbonyl)amino)-5-fluoro-4-oxopentanoic acid as pharmacologically active compounds.

DE 4026018 A1, EP 0 520 371 A2 and DE 4017665 disclose 3-phenylisoxazoline-5-carboxamides bearing a hydrogen atom in the 5 position of the isoxazoline ring. These compounds are described therein as agrochemically active safeners, i.e. as compounds which eliminate the unwanted herbicidal action of herbicides on crop plants. No herbicidal action of these compounds is disclosed. European patent application No. 10170238, which has an earlier priority date but was yet to be published at the priority date of the present application, discloses herbicidally and fungicidally active 3-phenylisoxazoline-5-carboxamides and 3-phenylisoxazoline-5-thioamides bearing a hydrogen atom in the 5 position of the isoxazoline ring. Monatshefte Chemie (2010) 141, 461 and Letters in Organic Chemistry (2010), 7, 502 also disclose 3-phenylisoxazoline-5-carboxamides bearing a hydrogen atom in the 5 position of the isoxazoline ring. Fungicidal action, but not herbicidal action, is disclosed for some of the compounds mentioned.

WO 2014/048827 describes the herbicidal action of 3-phenylisoxazoline-5-carboxylic acids, -5-carboxylic esters, -5-carbaldehydes and -5-nitriles.

WO 2014/048853 discloses isoxazoline-5-carboxamides and -5-thioamides having heterocycles in the 3-position which have herbicidal and fungicidal action.

WO 2014/048940 discloses fungicidally active isoxazolinecarboxamides having a quinolone as specific heterocycle in the 3-position.

WO 2014/048882 discloses isoxazolinecarboxamides having alkoxy as specific radical in the 5-position.

WO 2012/130798 describes herbicidally and fungicidally active 3-phenylisoxazoline-5-carboxamides and -5-thioamides of substituted heterocycles.

The herbicidal activity of these known compounds, in particular at low application rates, and/or their compatibility with crop plants remain deserving of improvement.

For the reasons stated, there is still a need for potent herbicides and/or plant growth regulators for the selective use in crop plants or the use on non-crop land, where these active ingredients preferably should have further advantageous properties in application, for example an improved compatibility with crop plants.

SUMMARY

Accordingly, it is an object of the present invention to provide compounds having herbicidal activity (herbicides) which are highly effective against economically important harmful plants even at relatively low application rates and can be used selectively in crop plants, preferably with good activity against harmful plants, and at the same time preferably have good compatibility with crop plants. Preferably, these herbicidal compounds should be particularly effective and efficient against a broad spectrum of weed grasses and preferably also have good activity against a large number of weeds.

In addition to a herbicidal action, numerous compound of the formula (I) also have fungicidal action which, however, is not very pronounced.

Surprisingly it has now been found that the 3-phenylisoxazoline-5-carboxamides of tetrahydro- and dihydrofurancarboxylic acids and esters of the formula (I) defined below and their salts have excellent herbicidal activity against a broad spectrum of economically important mono- and dicotyledonous annual harmful plants.

The present invention therefore provides compounds of the general formula (I)

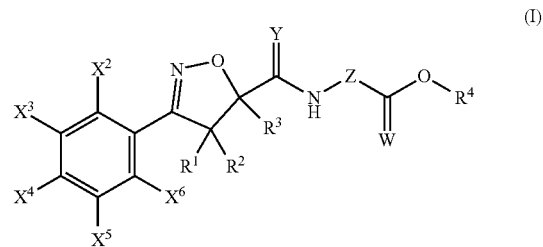

and the agrochemically acceptable salts thereof in which
$R^1$ and $R^2$ independently of one another represent hydrogen, fluorine, chlorine or cyano, or
represent $(C_1-C_3)$-alkyl or $(C_1-C_3)$-alkoxy, each of which is substituted by m radicals from the group consisting of fluorine, chlorine, bromine and cyano.
$R^3$ represents $(C_1-C_4)$-alkyl, $(C_3-C_5)$-cycloalkyl, $(C_2-C_4)$-alkenyl, $(C_2-C_4)$-alkynyl or $(C_1-C_4)$-alkoxy, each of which is substituted by m radicals from the group consisting of fluorine, chlorine, bromine, cyano, $(C_1-C_4)$-alkoxy and hydroxy;

$R^4$ represents hydrogen,
or
represents $(C_1-C_{12})$-alkyl, $(C_3-C_7)$-cycloalkyl, $(C_3-C_7)$-cycloalkyl-$(C_1-C_8)$-alkyl, $(C_2-C_8)$-alkenyl, $(C_5-C_6)$-cycloalkenyl or $(C_2-C_8)$-alkynyl, each of which is substituted by m radicals from the group consisting of halogen, cyano, $(C_1-C_6)$-alkoxy, hydroxy and aryl;

Y represents oxygen or sulfur;
W represents oxygen or sulfur;
Z represents a fully saturated or partly saturated furan ring substituted
by k radicals of group $R^5$

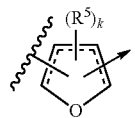

where the arrow in each case denotes a bond to the group C=W of the formula (I);

$R^5$ represents fluorine, chlorine, cyano or $CO_2R^7$,
or
represents $(C_1-C_2)$-alkyl or $(C_1-C_2)$-alkoxy, each of which is substituted by m radicals from the group consisting of fluorine and chlorine;

$X^2$, $X^4$ and $X^6$ independently of one another each represent hydrogen, fluorine, chlorine, bromine or cyano,
or
represent $(C_1-C_2)$-alkyl, in each case substituted by m radicals from the group consisting of fluorine, chlorine, bromine and $(C_1-C_2)$-alkoxy;

$X^3$ and $X^5$ independently of one another represent hydrogen, fluorine, chlorine, bromine, iodine, hydroxy, cyano, nitro, $S(O)_nR^6$ or $CO_2R^7$,
or
represent $(C_1-C_3)$-alkyl, $(C_1-C_3)$-alkoxy, $(C_3-C_4)$-cycloalkyl, $(C_2-C_3)$-alkenyl or $(C_2-C_3)$-alkynyl, each of which is substituted by m radicals from the group consisting of fluorine, chlorine and bromine;

$R^6$ represents $(C_1-C_2)$-alkyl or $(C_3-C_4)$-cycloalkyl, each of which is substituted by m radicals from the group consisting of fluorine and chlorine;

$R^7$ represents hydrogen,
or
represents $(C_1-C_3)$-alkyl or $(C_3-C_5)$-cycloalkyl, each of which is substituted by m radicals from the group consisting of fluorine, chlorine and $(C_1-C_2)$-alkoxy;

k represents the running number 0, 1 or 2;
m represents the running number 0, 1, 2, 3, 4 or 5; and
n represents the running number 0, 1 or 2.

DETAILED DESCRIPTION OF A PREFERRED EMBODIMENT

Alkyl means saturated straight-chain or branched hydrocarbyl radicals having the number of carbon atoms specified in each case, e.g. $C_1-C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl.

Halogen-substituted alkyl means straight-chain or branched alkyl groups where some or all of the hydrogen atoms in these groups may be replaced by halogen atoms, e.g. $C_1-C_2$-haloalkyl such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro, 2-difluoroethyl, 2,2-dichloro-2-fluoroethyl, 2,2,2-trichloroethyl, pentafluoroethyl and 1,1,1-trifluoroprop-2-yl.

Alkenyl means unsaturated straight-chain or branched hydrocarbyl radicals having the number of carbon atoms specified in each case and one double bond in any position, e.g. $C_2-C_6$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

Alkynyl means straight-chain or branched hydrocarbyl radicals having the number of carbon atoms specified in each case and one triple bond in any position, e.g. $C_2-C_6$-alkynyl such as ethynyl, 1-propynyl, 2-propynyl (or propargyl), 1-butynyl, 2-butynyl, 3-butynyl, 1-methyl-2-propynyl, 1-pentynyl, 2-pentynyl, 3-pentynyl, 4-pentynyl, 3-methyl-1-butynyl, 1-methyl-2-butynyl, 1-methyl-3-butynyl, 2-methyl-3-butynyl, 1,1-dimethyl-2-propynyl, 1-ethyl-2-propynyl, 1-hexynyl, 2-hexynyl, 3-hexynyl, 4-hexynyl, 5-hexynyl, 3-methyl-1-pentynyl, 4-methyl-1-pentynyl, 1-methyl-2-pentynyl, 4-methyl-2-pentynyl, 1-methyl-3-pentynyl, 2-methyl-3-pentynyl, 1-methyl-4-pentynyl, 2-methyl-4-pentynyl, 3-methyl-4-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl.

Cycloalkyl means a carbocyclic saturated ring system having preferably 3-8 ring carbon atoms, for example cyclopropyl, cyclobutyl, cyclopentyl or cyclohexyl. In the case of optionally substituted cycloalkyl, cyclic systems with substituents are included, also including substituents with a double bond on the cycloalkyl radical, for example an alkylidene group such as methylidene.

In the case of optionally substituted cycloalkyl, polycyclic aliphatic systems are also included, for example bicyclo[1.1.0]butan-1-yl, bicyclo[1.1.0]butan-2-yl, bicyclo[2.1.0]pentan-1-yl, bicyclo[2.1.0]pentan-2-yl, bicyclo[2.1.0]pentan-5-yl, bicyclo[2.2.1]hept-2-yl (norbornyl), adamantan-1-yl and adamantan-2-yl.

In the case of substituted cycloalkyl, spirocyclic aliphatic systems are also included, for example spiro[2.2]pent-1-yl, spiro[2.3]hex-1-yl and spiro[2.3]hex-4-yl, 3-spiro[2.3]hex-5-yl.

Cycloalkenyl means a carbocyclic, nonaromatic, partially unsaturated ring system having preferably 4-8 carbon atoms, e.g. 1-cyclobutenyl, 2-cyclobutenyl, 1-cyclopentenyl, 2-cyclopentenyl, 3-cyclopentenyl, or 1-cyclohexenyl, 2-cyclohexenyl, 3-cyclohexenyl, 1,3-cyclohexadienyl or 1,4-cyclohexadienyl, also including substituents with a double bond on the cycloalkenyl radical, for example an alkylidene group such as methylidene. In the case of optionally substituted cycloalkenyl, the elucidations for substituted cycloalkyl apply correspondingly.

Alkoxy means saturated straight-chain or branched alkoxy radicals having the number of carbon atoms specified in each case, for example $C_1$-$C_6$-alkoxy such as methoxy, ethoxy, propoxy, 1-methylethoxy, butoxy, 1-methylpropoxy, 2-methylpropoxy, 1,1-dimethylethoxy, pentoxy, 1-methylbutoxy, 2-methylbutoxy, 3-methylbutoxy, 2,2-dimethylpropoxy, 1-ethylpropoxy, hexoxy, 1,1-dimethylpropoxy, 1,2-dimethylpropoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy. Halogen-substituted alkoxy means straight-chain or branched alkoxy radicals having the number of carbon atoms specified in each case, where some or all of the hydrogen atoms in these groups may be replaced by halogen atoms as specified above, e.g. $C_1$-$C_2$-haloalkoxy such as chloromethoxy, bromomethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro-1,2-difluoroethoxy, 2,2-dichloro-2-fluoroethoxy, 2,2,2-trichloroethoxy, pentafluoroethoxy and 1,1,1-trifluoroprop-2-oxy.

Aryl means phenyl which is optionally substituted by 0-5 radicals from the group consisting of fluorine, chlorine, bromine, iodine, cyano, hydroxy, $(C_1$-$C_3)$-alkyl, $(C_1$-$C_3)$-alkoxy, $(C_3$-$C_4)$-cycloalkyl, $(C_2$-$C_3)$-alkenyl and $(C_2$-$C_3)$-alkynyl.

The term "halogen" means fluorine, chlorine, bromine or iodine. If the term is used for a radical, "halogen" means a fluorine, chlorine, bromine or iodine atom.

According to the nature of the substituents and the way in which they are joined, the compounds of the formula (I) may be present as stereoisomers. If, for example, one or more asymmetrically substituted carbon atoms and/or sulfoxides are present, enantiomers and diastereomers may occur. Stereoisomers can be obtained from the mixtures obtained in the preparation by customary separation methods, for example by chromatographic separation processes. It is likewise possible to selectively prepare stereoisomers by using stereoselective reactions with use of optically active starting materials and/or auxiliaries.

The invention also relates to all stereoisomers and mixtures thereof which are encompassed by the formula (I) but not defined specifically. However, the following text will, for the sake of simplicity, always mention compounds of the formula (I), even though this is understood as meaning not only the pure compounds, but also, if appropriate, mixtures with various amounts of isomeric compounds.

According to the nature of the substituents defined above, the compounds of the formula (I) have acidic properties and can form salts, and if appropriate also internal salts or adducts with inorganic or organic bases or with metal ions. If the compounds of the formula (I) carry hydroxyl, carboxyl or other groups which induce acidic properties, these compounds can be reacted with bases to give salts. Suitable bases are, for example, hydroxides, carbonates, bicarbonates of the alkali metals and alkaline earth metals, in particular those of sodium, potassium, magnesium and calcium, furthermore ammonia, primary, secondary and tertiary amines having $(C_1$-$C_4)$-alkyl groups, mono-, di- and trialkanolamines of $(C_1$-$C_4)$-alkanols, choline and chlorocholine, and also organic amines such as trialkylamines, morpholine, piperidine or pyridine. These salts are compounds in which the acidic hydrogen is replaced by an agriculturally suitable cation, for example metal salts, especially alkali metal salts or alkaline earth metal salts, in particular sodium and potassium salts, or else ammonium salts, salts with organic amines or quaternary ammonium salts, for example with cations of the formula [NRR'R"R'''] in which R to R''' each independently of one another represent an organic radical, in particular alkyl, aryl, aralkyl or alkylaryl. Also suitable are alkylsulfonium and alkylsulfoxonium salts, such as $(C_1$-$C_4)$-trialkylsulfonium and $(C_1$-$C_4)$-trialkylsulfoxonium salts.

The compounds of the formula (I) can form salts by addition of a suitable inorganic or organic acid, for example mineral acids, for example HCl, HBr, $H_2SO_4$, $H_3PO$ or $HNO_3$, or organic acids, for example carboxylic acids such as formic acid, acetic acid, propionic acid, oxalic acid, lactic acid or salicylic acid or sulfonic acids, for example p-toluenesulfonic acid, onto a basic group, for example amino, alkylamino, dialkylamino, piperidino, morpholino or pyridino. In such a case, these salts comprise the conjugated base of the acid as the anion.

Suitable substituents present in deprotonated form, such as, for example, sulfonic acids or carboxylic acids, may form inner salts with groups which for their part can be protonated, such as amino groups.

If a group is polysubstituted by radicals, this means that this group is substituted by one or more identical or different radicals from those mentioned.

In all the formulae specified hereinafter, the substituents and symbols have the same meaning as described in formula (I), unless defined differently. Arrows in a chemical formula denote the points at which it is joined to the rest of the molecule.

There follows a description of preferred, particularly preferred and very particularly preferred definitions of each of the individual substituents. The other substituents of the general formula (I) which are not specified hereinafter have the definition given above.

According to a first embodiment of the present invention, $R^1$ and $R^2$ preferably independently of one another each represent hydrogen, fluorine, chlorine or cyano, or represent methyl or methoxy which are in each case substituted by m radicals from the group consisting of fluorine and chlorine.

Particularly preferably, $R^1$ and $R^2$ each represent hydrogen.

According to a second embodiment of the present invention, $R^3$ preferably represents $(C_1-C_3)$-alkyl, $(C_3-C_4)$-cycloalkyl, $(C_2-C_3)$-alkenyl, $(C_2-C_3)$-alkynyl or $(C_1-C_3)$-alkoxy, each of which is substituted by m radicals from the group consisting of fluorine, chlorine, bromine, cyano, $(C_1-C_2)$-alkoxy and hydroxy.

According to a third embodiment of the present invention, $R^4$ preferably represents $(C_1-C_6)$-alkyl, $(C_3-C_6)$-cycloalkyl, $(C_3-C_6)$-cycloalkyl-$(C_1-C_6)$-alkyl, $(C_2-C_6)$-alkenyl, $(C_5-C_6)$-cycloalkenyl or $(C_2-C_6)$-alkynyl, each of which is substituted by m radicals from the group consisting of fluorine, chlorine, bromine, cyano, $(C_1-C_4)$-alkoxy, hydroxy and aryl.

According to a fourth embodiment of the present invention,

Y preferably represents oxygen.

According to a fifth embodiment of the present invention,

W preferably represents oxygen.

According to a sixth embodiment of the present invention,

Z preferably represents a group Z-1 to Z-33, where Z-1 to Z-33 have the following meaning:

Z-1

Z-2

Z-3

Z-4

Z-5

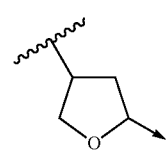

Z-6

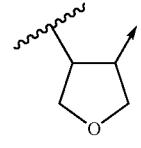

Z-7

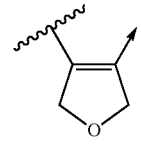

Z-8

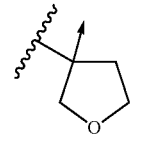

Z-9

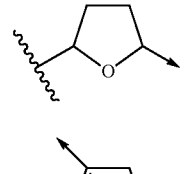

Z-10

-continued

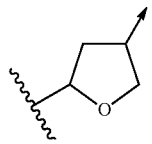

Z-7

Z-8

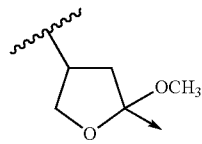

Z-9

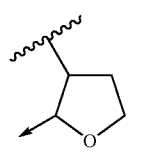

Z-10

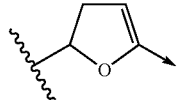

Z-11

Z-12

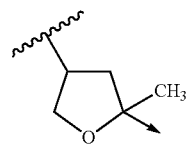

Z-13

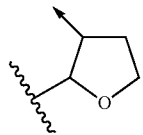

Z-14

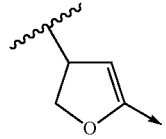

Z-15

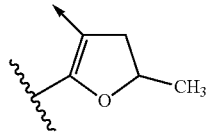

Z-16

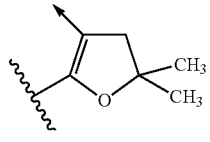

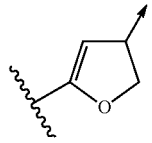

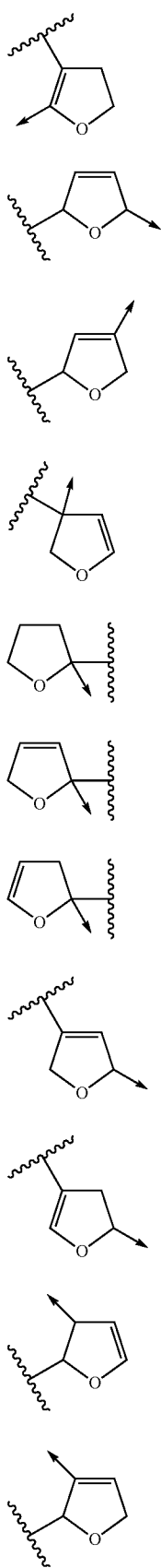
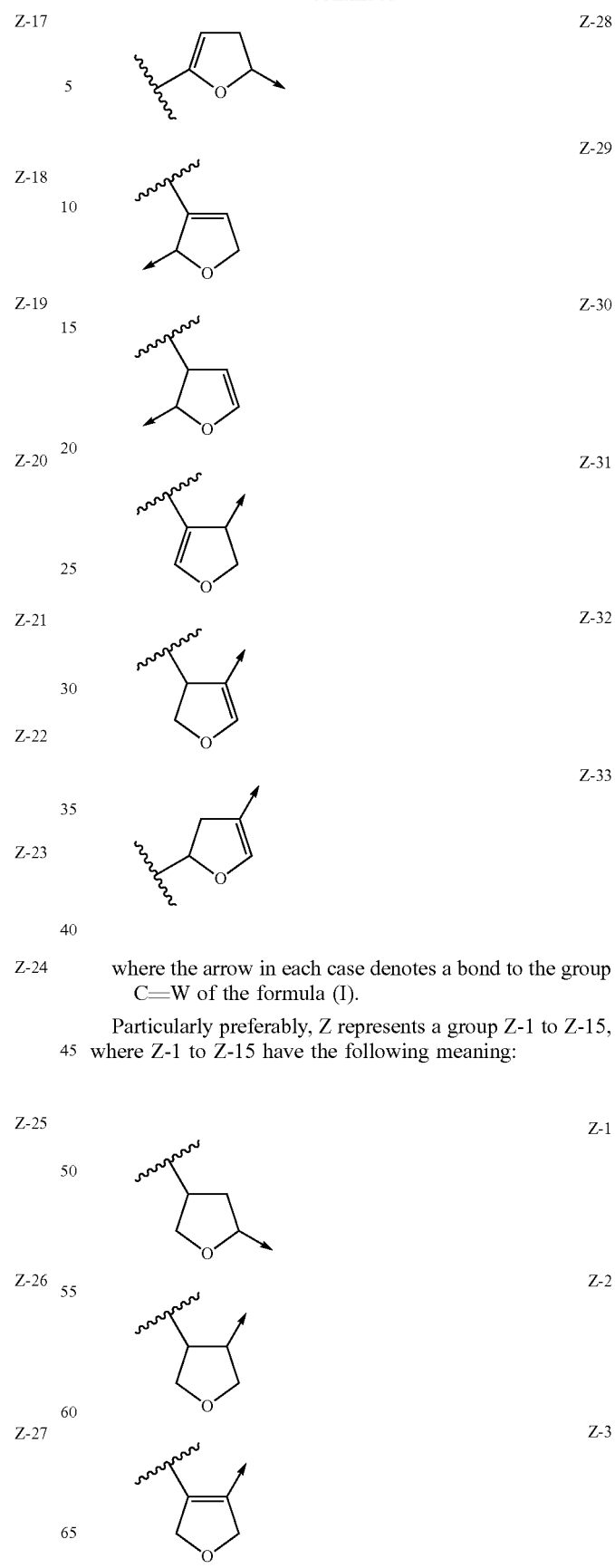
where the arrow in each case denotes a bond to the group C=W of the formula (I).
Particularly preferably, Z represents a group Z-1 to Z-15, where Z-1 to Z-15 have the following meaning:

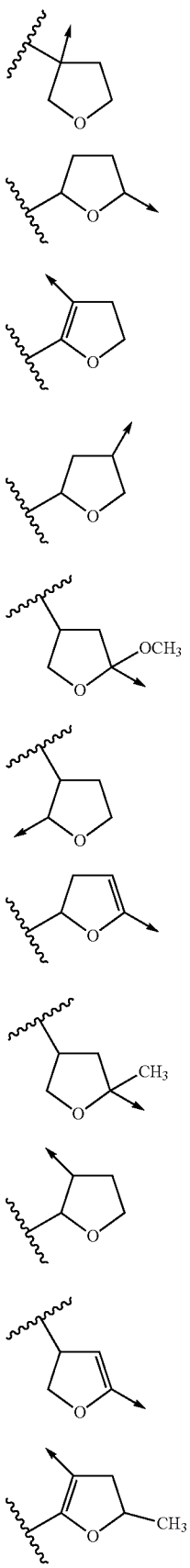
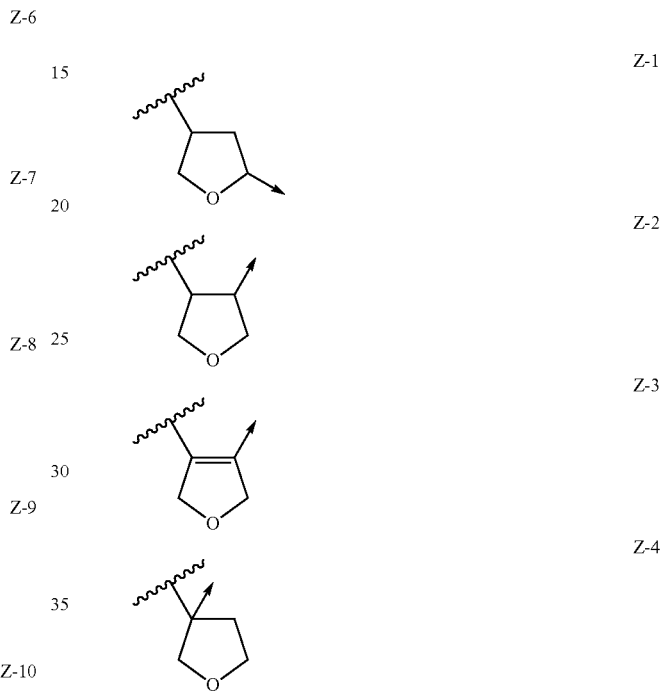

where the arrow in each case denotes a bond to the group C=W of the formula (I).

Most preferably, Z represents Z-1 to Z-4 where the arrow in each case denotes a bond to the group C=W of the formula (I).

According to a seventh embodiment of the present invention, $R^5$ preferably represents fluorine, chlorine, cyano, $CO_2H$, $CO_2CH_3$ or $CO_2CH_2CH_3$, or represents $(C_1-C_2)$-alkyl or $(C_1-C_2)$-alkoxy, each of which is substituted by m radicals from the group consisting of fluorine and chlorine.

According to an eighth embodiment of the present invention, $X^2$, $X^4$ and $X^6$ preferably independently of one another each represent hydrogen, fluorine, chlorine, bromine or cyano, or represent methyl or methoxy, each of which is substituted by m radicals from the group consisting of fluorine and chlorine.

Particularly preferably, $X^2$, $X^4$ and $X^6$ independently of one another represent hydrogen or fluorine.

According to a ninth embodiment of the present invention, $X^3$ and $X^5$ preferably independently of one another represent hydrogen, fluorine, chlorine, bromine, hydroxy or cyano, or represent $(C_1-C_3)$-alkyl, $(C_1-C_3)$-alkoxy, $(C_3-C_4)$-cycloalkyl, $(C_2-C_3)$-alkenyl or $(C_2-C_3)$-alkynyl, each of which is substituted by m radicals from the group consisting of fluorine, chlorine and bromine.

According to a tenth embodiment of the present invention, $R^7$ preferably represents hydrogen, or represents $(C_1\text{-}C_3)$-alkyl in each case substituted by m radicals from the group consisting of fluorine and chlorine.

According to an eleventh embodiment of the present invention, m preferably represents 0, 1, 2 or 3.

In the context of the present invention, the individual preferred, particularly preferred and most preferred meanings of the substituents $R^1$ to $R^7$, $X^2$ to $X^6$, W, Y and Z, and the running numbers k, m and n can be combined with one another as desired.

This means that the present invention encompasses compounds of the general formula (I) in which, for example, the substituent $R^1$ has a preferred definition and the substituents $R^2$ to $R^7$ have the general definition or else the substituent $R^2$ has a preferred definition, the substituent $R^3$ has a particularly preferred or very particularly preferred definition and the remaining substituents have a general definition.

Three of these combinations of the definitions given above for the substituents $R^1$ to $R^7$, $X^2$ to $X^6$, W, Y and Z, and the running numbers k, m and n are illustrated below by way of example, and each of them is disclosed as a further embodiment:

According to a twelfth embodiment of the present invention, $R^1$ and $R^2$ independently of one another represent hydrogen, fluorine, chlorine or cyano, or represent $(C_1\text{-}C_3)$-alkyl or $(C_1\text{-}C_3)$-alkoxy, each of which is substituted by m radicals from the group consisting of fluorine, chlorine, bromine and cyano;

$R^3$ represents $(C_1\text{-}C_4)$-alkyl, $(C_3\text{-}C_5)$-cycloalkyl, $(C_2\text{-}C_4)$-alkenyl, $(C_2\text{-}C_4)$-alkynyl or $(C_1\text{-}C_4)$-alkoxy, each of which is substituted by m radicals from the group consisting of fluorine, chlorine, bromine, cyano, $(C_1\text{-}C_4)$-alkoxy and hydroxy;

$R^4$ represents hydrogen, or represents $(C_1\text{-}C_6)$-alkyl, $(C_3\text{-}C_6)$-cycloalkyl, $(C_3\text{-}C_6)$-cycloalkyl-$(C_1\text{-}C_6)$-alkyl, $(C_2\text{-}C_6)$-alkenyl, $(C_5\text{-}C_6)$-cycloalkenyl or $(C_2\text{-}C_6)$-alkynyl, each of which is substituted by m radicals from the group consisting of fluorine, chlorine, bromine, cyano, $(C_1\text{-}C_4)$-alkoxy, hydroxy and aryl;

Y represents oxygen;

W represents oxygen;

Z represents a group Z-1 to Z-33, where Z-1 to Z-33 have the following meaning:

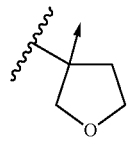

Z-1

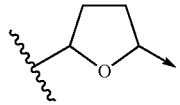

Z-2

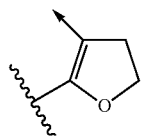

Z-3

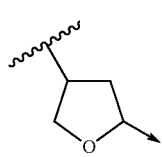

Z-4

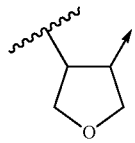

Z-5

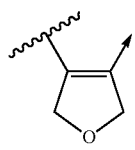

Z-6

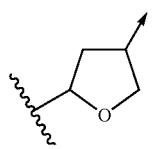

Z-7

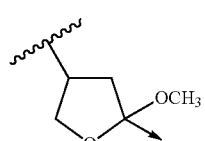

Z-8

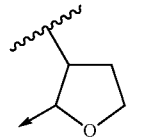

Z-9

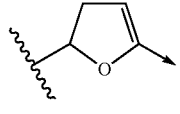

Z-10

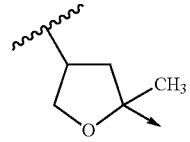

Z-11

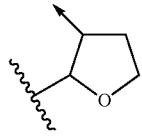

Z-12

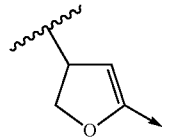

Z-13

Z-14

-continued

Z-15 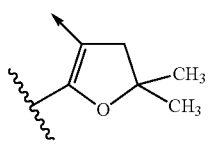

Z-16 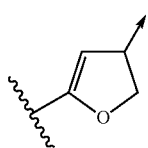

Z-17 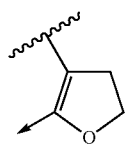

Z-18 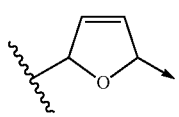

Z-19 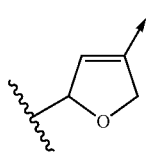

Z-20 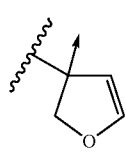

Z-21 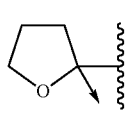

Z-22 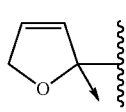

Z-23 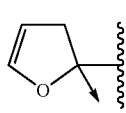

Z-24 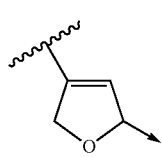

Z-25 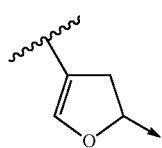

-continued

Z-26 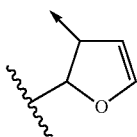

Z-27 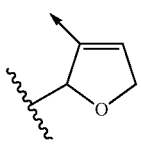

Z-28 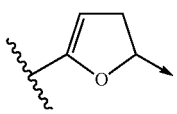

Z-29 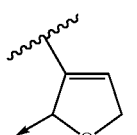

Z-30 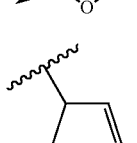

Z-31 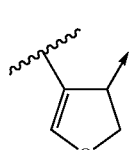

Z-32 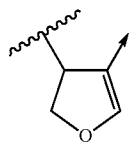

Z-33 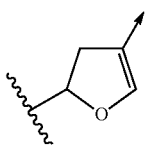

where the arrow in each case denotes a bond to the group C=W of the formula (I);

$X^2$, $X^4$ and $X^6$ independently of one another each represent hydrogen, fluorine, chlorine, bromine or cyano, or represent ($C_1$-$C_2$)-alkyl, in each case substituted by m radicals from the group consisting of fluorine, chlorine, bromine and ($C_1$-$C_2$)-alkoxy;

$X^3$ and $X^5$ independently of one another represent hydrogen, fluorine, chlorine, bromine, iodine, hydroxy, cyano, nitro, $S(O)_nR^6$ or $CO^2R^7$, or represent ($C_1$-$C_3$)-alkyl, ($C_1$-$C_3$)-alkoxy, ($C_3$-$C_4$)-cycloalkyl, ($C_2$-$C_3$)-alkenyl or ($C_2$-$C_3$)-alkynyl, each of which is substituted by m radicals from the group consisting of fluorine, chlorine and bromine;

$R^6$ represents $(C_1-C_2)$-alkyl or $(C_3-C_4)$-cycloalkyl, each of which is substituted by m radicals from the group consisting of fluorine and chlorine;

$R^7$ represents hydrogen,
or
represents $(C_1-C_3)$-alkyl or $(C_3-C_5)$-cycloalkyl, each of which is substituted by m radicals from the group consisting of fluorine, chlorine and $(C_1-C_2)$-alkoxy;

m represents the running number 0, 1, 2 or 3; and n represents the running number 0, 1 or 2.

According to a thirteenth embodiment of the present invention, $R^1$ and $R^2$ independently of one another represent hydrogen, fluorine, chlorine or cyano,
or
represent methyl or methoxy, each of which is substituted by m radicals from the group consisting of fluorine and chlorine;

$R^3$ represents $(C_1-C_3)$-alkyl, $(C_3-C_4)$-cycloalkyl, $(C_2-C_3)$-alkenyl, $(C_2-C_3)$-alkynyl or $(C_1-C_3)$-alkoxy, each of which is substituted by m radicals from the group consisting of fluorine, chlorine, bromine, cyano, $(C_1-C_2)$-alkoxy and hydroxy;

$R^4$ represents hydrogen,
or
represents $(C_1-C_6)$-alkyl, $(C_3-C_6)$-cycloalkyl, $(C_3-C_6)$-cycloalkyl-$(C_1-C_6)$-alkyl, $(C_2-C_6)$-alkenyl, $(C_5-C_6)$-cycloalkenyl or $(C_2-C_6)$-alkynyl, each of which is substituted by m radicals from the group consisting of fluorine, chlorine, bromine, cyano, $(C_1-C_4)$-alkoxy, hydroxy and aryl;

Y represents oxygen;

W represents oxygen;

Z represents a group Z-1 to Z-15, where Z-1 to Z-15 have the following meaning:

Z-1
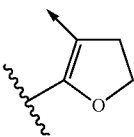

Z-2
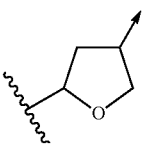

Z-3
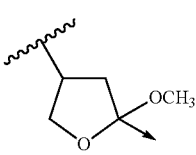

Z-4
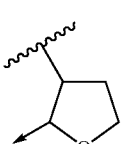

Z-5
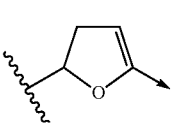

-continued

Z-6
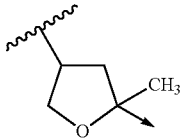

Z-7
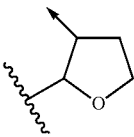

Z-8
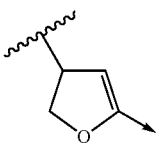

Z-9
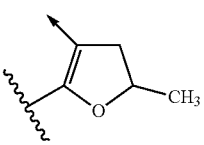

Z-10
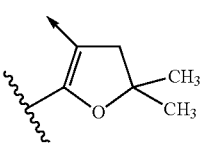

Z-11
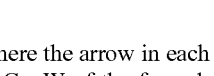

Z-12
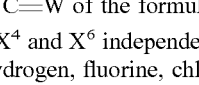

Z-13

Z-14

Z-15

where the arrow in each case denotes a bond to the group C=W of the formula (I);

$X^2$, $X^4$ and $X^6$ independently of one another each represent hydrogen, fluorine, chlorine, bromine or cyano, or
represent methyl or methoxy, each of which is substituted by m radicals from the group consisting of fluorine and chlorine;

$X^3$ and $X^5$ independently of one another represent hydrogen, fluorine, chlorine, bromine, iodine, hydroxy or cyano,
or
represent $(C_1-C_3)$-alkyl, $(C_1-C_3)$-alkoxy, $(C_3-C_4)$-cycloalkyl, $(C_2-C_3)$-alkenyl or $(C_2-C_3)$-alkynyl, each of which is substituted by m radicals from the group consisting of fluorine, chlorine and bromine; and m represents the running number 0, 1, 2 or 3.

According to a fourteenth embodiment of the present invention, $R^1$ and $R^2$ each represent hydrogen;
$R^3$ represents $(C_1-C_3)$-alkyl, $(C_3-C_4)$-cycloalkyl, $(C_2-C_3)$-alkenyl, $(C_2-C_3)$-alkynyl or $(C_1-C_3)$-alkoxy, each of which is substituted by m radicals from the group consisting of fluorine, chlorine, bromine, cyano, $(C_1-C_2)$-alkoxy and hydroxy;
$R^4$ represents hydrogen,
or
represents $(C_1-C_6)$-alkyl, $(C_3-C_6)$-cycloalkyl, $(C_3-C_6)$-cycloalkyl-$(C_1-C_6)$-alkyl, $(C_2-C_6)$-alkenyl, $(C_5-C_6)$-cycloalkenyl or $(C_2-C_6)$-alkynyl, each of which is substituted by m radicals from the group consisting of fluorine, chlorine, bromine, cyano, $(C_1-C_4)$-alkoxy, hydroxy and aryl;
Y represents oxygen;
W represents oxygen;
Z represents a group Z-1 to Z-4, where Z-1 to Z-4 have the following meaning:

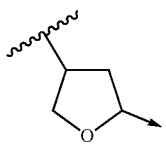

Z-1

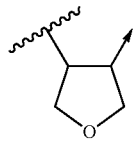

Z-2

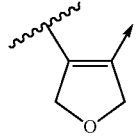

Z-3

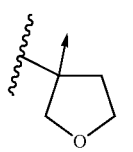

Z-4 where the arrow in each case denotes a bond to the group C=W of the formula (I);

$X^2$, $X^4$ and $X^6$ independently of one another represent hydrogen or fluorine;

$X^3$ and $X^5$ independently of one another represent hydrogen, fluorine, chlorine, bromine, hydroxy or cyano,
or
represent $(C_1-C_3)$-alkyl, $(C_1-C_3)$-alkoxy, $(C_3-C_4)$-cycloalkyl, $(C_2-C_3)$-alkenyl or $(C_2-C_3)$-alkynyl, each of which is substituted by m radicals from the group consisting of fluorine, chlorine and bromine; and m represents the running number 0, 1, 2 or 3.

Examples of the compounds of the general formula (I) are shown below in tabular form. Table 1 below specifies the substituents defined in general terms in formula (I).

TABLE 1

| Compounds of the general formula (1) in which $X^2=X^4=X^6=R^1=R^2=H$ and represents $Y=W=O$ |||||||
|---|---|---|---|---|---|---|
| Example No. | $X^3$ | $X^5$ | $R^3$ | $R^4$ | Z | Comment |
| I-1 | F | F | $CH_3$ | $CH_3$ | Z-1 | Z-1 of 2,4-cis configuration |
| I-2 | Cl | Cl | $OCH_3$ | $CH_3$ | Z-1 | Z-1 of 2,4-cis configuration |
| I-3 | Cl | Cl | $CH=CH_2$ | $CH_3$ | Z-1 | Z-1 of 2,4-cis configuration |
| I-4 | Br | $CH_3$ | $CH_3$ | $CH_3$ | Z-1 | Z-1 of 2,4-cis configuration |
| I-5 | F | F | $OCH_3$ | $CH_3$ | Z-1 | Z-1 of 2,4-cis configuration |
| I-6 | F | F | $CF_3$ | $CH_3$ | Z-1 | Z-1 of 2,4-cis configuration |
| I-7 | F | H | $CH=CH_2$ | $CH_3$ | Z-1 | Z-1 of 2,4-cis configuration |
| I-8 | Br | $CH_3$ | $OCH_3$ | $CH_3$ | Z-1 | Z-1 of 2,4-cis configuration |
| I-9 | F | F | (R) – $CH_3$ | $CH_3$ | Z-1 | Z-1 of 2,4-cis configuration |
| I-10 | F | F | (S)—$CH=CH_2$ | $CH_3$ | Z-1 | Z-1 of 2,4-cis configuration; 2 diastereomers |
| I-11 | F | F | (S)—$CH=CH_2$ | $CH_3$ | Z-1 | Z-1 of 2,4-cis configuration; diastereomer 1 of I-10 (individual enantiomer) |
| I-12 | F | F | (S)—$CH=CH_2$ | $CH_3$ | Z-1 | Z-1 of 2,4-cis configuration; diastereomer 2 of I-10 (individual enantiomer) |
| I-13 | F | H | $CH_3$ | $CH_3$ | Z-1 | Z-1 of 2,4-cis configuration |
| I-14 | H | H | $OCH_3$ | $CH_3$ | Z-1 | Z-1 of 2,4-cis configuration |
| I-15 | F | F | (R)—$CH_3$ | $CH_3$ | Z-1 | Z-1 of 2,4-cis configuration; diastereomer 1 (individual enantiomer) |
| I-16 | F | F | (R)—$CH_3$ | $CH_3$ | Z-1 | Z-1 of 2,4-cis configuration; diastereomer 2 (individual enantiomer) |
| I-17 | F | F | $CH_3$ | $CH_3$ | Z-4 | |
| I-18 | F | F | $CH_3$ | $CH_2CH_3$ | Z-4 | |
| I-19 | F | F | $CH_3$ | $CH_3$ | Z-2 | |

TABLE 1-continued

Compounds of the general formula (1) in which $X^2=X^4=X^6=R^1=R^2=H$ and represents $Y=W=O$

| Example No. | $X^3$ | $X^5$ | $R^3$ | $R^4$ | Z | Comment |
|---|---|---|---|---|---|---|
| I-20 | F | H | $CH_3$ | H | Z-1 | Z-1 of 2,4-cis configuration |
| I-21 | F | F | $CH=CH_2$ | H | Z-1 | Z-1 of 2,4-cis configuration |
| I-22 | F | F | (R)—$CH=CH_2$ | $CH_3$ | Z-1 | Z-1 of 2,4-cis configuration |
| I-23 | F | F | $CH=CH_2$ | $CH_2CH_3$ | Z-3 | |
| I-24 | F | F | $CH_3$ | $CH_2CH_3$ | Z-3 | |
| I-25 | F | F | $CH_3$ | $CH_3$ | Z-3 | |
| I-26 | F | F | (S)—$CH=CH_2$ | $CH_3$ | Z-2 | |
| I-27 | F | F | $OCH_3$ | $CH_3$ | Z-2 | |
| I-28 | F | F | (R)—$CH_3$ | $CH_3$ | Z-2 | |
| I-29 | Cl | Cl | $OCH_3$ | $CH_3$ | Z-2 | |
| I-30 | F | H | $CH_3$ | $CH_2CH_3$ | Z-1 | Z-1 of 2,4-cis configuration |
| I-31 | F | F | (S)—$CH=CH_2$ | H | Z-1 | Z-1 of 2,4-cis configuration |
| I-32 | F | H | $CH_3$ | $CH(CH_3)_2$ | Z-1 | Z-1 of 2,4-cis configuration |
| I-33 | F | H | $CH_3$ | $C(CH_3)_3$ | Z-1 | Z-1 of 2,4-cis configuration |
| I-34 | F | H | $CH_3$ | $CH_2Ph$ | Z-1 | Z-1 of 2,4-cis configuration |
| I-35 | F | F | (S)—$CH=CH_2$ | $CH_2CH_3$ | Z-1 | Z-1 of 2,4-cis configuration |
| I-36 | F | F | (S)—$CH=CH_2$ | $CH(CH_3)_2$ | Z-1 | Z-1 of 2,4-cis configuration |
| I-37 | F | F | (S)—$CH=CH_2$ | $CH_2Ph$ | Z-1 | Z-1 of 2,4-cis configuration |
| I-38 | F | F | (S)—$CH=CH_2$ | $C(CH_3)_3$ | Z-1 | Z-1 of 2,4-cis configuration |
| I-39 | F | H | $CH_3$ | $CH_3$ | Z-13 | (4S)-4-amino-4,5-dihydrofuran-2-carboxylate |
| I-40 | F | H | $CH_3$ | $CH_3$ | Z-8 | (2S,4S)-4-aminotetrahydrofuran-2-carboxylate |
| I-41 | F | F | (R)—$CH_3$ | H | Z-1 | Z-1 of 2,4-cis configuration |
| I-42 | F | F | (R)—$CH_3$ | $C(CH_3)_3$ | Z-1 | Z-1 of 2,4-cis configuration |
| I-43 | F | F | (R)—$CH_3$ | $CH_2CH_3$ | Z-1 | Z-1 of 2,4-cis configuration |
| I-44 | F | F | (R)—$CH_3$ | $CH_2(CH_3)_2$ | Z-1 | Z-1 of 2,4-cis configuration |
| I-45 | F | F | (R)—$CH_3$ | $CH_2Ph$ | Z-1 | Z-1 of 2,4-cis configuration |
| I-46 | F | H | $CH_3$ | $CH_3$ | Z-13 | (4R)-4-amino-4,5-dihydrofuran-2-carboxylate |
| I-47 | F | H | $CH_3$ | $CH_3$ | Z-8 | (2R,4R)-4-aminotetrahydrofuran-2-carboxylate |
| I-48 | F | F | (R)—$CH_3$ | $CH_3$ | Z-1 | Z-1 of 2,4-cis configuration |
| I-49 | F | F | (R)—$CF_2CH_3$ | $CH_3$ | Z-1 | Z-1 of 2,4-cis configuration |
| I-50 | F | F | (R)—$CF_2CH_3$ | H | Z-1 | Z-1 of 2,4-cis configuration |
| I-51 | F | F | (R)—$CF_2CH_3$ | $CH(CH_3)_2$ | Z-1 | Z-1 of 2,4-cis configuration |
| I-52 | F | F | (S)—$CH=CH_2$ | $CH_2(3\text{-}F\text{—}Ph)$ | Z-1 | Z-1 of 2,4-cis configuration |
| I-53 | F | F | (R)—$CH_3$ | $CH_2(3\text{-}F\text{—}Ph)$ | Z-1 | Z-1 of 2,4-cis configuration |
| I-54 | F | F | (S)—$CH=CH_2$ | $CH_2(4\text{-}OMe\text{—}Ph)$ | Z-1 | Z-1 of 2,4-cis configuration |
| I-55 | F | F | (R)—$CH_3$ | $CH_3$ | Z-1 | Z-1 of 2,4-trans configuration |
| I-56 | F | F | (S)—$CH=CH_2$ | $CH_3$ | Z-1 | Z-1 of 2,4-trans configuration |

The compounds according to the invention can be prepared by various processes listed below:

Scheme 1

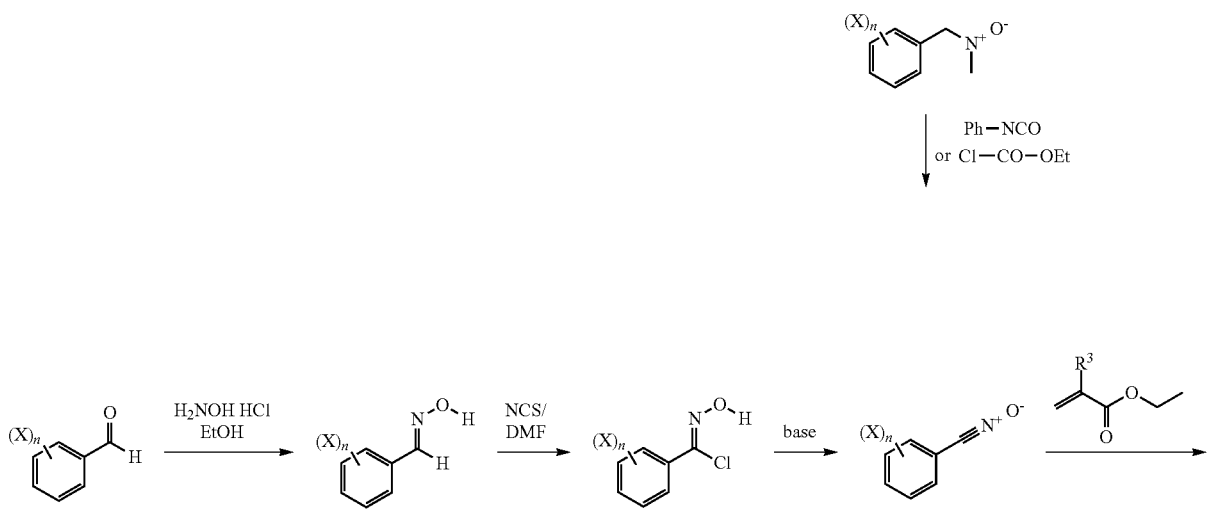

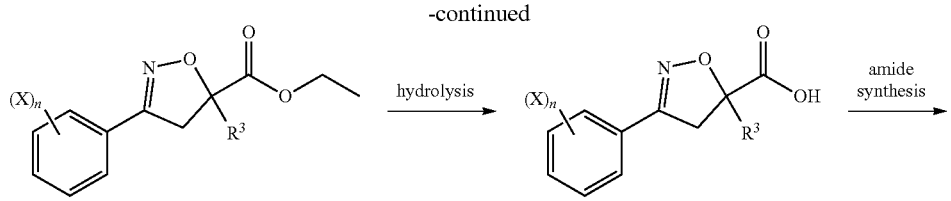

-continued

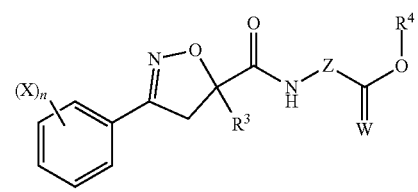

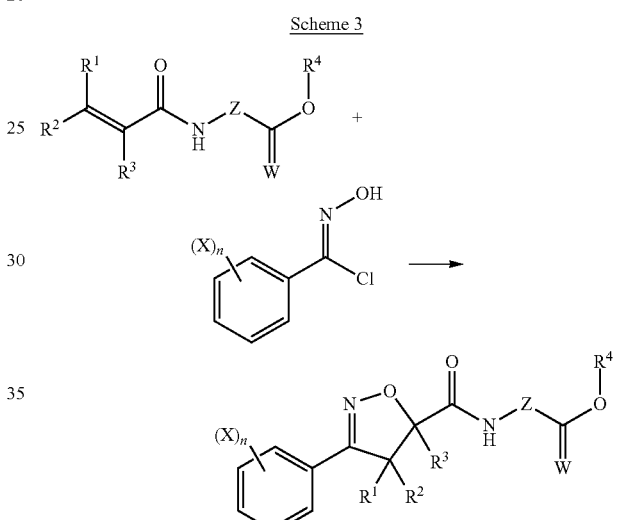

In Scheme 1 and the schemes which follow, (X) represents the substituents X, $X^3$, $X^4$, $X^5$ and $X^6$. Such 1,3-dipolar cycloadditions of nitrile oxides with suitable dipolarophiles are described, for example, in Reviews: 1,3 dipolar Cycloaddition Chemistry, Padwa, ed. Wiley, New York, 1984; Kanemasa and Tsuge, Heterocycles 1990, 30, 719. For preparation of chloroximes, see Kim, Jae N., Ryu, Eung K. J. Org. Chem. 1992, 57, 6649).

Compounds according to the invention substituted in the 4 and 5 positions of the isoxazoline ring system can likewise be prepared by 1,3-dipolar cycloaddition by using suitable 1,2-disubstituted olefins as dipolarophiles. Usually, this reaction gives diastereomer mixtures which can be separated by column chromatography. Optically active isoxazolines can be obtained by chiral HPLC of suitable precursors or end products and also by enantioselective reactions such as, for example, enzymatic ester or amide cleavage or by using chiral auxiliaries at the dipolarophile, as described by Olssen (J. Org. Chem. 1988, 53, 2468).

For preparation of the compounds according to the invention, it is also possible to use suitably substituted 2-alkoxyacrylamides (Scheme 3). These are obtainable from the acrylic esters described in Scheme 2 after hydrolysis and amide formation.

Scheme 2

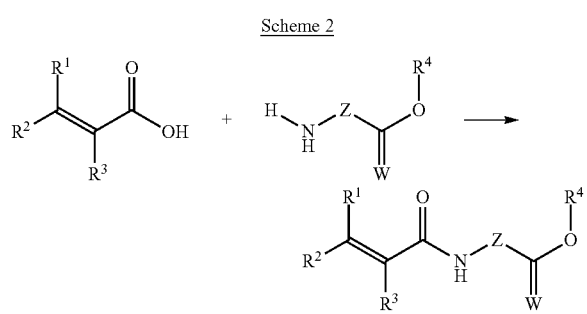

One option for activating the acrylic acid is carbodiimides, for example EDCl (Chen, F. M. F.; Benoiton, N. L. Synthesis 1979, 709). For preparation of acrylamides, see U.S. Pat. No. 2,521,902, JP60112746, J. of Polymer Science 1979, 17 (6), 1655. Suitably substituted acrylamides can be reacted in a 1,3-cycloaddition reaction with nitrile oxides to give the compounds according to the invention (Scheme 3).

Transformations of the functional groups $R^3$ are possible either at the alkene stage or at the isoxazoline stage.

Collections of compounds of the formula (I) and/or salts thereof which can be synthesized by the abovementioned reactions can also be prepared in a parallelized manner, in which case this may be accomplished in a manual, partly automated or fully automated manner. It is possible, for example, to automate the conduct of the reaction, the workup or the purification of the products and/or intermediates. Overall, this is understood to mean a procedure as described, for example, by D. Tiebes in Combinatorial Chemistry—Synthesis, Analysis, Screening (editor: Gunther Jung), Wiley, 1999, on pages 1 to 34.

The compounds of the formula (I) according to the invention (and/or salts thereof), referred to collectively as "compounds according to the invention" hereinafter, have excellent herbicidal efficacy against a broad spectrum of economically important monocotyledonous and dicotyledonous annual harmful plants.

The present invention therefore also provides a method for controlling unwanted plants or for regulating the growth of plants, preferably in plant crops, in which one or more compound(s) of the invention is/are applied to the plants (for example harmful plants such as monocotyledonous or dicotyledonous weeds or unwanted crop plants), the seed (for example grains, seeds or vegetative propagules such as tubers or shoot parts with buds) or the area on which the plants grow (for example the area under cultivation). The compounds of the invention can be deployed, for example, prior to sowing (if appropriate also by incorporation into the soil), prior to emergence or after emergence. Specific examples of some representatives of the monocotyledonous and dicotyledonous weed flora which can be controlled by the compounds of the invention are as follows, though the enumeration is not intended to impose a restriction to particular species.

Monocotyledonous harmful plants of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Dicotyledonous weeds of the genera: *Abutilon, Amaranthus, Ambrosia, Anoda, Anthemis, Aphanes, Artemisia, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

When the compounds according to the invention are applied to the soil surface before germination, either the weed seedlings are prevented completely from emerging or the weeds grow until they have reached the cotyledon stage, but then stop growing.

If the active compounds are applied post-emergence to the green parts of the plants, growth stops after the treatment, and the harmful plants remain at the growth stage at the time of application, or they die completely after a certain time, so that in this manner competition by the weeds, which is harmful to the crop plants, is eliminated very early and in a sustained manner.

The compounds according to the invention can be selective in crops of useful plants and can also be employed as non-selective herbicides.

By virtue of their herbicidal and plant growth regulatory properties, the active compounds can also be used to control harmful plants in crops of genetically modified plants which are known or are yet to be developed. In general, the transgenic plants are characterized by particular advantageous properties, for example by resistances to certain active compounds used in agroindustry, in particular certain herbicides, resistances to plant diseases or pathogens of plant diseases, such as certain insects or microorganisms such as fungi, bacteria or viruses. Other specific characteristics relate, for example, to the harvested material with regard to quantity, quality, storability, composition and specific constituents. For instance, there are known transgenic plants with an elevated starch content or altered starch quality, or those with a different fatty acid composition in the harvested material. Further particular properties lie in tolerance or resistance to abiotic stress factors, for example heat, cold, drought, salinity and ultraviolet radiation.

Preference is given to using the compounds of the formula (I) according to the invention or salts thereof in economically important transgenic crops of useful and ornamental plants.

The compounds of the formula (I) can be used as herbicides in crops of useful plants which are resistant, or have been made resistant by genetic engineering, to the phytotoxic effects of the herbicides.

Conventional ways of producing novel plants which have modified properties in comparison to existing plants consist, for example, in traditional cultivation methods and the generation of mutants. Alternatively, novel plants with altered properties can be generated with the aid of recombinant methods (see, for example, EP 0221044, EP 0131624). What has been described are, for example, several cases of genetic modifications of crop plants for the purpose of modifying the starch synthesized in the plants (e.g. WO 92/011376 A, WO 92/014827 A, WO 91/019806 A), transgenic crop plants which are resistant to certain herbicides of the glufosinate type (cf., for example, EP 0242236 A, EP 0242246 A) or of the glyphosate type (WO 92/000377A) or of the sulfonylurea type (EP 0257993 A, U.S. Pat. No. 5,013,659) or to combinations or mixtures of these herbicides through "gene stacking", such as transgenic crop plants, for example corn or soya with the trade name or the designation Optimum™ GAT™ (Glyphosate ALS Tolerant),
- transgenic crop plants, for example cotton, capable of producing *Bacillus thuringiensis* toxins (Bt toxins), which make the plants resistant to particular pests (EP 0142924 A, EP 0193259 A),
- transgenic crop plants having a modified fatty acid composition (WO 91/013972 A),
- genetically modified crop plants having novel constituents or secondary metabolites, for example novel phytoalexins, which cause an increase in disease resistance (EP 0309862 A, EP 0464461 A),
- genetically modified plants having reduced photorespiration, which have higher yields and higher stress tolerance (EP 0305398 A),
- transgenic crop plants which produce pharmaceutically or diagnostically important proteins ("molecular pharming"),
- transgenic crop plants which feature higher yields or better quality,
- transgenic crop plants which are distinguished by a combination, for example of the abovementioned novel properties ("gene stacking").

Numerous molecular biology techniques which can be used to produce novel transgenic plants with modified properties are known in principle; see, for example, I. Potrykus and G. Spangenberg (eds), Gene Transfer to Plants, Springer Lab Manual (1995), Springer Verlag Berlin, Heidelberg or Christou, "Trends in Plant Science" 1 (1996) 423-431).

For such genetic manipulations, nucleic acid molecules which allow mutagenesis or sequence alteration by recombination of DNA sequences can be introduced into plasmids. With the aid of standard methods, it is possible, for example, to undertake base exchanges, remove parts of sequences or add natural or synthetic sequences. To join the DNA fragments with one another, adapters or linkers can be placed onto the fragments, see, for example, Sambrook et al., 1989, Molecular Cloning, A Laboratory Manual, 2nd ed. Cold Spring Harbor Laboratory Press, Cold Spring Harbor, N.Y.; or Winnacker "Gene und Klone" [Genes and Clones], VCH Weinheim 2nd edition 1996.

For example, the generation of plant cells with a reduced activity of a gene product can be achieved by expressing at least one corresponding antisense RNA, a sense RNA for achieving a cosuppression effect, or by expressing at least one suitably constructed ribozyme which specifically cleaves transcripts of the abovementioned gene product. To this end, it is firstly possible to use DNA molecules which encompass the entire coding sequence of a gene product inclusive of any flanking sequences which may be present, and also DNA molecules which only encompass portions of the coding sequence, in which case it is necessary for these portions to be long enough to have an antisense effect in the cells. It is also possible to use DNA sequences which have a high degree of homology to the coding sequences of a gene product, but are not completely identical to them.

When expressing nucleic acid molecules in plants, the protein synthesized may be localized in any desired compartment of the plant cell. However, to achieve localization in a particular compartment, it is possible, for example, to join the coding region to DNA sequences which ensure localization in a particular compartment. Such sequences are known to those skilled in the art (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106). The nucleic acid molecules can also be expressed in the organelles of the plant cells.

The transgenic plant cells can be regenerated by known techniques to give rise to entire plants. In principle, the transgenic plants may be plants of any desired plant species, i.e. not only monocotyledonous but also dicotyledonous plants. Thus, transgenic plants can be obtained whose properties are altered by overexpression, suppression or inhibition of homologous (=natural) genes or gene sequences or expression of heterologous (=foreign) genes or gene sequences.

The compounds (I) according to the invention can be used with preference in transgenic crops which are resistant to growth regulators, for example 2,4-D, dicamba, or to herbicides which inhibit essential plant enzymes, for example acetolactate synthases (ALS), EPSP synthases, glutamine synthases (GS) or hydroxyphenylpyruvate dioxygenases (HPPD), or to herbicides from the group of the sulfonylureas, the glyphosates, glufosinates or benzoylisoxazoles and analogous active compounds, or to any desired combinations of these active compounds.

The compounds of the invention can be used with particular preference in transgenic crop plants which are resistant to a combination of glyphosates and glufosinates, glyphosates and sulfonylureas or imidazolinones. Most preferably, the compounds according to the invention can be used in transgenic crop plants such as corn or soya bean with the trade name or the designation Optimum™ GAT™ (glyphosate ALS tolerant), for example.

When the active compounds of the invention are employed in transgenic crops, not only do the effects towards harmful plants observed in other crops occur, but frequently also effects which are specific to the application in the particular transgenic crop, for example an altered or specifically widened spectrum of weeds which can be controlled, altered application rates which can be used for the application, preferably good combinability with the herbicides to which the transgenic crop is resistant, and influencing of growth and yield of the transgenic crop plants.

The invention therefore also relates to the use of the compounds according to the invention of the formula (I) as herbicides for controlling harmful plants in transgenic crop plants.

The compounds of the invention can be applied in the form of wettable powders, emulsifiable concentrates, sprayable solutions, dusting products or granules in the customary formulations. The invention therefore also provides herbicidal and plant-growth-regulating compositions which comprise the compounds of the invention.

The compounds of the invention can be formulated in various ways, according to the biological and/or physicochemical parameters required. Possible formulations include, for example: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), dispersions based on oil or water, oil-miscible solutions, capsule suspensions (CS), dusting products (DP), dressings, granules for scattering and soil application, granules (GR) in the form of microgranules, spray granules, absorption and adsorption granules, water-dispersible granules (WG), water-soluble granules (SG), ULV formulations, microcapsules and waxes. These individual formulation types are known in principle and are described, for example, in: Winnacker-Küchler, "Chemische Technologie" [Chemical Technology], Volume 7, C. Hanser Verlag Munich, 4th Ed. 1986, Wade van Valkenburg, "Pesticide Formulations", Marcel Dekker, N.Y., 1973, K. Martens, "Spray Drying" Handbook, 3rd Ed. 1979, G. Goodwin Ltd. London.

The formulation auxiliaries required, such as inert materials, surfactants, solvents and further additives, are likewise known and are described, for example, in: Watkins, "Handbook of Insecticide Dust Diluents and Carriers", 2nd Ed., Darland Books, Caldwell N.J.; H.v. Olphen, "Introduction to Clay Colloid Chemistry", 2nd Ed., J. Wiley & Sons, N.Y.; C. Marsden, "Solvents Guide", 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflachenaktive Äthylenoxidaddukte" [Interface-active Ethylene Oxide Adducts], Wiss. Verlagsgesell., Stuttgart 1976; Winnacker-Küchler, "Chemische Technologie", volume 7, C. Hanser Verlag Munich, 4th Ed. 1986.

On the basis of these formulations, it is also possible to produce combinations with other active compounds, for example insecticides, acaricides, herbicides, fungicides, and also with safeners, fertilizers and/or growth regulators, for example in the form of a finished formulation or as a tank mix.

Active compounds which can be employed in combination with the compounds according to the invention in mixed formulations or in the tank mix are, for example, known active compounds which are based on the inhibition of, for example, acetolactate synthase, acetyl-CoA carboxylase, cellulose synthase, enolpyruvylshikimate-3-phosphate synthase, glutamine synthetase, p-hydroxyphenylpyruvate dioxygenase, phytoene desaturase, photosystem I, photosystem II or protoporphyrinogen oxidase, as are described in, for example, Weed Research 26 (1986) 441-445 or "The Pesticide Manual", 16th edition, The British Crop Protection Council and the Royal Soc. of Chemistry, 2006 and the literature cited therein. Known herbicides or plant growth regulators which can be combined with the compounds according to the invention are, for example, the following active compounds, where said compounds are designated either with their "common name" in accordance with the International Organization for Standardization (ISO) or with the chemical name or with the code number. They always encompass all of the application forms such as, for example, acids, salts, esters and also all isomeric forms such as stereoisomers and optical isomers, even if not explicitly mentioned.

Examples of such herbicidal mixing partners are:

acetochlor, aciflurofen, aciflurofen-sodium, alachlor, allidochlor, alloxydim, alloxydim-sodium, ametryn, amicarbazone, amidochlor, amidosulfuron, 4-amino-3-chloro-6-(4-chloro-2-fluoro-3-methylphenyl)-5-fluoropyridine-2-carboxylic acid, aminocyclopyrachlor, aminocyclopyrachlor-potassium, aminocyclopyrachlor-methyl, aminopyralid, amitrole, ammoniumsulfamate, anilofos, asulam, atrazine, azafenidin, azimsulfuron, beflubutamid, benazolin, benazolin-ethyl, benfluralin, benfuresate, bensulfuron, bensulfuron-methyl, bensulide, bentazone, benzobicyclon, benzofenap, bicyclopyron, bifenox, bilanafos, bilanafos-sodium, bispyribac, bispyribac-sodium, bromacil, bromobutide, bromofenoxim, bromoxynil, bromoxynil-butyrate, -potassium, -heptanoate and -octanoate, busoxinone, butachlor, butafenacil, butamifos, butenachlor, butralin, butroxydim, butylate, cafenstrole, carbetamide, carfentrazone, carfentrazone-ethyl, chloramben, chlorbromuron, chlorfenac, chlorfenac-sodium, chlorfenprop, chlorflurenol, chlorflurenol-methyl, chloridazon, chlorimuron, chlorimuron-ethyl, chlorophthalim, chlorotoluron, chlorthal-dimethyl, chlorsulfuron, cinidon, cinidon-ethyl, cinmethylin, cinosulfuron, clacyfos, clethodim, clodinafop, clodinafop-propargyl, clomazone, clomeprop, clopyralid, cloransulam, cloransulam-methyl, cumyluron, cyanamide, cyanazine, cycloate, cyclopyrimorate, cyclosulfamuron, cycloxydim, cyhalofop, cyhalofop-butyl, cyprazine, 2,4-D, 2,4-D-butotyl, -butyl, -dimethylammonium, -diolamine, -ethyl, -2-ethylhexyl, -isobutyl, -isooctyl, -isopropylammonium, -potassium, -triisopropanolammonium and -trolamine, 2,4-DB, 2,4-DB-butyl, -dimethylammonium, -isooctyl, -potassium and -sodium, daimuron (dymron), dalapon, dazomet, n-decanol, desmedipham, detosyl-pyrazolate (DTP), dicamba, dichlobenil, 2-(2,4-dichlorobenzyl)-4,4-dimethyl-1,2-oxazolidin-3-one, 2-(2,5-dichlorobenzyl)-4,4-dimethyl-1,2-oxazolidin-3-one, dichlorprop, dichlorprop-P, diclofop, diclofop-methyl, diclofop-P-methyl, diclosulam, difenzoquat, diflufenican, diflufenzopyr, diflufenzopyr-sodium, dimefuron, dimepiperate, dimethachlor, dimethametryn, dimethenamid, dimethenamid-P, dimetrasulfuron, dinitramine, dinoterb, diphenamid, diquat, diquat dibromide, dithiopyr, diuron, DNOC, endothal, EPTC, esprocarb, ethalfluralin, ethametsulfuron, ethametsulfuron-methyl, ethiozin, ethofumesate, ethoxyfen, ethoxyfen-ethyl, ethoxysulfuron, etobenzanid, F-9600, F-5231, i.e. N-[2-chloro-4-fluoro-5-[4-(3-fluoropropyl)-4,5-dihydro-5-oxo-1H-tetrazol-1-yl]phenyl]ethansulfonamide, F-7967, i.e. 3-[7-chloro-5-fluoro-2-(trifluoromethyl)-1H-benzimidazol-4-yl]-1-methyl-6-(trifluoromethyl)pyrimidine-2,4(1H,3H)-dione, fenoxaprop, fenoxaprop-P, fenoxaprop-ethyl, fenoxaprop-P-ethyl, fenoxasulfone, fenquinotrione, fentrazamide, flamprop, flamprop-M-isopropyl, flamprop-M-methyl, flazasulfuron, florasulam, fluazifop, fluazifop-P, fluazifop-butyl, fluazifop-P-butyl, flucarbazone, flucarbazone-sodium, flucetosulfuron, fluchloralin, flufenacet, flufenpyr, flufenpyr-ethyl, flumetsulam, flumiclorac, flumiclorac-pentyl, flumioxazin, fluometuron, flurenol, flurenol-butyl, -dimethylammonium and -methyl, fluoroglycofen, fluoroglycofen-ethyl, flupropanate, flupyrsulfuron, flupyrsulfuron-methyl-sodium, fluridone, flurochloridone, fluroxypyr, fluroxypyr-meptyl, flurtamone, fluthiacet, fluthiacet-methyl, fomesafen, fomesafen-sodium, foramsulfuron, fosamine, glufosinate, glufosinate-ammonium, glufosinate-P-sodium, glufosinate-P-ammonium, glufosinate-P-sodium, glyphosate, glyphosate-ammonium, -isopropylammonium, -diammonium, -dimethylammonium, -potassium, -sodium and -trimesium, H-9201, i.e. O-(2,4-dimethyl-6-nitrophenyl)O-ethyl isopropylphosphoramidothioate, halauxifen, halauxifen-methyl, halosafen, halosulfuron, halosulfuron-methyl, haloxyfop, haloxyfop-P, haloxyfop-ethoxyethyl, haloxyfop-P-ethoxyethyl, haloxyfop-methyl, haloxyfop-P-methyl, hexazinone, HW-02, i.e. 1-(dimethoxyphosphoryl)ethyl (2,4-dichlorophenoxy)acetate, imazamethabenz, imazamethabenz-methyl, imazamox, imazamox-ammonium, imazapic, imazapic-ammonium, imazapyr, imazapyr-isopropylammonium, imazaquin, imazaquin-ammonium, imazethapyr, imazethapyr-immonium, imazosulfuron, indanofan, indaziflam, iodosulfuron, iodosulfuron-methyl-sodium, ioxynil, ioxynil-octanoate, -potassium and -sodium, ipfencarbazone, isoproturon, isouron, isoxaben, isoxaflutole, karbutilate, KUH-043, i.e. 3-({[5-(difluoromethyl)-1-methyl-3-(trifluoromethyl)-1H-pyrazol-4-yl]methyl}sulfonyl)-5,5-dimethyl-4,5-dihydro-1,2-oxazole, ketospiradox, lactofen, lenacil, linuron, MCPA, MCPA-butotyl, -dimethylammonium, -2-ethylhexyl, -isopropylammonium, -potassium and -sodium, MCPB, MCPB-methyl, -ethyl and -sodium, mecoprop, mecoprop-sodium and -butotyl, mecoprop-P, mecoprop-P-butotyl, -dimethylammonium, -2-ethylhexyl and -potassium, mefenacet, mefluidide, mesosulfuron, mesosulfuron-methyl, mesotrione, methabenzthiazuron, metam, metamifop, metamitron, metazachlor, metazosulfuron, methabenzthiazuron, methiopyrsulfuron, methiozolin, methyl isothiocyanate, metobromuron, metolachlor, S-metolachlor, metosulam, metoxuron, metribuzin, metsulfuron, metsulfuron-methyl, molinate, monolinuron, monosulfuron, monosulfuron-ester, MT-5950, i.e. N-[3-chloro-4-(1-methylethyl)phenyl]-2-methylpentanamide, NGGC-011, napropamide, NC-310, i.e. 4-(2,4-dichlorobenzoyl)-1-methyl-5-benzyloxypyrazole, neburon, nicosulfuron, nonanoic acid (pelargonic acid), norflurazon, oleic acid (fatty acids), orbencarb, orthosulfamuron, oryzalin, oxadiargyl, oxadiazon, oxasulfuron, oxaziclomefon, oxyfluorfen, paraquat, paraquat dichloride, pebulate, pendimethalin, penoxsulam, pentachlorphenol, pentoxazone, pethoxamid, petroleum oils, phenmedipham, picloram, picolinafen, pinoxaden, piperophos, pretilachlor, primisulfuron, primisulfuron-methyl, prodiamine, profoxydim, prometon, prometryn, propachlor, propanil, propaquizafop, propazine, propham, propisochlor, propoxycarbazone, propoxycarbazone-sodium, propyrisulfuron, propyzamide, prosulfocarb, prosulfuron, pyraclonil, pyraflufen, pyraflufen-ethyl, pyrasulfotole, pyrazolynate (pyrazolate), pyrazosulfuron, pyrazosulfuron-ethyl, pyrazoxyfen, pyribambenz, pyribambenz-isopropyl, pyribambenz-propyl, pyribenzoxim, pyributicarb, pyridafol, pyridate, pyriftalid, pyriminobac, pyriminobac-methyl, pyrimisulfan, pyrithiobac, pyrithiobac-sodium, pyroxasulfone, pyroxsulam, quinclorac, quinmerac, quinoclamine, quizalofop, quizalofop-ethyl, quizalofop-P, quizalofop-P-ethyl, quizalofop-P-tefuryl, rimsulfuron, saflufenacil, sethoxydim, siduron, simazine, simetryn, SL-261, sulcotrion, sulfentrazone, sulfometuron, sulfometuron-methyl, sulfosulfuron, SYN-523, SYP-249, i.e. 1-ethoxy-3-methyl-1-oxobut-3-en-2-yl 5-[2-chloro-4-(trifluoromethyl)phenoxy]-2-nitrobenzoate, SYP-300, i.e. 1-[7-fluoro-3-oxo-4-(prop-2-yn-1-yl)-3,4-dihydro-2H-1,4-benzoxazin-6-yl]-3-propyl-2-thioxoimidazolidine-4,5-dione, 2,3,6-TBA, TCA (trifluoroacetic acid), TCA-sodium, tebuthiuron, tefuryltrione, tembotrione, tepraloxydim, terbacil, terbucarb, terbumeton, terbuthylazin, terbutryn, thenylchlor, thiazopyr, thiencarbazone, thiencarbazone-methyl, thifensulfuron, thifensulfuron-methyl, thiobencarb, tiafenacil, tolpyralate, topramezone, tralkoxydim, triafamone, tri-allate, triasulfuron, triaziflam, tribenuron, tribenuron-methyl, triclopyr, trietazine, trifloxysulfuron, trifloxysulfuron-sodium, trifludimoxazin, trifluralin, triflusulfuron, triflusulfuron-methyl, tritosulfuron, urea sulfate, vernolate, XDE-848, ZJ-0862, i.e. 3,4-dichloro-N-{2-[(4,6-dimethoxypyrimidin-2-yl)oxy]benzyl}aniline, and also the following compounds:

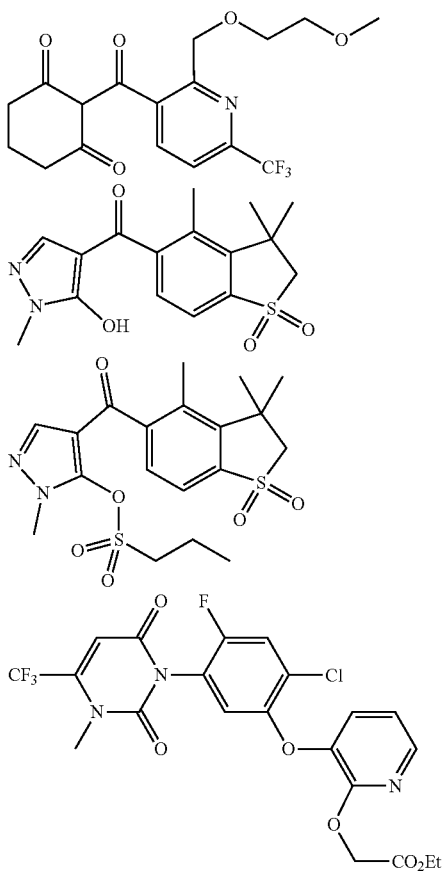

Examples of plant growth regulators as possible mixing partners are:

acibenzolar, acibenzolar-S-methyl, 5-aminolevulinic acid, ancymidol, 6-benzylaminopurine, brassinolide, catechol, chlormequat chloride, cloprop, cyclanilide, 3-(cycloprop-1-enyl)propionic acid, daminozide, dazomet, n-decanol, dikegulac, dikegulac-sodium, endothal, endothal-dipotassium, -disodium, and mono(N,N-dimethylalkylammonium), ethephon, flumetralin, flurenol, flurenol-butyl, flurprimidol, forchlorfenuron, gibberellic acid, inabenfide, indole-3-acetic acid (IAA), 4-indol-3-ylbutyric acid, isoprothiolane, probenazole, jasmonic acid, jasmonic acid methyl ester, maleic hydrazide, mepiquat chloride, 1-methylcyclopropene, 2-(1-naphthyl)acetamide, 1-naphthylacetic acid, 2-naphthyloxyacetic acid, nitrophenoxide mixture, 4-oxo-4 [(2-phenylethyl)amino]butyric acid, paclobutrazole, N-phenylphthalamic acid, prohexadione, prohexadione-calcium, prohydrojasmone, salicylic acid, strigolactone, tecnazene, thidiazuron, triacontanol, trinexapac, trinexapac-ethyl, tsitodef, uniconazole, uniconazole-P.

Safeners which can be employed in combination with the compounds of the formula (I) according to the invention and optionally in combination with further active compounds such as insecticides, acaricides, herbicides, fungicides as listed above are preferably selected from the group consisting of:

S1) Compounds of the formula (S1)

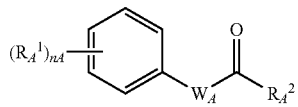

where the symbols and indices are defined as follows:

$n_A$ represents a natural number from 0 to 5, preferably from 0 to 3;

$R_A^1$ represents halogen, $(C_1-C_4)$-alkyl, $(C_1-C_4)$-alkoxy, nitro or $(C_1-C_4)$-haloalkyl;

$W_A$ represents an unsubstituted or substituted divalent heterocyclic radical from the group of the partially unsaturated or aromatic five-membered heterocycles having 1 to 3 ring heteroatoms from the N and O group, where at least one nitrogen atom and at most one oxygen atom is present in the ring, preferably a radical from the group of $(W_A^1)$ to $(W_A^4)$,

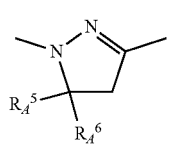

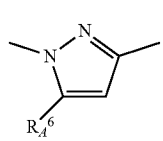

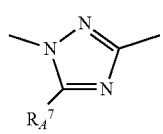

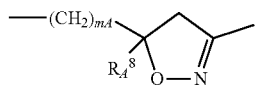

$m_A$ represents 0 or 1;

$R_A^2$ represents $OR_A^3$, $SR_A^3$ or $NR_A^3R_A^4$ or a saturated or unsaturated 3- to 7-membered heterocycle having at least one nitrogen atom and up to 3 heteroatoms, preferably from the group consisting of O and S, which is joined to the carbonyl group in (S1) via the nitrogen atom and is unsubstituted or substituted by radicals from the group consisting of $(C_1-C_4)$-alkyl, $(C_1-C_4)$-alkoxy or optionally substituted phenyl, preferably a radical of the formula $OR_A^3$, $NHR_A^4$ or $N(CH_3)_2$, especially of the formula $OR_A^3$;

$R_A^3$ represents hydrogen or an unsubstituted or substituted aliphatic hydrocarbon radical preferably having a total of 1 to 18 carbon atoms;

$R_A^4$ represents hydrogen, $(C_1-C_6)$-alkyl, $(C_1-C_6)$-alkoxy or substituted or unsubstituted phenyl;

$R_A^5$ represents H, $(C_1-C_8)$-alkyl, $(C_1-C_8)$-haloalkyl, $(C_1-C_4)$-alkoxy-$(C_1-C_8)$-alkyl, cyano or $COOR_A^9$, where $R_A^9$ represents hydrogen, $(C_1-C_8)$-alkyl, $(C_1-C_8)$-haloalkyl, $(C_1-$ $C_4$)-alkoxy-($C_1$-$C_4$)-alkyl, ($C_1$-$C_6$)-hydroxyalkyl, ($C_3$-$C_{12}$)-cycloalkyl or tri-($C_1$-$C_4$)-alkylsilyl;

$R_A^6$, $R_A^7$, $R_A^8$ are identical or different and represent hydrogen, ($C_1$-$C_8$)-alkyl, ($C_1$-$C_8$)-haloalkyl, ($C_3$-$C_{12}$)-cycloalkyl or substituted or unsubstituted phenyl;

preferably:

a) compounds of the dichlorophenylpyrazoline-3-carboxylic acid type (S1$^a$), preferably compounds such as 1-(2,4-dichlorophenyl)-5-(ethoxycarbonyl)-5-methyl-2-pyrazoline-3-carboxylic acid, ethyl 1-(2,4-dichlorophenyl)-5-(ethoxycarbonyl)-5-methyl-2-pyrazoline-3-carboxylate (S1-1) ("mefenpyr-diethyl"), and related compounds as described in WO-A-91/07874;

b) derivatives of dichlorophenylpyrazolecarboxylic acid (S1$^b$), preferably compounds such as ethyl 1-(2,4-dichlorophenyl)-5-methylpyrazole-3-carboxylate (S1-2), ethyl 1-(2,4-dichlorophenyl)-5-isopropylpyrazole-3-carboxylate (S1-3), ethyl 1-(2,4-dichlorophenyl)-5-(1,1-dimethylethyl)pyrazole-3-carboxylate (S1-4) and related compounds as described in EP-A-333 131 and EP-A-269 806;

c) derivatives of 1,5-diphenylpyrazole-3-carboxylic acid (S1$^c$), preferably compounds such as ethyl 1-(2,4-dichlorophenyl)-5-phenylpyrazole-3-carboxylate (S1-5), methyl 1-(2-chlorophenyl)-5-phenylpyrazole-3-carboxylate (S1-6) and related compounds as described in EP-A-268 554, for example;

d) compounds of the triazolecarboxylic acid type (S1$^d$), preferably compounds such as fenchlorazole(-ethyl ester), i.e. ethyl 1-(2,4-dichlorophenyl)-5-trichloromethyl-(1H)-1,2,4-triazole-3-carboxylate (S1-7), and related compounds as described in EP-A-174 562 and EP-A-346 620;

e) compounds of the 5-benzyl- or 5-phenyl-2-isoxazoline-3-carboxylic acid or of the 5,5-diphenyl-2-isoxazoline-3-carboxylic acid type (S1$^e$), preferably compounds such as ethyl 5-(2,4-dichlorobenzyl)-2-isoxazoline-3-carboxylate (S1-8) or ethyl 5-phenyl-2-isoxazoline-3-carboxylate (S1-9) and related compounds as described in WO-A-91/08202, or 5,5-diphenyl-2-isoxazoline-3-carboxylic acid (S1-10) or ethyl 5,5-diphenyl-2-isoxazoline-3-carboxylate (S1-11) ("isoxadifen-ethyl") or n-propyl 5,5-diphenyl-2-isoxazoline-3-carboxylate (S1-12) or ethyl 5-(4-fluorophenyl)-5-phenyl-2-isoxazoline-3-carboxylate (S1-13), as described in patent application WO-A-95/07897.

S2) Quinoline derivatives of the formula (S2)

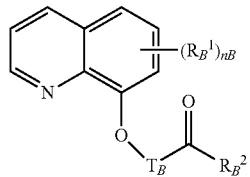

(S2)

where the symbols and indices have the meanings below:

$R_B^1$ represents halogen, ($C_1$-$C_4$)-alkyl, ($C_1$-$C_4$)-alkoxy, nitro or ($C_1$-$C_4$)-haloalkyl;

$n_B$ represents a natural number from 0 to 5, preferably from 0 to 3;

$R_B^2$ represents $OR_B^3$, $SR_B^3$ or $NR_B^3 R_B^4$ or a saturated or unsaturated 3- to 7-membered heterocycle having at least one nitrogen atom and up to 3 heteroatoms, preferably from the group of O and S, which is joined via the nitrogen atom to the carbonyl group in (S2) and is unsubstituted or substituted by radicals from the group of ($C_1$-$C_4$)-alkyl, ($C_1$-$C_4$)-alkoxy or optionally substituted phenyl, preferably a radical of the formula $OR_B^3$, $NHR_B^4$ or $N(CH_3)_2$, especially of the formula $OR_B^3$;

$R_B^3$ represents hydrogen or an unsubstituted or substituted aliphatic hydrocarbon radical preferably having a total of 1 to 18 carbon atoms;

$R_B^4$ represents hydrogen, ($C_1$-$C_6$)-alkyl, ($C_1$-$C_6$)-alkoxy or substituted or unsubstituted phenyl;

$T_B$ represents a ($C_1$ or $C_2$)-alkanediyl chain which is unsubstituted or substituted by one or two ($C_1$-$C_4$)-alkyl radicals or by [($C_1$-$C_3$)-alkoxy]carbonyl;

preferably:

a) compounds of the 8-quinolinoxyacetic acid type (S2a), preferably 1-methylhexyl (5-chloro-8-quinolinoxy)acetate ("cloquintocet-mexyl") (S2-1), (1,3-dimethylbut-1-yl) (5-chloro-8-quinolinoxy)acetate (S2-2), 4-allyloxybutyl (5-chloro-8-quinolinoxy)acetate (S2-3), 1-allyloxyprop-2-yl (5-chloro-8-quinolinoxy)acetate (S2-4), ethyl (5-chloro-8-quinolinoxy)acetate (S2-5), methyl (5-chloro-8-quinolinoxy)acetate (S2-6), allyl (5-chloro-8-quinolinoxy)acetate (S2-7), 2-(2-propylideneiminoxy)-1-ethyl (5-chloro-8-quinolinoxy)acetate (S2-8), 2-oxoprop-1-yl (5-chloro-8-quinolinoxy)acetate (S2-9) and related compounds, as described in EP-A-86 750, EP-A-94 349 and EP-A-191 736 or EP-A-0 492 366, and also (5-chloro-8-quinolinoxy)acetic acid (S2-10), hydrates and salts thereof, for example the lithium, sodium, potassium, calcium, magnesium, aluminum, iron, ammonium, quaternary ammonium, sulfonium or phosphonium salts thereof, as described in WO-A-2002/34048;

b) compounds of the (5-chloro-8-quinolinoxy)malonic acid type (S2$^b$), preferably compounds such as diethyl (5-chloro-8-quinolinoxy)malonate, diallyl (5-chloro-8-quinolinoxy)malonate, methyl ethyl (5-chloro-8-quinolinoxy)malonate and related compounds, as described in EP-A-0 582 198.

S3) Compounds of the formula (S3)

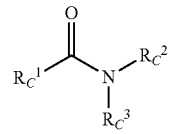

(S3)

where the symbols and indices are defined as follows:

$R_C^1$ represents ($C_1$-$C_4$)-alkyl, ($C_1$-$C_4$)-haloalkyl, ($C_2$-$C_4$)-alkenyl, ($C_2$-$C_4$)-haloalkenyl, ($C_3$-$C_7$)-cycloalkyl, preferably dichloromethyl;

$R_C^2$, $R_C^3$ are identical or different and represent hydrogen, ($C_1$-$C_4$)-alkyl, ($C_2$-$C_4$)-alkenyl, ($C_2$-$C_4$)-alkynyl, ($C_1$-$C_4$)-haloalkyl, ($C_2$-$C_4$)-haloalkenyl, ($C_1$-$C_4$)-alkylcarbamoyl-($C_1$-$C_4$)-alkyl, ($C_2$-$C_4$)-alkenylcarbamoyl-($C_1$-$C_4$)-alkyl, ($C_1$-$C_4$)-alkoxy-($C_1$-$C_4$)-alkyl, dioxolanyl-($C_1$-$C_4$)-alkyl, thiazolyl, furyl, furylalkyl, thienyl, piperidyl, substituted or unsubstituted phenyl, or $R_C^2$ and $R_C^3$ together form a substituted or unsubstituted heterocyclic ring, preferably an oxazolidine, thiazolidine, piperidine, morpholine, hexahydropyrimidine or benzoxazine ring;

preferably:

active compounds of the dichloroacetamide type, which are frequently used as pre-emergence safeners (soil-acting safeners), for example "dichlormid" (N,N-diallyl-2,2-dichloroacetamide) (S3-1), "R-29148" (3-dichloroacetyl-2,2,5-trimethyl-1,3-oxazolidine) from Stauffer (S3-2), "R-28725" (3-dichloroacetyl-2,2-dimethyl-1,3-oxazolidine) from Stauffer (S3-3), "benoxacor" (4-dichloroacetyl-3,4-dihydro-3-methyl-2H-1,4-benzoxazine) (S3-4), "PPG-1292" (N-allyl-N-[(1,3-dioxolan-2-yl)methyl]dichloroacetamide) from PPG Industries (S3-5), "DKA-24" (N-allyl-N-[(allylaminocarbonyl)methyl]dichloroacetamide) from Sagro-Chem (S3-6), "AD-67" or "MON 4660" (3-dichloroacetyl-1-oxa-3-azaspiro[4.5]decane) from Nitrokemia or Monsanto (S3-7), "TI-35" (1-dichloroacetylazepane) from TRI-Chemical RT (S3-8), "diclonon" (dicyclonon) or "BAS145138" or "LAB145138" (S3-9)

((RS)-1-dichloroacetyl-3,3,8a-trimethylperhydropyrrolo[1,2-a]pyrimidin-6-one) from BASF, "furilazole" or "MON 13900" ((RS)-3-dichloroacetyl-5-(2-furyl)-2,2-dimethyloxazolidine) (S3-10); and the (R) isomer thereof (S3-11).

S4) N-acylsulfonamides of the formula (S4) and salts thereof,

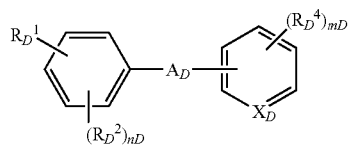

(S4)

in which the symbols and indices are defined as follows:

$A_D$ represents $SO_2$—$NR_D^3$—CO or CO—$NR_D^3$—$SO_2$ $X_D$ represents CH or N;

$R_D^1$ represents CO—$NR_D^5R_D^6$ or NHCO—$R_D^7$;

$R_D^2$ represents halogen, $(C_1-C_4)$-haloalkyl, $(C_1-C_4)$-haloalkoxy, nitro, $(C_1-C_4)$-alkyl, $(C_1-C_4)$-alkoxy, $(C_1-C_4)$-alkylsulfonyl, $(C_1-C_4)$-alkoxycarbonyl or $(C_1-C_4)$-alkylcarbonyl;

$R_D^3$ represents hydrogen, $(C_1-C_4)$-alkyl, $(C_2-C_4)$-alkenyl or $(C_2-C_4)$-alkynyl;

$R_D^4$ represents halogen, nitro, $(C_1-C_4)$-alkyl, $(C_1-C_4)$-haloalkyl, $(C_1-C_4)$-haloalkoxy, $(C_3-C_6)$-cycloalkyl, phenyl, $(C_1-C_4)$-alkoxy, cyano, $(C_1-C_4)$-alkylthio, $(C_1-C_4)$-alkylsulfinyl, $(C_1-C_4)$-alkylsulfonyl, $(C_1-C_4)$-alkoxycarbonyl or $(C_1-C_4)$-alkylcarbonyl;

$R_D^5$ represents hydrogen, $(C_1-C_6)$-alkyl, $(C_3-C_6)$-cycloalkyl, $(C_2-C_6)$-alkenyl, $(C_2-C_6)$-alkynyl, $(C_5-C_6)$-cycloalkenyl, phenyl or 3- to 6-membered heterocyclyl containing $v_D$ heteroatoms from the group consisting of nitrogen, oxygen and sulfur, where the seven last-mentioned radicals are substituted by $v_D$ substituents from the group consisting of halogen, $(C_1-C_6)$-alkoxy, $(C_1-C_6)$-haloalkoxy, $(C_1-C_2)$-alkylsulfinyl, $(C_1-C_2)$-alkylsulfonyl, $(C_3-C_6)$-cycloalkyl, $(C_1-C_4)$-alkoxycarbonyl, $(C_1-C_4)$-alkylcarbonyl and phenyl and, in the case of cyclic radicals, also $(C_1-C_4)$-alkyl and $(C_1-C_4)$-haloalkyl;

$R_D^6$ represents hydrogen, $(C_1-C_6)$-alkyl, $(C_2-C_6)$-alkenyl or $(C_2-C_6)$-alkynyl, where the three last-mentioned radicals are substituted by $v_D$ radicals from the group consisting of halogen, hydroxy, $(C_1-C_4)$-alkyl, $(C_1-C_4)$-alkoxy and $(C_1-C_4)$-alkylthio, or $R_D^5$ and $R_D^6$ together with the nitrogen atom carrying them form a pyrrolidinyl or piperidinyl radical;

$R_D^7$ represents hydrogen, $(C_1-C_4)$-alkylamino, di-$(C_1-C_4)$-alkylamino, $(C_1-C_6)$-alkyl, $(C_3-C_6)$-cycloalkyl, where the 2 last-mentioned radicals are substituted by $v_D$ substituents from the group consisting of halogen, $(C_1-C_4)$-alkoxy, $(C_1-C_6)$-haloalkoxy and $(C_1-C_4)$-alkylthio and, in the case of cyclic radicals, also $(C_1-C_4)$-alkyl and $(C_1-C_4)$-haloalkyl;

$n_D$ represents 0, 1 or 2;

$m_D$ represents 1 or 2;

$v_D$ represents 0, 1, 2 or 3;

among these, preference is given to compounds of the N-acylsulfonamide type, for example of the formula (S4a) below, which are known, for example, from WO-A-97/45016

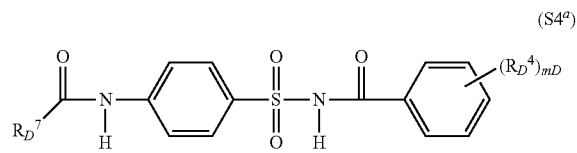

(S4$^a$)

in which $R_D^7$ is $(C_1-C_6)$-alkyl, $(C_3-C_6)$-cycloalkyl, where the 2 last-mentioned radicals are substituted by $v_D$ substituents from the group consisting of halogen, $(C_1-C_4)$-alkoxy, $(C_1-C_6)$-haloalkoxy and $(C_1-C_4)$-alkylthio and, in the case of cyclic radicals, also $(C_1-C_4)$-alkyl and $(C_1-C_4)$-haloalkyl;

$R_D^4$ represents halogen, $(C_1-C_4)$-alkyl, $(C_1-C_4)$-alkoxy, $CF_3$;

$m_D$ represents 1 or 2;

$v_D$ represents 0, 1, 2 or 3;

and acylsulfamoylbenzamides, for example of the formula (S4$^b$) below, which are known, for example, from WO-A-99/16744,

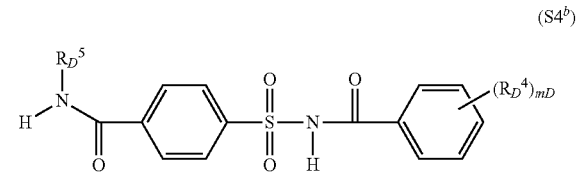

(S4$^b$)

for example those in which $R_D^5$=cyclopropyl and $(R_D^4)$=2-OMe ("cyprosulfamide", S4-1), $R_D^5$=cyclopropyl and $(R_D^4)$=5-Cl-2-OMe (S4-2), $R_D^5$=ethyl and $(R_D^4)$=2-OMe (S4-3), $R_D^5$=isopropyl and $(R_D^4)$=5-Cl-2-OMe (S4-4) and $R_D^5$=isopropyl and $(R_D^4)$=2-OMe (S4-5)

and compounds of the N-acylsulfamoylphenylurea type, of the formula (S4$^c$), which are known, for example, from EP-A-365484,

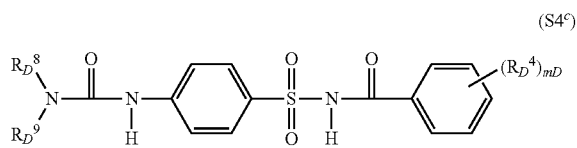

(S4$^c$)

in which $R_D^8$ and $R_D^9$ independently of one another represent hydrogen, $(C_1-C_8)$-alkyl, $(C_3-C_8)$-cycloalkyl, $(C_3-C_6)$-alkenyl, $(C_3-C_6)$-alkynyl, $R_D^4$ represents halogen, $(C_1-C_4)$-alkyl, $(C_1-C_4)$-alkoxy, $CF_3$, $m_D$ represents 1 or 2;

for example

1-[4-(N-2-methoxybenzoylsulfamoyl)phenyl]-3-methylurea,

1-[4-(N-2-methoxybenzoylsulfamoyl)phenyl]-3,3-dimethylurea,

1-[4-(N-4,5-dimethylbenzoylsulfamoyl)phenyl]-3-methylurea, and

N-phenylsulfonylterephthalamides of the formula (S4$^d$), which are known, for example, from CN 101838227,

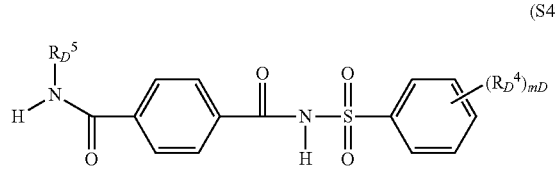

(S4$^d$)

for example those in which $R_D^4$ represents halogen, $(C_1-C_4)$-alkyl, $(C_1-C_4)$-alkoxy, $CF_3$;

$m_D$ represents 1 or 2;

$R_D^5$ represents hydrogen, $(C_1-C_6)$-alkyl, $(C_3-C_6)$-cycloalkyl, $(C_2-C_6)$-alkenyl, $(C_2-C_6)$-alkynyl, $(C_5-C_6)$-cycloalkenyl.

S5) Active compounds from the class of the hydroxyaromatics and the aromatic-aliphatic carboxylic acid derivatives (S5), for example ethyl 3,4,5-triacetoxybenzoate, 3,5-dimethoxy-4-hydroxybenzoic acid, 3,5-dihydroxybenzoic acid, 4-hydroxysalicylic acid, 4-fluorosalicylic acid, 2-hydroxycinnamic acid, 2,4-dichlorocinnamic acid, as described in WO-A-2004/084631, WO-A-2005/015994, WO-A-2005/016001.

S6) Active compounds from the class of the 1,2-dihydroquinoxalin-2-ones (S6), for example 1-methyl-3-(2-thienyl)-1,2-dihydroquinoxalin-2-one, 1-methyl-3-(2-thienyl)-1,2-dihydroquinoxaline-2-thione, 1-(2-aminoethyl)-3-(2-thienyl)-1,2-dihydroquinoxalin-2-one hydrochloride, 1-(2-methylsulfonylaminoethyl)-3-(2-thienyl)-1,2-dihydroquinoxalin-2-one, as described in WO-A-2005/112630.

S7) Compounds of the formula (S7), as described in WO-A-1998/38856,

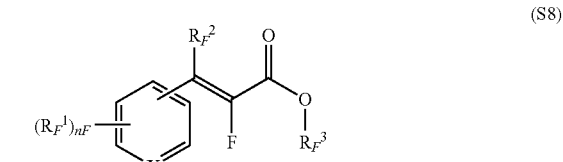

(S7)

in which the symbols and indices are defined as follows:

$R_E^1$, $R_E^2$ independently of one another represent halogen, $(C_1-C_4)$-alkyl, $(C_1-C_4)$-alkoxy, $(C_1-C_4)$-haloalkyl, $(C_1-C_4)$-alkylamino, di-$(C_1-C_4)$-alkylamino, nitro;

$A_E$ represents $COOR_E^3$ or $COSR_E^4$ $R_E^3$, $R_E^4$ independently of one another represent hydrogen, $(C_1-C_4)$-alkyl, $(C_2-C_6)$-alkenyl, $(C_2-C_4)$-alkynyl, cyanoalkyl, $(C_1-C_4)$-haloalkyl, phenyl, nitrophenyl, benzyl, halobenzyl, pyridinylalkyl and alkylammonium, $n_E^1$ represents 0 or 1

$n_E^2$, $n_E^3$ independently of one another represent 0, 1 or 2, preferably:

diphenylmethoxyacetic acid, ethyl diphenylmethoxyacetate, methyl diphenylmethoxyacetate (CAS reg. no. 41858-19-9) (S7-1).

S8) Compounds of the formula (S8), as described in WO-A-98/27049, (S8)

in which $X_F$ represents CH or N, $n_F$ in the case that $X_F$=N is an integer from 0 to 4 and in the case that $X_F$=CH is an integer from 0 to 5, $R_F^1$ represents halogen, $(C_1-C_4)$-alkyl, $(C_1-C_4)$-haloalkyl, $(C_1-C_4)$-alkoxy, $(C_1-C_4)$-haloalkoxy, nitro, $(C_1-C_4)$-alkylthio, $(C_1-C_4)$-alkylsulfonyl, $(C_1-C_4)$-alkoxycarbonyl, optionally substituted phenyl, optionally substituted phenoxy, $R_F^2$ represents hydrogen or $(C_1-C_4)$-alkyl, $R_F^3$ represents hydrogen, $(C_1-C_8)$-alkyl, $(C_2-C_4)$-alkenyl, $(C_2-C_4)$-alkynyl or aryl, where each of the abovementioned carbon-containing radicals is unsubstituted or substituted by one or more, preferably up to three identical or different radicals from the group consisting of halogen and alkoxy; or salts thereof, preferably compounds in which $X_F$ represents CH, $n_F$ represents an integer from 0 to 2, $R_F^1$ represents halogen, $(C_1-C_4)$-alkyl, $(C_1-C_4)$-haloalkyl, $(C_1-C_4)$-alkoxy, $(C_1-C_4)$-haloalkoxy, $R_F^2$ represents hydrogen or $(C_1-C_4)$-alkyl, $R_F^3$ represents hydrogen, $(C_1-C_8)$-alkyl, $(C_2-C_4)$-alkenyl, $(C_2-C_4)$-alkynyl or aryl, where each of the abovementioned carbon-containing radicals is unsubstituted or substituted by one or more, preferably up to three identical or different radicals from the group consisting of halogen and alkoxy, or salts thereof.

S9) Active compounds from the class of the 3-(5-tetrazolylcarbonyl)-2-quinolones (S9), for example 1,2-dihydro-4-hydroxy-1-ethyl-3-(5-tetrazolylcarbonyl)-2-quinolone (CAS reg. no. 219479-18-2), 1,2-dihydro-4-hydroxy-1-methyl-3-(5-tetrazolylcarbonyl)-2-quinolone (CAS Reg. no. 95855-00-8), as described in WO-A-1999/000020.

S10) Compounds of the formula (S10$^a$) or (S10$^b$) as described in WO-A-2007/023719 and WO-A-2007/023764

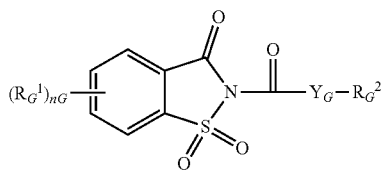

(S10$^a$)

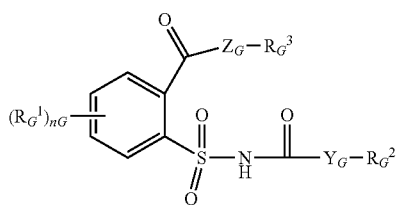

(S10$^b$)

in which $R_G^1$ represents halogen, $(C_1-C_4)$-alkyl, methoxy, nitro, cyano, $CF_3$, $OCF_3$, $Y_G$, $Z_G$ independently of one another represent O or S, $n_G$ represents an integer from 0 to 4, $R_G^2$ represents $(C_1-C_{16})$-alkyl, $(C_2-C_6)$-alkenyl, $(C_3-C_6)$-cycloalkyl, aryl; benzyl, halobenzyl, $R_G^3$ represents hydrogen or $(C_1-C_6)$-alkyl.

S11) Active compounds of the oxyimino compound type (S11), which are known as seed-dressing agents, for example "oxabetrinil" ((Z)-1,3-dioxolan-2-ylmethoxyimino(phenyl)acetonitrile) (S11-1), which is known as a seed-dressing safener for millet/sorghum against metolachlor damage, "fluxofenim" (1-(4-chlorophenyl)-2,2,2-trifluoro-1-ethanone 0-(1,3-dioxolan-2-ylmethyl)oxime) (S11-2), which is known as a seed-dressing safener for millet/sorghum against metolachlor damage, and "cyometrinil" or "CGA-43089" ((Z)-cyanomethoxyimino(phenyl)acetonitrile) (S11-3), which is known as a seed-dressing safener for millet/sorghum against metolachlor damage.

S12) Active compounds from the class of the isothiochromanones (S12), for example methyl [(3-oxo-1H-2-benzothiopyran-4(3H)-ylidene)methoxy]acetate (CAS Reg. No. 205121-04-6) (S12-1) and related compounds from WO-A-1998/13361.

S13) One or more compounds from group (S13):

"naphthalic anhydride" (1,8-naphthalenedicarboxylic anhydride) (S13-1), which is known as a seed-dressing safener for corn against thiocarbamate herbicide damage, "fenclorim" (4,6-dichloro-2-phenylpyrimidine) (S13-2), which is known as a safener for pretilachlor in sown rice, "flurazole" (benzyl 2-chloro-4-trifluoromethyl-1,3-thiazole-5-carboxylate) (S13-3), which is known as a seed-dressing safener for millet/sorghum against alachlor and metolachlor damage, "CL 304415" (CAS Reg. No. 31541-57-8) (4-carboxy-3,4-dihydro-2H-1-benzopyran-4-acetic acid) (S13-4) from American Cyanamid, which is known as a safener for corn against damage by imidazolinones, "MG 191" (CAS Reg. No. 96420-72-3) (2-dichloromethyl-2-methyl-1,3-dioxolane) (S13-5) from Nitrokemia, which is known as a safener for corn, "MG 838" (CAS Reg. No. 133993-74-5) (2-propenyl 1-oxa-4-azaspiro[4.5]decane-4-carbodithioate) (S13-6) from Nitrokemia, "disulfoton" (0,0-diethyl S-2-ethylthioethyl phosphorodithioate) (S13-7), "dietholate" (0,0-diethyl O-phenyl phosphorothioate) (S13-8), "mephenate" (4-chlorophenyl methylcarbamate) (S13-9).

S14) Active compounds which, in addition to herbicidal action against harmful plants, also have safener action on crop plants such as rice, for example "dimepiperate" or "MY 93" (S-1-methyl 1-phenylethylpiperidine-1-carbothioate), which is known as a safener for rice against damage by the herbicide molinate, "daimuron" or "SK 23" (1-(1-methyl-1-phenylethyl)-3-p-tolylurea), which is known as a safener for rice against imazosulfuron herbicide damage, "cumyluron"="JC 940" (3-(2-chlorophenylmethyl)-1-(1-methyl-1-phenylethyl)urea, see JP-A-60087254), which is known as safener for rice against damage by some herbicides, "methoxyphenone" or "NK 049" (3,3'-dimethyl-4-methoxybenzophenone), which is known as a safener for rice against damage by some herbicides, "CSB" (1-bromo-4-(chloromethylsulfonyl)benzene) from Kumiai, (CAS Reg. No. 54091-06-4), which is known as a safener against damage by some herbicides in rice.

S15) Compounds of the formula (S15) or tautomers thereof

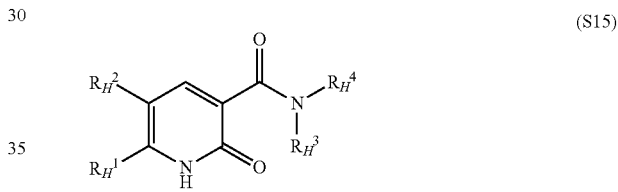

(S15)

as described in WO-A-2008/131861 and WO-A-2008/131860 in which $R_H^1$ represents a $(C_1-C_6)$-haloalkyl radical and $R_H^2$ represents hydrogen or halogen and $R_H^3$, $R_H^4$ independently of one another represent hydrogen, $(C_1-C_{16})$-alkyl, $(C_2-C_{16})$-alkenyl or $(C_2-C_{16})$-alkynyl, where each of the 3 last-mentioned radicals is unsubstituted or substituted by one or more radicals from the group of halogen, hydroxyl, cyano, $(C_1-C_4)$-alkoxy, $(C_1-C_4)$-haloalkoxy, $(C_1-C_4)$-alkylthio, $(C_1-C_4)$-alkylamino, di[$(C_1-C_4)$-alkyl]amino, [$(C_1-C_4)$-alkoxy]carbonyl, [$(C_1-C_4)$-haloalkoxy]carbonyl, $(C_3-C_6)$-cycloalkyl which is unsubstituted or substituted, phenyl which is unsubstituted or substituted, and heterocyclyl which is unsubstituted or substituted, or $(C_3-C_6)$-cycloalkyl, $(C_4-C_6)$-cycloalkenyl, $(C_3-C_6)$-cycloalkyl fused on one side of the ring to a 4 to 6-membered saturated or unsaturated carbocyclic ring, or $(C_4-C_6)$-cycloalkenyl fused on one side of the ring to a 4 to 6-membered saturated or unsaturated carbocyclic ring, where each of the 4 last-mentioned radicals is unsubstituted or substituted by one or more radicals from the group consisting of halogen, hydroxyl, cyano, $(C_1-C_4)$-alkyl, $(C_1-C_4)$-haloalkyl, $(C_1-C_4)$-alkoxy, $(C_1-C_4)$-haloalkoxy, $(C_1-C_4)$-alkylthio, $(C_1-C_4)$-alkylamino, di[$(C_1-C_4)$-alkyl]amino, [$(C_1-C_4)$-alkoxy]carbonyl, [$(C_1-C_4)$-haloalkoxy]carbonyl, $(C_3-C_6)$-cycloalkyl which is unsubstituted or substituted, phenyl which is unsubstituted or substituted, and heterocyclyl which is unsubstituted or substituted, or $R_H^3$ represents $(C_1-C_4)$-alkoxy, $(C_2-C_4)$-alkenyloxy, $(C_2-C_6)$-alkynyloxy or $(C_2-C_4)$-haloalkoxy and $R_H^4$ represents hydrogen or $(C_1-C_4)$-alkyl or $R_H^3$ and $R_H^4$ together with the directly attached nitrogen atom represent a four- to eight-membered heterocyclic ring which, as well as the nitrogen atom, may also contain further ring heteroatoms, preferably up to two further ring heteroatoms from the group of N, O and S, and which is unsubstituted or substituted by one or more radicals from the group of halogen, cyano, nitro, $(C_1-C_4)$-alkyl, $(C_1-C_4)$-haloalkyl, $(C_1-C_4)$-alkoxy, $(C_1-C_4)$-haloalkoxy and $(C_1-C_4)$-alkylthio.

S16) Active compounds which are used primarily as herbicides but also have safener action on crop plants, for example (2,4-dichlorophenoxy)acetic acid (2,4-D),
(4-chlorophenoxy)acetic acid,
(R,S)-2-(4-chloro-o-tolyloxy)propionic acid (mecoprop),
4-(2,4-dichlorophenoxy)butyric acid (2,4-DB),
(4-chloro-o-tolyloxy)acetic acid (MCPA),
4-(4-chloro-o-tolyloxy)butyric acid,
4-(4-chlorophenoxy)butyric acid,
3,6-dichloro-2-methoxybenzoic acid (dicamba),
1-(ethoxycarbonyl)ethyl 3,6-dichloro-2-methoxybenzoate (lactidichlor-ethyl).

Particularly preferred safeners are mefenpyr-diethyl, cyprosulfamide, isoxadifen-ethyl, cloquintocet-mexyl and dichlormid.

Wettable powders are preparations which can be dispersed uniformly in water and, in addition to the active compound, apart from a diluent or inert substance, also comprise surfactants of the ionic and/or nonionic type (wetting agents, dispersants), for example polyoxyethylated alkylphenols, polyoxyethylated fatty alcohols, polyoxyethylated fatty amines, fatty alcohol polyglycol ether sulfates, alkanesulfonates, alkylbenzenesulfonates, sodium lignosulfonate, sodium 2,2'-dinaphthylmethane-6,6'-disulfonate, sodium dibutylnaphthalenesulfonate or else sodium oleoylmethyltaurate. To produce the wettable powders, the herbicidally active compounds are finely ground, for example in customary apparatuses such as hammer mills, blower mills and air-jet mills, and simultaneously or subsequently mixed with the formulation auxiliaries.

Emulsifiable concentrates are produced by dissolving the active compound in an organic solvent, for example butanol, cyclohexanone, dimethylformamide, xylene, or else relatively high-boiling aromatics or hydrocarbons or mixtures of the organic solvents, with addition of one or more ionic and/or nonionic surfactants (emulsifiers). Examples of emulsifiers which may be used are: calcium alkylarylsulfonates such as calcium dodecylbenzenesulfonate, or nonionic emulsifiers such as fatty acid polyglycol esters, alkylaryl polyglycol ethers, fatty alcohol polyglycol ethers, propylene oxide-ethylene oxide condensation products, alkyl polyethers, sorbitan esters, for example sorbitan fatty acid esters, or polyoxyethylene sorbitan esters, for example polyoxyethylene sorbitan fatty acid esters.

Dusting products are obtained by grinding the active compound with finely distributed solids, for example talc, natural clays, such as kaolin, bentonite and pyrophyllite, or diatomaceous earth.

Suspension concentrates may be water- or oil-based. They may be prepared, for example, by wet-grinding by means of commercial bead mills and optional addition of surfactants as have, for example, already been listed above for the other formulation types.

Emulsions, for example oil-in-water emulsions (EW), can be produced, for example, by means of stirrers, colloid mills and/or static mixers using aqueous organic solvents and optionally surfactants as already listed above, for example, for the other formulation types.

Granules can be produced either by spraying the active compound onto adsorptive granular inert material or by applying active compound concentrates to the surface of carriers, such as sand, kaolinites or granular inert material, by means of adhesives, for example polyvinyl alcohol, sodium polyacrylate or else mineral oils. Suitable active compounds can also be granulated in the manner customary for the production of fertilizer granules—if desired as a mixture with fertilizers.

Water-dispersible granules are produced generally by the customary processes such as spray-drying, fluidized-bed granulation, pan granulation, mixing with high-speed mixers and extrusion without solid inert material.

For the production of pan, fluidized-bed, extruder and spray granules, see e.g. processes in "Spray-Drying Handbook" 3rd Ed. 1979, G. Goodwin Ltd., London, J. E. Browning, "Agglomeration", Chemical and Engineering 1967, pages 147 ff.; "Perry's Chemical Engineer's Handbook", 5th Ed., McGraw-Hill, New York 1973, pp. 8-57.

For further details regarding the formulation of crop protection compositions, see, for example, G. C. Klingman, "Weed Control as a Science", John Wiley and Sons, Inc., New York, 1961, pages 81-96 and J. D. Freyer, S. A. Evans, "Weed Control Handbook", 5th Ed., Blackwell Scientific Publications, Oxford, 1968, pages 101-103.

The agrochemical preparations contain generally 0.1 to 99% by weight, especially 0.1 to 95% by weight, of compounds of the invention. In wettable powders, the active compound concentration is, for example, about 10 to 90% by weight, the remainder to 100% by weight consisting of customary formulation constituents. In emulsifiable concentrates, the active compound concentration may be about 1% to 90% and preferably 5% to 80% by weight. Formulations in the form of dusts comprise 1% to 30% by weight of active compound, preferably usually 5% to 20% by weight of active compound; sprayable solutions contain about 0.05% to 80% by weight, preferably 2% to 50% by weight of active compound. In the case of water-dispersible granules, the active compound content depends partially on whether the active compound is in liquid or solid form and on which granulation auxiliaries, fillers, etc., are used. In the water-dispersible granules, the content of active compound is, for example, between 1% and 95% by weight, preferably between 10% and 80% by weight.

In addition, the active compound formulations mentioned optionally comprise the respective customary stickers, wetters, dispersants, emulsifiers, penetrants, preservatives, antifreeze agents and solvents, fillers, carriers and dyes, defoamers, evaporation inhibitors and agents which influence the pH and the viscosity.

On the basis of these formulations, it is also possible to produce combinations with other pesticidally active substances, for example insecticides, acaricides, herbicides, fungicides, and also with safeners, fertilizers and/or growth regulators, for example in the form of a finished formulation or as a tank mix.

For application, the formulations in commercial form are, if appropriate, diluted in a customary manner, for example in the case of wettable powders, emulsifiable concentrates, dispersions and water-dispersible granules with water. Dust-type preparations, granules for soil application or granules for scattering and sprayable solutions are not normally diluted further with other inert substances prior to application.

The required application rate of the compounds of the formula (I) varies with the external conditions, including, inter alia, temperature, humidity and the type of herbicide used. It can vary within wide limits, for example between 0.001 and 1.0 kg/ha or more of active substance, but it is preferably between 0.005 and 750 g/ha.

A carrier is a natural or synthetic organic or inorganic substance with which the active compounds are mixed or combined for better applicability, in particular for application to plants or plant parts or seed. The carrier, which may be solid or liquid, is generally inert and should be suitable for use in agriculture.

Useful solid or liquid carriers include: for example ammonium salts and natural rock dusts, such as kaolins, clays, talc, chalk, quartz, attapulgite, montmorillonite or diatomaceous earth, and synthetic rock dusts, such as finely divided silica, alumina and natural or synthetic silicates, resins, waxes, solid fertilizers, water, alcohols, especially butanol, organic solvents, mineral and vegetable oils, and derivatives thereof. It is likewise possible to use mixtures of such carriers. Useful solid carriers for granules include: for example crushed and fractionated natural rocks such as calcite, marble, pumice, sepiolite, dolomite, and synthetic granules of inorganic and organic meals, and also granules of organic material such as sawdust, coconut shells, corn cobs and tobacco stalks.

Suitable liquefied gaseous extenders or carriers are liquids which are gaseous at standard temperature and under atmospheric pressure, for example aerosol propellants such as halogenated hydrocarbons, or else butane, propane, nitrogen and carbon dioxide.

In the formulations, it is possible to use tackifiers such as carboxymethylcellulose, natural and synthetic polymers in the form of powders, granules or latices, such as gum arabic, polyvinyl alcohol and polyvinyl acetate, or else natural phospholipids such as cephalins and lecithins and synthetic phospholipids. Further additives may be mineral and vegetable oils.

When the extender used is water, it is also possible to use, for example, organic solvents as auxiliary solvents. Suitable liquid solvents are essentially: aromatics such as xylene, toluene or alkylnaphthalenes, chlorinated aromatics and chlorinated aliphatic hydrocarbons such as chlorobenzenes, chloroethylenes or dichloromethane, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulfoxide, and also water.

The compositions according to the invention may additionally comprise further components, for example surfactants. Useful surfactants are emulsifiers and/or foam formers, dispersants or wetting agents having ionic or nonionic properties, or mixtures of these surfactants. Examples thereof are salts of polyacrylic acid, salts of lignosulfonic acid, salts of phenolsulfonic acid or naphthalenesulfonic acid, polycondensates of ethylene oxide with fatty alcohols or with fatty acids or with fatty amines, substituted phenols (preferably alkylphenols or arylphenols), salts of sulfosuccinic esters, taurine derivatives (preferably alkyl taurates), phosphoric esters of polyethoxylated alcohols or phenols, fatty acid esters of polyols, and derivatives of the compounds containing sulfates, sulfonates and phosphates, for example alkylaryl polyglycol ethers, alkylsulfonates, alkyl sulfates, arylsulfonates, protein hydrolyzates, lignosulfite waste liquors and methylcellulose. The presence of a surfactant is necessary if one of the active compounds and/or one of the inert carriers is insoluble in water and when application is effected in water. The proportion of surfactants is between 5 and 40 percent by weight of the inventive composition. It is possible to use dyes such as inorganic pigments, for example iron oxide, titanium oxide and Prussian Blue, and organic dyes such as alizarin dyes, azo dyes and metal phthalocyanine dyes, and trace nutrients such as salts of iron, manganese, boron, copper, cobalt, molybdenum and zinc.

If appropriate, it is also possible for other additional components to be present, for example protective colloids, binders, adhesives, thickeners, thixotropic substances, penetrants, stabilizers, sequestrants, complexing agents. In general, the active compounds can be combined with any solid or liquid additive commonly used for formulation purposes. In general, the compositions and formulations according to the invention contain between 0.05 and 99% by weight, 0.01 and 98% by weight, preferably between 0.1 and 95% by weight and more preferably between 0.5 and 90% active compound, most preferably between 10 and 70 percent by weight. The active compounds or compositions according to the invention can be used as such or, depending on their respective physical and/or chemical properties, in the form of their formulations or the use forms prepared therefrom, such as aerosols, capsule suspensions, cold-fogging concentrates, warm-fogging concentrates, encapsulated granules, fine granules, flowable concentrates for the treatment of seed, ready-to-use solutions, dustable powders, emulsifiable concentrates, oil-in-water emulsions, water-in-oil emulsions, macrogranules, microgranules, oil-dispersible powders, oil-miscible flowable concentrates, oil-miscible liquids, foams, pastes, pesticide coated seed, suspension concentrates, suspoemulsion concentrates, soluble concentrates, suspensions, wettable powders, soluble powders, dusts and granules, water-soluble granules or tablets, water-soluble powders for the treatment of seed, wettable powders, natural products and synthetic substances impregnated with active compound, and also microencapsulations in polymeric substances and in coating materials for seed, and also ULV cold-fogging and warm-fogging formulations.

The formulations mentioned can be produced in a manner known per se, for example by mixing the active compounds with at least one customary extender, solvent or diluent, emulsifier, dispersant and/or binder or fixative, wetting agent, water repellent, optionally siccatives and UV stabilizers and optionally dyes and pigments, antifoams, preservatives, secondary thickeners, tackifiers, gibberellins and other processing auxiliaries.

The compositions according to the invention include not only formulations which are already ready for use and can be deployed with a suitable apparatus onto the plant or the seed, but also commercial concentrates which have to be diluted with water prior to use.

The active compounds according to the invention may be present as such or in their (commercial standard) formulations, or else in the use forms prepared from these formulations as a mixture with other (known) active compounds, such as insecticides, attractants, sterilants, bactericides, acaricides, nematicides, fungicides, growth regulators, herbicides, fertilizers, safeners or semiochemicals.

The treatment according to the invention of the plants and plant parts with the active compounds or compositions is carried out directly or by action on their surroundings, habitat or storage space using customary treatment methods, for example by dipping, spraying, atomizing, irrigating, evaporating, dusting, fogging, broadcasting, foaming, painting, spreading-on, watering (drenching), drip irrigating and, in the case of propagation material, in particular in the case of seeds, furthermore as a powder for dry seed treatment, a solution for seed treatment, a water-soluble powder for slurry treatment, by incrusting, by coating with one or more coats, etc. It is furthermore possible to apply the active compounds by the ultra-low volume method or to inject the active compound preparation or the active compound itself into the soil.

As also described below, the treatment of transgenic seed with the active compounds according to the invention or compositions is of particular significance. This relates to the seed of plants containing at least one heterologous gene which enables the expression of a polypeptide or protein having insecticidal properties. The heterologous gene in transgenic seed can originate, for example, from microorganisms of the species *Bacillus, Rhizobium, Pseudomonas, Serratia, Trichoderma, Clavibacter, Glomus* or *Gliocladium*. This heterologous gene preferably originates from *Bacillus* sp., in which case the gene product is effective against the European corn borer and/or the Western corn rootworm. The heterologous gene more preferably originates from *Bacillus thuringiensis*.

In the context of the present invention, the inventive composition is applied to the seed alone or in a suitable formulation. Preferably, the seed is treated in a state in which it is sufficiently stable for no damage to occur in the course of treatment. In general, the seed can be treated at any time between harvest and sowing. It is customary to use seed which has been separated from the plant and freed from cobs, shells, stalks, coats, hairs or the flesh of the fruits. For example, it is possible to use seed which has been harvested, cleaned and dried down to a moisture content of less than 15% by weight. Alternatively, it is also possible to use seed which, after drying, for example, has been treated with water and then dried again.

In general, when treating the seed, it has to be ensured that the amount of the composition according to the invention and/or further additives applied to the seed is chosen such that the germination of the seed is not impaired and the plant which arises therefrom is not damaged. This has to be ensured particularly in the case of active compounds which can exhibit phytotoxic effects at certain application rates.

The compositions according to the invention can be applied directly, i.e. without containing any other components and without having been diluted. In general, it is preferable to apply the compositions to the seed in the form of a suitable formulation. Suitable formulations and methods for seed treatment are known to those skilled in the art and are described, for example, in the following documents: U.S. Pat. Nos. 4,272,417 A, 4,245,432 A, 4,808,430, 5,876,739, US 2003/0176428 A1, WO 2002/080675 A1, WO 2002/028186 A2.

The active compounds which can be used in accordance with the invention can be converted to the customary seed-dressing formulations, such as solutions, emulsions, suspensions, powders, foams, slurries or other coating compositions for seed, and also ULV formulations.

These formulations are produced in a known manner, by mixing the active compounds with customary additives, for example customary extenders and solvents or diluents, dyes, wetting agents, dispersants, emulsifiers, antifoams, preservatives, secondary thickeners, adhesives, gibberellins, and also water. Dyes which may be present in the seed-dressing formulations usable in accordance with the invention are all dyes which are customary for such purposes. It is possible to use either pigments, which are sparingly soluble in water, or dyes, which are soluble in water. Examples include the dyes known by the names Rhodamine B, C.I. Pigment Red 112 and C.I. Solvent Red 1.

Useful wetting agents which may be present in the seed-dressing formulations usable in accordance with the invention are all substances which promote wetting and which are customary for the formulation of agrochemically active compounds. Alkyl naphthalenesulfonates, such as diisopropyl or diisobutyl naphthalenesulfonates, can be used with preference.

Suitable dispersants and/or emulsifiers which may be present in the seed-dressing formulations usable in accordance with the invention are all nonionic, anionic and cationic dispersants customary for the formulation of agrochemically active compounds. Preference is given to using nonionic or anionic dispersants or mixtures of nonionic or anionic dispersants. Suitable nonionic dispersants include especially ethylene oxide/propylene oxide block polymers, alkylphenol polyglycol ethers and tristryrylphenol polyglycol ether, and the phosphated or sulfated derivatives thereof. Suitable anionic dispersants are especially lignosulfonates, polyacrylic acid salts and arylsulfonate-formaldehyde condensates.

Antifoams which may be present in the seed-dressing formulations usable in accordance with the invention are all foam-inhibiting substances customary for the formulation of agrochemically active compounds. Silicone antifoams and magnesium stearate can be used with preference.

Preservatives which may be present in the seed-dressing formulations usable in accordance with the invention are all substances usable for such purposes in agrochemical compositions. Examples include dichlorophene and benzyl alcohol hemiformal.

Secondary thickeners which may be present in the seed-dressing formulations usable in accordance with the invention are all substances usable for such purposes in agrochemical compositions. Preferred examples include cellulose derivatives, acrylic acid derivatives, xanthan, modified clays and finely divided silica.

Useful stickers which may be present in the seed-dressing formulations usable in accordance with the invention are all customary binders usable in seed-dressing products. Preferred examples include polyvinylpyrrolidone, polyvinyl acetate, polyvinyl alcohol and tylose.

The seed-dressing formulations usable in accordance with the invention can be used, either directly or after previously having been diluted with water, for the treatment of a wide range of different seed, including the seed of transgenic plants. In this case, additional synergistic effects may also occur in interaction with the substances formed by expression.

For the treatment of seed with the seed-dressing formulations usable in accordance with the invention or with the preparations prepared therefrom by addition of water, useful equipment is all mixing units usable customarily for seed dressing. Specifically, the seed dressing procedure is to place the seed into a mixer, to add the particular desired amount of seed-dressing formulations, either as such or after prior dilution with water, and to mix them until the formulation is distributed homogeneously on the seed. If appropriate, this is followed by a drying operation.

The active compounds according to the invention, given good plant compatibility, favorable homotherm toxicity and good environmental compatibility, are suitable for protection of plants and plant organs, for increasing harvest yields, and for improving the quality of the harvested crop. They can preferably be used as crop protection agents. They are active against normally sensitive and resistant species and also against all or specific stages of development.

Plants which can be treated in accordance with the invention include the following main crop plants: corn, soya bean, cotton, *Brassica* oil seeds such as *Brassica napus* (e.g. Canola), *Brassica rapa, B. juncea* (e.g. (field) mustard) and *Brassica carinata*, rice, wheat, sugar beet, sugar cane, oats, rye, barley, millet and sorghum, triticale, flax, grapes and various fruit and vegetables from various botanic taxa, for example *Rosaceae* sp. (for example pome fruits such as apples and pears, but also stone fruits such as apricots, cherries, almonds and peaches, and berry fruits such as strawberries), *Ribesioidae* sp., *Juglandaceae* sp., *Betulaceae* sp., *Anacardiaceae* sp., *Fagaceae* sp., *Moraceae* sp., *Oleaceae* sp., *Actinidaceae* sp., *Lauraceae* sp., *Musaceae* sp. (for example banana trees and plantations), *Rubiaceae* sp. (for example coffee), *Theaceae* sp., *Sterculiceae* sp., *Rutaceae* sp. (for example lemons, oranges and grapefruit); *Solanaceae* sp. (for example tomatoes, potatoes, peppers, eggplants), *Liliaceae* sp., *Compositae* sp. (for example lettuce, artichokes and chicory—including root chicory, endive or common chicory), *Umbelliferae* sp. (for example carrots, parsley, celery and celeriac), Cucurbitaceae sp. (for example cucumbers—including gherkins, pumpkins, watermelons, calabashes and melons), *Alliaceae* sp. (for example leeks and onions), *Cruciferae* sp. (for example white cabbage, red cabbage, broccoli, cauliflower, Brussels sprouts, pak choi, kohlrabi, radishes, horseradish, cress and chinese cabbage), *Leguminosae* sp. (for example peanuts, peas, and beans—for example common beans and broad beans), *Chenopodiaceae* sp. (for example Swiss chard, fodder beet, spinach, beetroot), Malvaceae (for example okra), *Asparagaceae* (for example asparagus); useful plants and ornamental plants in the garden and woods; and in each case genetically modified types of these plants.

As mentioned above, it is possible to treat all plants and their parts in accordance with the invention. In a preferred embodiment, wild plant species and plant cultivars, or those obtained by conventional biological breeding techniques, such as crossing or protoplast fusion, and parts thereof, are treated. In a further preferred embodiment, transgenic plants and plant cultivars obtained by genetic engineering methods, if appropriate in combination with conventional methods (genetically modified organisms), and parts thereof are treated. The term "parts" or "parts of plants" or "plant parts" has been explained above. Particular preference is given in accordance with the invention to treating plants of the respective commercially customary plant cultivars or those that are in use. Plant cultivars are understood to mean plants having new properties ("traits") which have been grown by conventional breeding, by mutagenesis or by recombinant DNA techniques. They may be cultivars, varieties, biotypes or genotypes.

The treatment method according to the invention can be used for the treatment of genetically modified organisms (GMOs), e.g. plants or seeds. Genetically modified plants (or transgenic plants) are plants in which a heterologous gene has been stably integrated into the genome. The term "heterologous gene" means essentially a gene which is provided or assembled outside a plant and which, upon introduction into the nuclear genome, the chloroplast genome or the mitochondrial genome, imparts to the transformed plant novel or improved agronomical or other traits because it expresses a protein or polypeptide of interest or another gene which is present in the plant, or other genes which are present in the plant are down-regulated or switched off (for example by means of antisense technology, co-suppression technologies or RNAi technologies [RNA interference]). A heterologous gene that is located in the genome is also called a transgene. A transgene that is defined by its specific presence in the plant genome is called a transformation or transgenic event.

Depending on the plant species or plant cultivars, their location and growth conditions (soils, climate, vegetation period, diet), the inventive treatment may also result in superadditive ("synergistic") effects. For example, the following effects which exceed the effects actually to be expected are possible: reduced application rates and/or widened spectrum of activity and/or increased efficacy of the active ingredients and compositions which can be used in accordance with the invention, better plant growth, increased tolerance to high or low temperatures, increased tolerance to drought or to water or soil salinity, increased flowering performance, easier harvesting, accelerated maturation, higher harvest yields, bigger fruits, greater plant height, greener leaf color, earlier flowering, higher quality and/or a higher nutritional value of the harvested products, higher sugar concentration within the fruits, better storage stability and/or processability of the harvested products.

Plants and plant cultivars which are preferably treated in accordance with the invention include all plants which have genetic material which imparts particularly advantageous, useful traits to these plants (whether obtained by breeding and/or biotechnological means).

Examples of nematode-resistant plants are described, for example, in the following U.S. patent application Ser. Nos. 11/765,491, 11/765,494, 10/926,819, 10/782,020, 12/032,479, 10/783,417, 10/782,096, 11/657,964, 12/192,904, 11/396,808, 12/166,253, 12/166,239, 12/166,124, 12/166,209, 11/762,886, 12/364,335, 11/763,947, 12/252,453, 12/209,354, 12/491,396 and 12/497,221.

Plants that may be treated according to the invention are hybrid plants that already express the characteristics of heterosis, or hybrid effect, which results in generally higher yield, vigor, better health and resistance towards biotic and abiotic stress factors. Such plants are typically produced by crossing an inbred male-sterile parent line (the female crossbreeding parent) with another inbred male-fertile parent line (the male crossbreeding parent). Hybrid seed is typically harvested from the male-sterile plants and sold to growers. Male-sterile plants can sometimes (e.g. in corn) be produced by detasseling (i.e. the mechanical removal of the male reproductive organs or male flowers) but, more typically, male sterility is the result of genetic determinants in the plant genome. In that case, and especially when seed is the desired product to be harvested from the hybrid plants, it is typically beneficial to ensure that male fertility in hybrid plants, which contain the genetic determinants responsible for male sterility, is fully restored. This can be accomplished by ensuring that the male crossbreeding parents have appropriate fertility restorer genes which are capable of restoring the male fertility in hybrid plants that contain the genetic determinants responsible for male sterility. Genetic determinants for male sterility may be located in the cytoplasm. Examples of cytoplasmic male sterility (CMS) were for instance described for *Brassica* species. However, genetic determinants for male sterility can also be located in the nuclear genome. Male-sterile plants can also be obtained by plant biotechnology methods such as genetic engineering. A particularly useful means of obtaining male-sterile plants is described in WO 89/10396 in which, for example, a ribonuclease such as a barnase is selectively expressed in the tapetum cells in the stamens. Fertility can then be restored by expression in the tapetum cells of a ribonuclease inhibitor such as barstar.

Plants or plant cultivars (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-tolerant plants are for example glyphosate-tolerant plants, i.e. plants made tolerant to the herbicide glyphosate or salts thereof. Plants can be made tolerant to glyphosate by various methods. Thus, for example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium* (Comai et al., 1983, Science, 221, 370-371), the CP4 gene of the bacterium *Agrobacterium* sp. (Barry et al., 1992, Curr. Topics Plant Physiol. 7, 139-145), the genes encoding a *petunia* EPSPS (Shah et al., 1986, Science 233, 478-481), a tomato EPSPS (Gasser et al., 1988, J. Biol. Chem. 263, 4280-4289) or an *Eleusine* EPSPS (WO 01/66704). It can also be a mutated EPSPS. Glyphosate-tolerant plants can also be obtained by expressing a gene that encodes a glyphosate oxidoreductase enzyme. Glyphosate-tolerant plants can also be obtained by expressing a gene that encodes a glyphosate acetyltransferase enzyme. Glyphosate-tolerant plants can also be obtained by selecting plants containing naturally-occurring mutations of the above mentioned genes. Plants which express EPSPS genes which impart glyphosate tolerance have been described. Plants which express other genes which impart glyphosate tolerance, for example decarboxylase genes, have been described.

Other herbicide-resistant plants are for example plants made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition. One example of such an effective detoxifying enzyme is an enzyme encoding a phosphinothricin acetyltransferase (such as the bar or pat protein from *Streptomyces* species). Plants expressing an exogenous phosphinothricin acetyltransferase have been described.

Further herbicide-tolerant plants are also plants that have been made tolerant to the herbicides inhibiting the enzyme hydroxyphenylpyruvate dioxygenase (HPPD). Hydroxyphenylpyruvate dioxygenases are enzymes that catalyze the reaction in which para-hydroxyphenylpyruvate (HPP) is converted to homogentisate. Plants tolerant to HPPD inhibitors can be transformed with a gene encoding a naturally-occurring resistant HPPD enzyme, or a gene encoding a mutated or chimeric HPPD enzyme, as described in WO 96/38567, WO 99/24585, WO 99/24586, WO 2009/144079, WO 2002/046387 or U.S. Pat. No. 6,768,044. Tolerance to HPPD inhibitors can also be obtained by transforming plants with genes encoding certain enzymes enabling the formation of homogentisate despite inhibition of the native HPPD enzyme by the HPPD inhibitor. Such plants are described in WO 99/34008 and WO 02/36787. Tolerance of plants to HPPD inhibitors can also be improved by transforming plants with a gene encoding a prephenate dehydrogenase enzyme in addition to a gene encoding an HPPD-tolerant enzyme, as described in WO 2004/024928. In addition, plants can be made more tolerant to HPPD inhibitors by inserting into the genome thereof a gene which encodes an enzyme which metabolizes or degrades HPPD inhibitors, for example CYP450 enzymes (see WO 2007/103567 and WO 2008/150473).

Other herbicide-resistant plants are plants which have been rendered tolerant to acetolactate synthase (ALS) inhibitors. Known ALS inhibitors include, for example, sulfonylurea, imidazolinone, triazolopyrimidines, pyrimidinyloxy(thio)benzoates, and/or sulfonylaminocarbonyltriazolinone herbicides. It is known that different mutations in the ALS enzyme (also known as acetohydroxy acid synthase, AHAS) confer tolerance to different herbicides and groups of herbicides, as described, for example, in Tranel and Wright (Weed Science 2002, 50, 700-712). The production of sulfonylurea-tolerant plants and imidazolinone-tolerant plants has been described. Further sulfonylurea- and imidazolinone-tolerant plants have also been described.

Further plants tolerant to imidazolinones and/or sulfonylureas can be obtained by induced mutagenesis, by selection in cell cultures in the presence of the herbicide or by mutation breeding (cf., for example, for soya beans U.S. Pat. No. 5,084,082, for rice WO 97/41218, for sugar beet U.S. Pat. No. 5,773,702 and WO 99/057965, for lettuce U.S. Pat. No. 5,198,599 or for sunflower WO 01/065922).

Plants or plant cultivars (obtained by plant biotechnology methods such as genetic engineering) which may also be treated according to the invention are tolerant to abiotic stress factors. Such plants can be obtained by genetic transformation, or by selection of plants containing a mutation imparting such stress resistance. Particularly useful stress-tolerant plants include the following:

a. plants which contain a transgene capable of reducing the expression and/or the activity of the poly(ADP-ribose) polymerase (PARP) gene in the plant cells or plants;

b. plants which contain a stress tolerance-enhancing transgene capable of reducing the expression and/or the activity of the PARG-encoding genes of the plants or plant cells;

c. plants which contain a stress tolerance-enhancing transgene coding for a plant-functional enzyme of the nicotinamide adenine dinucleotide salvage biosynthesis pathway, including nicotinamidase, nicotinate phosphoribosyltransferase, nicotinic acid mononucleotide adenyltransferase, nicotinamide adenine dinucleotide synthetase or nicotinamide phosphoribosyltransferase.

Plants or plant cultivars (obtained by plant biotechnology methods such as genetic engineering) which may also be treated according to the invention show altered quantity, quality and/or storage stability of the harvested product and/or altered properties of specific components of the harvested product such as, for example:

1) Transgenic plants which synthesize a modified starch which, in its physicochemical characteristics, in particular the amylose content or the amylose/amylopectin ratio, the degree of branching, the average chain length, the side chain distribution, the viscosity behavior, the gelling strength, the starch granule size and/or the starch granule morphology, is changed in comparison with the synthesized starch in wild-type plant cells or plants, so that this modified starch is better suited to specific applications.

2) Transgenic plants which synthesize non-starch carbohydrate polymers or which synthesize non-starch carbohydrate polymers with altered properties in comparison to wild-type plants without genetic modification. Examples are plants which produce polyfructose, especially of the inulin and levan type, plants which produce alpha-1,4-glucans, plants which produce alpha-1,6-branched alpha-1,4-glucans, and plants producing alternan.

3) Transgenic plants which produce hyaluronan.

4) Transgenic plants or hybrid plants such as onions with particular properties, such as "high soluble solids content", "low pungency" (LP) and/or "long storage" (LS).

Plants or plant cultivars (obtained by plant biotechnology methods such as genetic engineering) which may also be treated according to the invention are plants, such as cotton plants, with altered fiber characteristics. Such plants can be obtained by genetic transformation, or by selection of plants containing a mutation imparting such altered fiber characteristics and include:

a) plants, such as cotton plants, containing an altered form of cellulose synthase genes;

b) plants, such as cotton plants, which contain an altered form of rsw2 or rsw3 homologous nucleic acids, such as cotton plants with an increased expression of sucrose phosphate synthase;

c) plants, such as cotton plants, with increased expression of sucrose synthase;

d) plants, such as cotton plants, wherein the timing of the plasmodesmatal gating at the base of the fiber cell is altered, for example through downregulation of fiber-selective β-1,3-glucanase;

e) plants, such as cotton plants, which have fibers with altered reactivity, for example through expression of the N-acetylglucosaminetransferase gene, including nodC, and chitin synthase genes.

Plants or plant cultivars (obtained by plant biotechnology methods such as genetic engineering) which may also be treated according to the invention are plants, such as oilseed rape or related *Brassica* plants, with altered oil profile characteristics. Such plants can be obtained by genetic transformation, or by selection of plants containing a mutation imparting such altered oil characteristics and include:

a) plants, such as oilseed rape plants, which produce oil having a high oleic acid content;

b) plants, such as oilseed rape plants, which produce oil having a low linolenic acid content;

c) plants, such as oilseed rape plants, producing oil having a low level of saturated fatty acids.

Plants or plant cultivars (which can be obtained by plant biotechnology methods such as genetic engineering) which may also be treated according to the invention are plants such as potatoes which are virus-resistant, for example to the potato virus Y (SY230 and SY233 events from Tecnoplant, Argentina), or which are resistant to diseases such as potato late blight (e.g. RB gene), or which exhibit reduced cold-induced sweetness (which bear the genes Nt-Inh, II-INV) or which exhibit the dwarf phenotype (A-20 oxidase gene).

Plants or plant cultivars (obtained by plant biotechnology methods such as genetic engineering) which may also be treated according to the invention are plants, such as oilseed rape or related *Brassica* plants, with altered seed shattering characteristics. Such plants can be obtained by genetic transformation, or by selection of plants containing a mutation imparting such altered characteristics, and include plants such as oilseed rape with retarded or reduced seed shattering.

Particularly useful transgenic plants which can be treated according to the invention are plants with transformation events or combinations of transformation events which are the subject of granted or pending petitions for nonregulated status in the USA at the Animal and Plant Health Inspection Service (APHIS) of the United States Department of Agriculture (USDA). Information relating to this is available at any time from APHIS (4700 River Road Riverdale, Md. 20737, USA), for example via the website http://www.aphis.usda.gov/brs/not_reg.html. At the filing date of this application, the petitions with the following information were either granted or pending at the APHIS:

Petition: Identification number of the petition. The technical description of the transformation event can be found in the specific petition document available from APHIS on the website via the petition number. These descriptions are hereby disclosed by reference.

Extension of a petition: Reference to an earlier petition for which an extension of scope or term is being requested.

Institution: Name of the person submitting the petition.

Regulated article: The plant species in question.

Transgenic phenotype: The trait imparted to the plant by the transformation event.

Transformation event or line: The name of the event(s) (sometimes also referred to as line(s)) for which non-regulated status is being requested.

APHIS documents: Various documents which have been published by APHIS with regard to the petition or can be obtained from APHIS on request.

Particularly useful transgenic plants which can be treated in accordance with the invention are plants which comprise one or more genes which code for one or more toxins, for example the transgenic plants which are sold under the following trade names: YIELD GARD® (for example corn, cotton, soya beans), KnockOut® (for example corn), BiteGard® (for example corn), BT-Xtra® (for example corn), StarLink® (for example corn), Bollgard® (cotton), Nucotn® (cotton), Nucotn 33B® (cotton), NatureGard® (for example corn), Protecta® and NewLeaf® (potato). Examples of herbicide-tolerant plants include corn varieties, cotton varieties and soya bean varieties which are available under the following trade names: Roundup Ready® (tolerance to glyphosates, for example corn, cotton, soya beans), Liberty Link® (tolerance to phosphinothricin, for example oilseed rape), IMI® (tolerance to imidazolinone) and SCS® (tolerance to sulfonylurea), for example corn. Herbicide-resistant plants (plants bred in a conventional manner for herbicide tolerance) which may be mentioned include the varieties sold under the name Clearfield® (for example corn).

Particularly useful transgenic plants which may be treated according to the invention are plants containing transformation events, or a combination of transformation events, and that are listed for example in the databases for various national or regional regulatory agencies (see for example http://gmoinfo.jrc.it/gmp_browse.aspx and http://cera-gmc.org/index.php?evidcode=&hstIDXCode=&gType=&AbbrCode=&atCode=&stCode=&coIDCode=&action=gm_crop_database&mode=Submit).

A. CHEMICAL EXAMPLES

The NMR data of disclosed examples are listed either in conventional form (δ values, number of hydrogen atoms, multiplet splitting) or as so-called NMR peak lists. In the NMR peak list method, the NMR data of selected examples are recorded in the form of NMR peak lists, where for each signal peak first the δ value in ppm and then, separated by a space, the signal intensity are listed. The δ value/signal intensity number pairs for different signal peaks are listed with separation from one another by semicolons.

The peak list for one example therefore takes the form of:

$\delta_1$ (intensity$_1$); $\delta_2$ (intensity$_2$); ...; $\beta_i$ (intensity$_i$); ...; $\delta_n$ (intensity$_n$)

The intensity of sharp signals correlates with the height of the signals in a printed example of an NMR spectrum in cm and shows the true ratios of the signal intensities. In the case of broad signals, several peaks or the middle of the signal and the relative intensity thereof may be shown in comparison to the most intense signal in the spectrum.

Calibration of the chemical shift of $^1$H NMR spectra is accomplished using tetramethylsilane and/or the chemical shift of the solvent, particularly in the case of spectra which are measured in DMSO.

Therefore, the tetramethylsilane peak may but need not occur in NMR peak lists.

The lists of the $^1$H NMR peaks are similar to the conventional $^1$H NMR printouts and thus usually contain all peaks listed in a conventional NMR interpretation.

In addition, like conventional $^1$H NMR printouts, they may show solvent signals, signals of stereoisomers of the target compounds which are likewise provided by the invention, and/or peaks of impurities.

In the reporting of compound signals within the delta range of solvents and/or water, our lists of $^1$H NMR peaks show the standard solvent peaks, for example peaks of DMSO in DMSO-D$_6$ and the peak of water, which usually have a high intensity on average.

Such stereoisomers and/or impurities may be typical of the particular preparation process. Their peaks can thus help in identifying reproduction of our preparation process with reference to "by-product fingerprints".

An expert calculating the peaks of the target compounds by known methods (MestreC, ACD simulation, but also with empirically evaluated expected values) can, if required, isolate the peaks of the target compounds, optionally using additional intensity filters. This isolation would be similar to the relevant peak picking in conventional 1H NMR interpretation.

Further details of $^1$H NMR peak lists can be found in the Research Disclosure Database Number 564025.

The examples which follow illustrate the invention in detail.

Intermediate 1

Preparation of 3,5-difluoro-N-hydroxybenzenecarboximidoyl chloride

Analogously to the procedure in WO2012/130798 for 3,5-dichloro-N-hydroxybenzenecarboximidoyl chloride, 3,5-difluoro-N-hydroxybenzenecarboximidoyl chloride was prepared from 3,5-difluorobenzaldehyde in two steps.

Intermediate 2

Preparation of methyl 3-(3,5-difluorophenyl)-5-methyl-4H-isoxazole-5-carboxylate Analogously to the procedure in WO2012/130798 for methyl 3-(3,5-difluorophenyl)-5-methyl-4H-isoxazole-5-carboxylate, methyl 3-(3,5-difluorophenyl)-5-methyl-4H-isoxazole-5-carboxylate was prepared from 3,5-difluorobenzaldehyde in three steps.

Intermediate 3

Preparation of 3-(3,5-difluorophenyl)-5-methyl-4H-isoxazole-5-carboxylic acid

Analogously to the procedure in WO2012/130798 for 3-(3,5-dichlorophenyl)-5-methyl-4H-isoxazole-5-carboxylic acid, 3-(3,5-difluorophenyl)-5-methyl-4H-isoxazole-5-carboxylic acid was prepared by hydrolysis of methyl 3-(3,5-difluorophenyl)-5-methyl-4H-isoxazole-5-carboxylate.

Intermediate 4

Preparation of 3-(3,5-difluorophenyl)-5-methyl-4H-isoxazole-5-carbonyl chloride

Analogously to the procedure in WO2012/130798 for N-tert-butyl-3-(3,5-dichlorophenyl)-5-methyl-4,5-dihydro-1,2-oxazole-5-carboxamide, 3-(3,5-difluorophenyl)-5-methyl-4H-isoxazole-5-carbonyl chloride was prepared from 3-(3,5-difluorophenyl)-5-methyl-4H-isoxazole-5-carboxylic acid by reaction with oxalyl chloride and used as crude product without further purification.

Intermediate 5

Preparation of methyl 3-(3,5-difluorophenyl)-5-(1-hydroxyethyl)-4H-isoxazole-5-carboxylate 19.9 g (104 mmol) of 3,5-difluoro-N-hydroxybenzimidoyl chloride (see Intermediate 1) were dissolved in 330 ml of 2-propanol, and 15.0 g (104 mmol) of methyl 3-hydroxy-2-methylenebutanoate were added. After addition of 43.8 g (522 mmol) of sodium bicarbonate, the suspension was heated to 50° C. and the temperature was maintained for 2 h until complete conversion of the starting material. The suspension was filtered and the filtrate was concentrated under reduced pressure. The resulting residue was taken up in dichloromethane and then washed with saturated sodium chloride solution and the organic phase was dried with sodium sulfate and, after filtration, concentrated under reduced pressure. The crude product thus obtained was taken up in toluene and, by addition of n-heptane, crystallized.

This gave 25.5 g (86%) of methyl 3-(3,5-difluorophenyl)-5-(1-hydroxyethyl)-4H-isoxazole-5-carboxylate in the form of colorless crystals.

Diastereomer 1: $^1$H NMR (CDCl3): δ=1.20 (d, 3H), 2.36 (d, 1H), 3.52 (d, 1H), 3.72 (d, 1H), 3.83 (s, 3H), 4.34 (m, 1H), 6.88 (m, 1H), 7.20 (m, 2H).

Diastereomer 2: $^1$H NMR (CDCl3): δ=1.29 (d, 3H), 2.12 (d, 1H), 3.58 (d, 1H), 3.68 (d, 1H), 3.83 (s, 3H), 4.23 (m, 1H), 6.88 (m, 1H), 7.20 (m, 2H).

Intermediate 6

Preparation of methyl 3-(3,5-difluorophenyl)-5-[1-(trifluoromethylsulfonyloxy)ethyl]-4H-isoxazole-5-carboxylate 29.9 (105 mmol) of methyl 3-(3,5-difluorophenyl)-5-(1-hydroxyethyl)-4H-isoxazole-5-carboxylate in 660 ml of dichloromethane were cooled to 0° C., and 16.3 g (210 mmol) of pyridine were added. A solution of 38.6 g (137 mmol) of trifluoromethanesulfonic anhydride in 80 ml of dichloromethane was then added slowly. After 30 minutes at 0° C., 300 ml of dichloromethane were added and the organic phase was washed three times with in each case 200 ml of a solution of saturated sodium chloride solution and 1 N hydrochloric acid (3:1). The organic phase was then washed twice with saturated sodium chloride solution and dried over sodium sulfate, and the solvent was removed under reduced pressure. The resulting crude product was used in the next step without further purification.

Diasteromer 1: $^1$H NMR (CDCl3): δ=1.54 (d, 3H), 3.44 (d, 1H), 3.89 (s, 3H), 3.94 (d, 1H), 5.49 (q, 1H), 6.91 (m, 1H), 7.20 (m, 2H).

Diastereomer 2: $^1$H NMR (CDCl3): δ=1.59 (d, 3H), 3.53 (d, 1H), 3.89 (s, 3H), 3.90 (d, 1H), 5.57 (q, 1H), 6.91 (m, 1H), 7.20 (m, 2H).

Intermediate 7

Preparation of methyl 3-(3,5-difluorophenyl)-5-vinyl-4H-isoxazole-5-carboxylate 43.0 g (103 mmol) of the crude product from the previous step (methyl 3-(3,5-difluorophenyl)-5-[1-(trifluoromethylsulfonyloxy)ethyl]-4H-isoxazole-5-carboxylate) were dissolved in 500 ml of dimethylacetamide, and a solution of 18.8 g (124 mmol) of DBU in 50 ml of dimethylacetamide was added dropwise over 20 minutes. The reaction mixture was stirred at room temperature for 2 h and then poured onto 1 l of ice-cooled 2 N hydrochloric acid and extracted twice with 500 ml of diethyl ether each time. The combined organic phases were dried over sodium sulfate, filtered and concentrated under reduced pressure. After chromatographic purification on silica gel using the mobile phase dichloromethane the crude product was crystallized from cyclohexane. This gave 23.4 g (85%) of colorless crystals.

$^1$H NMR (CDCl3): δ=3.34 (d, 1H), 3.84 (s, 3H), 3.93 (d, 1H), 5.38 (d, 1H), 5.55 (d, 1H), 6.14 (dd, 1H), 6.88 (m, 1H), 7.19 (m, 2H).

Intermediate 8

Preparation of 3-(3,5-difluorophenyl)-5-vinyl-4H-isoxazole-5-carboxylic acid 21 ml of 2 N aqueous sodium hydroxide solution were added to 7.5 g (28.0 mmol) of methyl 3-(3,5-difluorophenyl)-5-vinyl-4H-isoxazole-5-carboxylate and the mixture was heated at reflux for 8 h. After cooling the reaction mixture was washed with ethyl acetate, the aqueous phase was acidified to pH 1 with 2 N hydrochloric acid and the colorless precipitate was filtered off and air-dried. The yield was 6.8 g (96%).

$^1$H NMR (CDCl3): δ=3.40 (d, 1H), 3.92 (d, 1H), 5.00 (dd, 1H), 5.45 (d, 1H), 5.63 (d, 1H), 6.16 (dd, 1H), 6.87-6.93 (m, 1H), 7.16-7.21 (m, 2H).

Intermediate 9

Preparation of 3-(3,5-difluorophenyl)-5-vinyl-4H-isoxazole-5-carbonyl chloride 2.70 g (10.6 mmol) of 3-(3,5-difluorophenyl)-5-vinyl-4H-isoxazole-5-carboxylic acid were added to 45 ml of dichloromethane, and three drops of dimethylformamide (DMF) followed by 2.03 g (15.9 mmol) of oxalyl chloride were then added. A vigorous evolution of gas was observed. The mixture was stirred at room temperature for 6 h and solvent and excess oxalyl chloride were then evaporated under reduced pressure. The resulting crude product was used in the next step without further purification.

Intermediate 10

Preparation of 3-(3,5-dichlorophenyl)-5-methoxy-4H-isoxazole-5-carbonyl chloride 282 mg (0.97 mmol) of 3-(3,5-dichlorophenyl)-5-methoxy-4H-isoxazole-5-carboxylic acid were added to 10 ml of dichloromethane, and three drops of dimethylformamide (DMF) followed by 185 mg (1.85 mmol) of oxalyl chloride dissolved in a little dichloromethane were then added. The mixture was stirred at room temperature for 6 h and the reaction mixture was then concentrated under reduced pressure. Subsequently, two more times dichloromethane was added to the residue and the mixture was concentrated under reduced pressure. The resulting crude product was used in the next step without further purification.

Intermediate 11

Preparation of methyl 4-amino-2,5-dihydrofuran-3-carboxylate

Methyl 4-amino-2,5-dihydrofuran-3-carboxylate can be prepared analogously to the method described by F. Cohen et al., *J. Med. Chem.* 2011, 54, 3426-3435.

Intermediate 12

Preparation of ethyl 4-amino-2,5-dihydrofuran-3-carboxylate

Ethyl 4-amino-2,5-dihydrofuran-3-carboxylate can be prepared analogously to the method described by F. Cohen et al., *J. Med. Chem.* 2011, 54, 3426-3435.

Intermediate 13

Preparation of methyl 4-aminotetrahydrofuran-3-carboxylate

Methyl 4-aminotetrahydrofuran-3-carboxylate can be prepared by the method described by G. R. Ott et al.; *Bioorg. Med. Chem. Lett.* 2008, 694-699.

Intermediate 14

Preparation of methyl cis-4-aminotetrahydrofuran-2-carboxylate hydrochloride

Methyl cis-4-aminotetrahydrofuran-2-carboxylate hydrochloride can be prepared by the method described by D. P. Walker et al., Synthesis 2011, 1113-1119.

Intermediate 15

Preparation of tert-butyl N,N'-diisopropylcarbamimidate

In a flask that had been dried by heating und under nitrogen, 27 mg of anhydrous copper(I) chloride were added to 2.33 g of tert-butanol and 3.44 g of N,N'-diisopropylcarbodiimide, and the mixture was stirred at room temperature for 2 h and allowed to stand for three days.

This crude product was used as such for the esterifications giving the tert-butyl esters and metered in using a syringe filter.

Intermediate 16

Preparation of methyl trans-4-aminotetrahydrofuran-2-carboxylate hydrochloride

Methyl trans-4-aminotetrahydrofuran-2-carboxylate hydrochloride can be prepared either from commercially available trans-aminocarboxylic acid by esterification with thionyl chloride/methanol or by the method described by Allan, Robin D.; Tran, Hue W. Australian Journal of Chemistry (1984), 37(5), 1123-6 from commercially available 2,5-anhydro-3-deoxypentonic acid.

Intermediate 17

Preparation of methyl (4S)-4-amino-4,5-dihydrofuran-2-carboxylate

Methyl (4S)-4-amino-4,5-dihydrofuran-2-carboxylate can be prepared by the method described by Joseph P. Burkhart, Gene W. Holbert, Brian W. Metcalf, Tetrahedron Lett., 25 (46), 1984, pp. 5267-5270 from commercially available methyl L-glutaminate.

Intermediate 18

Preparation of methyl (4R)-4-amino-4,5-dihydrofuran-2-carboxylate

Methyl (4R)-4-amino-4,5-dihydrofuran-2-carboxylate can be prepared by the method described by Joseph P. Burkhart, Gene W. Holbert, Brian W. Metcalf, Tetrahedron Lett., 25 (46), 1984, pp. 5267-5270 from commercially available methyl D-glutaminate.

Example I-01

Preparation of methyl cis-4-[[3-(3,5-difluorophenyl)-5-methyl-4H-isoxazole-5-carbonyl]amino]tetrahydrofuran-2-carboxylate 292 mg (2.88 mmol) of triethylamine were added to 262 mg (1.44 mmol) of Intermediate 14 in 5 ml of dichloromethane, 250 mg (0.96 mmol) of carbonyl chloride (intermediate 4) in 6 ml of dichloromethane were then added at 0° C., the mixture was stirred for 6 h warming to room temperature and finally water was added. The organic phase was removed, dried with sodium sulfate and concentrated under reduced pressure. Chromatography of the evaporation residue on silica gel (mobile phase n-heptane/ethyl acetate) gave 75 mg (21%) of methyl cis-4-[[3-(3,5-difluorophenyl)-5-methyl-4H-isoxazole-5-carbonyl]amino]tetrahydrofuran-2-carboxylate.

Example I-02

Preparation of methyl cis-4-[[3-(3,5-dichlorophenyl)-5-methoxy-4H-isoxazole-5-carbonyl]amino]tetrahydrofuran-2-carboxylate 277 mg (2.74 mmol) of triethylamine were added to 249 mg (1.37 mmol) of Intermediate 14 in 5 ml of dichloromethane, 282 mg (0.91 mmol) of 3-(3,5-dichlorophenyl)-5-methoxy-4H-isoxazole-5-carbonyl chloride in 5 ml of dichloromethane were then added at 0° C., the mixture was stirred for 6 h warming to room temperature and finally water was added. The organic phase was removed, dried with sodium sulfate and concentrated under reduced pressure. Chromatography of the evaporation residue on silica gel (mobile phase n-heptane/ethyl acetate) gave 41 mg (11%) of methyl cis-4-[[3-(3,5-dichlorophenyl)-5-methoxy-4H-isoxazole-5-carbonyl]amino]tetrahydrofuran-2-carboxylate.

Example I-03

Preparation of methyl cis-4-[[3-(3,5-dichlorophenyl)-5-vinyl-4H-isoxazole-5-carbonyl]amino]tetrahydrofuran-2-carboxylate Starting with 3,5-dichlorobenzaldehyde, first the corresponding carbonyl chloride was prepared analogously to the preparation of Intermediate 9. This was then converted analogously to Example I-02 into the target compound.

In this manner, 317 mg (1.74 mmol) of Intermediate 14 and 400 mg (1.39 mmol) of carbonyl chloride gave 10 mg (2%) of methyl cis-4-[[3-(3,5-dichlorophenyl)-5-vinyl-4H-isoxazole-5-carbonyl]amino]tetrahydrofuran-2-carboxylate.

Example I-04

Preparation of methyl cis-4-[[3-(3-bromo-5-methylphenyl)-5-methyl-4H-isoxazole-5-carbonyl]amino]tetrahydrofuran-2-carboxylate Starting with 3-bromo-5-methylbenzaldehyde, first the corresponding carbonyl chloride was prepared analogously to the preparation of Intermediate 4. This was then converted analogously to Example I-02 into the target compound.

In this manner, 129 mg (0.71 mmol) of Intermediate 14 and 150 mg (0.47 mmol) of carbonyl chloride gave 22 mg (11%) of methyl cis-4-[[3-(3-bromo-5-methylphenyl)-5-methyl-4H-isoxazole-5-carbonyl]amino]tetrahydrofuran-2-carboxylate.

Example I-05

Preparation of methyl cis-4-[[3-(3,5-difluorophenyl)-5-methoxy-4H-isoxazole-5-carbonyl]amino]tetrahydrofuran-2-carboxylate Starting with 3,5-difluorobenzaldehyde, analogously to the preparation of Intermediate 4, first the corresponding carbonyl chloride was prepared which was then converted analogously to Example I-02 into the target compound.

In this manner, 247 mg (1.36 mmol) of Intermediate 14 and 250 mg (0.90 mmol) of carbonyl chloride gave 63 mg (18%) of methyl cis-4-[[3-(3,5-difluorophenyl)-5-methoxy-4H-isoxazole-5-carbonyl]amino]tetrahydrofuran-2-carboxylate.

Example I-06

Preparation of methyl cis-4-[[3-(3,5-difluorophenyl)-5-(trifluoromethyl)-4H-isoxazole-5-carbonyl]amino]tetrahydrofuran-2-carboxylate Analogously to the preparation of Intermediate 4, first the corresponding carbonyl chloride was prepared which was then converted analogously to Example I-02 into the target compound.

In this manner, 184 mg (1.01 mmol) of Intermediate 14 and 212 mg (0.67 mmol) of carbonyl chloride gave 39 mg (13%) of methyl cis-4-[[3-(3,5-difluorophenyl)-5-(trifluoromethyl)-4H-isoxazole-5-carbonyl]amino]tetrahydrofuran-2-carboxylate.

Example I-07

Preparation of methyl cis-4-[[3-(3-fluorophenyl)-5-vinyl-4H-isoxazole-5-carbonyl]amino]tetrahydrofuran-2-carboxylate Analogously to the preparation of Intermediate 9, first the corresponding carbonyl chloride was prepared which was converted analogously to Example I-02 into the target compound.

In this manner, 184 mg (1.01 mmol) of Intermediate 14 and 212 mg (0.67 mmol) of carbonyl chloride gave 64 mg (26%) of methyl cis-4-[[3-(3-fluorophenyl)-5-vinyl-4H-isoxazole-5-carbonyl]amino]tetrahydrofuran-2-carboxylate.

Example I-08

Preparation of methyl cis-4-[[3-(3-bromo-5-methylphenyl)-5-methoxy-4H-isoxazole-5-carbonyl]amino]tetrahydrofuran-2-carboxylate Analogously to the preparation of Intermediate 4, first the corresponding carbonyl chloride was prepared which was converted analogously to Example I-02 into the target compound.

In this manner, 184 mg (1.01 mmol) of Intermediate 14 and 212 mg (0.67 mmol) of carbonyl chloride gave 64 mg (26%) of methyl cis-4-[[3-(3-fluorophenyl)-5-vinyl-4H-isoxazole-5-carbonyl]amino]tetrahydrofuran-2-carboxylate.

Example I-09

Preparation of methyl cis-4-[[(5R)-3-(3,5-difluorophenyl)-5-methyl-4H-isoxazole-5-carbonyl]amino]tetrahydrofuran-2-carboxylate Analogously to the preparation of Intermediate 4, first the corresponding carbonyl chloride was prepared which was converted analogously to Example I-01 into the target compound.

In this manner, 227 mg (1.24 mmol) of Intermediate 14 and 216 mg (0.83 mmol) of carbonyl chloride gave 79 mg (25%) of methyl cis-4-[[(5R)-3-(3,5-difluorophenyl)-5-methyl-4H-isoxazole-5-carbonyl]amino]tetrahydrofuran-2-carboxylate.

The mixture of the individual diastereomers was separated by HPLC into I-15 and I-16.

Example I-10

Preparation of methyl cis-4-[[(5S)-3-(3,5-difluorophenyl)-5-vinyl-4H-isoxazole-5-carbonyl]amino]tetrahydrofuran-2-carboxylate Analogously to the preparation of Intermediate 9, first the corresponding carbonyl chloride was prepared which was converted analogously to Example I-01 into the target compound.

In this manner, 246 mg (1.35 mmol) of Intermediate 14 and 228 mg (0.90 mmol) of carbonyl chloride gave 110 mg (31%) of methyl cis-4-[[(5S)-3-(3,5-difluorophenyl)-5-vinyl-4H-isoxazole-5-carbonyl]amino]tetrahydrofuran-2-carboxylate.

The mixture of the individual diastereomers was separated by HPLC into I-11 and I-12.

Example I-11: Diastereomer 1 of I-10

Preparation of methyl cis-4-[[(5S)-3-(3,5-difluorophenyl)-5-vinyl-4H-isoxazole-5-carbonyl]amino]tetrahydrofuran-2-carboxylate H-NMR data: see table for the analytical data.

Example I-12: Diastereomer 2 of I-10

Preparation of methyl cis-4-[[(5S)-3-(3,5-difluorophenyl)-5-vinyl-4H-isoxazole-5-carbonyl]amino]tetrahydrofuran-2-carboxylate H-NMR data: see table for the analytical data.

Example I-13

Preparation of methyl cis-4-[[3-(3-fluorophenyl)-5-methyl-4H-isoxazole-5-carbonyl]amino]tetrahydrofuran-2-carboxylate Analogously to the preparation of Intermediate 4, first the corresponding carbonyl chloride was prepared which was converted analogously to Example I-01 into the target compound.

In this manner, 169 mg (0.93 mmol) of Intermediate 14 and 150 mg (0.62 mmol) of carbonyl chloride gave 171 mg (75%) of methyl cis-4-[[3-(3-fluorophenyl)-5-methyl-4H-isoxazole-5-carbonyl]amino]tetrahydrofuran-2-carboxylate.

Example I-14

Preparation of methyl cis-4-[(5-methoxy-3-phenyl-4H-isoxazole-5-carbonyl)amino]tetrahydrofuran-2-carboxylate Analogously to the preparation of Intermediate 10, first the corresponding carbonyl chloride was prepared which was converted analogously to Example I-03 into the target compound.

In this manner, 247 mg (1.35 mmol) of Intermediate 14 and 217 mg (0.90 mmol) of carbonyl chloride gave 75 mg (23%) of methyl cis-4-[(5-methoxy-3-phenyl-4H-isoxazole-5-carbonyl)amino]tetrahydrofuran-2-carboxylate.

Example I-15: Diastereomer 1 of I-09

Preparation of methyl cis-4-[[(5R)-3-(3,5-difluorophenyl)-5-methyl-4H-isoxazole-5-carbonyl]amino]tetrahydrofuran-2-carboxylate H-NMR data: see table for the analytical data.

Example I-16: Diastereomer 2 of I-09

Methyl cis-4-[[(5R)-3-(3,5-difluorophenyl)-5-methyl-4H-isoxazole-5-carbonyl]amino]tetrahydrofuran-2-carboxylate H-NMR data: see table for the analytical data.

Example I-17

Preparation of methyl 3-[[3-(3,5-difluorophenyl)-5-methyl-4H-isoxazole-5-carbonyl]amino]tetrahydrofuran-3-carboxylate First, the corresponding carbonyl chloride was prepared, which was reacted analogously to Example I-01 to give the target compound.

In this manner, 1.57 g (8.66 mmol) of methyl 3-amino-tetrahydrofuran-3-carboxylate hydrochloride and 1.50 g (5.77 mmol) of carbonyl chloride gave 477 mg (22%) of methyl 3-[[3-(3,5-difluorophenyl)-5-methyl-4H-isoxazole-5-carbonyl]amino]tetrahydrofuran-3-carboxylate.

Example I-18

Preparation of ethyl 3-[[3-(3,5-difluorophenyl)-5-methyl-4H-isoxazole-5-carbonyl]amino]tetrahydrofuran-3-carboxylate The title compound can be prepared analogously to Example I-17

Example I-19

Preparation of methyl 4-[[3-(3,5-difluorophenyl)-5-methyl-4H-isoxazole-5-carbonyl]amino]tetrahydrofuran-3-carboxylate First, the corresponding carbonyl chloride was prepared, which was reacted analogously to Example I-01 with methyl 4-aminotetrahydrofuran-3-carboxylate to give the target compound.

In this manner, 419 mg (8.66 mmol) of methyl 4-amino-tetrahydrofuran-3-carboxylate and 500 mg (1.92 mmol) of carbonyl chloride gave 657 mg (91%) of methyl 4-[[3-(3,5-difluorophenyl)-5-methyl-4H-isoxazole-5-carbonyl]amino]tetrahydrofuran-3-carboxylate.

Example I-20

Preparation of cis-4-[[3-(3-fluorophenyl)-5-methyl-4H-isoxazole-5-carbonyl]amino]tetrahydrofuran-2-carboxylic acid 1 ml of 2 N hydrochloric acid was added to 85 mg (0.24 mmol) of methyl cis-4-[[3-(3-fluorophenyl)-5-methyl-4H-isoxazole-5-carbonyl]amino]tetrahydrofuran-2-carboxylate and the mixture was kept at room temperature for 3 days. The reaction mixture was then concentrated on a rotary evaporator. In this manner, 33 mg (40%) of cis-4-[[3-(3-fluorophenyl)-5-methyl-4H-isoxazole-5-carbonyl]amino]tetrahydrofuran-2-carboxylic acid were obtained.

Example I-21

Preparation of cis-4-[[3-(3,5-difluorophenyl)-5-vinyl-4H-isoxazole-5-carbonyl]amino]tetrahydrofuran-2-carboxylic acid 650 mg (1.70 mmol) of methyl cis-4-[[3-(3,5-difluorophenyl)-5-vinyl-4H-isoxazole-5-carbonyl]amino]tetrahydrofuran-2-carboxylate were added to 10 ml of tetrahydrofuran, 0.64 ml of a 2 N aqueous sodium hydroxide solution were added at room temperature and the mixture was stirred for 6 h. The mixture was then acidified with conc. hydrochloric acid and extracted with ethyl acetate and the organic phase was dried with sodium sulfate. Evaporation of the organic phase gave 530 mg (83%) of cis-4-[[3-(3,5-difluorophenyl)-5-vinyl-4H-isoxazole-5-carbonyl]amino]tetrahydrofuran-2-carboxylic acid.

Example I-22

Preparation of methyl cis-4-[[(5R)-3-(3,5-difluorophenyl)-5-vinyl-4H-isoxazole-5-carbonyl]amino]tetrahydrofuran-2-carboxylate The title compound was prepared analogously to Example I-01 from 268 mg (0.98 mmol) of the corresponding carbonyl chloride and 215 mg (1.48 mmol) of the amine (Intermediate 14).

In this manner, 64 mg (17%) of methyl cis-4-[[(5R)-3-(3,5-difluorophenyl)-5-vinyl-4H-isoxazole-5-carbonyl]amino]tetrahydrofuran-2-carboxylate were obtained.

Example I-23

Preparation of ethyl 4-[[3-(3,5-difluorophenyl)-5-vinyl-4H-isoxazole-5-carbonyl]amino]-2,5-dihydrofuran-3-carboxylate First, ethyl 4-amino-2,5-dihydrofuran-3-carboxylate was prepared analogously to F. Cohen et al., *J. Med. Chem.* 2011, 54, 3426-3435 from ethyl 4-oxotetrahydrofurancarboxylate, and then reacted with the corresponding carbonyl chloride (Intermediate 9) analogously to procedure I-01.

In this manner, 230 mg (0.84 mmol) of carbonyl chloride and 166 mg (1.05 mmol) of amine gave 52 mg (15%) of ethyl 4-[[3-(3,5-difluorophenyl)-5-vinyl-4H-isoxazole-5-carbonyl]amino]-2,5-dihydrofuran-3-carboxylate.

Example I-24

Preparation of ethyl 4-[[3-(3,5-difluorophenyl)-5-methyl-4H-isoxazole-5-carbonyl]amino]-2,5-dihydrofuran-3-carboxylate First, ethyl 4-amino-2,5-dihydrofuran-3-carboxylate was prepared analogously to F. Cohen et al., *J. Med. Chem.* 2011, 54, 3426-3435 from ethyl 4-oxotetrahydrofurancarboxylate, and then reacted with the corresponding carbonyl chloride (Intermediate 4) analogously to procedure I-01.

In this manner, 220 mg (0.84 mmol) of carbonyl chloride and 166 mg (1.05 mmol) of amine gave 175 mg (53%) of ethyl 4-[[3-(3,5-difluorophenyl)-5-methyl-4H-isoxazole-5-carbonyl]amino]-2,5-dihydrofuran-3-carboxylate.

Example I-25

Preparation of methyl 4-[[3-(3,5-difluorophenyl)-5-methyl-4H-isoxazole-5-carbonyl]amino]-2,5-dihydrofuran-3-carboxylate First, methyl 4-amino-2,5-dihydrofuran-3-carboxylate was prepared analogously to F. Cohen et al., *J. Med. Chem.* 2011, 54, 3426-3435 from methyl 4-oxotetrahydrofurancarboxylate, and then reacted with the corresponding carbonyl chloride (Intermediate 4) analogously to procedure I-01.

In this manner, 200 mg (0.77 mmol) of carbonyl chloride and 165 mg (1.15 mmol) of amine gave 94 mg (33%) of methyl 4-[[3-(3,5-difluorophenyl)-5-methyl-4H-isoxazole-5-carbonyl]amino]-2,5-dihydrofuran-3-carboxylate.

Example I-26

Preparation of methyl 4-[[(5S)-3-(3,5-difluorophenyl)-5-vinyl-4H-isoxazole-5-carbonyl]amino]tetrahydrofuran-3-carboxylate First, the corresponding carbonyl chloride was prepared, which was reacted analogously to Example I-01 with methyl 4-aminotetrahydrofuran-3-carboxylate to give the target compound.

In this manner, 110 mg (0.40 mmol) of carbonyl chloride and 88 mg (0.60 mmol) of methyl cis-4-aminotetrahydrofuran-3-carboxylate gave 7 mg (4%) of methyl 4-[[(5S)-3-(3,5-difluorophenyl)-5-vinyl-4H-isoxazole-5-carbonyl]amino]tetrahydrofuran-3-carboxylate.

Example I-27

Preparation of methyl 4-[[3-(3,5-difluorophenyl)-5-methoxy-4H-isoxazole-5-carbonyl]amino]tetrahydrofuran-3-carboxylate First, the corresponding carbonyl chloride was prepared, which was reacted analogously to Example I-02 with methyl 4-aminotetrahydrofuran-3-carboxylate to give the target compound.

In this manner, 112 mg (0.40 mmol) of carbonyl chloride and 88 mg (0.60 mmol) of methyl 4-aminotetrahydrofuran-3-carboxylate gave 28 mg (17%) of methyl 4-[[3-(3,5-difluorophenyl)-5-methoxy-4H-isoxazole-5-carbonyl]amino]tetrahydrofuran-3-carboxylate.

Example I-28

Preparation of methyl 4-[[(5R)-3-(3,5-difluorophenyl)-5-methyl-4H-isoxazole-5-carbonyl]amino]tetrahydrofuran-3-carboxylate Analogously to the preparation of Intermediate 4, first the corresponding carbonyl chloride was prepared which was converted according to Example I-01 using methyl 4-aminotetrafuran-3-carboxylate into the target compound.

In this manner, 110 mg (0.42 mmol) of carbonyl chloride and 92 mg (0.63 mmol) of methyl 4-aminotetrahydrofuran-3-carboxylate gave 36 mg (23%) of methyl 4-[[(5R)-3-(3,5-difluorophenyl)-5-methyl-4H-isoxazole-5-carbonyl]amino]tetrahydrofuran-3-carboxylate.

Example I-29

Preparation of methyl 4-[[3-(3,5-dichlorophenyl)-5-methoxy-4H-isoxazole-5-carbonyl]amino]tetrahydrofuran-3-carboxylate First, the corresponding carbonyl chloride (Intermediate 10) was prepared, which was reacted analogously to Example I-02 with methyl 4-aminotetrahydrofuran-3-carboxylate to give the target compound.

In this manner, 110 mg (0.35 mmol) of carbonyl chloride and 78 mg (0.53 mmol) of methyl 4-aminotetrahydrofuran-3-carboxylate gave 80 mg (53%) of methyl 4-[[3-(3,5-dichlorophenyl)-5-methoxy-4H-isoxazole-5-carbonyl]amino]tetrahydrofuran-3-carboxylate.

Example I-30

Preparation of ethyl cis-4-[[(5RS)-3-(3-fluorophenyl)-5-methyl-4H-isoxazole-5-carbonyl]amino]tetrahydrofuran-2-carboxylate 0.10 g of carboxylic acid, 85 mg of 1-(3-dimethylaminopropyl)-3-ethylcarbodiimide hydrochloride and 4 mg of 4-dimethylaminopyridine were dissolved in 5 ml of dichloromethane.

With stirring at room temperature, 68 mg of ethanol were then added and the reaction mixture was stirred at room temperature for 8 h and then overnight.

The reaction mixture was washed with 0.5 M aqueous hydrochloric acid, dried and concentrated under reduced pressure. The crude product was then purified by chromatography.

This gave 55 mg of ethyl ester (49% yield).

Example I-31

Preparation of cis-4-[[(5S)-3-(3,5-difluorophenyl)-5-vinyl-4H-isoxazole-5-carbonyl]amino]tetrahydrofuran-2-carboxylic acid 0.52 g of the methyl ester was dissolved in 8 ml of tetrahydrofuran and cooled to 0° C. A solution of 98 mg of lithium hydroxide in 4 ml of water was added dropwise with stirring. With stirring, the reaction mixture was brought to room temperature over 1 h. Then the reaction mixture was diluted with water, acidified with 0.5 M aqueous hydrochloric acid and extracted with ethyl acetate. The resulting ethyl acetate phase was then dried and concentrated under reduced pressure.

For further purification, the crude product was then taken up in 2 M aqueous sodium hydroxide solution and washed with ethyl acetate. The aqueous phase was subsequently acidified with 2 M aqueous hydrochloric acid and extracted with dichloromethane. The dichloromethane phase was dried and concentrated. This gave 0.53 g of carboxylic acid (84% yield).

Example I-32

Preparation of isopropyl cis-4-[[(5RS)-3-(3-fluorophenyl)-5-methyl-4H-isoxazole-5-carbonyl]amino]tetrahydrofuran-2-carboxylate 0.12 g of carboxylic acid, 98 mg of 1-(3-dimethylaminopropyl)-3-ethylcarbodiimide hydrochloride and 4 mg of 4-dimethylaminopyridine were dissolved in 5 ml of dichloromethane.

With stirring at room temperature, 0.41 g of 2-propanol were then added and the reaction mixture was stirred at room temperature for 1.5 h and then for three days.

The reaction mixture was washed with 0.5 M aqueous hydrochloric acid, dried and concentrated under reduced pressure. The crude product was then purified by chromatography.

This gave 82 mg of 2-propyl ester (61% yield).

Example I-33

Preparation of tert-butyl cis-4-[[(5RS)-3-(3-fluorophenyl)-5-methyl-4H-isoxazole-5-carbonyl]amino]tetrahydrofuran-2-carboxylate 0.11 g of carboxylic acid was dissolved in 2 ml of tetrahydrofuran and placed under nitrogen. Via a syringe filter, 0.2 ml of tert-butyl N,N'-diisopropylcarbamimidate was added. The reaction mixture was heated under reflux for 3 h and cooled, and a further 0.2 ml of tert-butyl N,N'-diisopropylcarbamimidate were added. The reaction mixture was heated under reflux for a further 2 h and subsequently cooled to room temperature.

The reaction mixture was then diluted with ethyl acetate and filtered through Celite, rinsing with additional ethyl acetate. The combined filtrates were concentrated under reduced pressure and purified by column chromatography. Further purification via HPLC gave 61 mg of tert-butyl ester (48% yield).

Example I-34

Preparation of benzyl cis-4-[[(5RS)-3-(3-fluorophenyl)-5-methyl-4H-isoxazole-5-carbonyl]amino]tetrahydrofuran-2-carboxylate 0.10 g of carboxylic acid, 89 mg of 1-(3-dimethylaminopropyl)-3-ethylcarbodiimide hydrochloride and 4 mg of 4-dimethylaminopyridine were dissolved in 5 ml of dichloromethane.

With stirring at room temperature, 0.67 g of benzyl alcohol were then added and the reaction mixture was stirred at room temperature for 1.5 h and then for three days.

The reaction mixture was washed with 0.5 M aqueous hydrochloric acid, dried and concentrated under reduced pressure. The crude product was then purified by chromatography.

This gave 84 mg (61%) of benzyl ester.

Example I-35

Preparation of ethyl cis-4-[[(5S)-3-(3,5-difluorophenyl)-5-vinyl-4H-isoxazole-5-carbonyl]amino]tetrahydrofuran-2-carboxylate 0.12 g of carboxylic acid and 8 mg of 4-dimethylaminopyridine were dissolved in 5 ml of dichloromethane. With stirring at room temperature, 92 mg of 1-(3-dimethylaminopropyl)-3-ethylcarbodiimide hydrochloride followed by 0.22 g of ethanol were then added, and the reaction mixture was left to stir at room temperature for 1.5 h and then at this temperature for 36 h.

The reaction mixture was washed with 0.5 M aqueous hydrochloric acid, dried and concentrated under reduced pressure. The crude product was then purified by chromatography.

This gave 82 mg of ethyl ester (64% yield).

Example I-36

Preparation of isopropyl cis-4-[[(5S)-3-(3,5-difluorophenyl)-5-vinyl-4H-isoxazole-5-carbonyl]amino]tetrahydrofuran-2-carboxylate 0.13 g of carboxylic acid and 9 mg of 4-dimethylaminopyridine were dissolved in 5 ml of dichloromethane. With stirring at room temperature, 104 mg of 1-(3-dimethylaminopropyl)-3-ethylcarbodiimide hydrochloride followed by 0.33 g of 2-propanol were then added, and the reaction mixture was left to stir at room temperature for 1.5 h and then at this temperature for 36 h.

The reaction mixture was washed with 0.5 M aqueous hydrochloric acid, dried and concentrated under reduced pressure. The crude product was then purified by chromatography.

This gave 106 mg of 2-propyl ester (71% yield).

Example I-37

Preparation of benzyl cis-4-[[(5S)-3-(3,5-difluorophenyl)-5-vinyl-4H-isoxazole-5-carbonyl]amino]tetrahydrofuran-2-carboxylate 0.10 g of carboxylic acid and 0.04 g of benzyl alcohol were dissolved in 5 ml of dichloromethane. With stirring at room temperature, 0.07 g of N,N-diisopropylethylamine followed by 0.26 g of a solution of propylphosphonic anhydride (50% strength) in tetrahydrofuran were added to this mixture, and the reaction mixture was then stirred at room temperature for 1 h.

The reaction mixture was washed with saturated aqueous sodium bicarbonate solution, dried and concentrated under reduced pressure.

This gave 100 mg of benzyl ester (73% yield).

Example I-38

Preparation of tert-butyl cis-4-[[(5S)-3-(3,5-difluorophenyl)-5-vinyl-4H-isoxazole-5-carbonyl]amino]tetrahydrofuran-2-carboxylate 0.13 g of carboxylic acid was dissolved in 2 ml of tetrahydrofuran and placed under nitrogen.

Via a syringe filter, 0.2 ml of tert-butyl N,N'-diisopropylcarbamimidate was added. The reaction mixture was heated under reflux for 3 hours and cooled, and a further 0.2 ml of tert-butyl N,N'-diisopropylcarbamimidate was added. The reaction mixture was heated under reflux for a further 2 h and subsequently cooled to room temperature.

The reaction mixture was then diluted with ethyl acetate and filtered through Celite, rinsing with additional ethyl acetate. The combined filtrates were concentrated under reduced pressure and purified by column chromatography. Further purification by HPLC gave 84 mg of tert-butyl ester (54% yield).

Example I-39 and Example I-40

Preparation of methyl (3S)-3-[[3-(3-fluorophenyl)-5-methyl-4H-isoxazole-5-carbonyl]amino]-2,3-dihydrofuran-5-carboxylate and methyl (2S,4S)-4-[[3-(3-fluorophenyl)-5-methyl-4H-isoxazole-5-carbonyl]amino]-2-methoxytetrahydrofuran-2-carboxylate 0.43 g of intermediate 17 (as hydrochloride) and 0.42 g of carboxylic acid were dissolved in 15 ml of dichloromethane. With stirring at room temperature, 0.78 ml of triethylamine followed by 3.34 ml of a solution of propylphosphonic anhydride (50% strength) in tetrahydrofuran were added to this mixture, and the reaction mixture was then stirred at room temperature for 3 h. The reaction mixture was washed with saturated aqueous sodium bicarbonate solution, dried and concentrated under reduced pressure.

The crude product was then purified by chromatography. This gave 40 mg (5% yield) of methyl (3S)-3-[[3-(3-fluorophenyl)-5-methyl-4H-isoxazole-5-carbonyl]amino]-2,3-dihydrofuran-5-carboxylate and 96 mg (13% yield) of methyl (2S,4S)-4-[[3-(3-fluorophenyl)-5-methyl-4H-isoxazole-5-carbonyl]amino]-2-methoxytetrahydrofuran-2-carboxylate

Example I-46 and Example I-47

Preparation of methyl (3R)-3-[[3-(3-fluorophenyl)-5-methyl-4H-isoxazole-5-carbonyl]amino]-2,3-dihydrofuran-5-carboxylate and methyl (2R,4R)-4-[[3-(3-fluorophenyl)-5-methyl-4H-isoxazole-5-carbonyl]amino]-2-methoxytetrahydrofuran-2-carboxylate The preparation was carried out analogously to Intermediate 18 (as hydrochloride) under the conditions specified in Example I-39 and Example I-40.

Example I-55

Preparation of methyl trans-4-[[(5R)-3-(3,5-difluorophenyl)-5-methyl-4H-isoxazole-5-carbonyl]amino] tetrahydrofuran-2-carboxylate 0.08 g of intermediate 16 and 0.11 mg of carboxylic acid were dissolved in 5 ml of dichloromethane.

With stirring at room temperature, 0.18 ml of triethylamine followed by 0.79 ml of a solution of propylphosphonic anhydride (50% strength) in tetrahydrofuran were added to this mixture, and the reaction mixture was then stirred at room temperature for 2 h. The reaction mixture was washed with saturated aqueous sodium bicarbonate solution, dried and concentrated under reduced pressure. The crude product was then purified by chromatography. This gave 90 mg (54% yield).

Example I-56

Preparation of methyl trans-4-[[(5S)-3-(3,5-difluorophenyl)-5-vinyl-4H-isoxazole-5-carbonyl]amino] tetrahydrofuran-2-carboxylate The preparation was carried out analogously to Example I-55 using 0.08 g of Intermediate 16 and 0.11 g of carboxylic acid. This gave 110 mg (64% yield).

| | Analytical data of Examples I-01-I-56. |
|---|---|
| No. | NMR |
| I-01 | $^1$H-NMR(400.0 MHz, CDCl3): δ = 7.518(1.0); 7.260(181.8); 7.171(1.8); 7.166(2.2); 7.162(1.3); 7.155(1.2); 7.151(2.2); 7.146(1.8); 6.996(1.0); 6.898(0.6); 6.883(0.7); 6.882(0.7); 6.878(1.2); 6.876(1.2); 6.870(0.6); 6.854(0.6); 4.578(1.1); 4.573(0.7); 4.569(1.1); 4.560(0.5); 4.554(1.6); 4.545(1.1); 4.530(1.0); 4.521(0.8); 4.065(0.8); 4.052(0.8); 4.042(1.3); 4.029(1.7); 4.017(0.8); 4.006(1.1); 3.993(1.0); 3.967(07); . 3.962(0.7); 3.900(0.6); 3.896(0.6); 3.834(14.5); 3.785(16.0); 3.773(2.0); 3.756(1.8); 3.730(2.2); 3.712(2.0); 3.190(1.9); 3.182(2.0); 3.146(1.6); 3.138(1.8); 2.558(0.7); 2.541(0.9); 2.524(0.8); 2.506(0.5); 2.019(0.5); 1.710(11.3); 1.687(10.3); 1.541(35.4); 0.008(2.1); 0.000(68.8); −0.008(1.9) |
| I-02 | $^1$H-NMR(400.0 MHz, CDCl3): δ = 7.556(5.0); 7.552(6.9); 7.552(6.5); 7.548(6.3); 7.518(1.0); 7.438(1.8); 7.437(1.6); 7.433(3.1); 7.432(2.8); 7.429(1.5); 7.427(1.4); 7.268(0.6); 7.267(0.7); 7.260(105.5); 6.996(0.6); 5.298(5.7); 4.677(0.6); 4.671(0.6); 4.590(0.8); 4.582(1.2); 4.574(0.7); 4.567(0.8); 4.558(1.3); 4.551(0.7); 4.061(0.6); 4.048(0.7); 4.045(1.3); 4.037(1.4); 4.033(1.2); 4.024(1.3); 4.014(0.6); 4.010(07); . 4.000(0.7); 3.994(0.8); 3.890(1.5); 3.848(1.9); 3.844(1.9); 3.810(15.9); 3.802(2.2); 3.792(13.4); 3.359(13.3); 3.355(16.0); 3.337(2.2); 3.320(1.8); 3.291(1.8); 3.274(1.6); 2.591(0.5); 2.573(0.6); 2.567(0.5); 2.126(0.5); 1.538(20.2); 0.008(1.3); 0.000(42.8); −0.008(1.2) |
| I-03 | $^1$H-NMR(400.0 MHz, CDCl3): δ = 7.595(2.6); 7.590(2.9); 7.526(7.9); 7.521(8.3); 7.518(2.3); 7.448(1.1); 7.445(1.4); 7.443(1.4); 7.419(2.0); 7.414(3.2); 7.409(1.7); 7.259(347.5); 6.995(1.9); 6.172(1.3); 6.145(1.6); 6.129(1.6); 6.102(1.7); 5.556(1.6); 5.555(1.8); 5.540(1.0); 5.513(1.5); 5.512(1.5); 5.497(0.8); 5.355(1.6); 5.341(0.8); 5.328(1.4); 5.314(0.8); 5.298(3.5); 4.594(0.6); 4.587(0.7); 4.572(0.8); 4.564(0.9); 4.556(1.0); 4.548(1.0); 4.541(0.5); 4.533(0.8); 4.524(0.8); 4.053(1.3); 4.040(1.6); 4.029(1.4); 4.016(1.7); 4.008(0.6); 4.003(0.8); 3.949(0.8); 3.924(2.5); 3.903(1.3); 3.881(2.1); 3.860(1.4); 3.857(5.2); 3.827(5.8); 3.814(9.6); 3.803(16.0); 3.326(1.0); 3.318(1.1); 3.315(1.0); 3.308(1.8); 3.301(1.0); 3.290(1.0); 3.274(0.8); 3.265(1.5); 2.837(0.7); 2.835(0.7); 2.526(0.6); 2.508(0.5); 2.039(0.6); 2.004(0.8); 1.532(84.5); 1.284(0.5); 1.256(0.5); 0.899(2.5); 0.896(2.3); 0.884(2.5); 0.880(2.3); 0.008(4.3); 0.000(146.4); −0.008(3.9) |
| I-04 | $^1$H-NMR(400.0 MHz, CDCl3): δ = 8.018(1.1); 7.569(1.2); 7.518(6.4); 7.384(2.3); 7.359(2.0); 7.322(2.1); 7.308(2.4); 7.295(2.9); 7.259(1071.8); 7.252(5.2); 7.251(1.9); 7.250(1.7); 7.249(1.6); 7.248(1.4); 7.248(1.5); 7.247(1.5); |

Analytical data of Examples I-01–I-56.

| No. | NMR |
|---|---|
| | 7.246(1.5); 7.245(1.3); 7.244(1.2); 7.244(1.2); 7.242(1.1); 7.241(1.2); 7.240(1.2); 7.239(1.1); 7.236(1.4); 7.232(1.6); 7.227(1.8); 7.221(1.6); 7.217(1.8); 7.209(2.1); 7.194(1.1); 7.150(0.6); 6.995(5.9); 5.298(16.0); 4.565(0.8); 4.541(0.8); 4.419(0.6); 4.392(0.6); 4.113(0.6); 4.043(0.8); 3.991(0.9); 3.947(0.9); 3.825(3.9); 3.786(4.3); 3.772(4.7); 3.760(4.6); 3.746(1.4); 3.706(1.6); 3.633(1.5); 3.589(0.6); 3.424(2.1); 3.203(2.3); 3.166(0.9); 3.142(0.9); 3.129(1.8); 3.124(2.2); 3.040(2.4); 2.992(2.0); 2.986(1.8); 2.955(11.0); 2.884(9.4); 2.882(9.4); 2.553(0.6); 2.352(6.6); 2.340(2.6); 2.321(1.4); 2.221(3.9); 2.043(2.2); 2.003(1.2); 1.714(6.2); 1.704(6.4); 1.686(6.9); 1.676(5.7); 1.664(6.0); 1.658(6.2); 1.495(2.1); 1.434(2.5); 1.333(1.0); 1.284(1.1); 1.258(1.9); 0.146(1.4); 0.008(13.6); 0.000(458.9); −0.008(12.8); −0.051(0.7); −0 149(1.4) |
| I-05 | $^1$H-NMR(400.0 MHz, CDCl3): δ = 7.518(1.6); 7.310(0.5); 7.259(217.2); 7.227(0.5); 7.211(1.3); 7.208(1.9); 7.205(2.0); 7.202(2.0); 7.191(2.0); 7.188(1.8); 7.186(1.9); 7.182(1.2); 6.995(1.2); 6.920(0.7); 6.904(0.8); 6.898(1.3); 6.894(0.7); 6.878(0.7); 4.678(0.6); 4.673(0.6); 4.667(0.5); 4.591(0.7); 4.583(1.3); 4.575(0.9); 4.568(0.8); 4.560(1.4); 4.552(0.6); 4.071(0.5); 4.059(0.7); 4.047(0.6); 4.035(1.6); 4.025(1.3); 4.015(0.8); 4.012(0.8); 4.002(0.7); 3.998(0.7); 3.884(1.8); 3.841(1.9); 3.838(2.3); 3.810(14.7); 3.796(2.4); 3.790(16.0); 3.366(15.8); 3.362(15.0); 3.343(2.1); 3.326(2.2); 3.298(1.8); 3.280(1.8); 2.593(0.5); 2.580(0.5); 2.573(0.6); 2.562(0.6); 2.556(0.5); 2.552(0.5); 2.545(0.5); 2.146(0.5); 2.128(0.5); 2.119(0.5); 1.539(11.2); 0.008(2.6); 0.000(88.3); −0.008(2.4) |
| I-06 | $^1$H-NMR(400.0 MHz, CDCl3): δ = 7.261(34.4); 7.205(1.5); 7.200(2.0); 7.196(1.2); 7.189(1.2); 7.185(1.9); 7.180(1.6); 6.960(0.8); 6.945(0.8); 6.939(1.5); 6.933(0.7); 6.917(0.7); 5.298(5.5); 4.678(0.5); 4.675(0.6); 4.663(0.6); 4.658(0.5); 4.606(0.6); 4.598(0.7); 4.585(0.8); 4.582(0.8); 4.577(0.7); 4.585(0.8); 4.561(0.8); 4.554(0.8); 4.074(0.7); 4.061(0.7); 4.050(1.4); 4.047(0.6); 4.037(1.3); 4.035(0.6); 4.022(1.2); 4.010(1.2); 4.000(0.7); 3.998(0.8); 3.993(1.2); 3.987(0.8); 3.985(0.7); 3.980(0.9); 3.969(0.6); 3.955(0.6); 3.934(1.1); 3.910(0.9); 3.829(12.4); 3.798(16.0); 3.752(2.0); 3.746(2.3); 3.707(1.3); 3.701(1.6); 2.521(0.5); 2.104(0.6); 2.099(0.6); 1.556(6.0); 0.000(14.2) |
| I-07 | $^1$H-NMR(400.0 MHz, CDCl3): δ = 7.405(0.7); 7.404(0.8); 7.402(1.0); 7.400(1.0); 7.398(1.0); 7.394(1.4); 7.393(1.4); 7.388(0.9); 7.385(1.5); 7.380(5.0); 7.377(2.9); 7.375(2.0); 7.372(2.8); 7.368(1.5); 7.261(32.6); 7.149(0.6); 7.143(0.6); 7.135(0.8); 7.133(0.7); 7.127(0.8); 7.114(0.5); 6.189(1.3); 6.163(1.4); 6.146(1.5); 6.119(1.6); 5.562(1.7); 5.561(1.7); 5.547(1.4); 5.545(1.4); 5.519(1.5); 5.518(1.5); 5.504(1.5); 5.502(1.2); 5.346(1.4); 5.345(1.4); 5.334(1.2); 5.332(1.2); 5.320(1.4); 5.318(1.4); 5.307(1.1); 5.305(1.1); 5.298(2.9); 4.572(0.9); 4.564(0.8); 4.554(0.9); 4.549(0.9); 4.545(0.9); 4.540(0.7); 4.531(0.8); 4.521(0.8); 4.062(0.8); 4.049(0.8); 4.044(0.7); 4.039(1.2); 4.031(0.7); 4.026(1.2); 4.020(1.0); 4.007(0.9); 3.952(0.7); 3.950(0.7); 3.946(2.5); 3.926(2.6); 3.921(1.0); 3.919(0.9); 3.903(2.6); 3.883(1.9); 3.815(13.3); 3.796(16.0); 3.357(1.6); 3.348(1.9); 3.314(1.4); 3.305(1.6); 2.542(0.6); 2.531(0.6); 2.513(0.5); 2.042(0.5); 1.572(4.6); 0.000(12.8) |
| I-08 | $^1$H-NMR(400.0 MHz, CDCl3): δ = 7.613(0.7); 7.611(0.8); 7.607(1.5); 7.605(1.4); 7.603(1.4); 7.598(0.7); 7.596(0.6); 7.413(2.8); 7.411(3.9); 7.409(4.0); 7.407(3.5); 7.262(34.4); 5.298(11.2); 4.675(0.6); 4.670(0.5); 4.667(0.5); 4.654(0.5); 4.589(0.7); 4.580(1.5); 4.572(0.8); 4.565(0.8); 4.557(1.5); 4.548(0.8); 4.074(0.6); 4.063(0.7); 4.062(0.7); 4.050(1.8); 4.039(1.6); 4.038(1.6); 4.027(1.2); 4.014(0.7); 4.012(0.7); 4.009(0.8); 4.006(0.7); 3.998(0.6); 3.996(0.7); 3.992(1.0); 3.989(0.9); 3.881(1.7); 3.836(2.1); 3.810(14.9); 3.795(2.1); 3.789(16.0); 3.360(2.5); 3.355(15.3); 3.351(14.7); 3.343(2.2); 3.315(1.7); 3.297(1.8); 2.594(0.5); 2.576(0.5); 2.574(0.5); 2.562(0.6); 2.363(11.5); 2.362(11.5); 2.143(0.5); 2.136(0.6); 2.130(0.5); 1.568(4.3); 0.000(14.6) |
| I-09 | $^1$H-NMR(400.0 MHz, CDCl3): δ = 7.263(29.0); 7.172(1.9); 7.166(2.3); 7.163(1.3); 7.155(1.3); 7.152(2.2); 7.146(1.9); 6.900(0.6); 6.898(0.6); 6.884(0.7); 6.882(0.7); 6.878(1.3); 6.876(1.2); 6.872(0.7); 6.870(0.6); 6.856(0.6); 6.854(0.6); 5.299(4.4); 4.579(1.2); 4.574(0.7); 4.569(1.2); 4.560(0.6); 4.554(1.7); 4.545(1.4); 4.530(0.9); 4.521(0.8); 4.066(0.7); 4.053(0.7); 4.042(1.2); 4.029(1.7); 4.017(0.8); 4.006(1.2); 3.993(1.1); 3.967(0.7); 3.963(0.6); 3.961(0.6); 3.902(0.6); 3.900(0.6); 3.896(0.6); 3.894(0.6); 3.834(16.0); 3.785(15.8); 3.779(0.7); 3.774(2.3); 3.757(1.9); 3.730(2.2); 3.714(2.2); 3.191(2.0); 3.183(1.9); 3.148(1.7); 3.140(1.7); 2.565(0.6); 2.559(0.7); 2.541(0.9); 2.524(0.8); 2.122(0.5); 2.020(0.5); 1.710(10.7); 1.687(10.9); 1.585(5.6); 0.000(11.5) |
| I-10 | $^1$H-NMR(400.0 MHz, CDCl3): δ = 7.262(28.6); 7.180(2.2); 7.174(2.6); 7.171(1.5); 7.163(1.5); 7.160(2.6); 7.154(2.1); 6.903(0.8); 6.887(0.9); 6.882(1.6); 6.876(0.8); 6.860(0.8); 6.176(2.0); 6.150(2.4); 6.133(2.4); 6.106(2.5); 5.560(1.8); 5.558(1.8); 5.544(1.7); 5.543(1.7); 5.517(1.5); 5.515(1.5); 5.501(1.5); 5.500(1.4); 5.357(1.6); 5.356(1.6); 5.343(1.5); 5.342(1.5); 5.330(1.5); 5.329(1.5); 5.316(1.4); 5.315(1.4); 5.299(9.2); 4.603(0.5); 4.596(0.6); 4.591(0.6); 4.585(0.6); 4.579(0.6); 4.574(1.1); 4.565(1.2); 4.558(1.1); 4.550(1.4); 4.542(0.9); 4.534(0.9); 4.525(0.8); 4.056(0.8); 4.043(0.9); 4.041(0.9); 4.033(1.3); 4.028(0.8); 4.020(1.3); 4.017(1.4); 4.004(1.1); 3.950(0.7); 3.946(0.7); 3.944(0.7); 3.929(1.1); 3.922(2.7); 3.905(0.5); 3.899(2.3); 3.878(2.2); 3.856(2.2); 3.814(15.9); 3.800(16.0); 3.322(1.9); 3.313(1.9); 3.279(1.6); 3.270(1.7); 2.566(0.5); 2.564(0.5); 2.555(0.6); 2.549(0.5); 2.546(0.5); 2.540(0.6); 2.538(0.6); 2.531(0.6); 2.529(0.6); 2.514(0.5); 2.511(0.6); 2.094(0.6); 2.060(0.5); 2.052(0.5); 2.044(0.6); 1.577(5.9); 0.000(11.4) |
| I-11 | $^1$H-NMR(400.6 MHz, CDCl3): δ = 7.494(0.6); 7.474(0.6); 7.278(0.9); 7.184(1.5); 7.178(2.0); 7.176(1.4); 7.167(1.3); 7.164(2.0); 7.159(1.7); 6.906(0.6); 6.890(0.7); 6.884(1.3); 6.879(0.7); 6.863(0.6); 6.180(1.1); 6.153(1.2); 6.137(1.4); 6.110(1.4); 5.560(2.2); 5.559(2.2); 5.516(1.9); 5.516(1.9); 5.358(2.1); 5.331(2.0); 4.622(0.5); 4.615(0.6); 4.611(0.6); 4.608(0.6); 4.602(0.6); 4.597(0.6); 4.562(1.0); 4.553(1.2); 4.539(1.2); 4.530(1.1); 4.060(0.9); 4.047(1.0); 4.036(1.5); 4.023(1.4); 3.955(1.1); 3.951(1.2); 3.928(2.9); 3.885(2.5); 3.801(16.0); 3.322(2.3); 3.279(2.0); 2.569(0.5); 2.551(0.6); 2.546(0.6); |

| No. | NMR |
|---|---|
| | 2.534(0.7); 2.528(0.6); 2.517(0.7); 2.511(0.7); 2.493(0.6); 2.056(0.5); 2.050(0.8); 2.043(0.6); 2.015(0.8); 2.009(0.5); 0.000(0.8) |
| I-12 | $^1$H-NMR(400.6 MHz, CDCl3): δ = 7.461(0.7); 7.442(0.7); 7.278(0.9); 7.184(1.6); 7.178(2.0); 7.164(2.1); 7.159(1.6); 6.907(0.6); 6.891(0.8); 6.885(1.3); 6.880(0.7); 6.864(0.7); 6.179(1.1); 6.152(1.3); 6.136(1.4); 6.109(1.4); 5.543(2.3); 5.500(2.0); 5.344(2.2); 5.317(2.1); 4.593(0.6); 4.587(0.7); 4.579(1.6); 4.570(1.8); 4.563(0.6); 4.555(1.5); 4.546(1.2); 4.043(1.0); 4.030(1.0); 4.019(1.6); 4.006(1.4); 3.935(1.2); 3.930(1.2); 3.905(3.0); 3.862(2.6); 3.814(16.0); 3.331(2.4); 3.288(2.1); 2.596(0.5); 2.579(0.6); 2.573(0.6); 2.562(0.7); 2.555(0.6); 2.544(0.7); 2.538(0.7); 2.521(0.6); 2.107(0.6); 2.101(0.9); 2.095(0.6); 2.073(0.5); 2.067(0.8); 2.060(0.5); 1.257(0.5); 0.000(0.8) |
| I-13 | $^1$H-NMR(400.0 MHz, CDCl3): δ = 7.518(1.2); 7.394(1.4); 7.389(2.4); 7.374(5.0); 7.365(4.2); 7.358(0.6); 7.310(0.7); 7.268(1.5); 7.265(3.0); 7.259(207.2); 7.253(1.0); 7.252(0.8); 7.251(0.6); 7.145(0.8); 7.140(0.6); 7.130(1.0); 7.121(0.9); 7.113(0.6); 7.110(0.6); 6.995(1.2); 4.577(1.2); 4.567(1.1); 4.557(0.6); 4.553(1.2); 4.550(1.2); 4.544(1.0); 4.540(1.1); 4.526(0.9); 4.517(0.8); 4.072(0.8); 4.059(0.8); 4.048(1.3); 4.035(1.6); 4.021(0.8); 4.010(1.1); 3.997(0.9); 3.966(0.7); 3.961(0.8); 3.896(0.6); 3.890(0.6); 3.835(14.3); 3.800(2.0); 3.785(2.1); 3.778(16.0); 3.762(0.6); 3.757(2.3); 3.742(2.1); 3.223(1.9); 3.215(2.1); 3.180(1.7); 3.172(1.9); 2.561(0.8); 2.549(0.5); 2.543(0.6); 2.526(0.5); 2.520(0.5); 2.509(0.5); 2.503(0.5); 2.018(0.6); 1.983(0.5); 1.725(0.6); 1.714(1.4); 1.708(11.3); 1.697(0.7); 1.686(10.3); 1.666(0.6); 1.606(2.7); 0.008(2.2); 0.000(86.6); −0.008(2.6) |
| I-14 | $^1$H-NMR(400.0 MHz, CDCl3): δ = 7.684(1.6); 7.680(2.9); 7.677(2.1); 7.670(1.0); 7.666(1.6); 7.665(1.5); 7.663(1.6); 7.660(2.4); 7.656(1.9); 7.520(0.6); 7.454(0.6); 7.452(0.7); 7.451(0.8); 7.450(0.8); 7.442(1.4); 7.440(1.6); 7.437(5.2); 7.432(2.3); 7.427(1.0); 7.422(1.3); 7.418(2.4); 7.404(0.8); 7.261(43.3); 5.298(3.7); 4.680(0.5); 4.672(0.5); 4.590(0.7); 4.581(1.3); 4.571(0.8); 4.567(0.8); 4.557(1.3); 4.548(0.8); 4.081(0.6); 4.068(1.0); 4.057(1.4); 4.055(0.8); 4.044(2.0); 4.031(1.2); 4.018(0.7); 4.016(0.7); 4.012(0.7); 4.009(0.7); 3.999(0.6); 3.997(0.7); 3.992(1.0); 3.904(1.9); 3.866(1.8); 3.858(2.2); 3.821(2.2); 3.813(14.8); 3.783(15.8); 3.438(2.2); 3.420(2.3); 3.393(1.9); 3.375(2.5); 3.370(16.0); 3.364(15.0); 2.600(0.8); 2.583(0.7); 2.577(0.8); 2.566(0.6); 2.560(0.7); 2.146(0.8); 2.143(0.6); 2.140(0.6); 2.137(0.7); 2.111(0.7); 2.108(0.5); 2.105(0.5); 2.102(0.6); 1.563(9.6); 0.008(0.5); 0.000(18.3); −0.008(0.5) |
| I-15 | $^1$H-NMR(400.0 MHz, CDCl3): δ = 7.518(1.2); 7.259(207.4); 7.210(0.6); 7.170(1.4); 7.165(1.8); 7.150(1.7); 7.145(1.4); 6.995(1.2); 6.898(0.6); 6.882(0.7); 6.876(1.2); 6.870(0.6); 6.854(0.6); 4.581(0.6); 4.554(1.2); 4.545(1.0); 4.530(1.2); 4.521(1.0); 4.066(0.9); 4.052(0.9); 4.042(1.5); 4.029(1.4); 3.968(1.0); 3.962(1.1); 3.945(0.7); 3.786(16.0); 3.773(2.3); 3.729(2.5); 3.182(2.4); 3.138(2.1); 2.559(0.5); 2.540(0.5); 2.536(0.6); 2.524(0.7); 2.518(0.6); 2.506(0.7); 2.501(0.6); 2.483(0.5); 2.019(0.8); 1.985(0.6); 1.710(13.0); 1.530(23.7); 0.008(2.5); 0.000(73.7); −0.008(2.3) |
| I-16 | $^1$H-NMR(400.0 MHz, CDCl3): δ = 7.519(0.5); 7.426(0.5); 7.260(91.8); 7.172(1.4); 7.166(1.8); 7.152(1.7); 7.146(1.4); 6.900(0.6); 6.884(0.7); 6.878(1.2); 6.872(0.6); 6.856(0.6); 4.580(1.3); 4.570(1.5); 4.556(1.6); 4.547(1.3); 4.030(1.0); 4.017(1.0); 4.006(1.4); 3.993(1.3); 3.901(1.0); 3.895(0.9); 3.878(0.7); 3.871(0.7); 3.834(16.0); 3.756(2.2); 3.713(2.5); 3.190(2.4); 3.147(2.0); 2.599(0.5); 2.581(0.6); 2.575(0.5); 2.564(0.6); 2.558(0.6); 2.547(0.6); 2.541(0.6); 2.524(0.6); 2.122(0.8); 2.087(0.6); 1.688(12.8); 1.536(5.7); 0.008(1.4); 0.000(33.1); −0.008(1.1) |
| I-17 | $^1$H-NMR(400.0 MHz, CDCl3): δ = 7.260(62.3); 7.217(0.8); 7.186(1.3); 7.181(2.3); 7.178(1.4); 7.175(1.5); 7.171(1.1); 7.167(1.6); 7.164(1.3); 7.161(2.3); 7.155(1.1); 6.919(0.5); 6.913(0.9); 6.897(1.1); 6.891(1.8); 6.886(0.9); 6.876(0.5); 6.870(0.9); 4.239(1.7); 4.215(2.1); 4.203(1.6); 4.179(1.9); 4.012(1.6); 4.002(2.5); 3.996(1.5); 3.993(2.0); 3.988(1.1); 3.982(2.1); 3.977(2.8); 3.968(0.9); 3.964(0.9); 3.946(1.3); 3.922(1.1); 3.769(1.9); 3.760(1.7); 3.724(14.8); 3.716(2.1); 3.706(16.0); 3.208(3.1); 3.165(2.8); 2.624(0.6); 2.603(0.5); 2.590(0.9); 2.584(0.6); 2.570(0.6); 2.551(0.8); 2.252(0.6); 2.236(0.5); 2.219(0.5); 2.190(0.6); 2.174(0.6); 1.723(14.0); 1.547(5.9); 0.008(0.7); 0.000(23.6); −0.008(0.7) |
| I-18 | $^1$H-NMR(400.0 MHz, CDCl3): δ = 7.262(30.8); 7.221(0.9); 7.184(1.4); 7.178(2.2); 7.173(1.6); 7.168(1.1); 7.164(1.8); 7.158(2.1); 7.153(1.0); 6.917(0.6); 6.911(1.0); 6.905(0.5); 6.895(1.2); 6.889(2.0); 6.884(1.0); 6.874(0.6); 6.868(1.0); 5.299(2.7); 4.230(1.9); 4.206(2.9); 4.198(1.6); 4.190(1.3); 4.188(2.9); 4.173(4.5); 4.170(3.3); 4.155(3.8); 4.152(1.2); 4.137(1.2); 4.009(1.5); 4.006(1.9); 3.997(1.9); 3.993(2.0); 3.990(1.4); 3.982(2.8); 3.978(2.6); 3.974(1.7); 3.962(1.8); 3.953(1.2); 3.928(1.0); 3.776(2.0); 3.766(1.6); 3.733(2.3); 3.723(1.8); 3.207(3.2); 3.164(2.8); 2.625(0.7); 2.610(0.8); 2.608(0.5); 2.592(1.0); 2.589(0.9); 2.575(0.6); 2.573(0.5); 2.570(0.5); 2.556(1.0); 2.245(0.6); 2.229(0.5); 2.184(0.7); 2.168(0.6); 2.151(0.6); 1.726(16.0); 1.215(3.2); 1.197(9.0); 1.180(10.3); 1.162(3.9); 0.000(12.2) |
| I-19 | $^1$H-NMR(400.0 MHz, CDCl3): δ = 7.263(33.4); 7.258(0.6); 7.179(0.5); 7.174(1.4); 7.168(1.8); 7.165(2.3); 7.159(2.1); 7.157(1.5); 7.154(2.0); 7.148(2.2); 7.145(1.7); 7.140(1.3); 7.040(0.7); 7.021(0.7); 6.916(0.8); 6.910(0.8); 6.900(0.8); 6.894(1.7); 6.888(1.5); 6.882(0.6); 6.879(0.7); 6.872(1.0); 6.866(0.8); 4.715(0.8); 4.710(0.6); 4.706(0.8); 4.700(0.6); 4.696(0.8); 4.690(0.5); 4.225(0.7); 4.203(1.7); 4.181(1.8); 4.159(0.9); 4.149(0.6); 4.131(1.6); 4.113(1.6); 4.095(0.6); 4.038(0.9); 4.023(0.9); 4.014(1.8); 4.000(1.8); 3.991(1.0); 3.976(1.1); 3.950(1.0); 3.934(1.0); 3.927(1.0); 3.922(1.0); 3.911(0.9); 3.907(1.1); 3.899(0.9); 3.884(0.9); 3.792(2.0); 3.780(2.0); 3.774(0.6); 3.772(0.5); 3.757(0.9); 3.746(16.0); 3.741(1.2); 3.737(6.0); 3.731(1.2); 3.725(1.0); 3.710(0.6); 3.704(0.6); 3.691(16.0); 3.680(1.1); 3.665(0.9); 3.656(0.8); 3.541(3.0); 3.211(2.8); 3.188(0.6); 3.168(2.4); 3.145(0.5); 3.007(1.0); 2.045(7.1); 1.722(10.8); 1.715(13.2); 1.688(2.5); 1.277(2.6); 1.264(1.8); 1.260(5.3); 1.242(2.3); 0.899(0.9); 0.882(3.1); 0.864(1.2); 0.000(13.7) |

Analytical data of Examples I-01-I-56.

| No. | NMR |
|---|---|
| I-20 | $^1$H-NMR(400.0 MHz, d$_6$-DMSO): δ = 8.147(0.6); 8.130(0.6); 8.087(0.6); 8.069(0.6); 7.526(2.2); 7.524(2.3); 7.517(3.2); 7.512(2.2); 7.498(2.4); 7.469(1.1); 7.465(0.9); 7.349(0.6); 7.341(0.6); 7.334(0.7); 7.326(1.0); 7.322(0.9); 7.315(0.6); 7.308(0.6); 7.303(0.7); 5.756(5.0); 4.380(0.6); 4.365(1.4); 4.359(0.8); 4.349(1.0); 4.343(1.5); 4.327(0.9); 4.318(0.8); 4.303(0.8); 3.911(0.7); 3.895(0.7); 3.889(0.9); 3.873(0.8); 3.868(0.7); 3.853(0.7); 3.847(0.8); 3.831(0.7); 3.761(1.3); 3.740(1.5); 3.717(1.6); 3.696(1.9); 3.678(0.8); 3.671(0.7); 3.660(0.8); 3.647(0.7); 3.638(0.6); 3.625(0.6); 3.390(1.8); 3.385(1.7); 3.346(1.9); 3.341(2.0); 3.322(43.8); 2.670(0.6); 2.544(0.8); 2.524(1.3); 2.519(2.0); 2.510(32.8); 2.506(72.0); 2.501(100.7); 2.497(70.3); 2.492(31.4); 2.468(0.8); 2.456(1.2); 2.451(1.0); 2.447(1.1); 2.436(0.5); 2.425(0.7); 2.328(0.6); 2.048(0.5); 1.979(0.6); 1.963(0.6); 1.947(0.6); 1.567(1.4); 1.534(16.0); 0.000(1.8) |
| I-21 | $^1$H-NMR(400.0 MHz, d-DMSO): δ = 7.428(4.5); 7.421(1.4); 7.410(3.4); 7.404(2.6); 7.386(0.6); 7.381(0.5); 6.160(1.0); 6.153(0.9); 6.134(1.1); 6.126(1.0); 6.117(1.2); 6.110(1.1); 6.091(1.2); 6.083(1.0); 5.398(2.3); 5.396(1.5); 5.355(2.1); 5.316(2.1); 5.288(2.0); 4.376(0.6); 4.367(0.8); 4.360(1.0); 4.354(1.0); 4.351(1.2); 4.346(1.3); 4.339(1.0); 4.330(1.3); 4.314(0.5); 4.056(1.0); 4.038(3.2); 4.020(3.2); 4.003(1.1); 3.908(0.7); 3.893(1.6); 3.887(1.0); 3.880(1.5); 3.871(0.8); 3.862(0.6); 3.856(0.8); 3.849(1.5); 3.840(0.8); 3.835(1.7); 3.667(1.4); 3.653(1.3); 3.645(1.2); 3.631(1.1); 3.574(3.0); 3.530(2.6); 3.431(1.9); 2.670(0.7); 2.524(2.1); 2.519(3.0); 2.510(39.7); 2.506(85.1); 2.501(118.3); 2.496(82.4); 2.492(36.6); 2.476(0.6); 2.464(0.6); 2.453(0.8); 2.432(0.6); 2.332(0.5); 2.328(0.7); 2.323(0.5); 2.014(0.6); 2.005(0.7); 1.996(0.6); 1.988(16.0); 1.973(0.6); 1.908(1.7); 1.760(0.5); 1.356(0.8); 1.192(4.1); 1.175(8.3); 1.157(4.0); 0.000(3.8) |
| I-22 | $^1$H-NMR(400.0 MHz, CDCl3): δ = 7.262(46.3); 7.180(2.1); 7.174(2.4); 7.171(1.4); 7.164(1.4); 7.160(2.4); 7.154(1.9); 6.904(0.8); 6.888(0.9); 6.882(1.5); 6.877(0.7); 6.860(0.7); 6.176(2.0); 6.150(2.2); 6.133(2.4); 6.106(2.4); 5.560(1.8); 5.559(1.8); 5.544(1.7); 5.543(1.7); 5.517(1.6); 5.516(1.6); 5.501(1.5); 5.500(1.4); 5.358(1.6); 5.356(1.6); 5.344(1.5); 5.342(1.4); 5.331(1.4); 5.330(1.4); 5.317(1.4); 5.316(1.4); 5.300(2.9); 4.586(0.5); 4.579(0.6); 4.576(1.1); 4.566(1.1); 4.559(1.1); 4.552(1.3); 4.543(0.8); 4.535(0.9); 4.526(0.8); 4.056(0.8); 4.043(0.9); 4.041(0.8); 4.033(1.3); 4.028(0.8); 4.020(1.3); 4.017(1.3); 4.004(1.1); 3.953(0.6); 3.951(0.7); 3.947(0.7); 3.945(0.6); 3.930(1.0); 3.927(1.0); 3.921(2.4); 3.899(2.0); 3.878(2.2); 3.856(2.1); 3.814(15.6); 3.801(16.0); 3.323(1.8); 3.313(1.9); 3.280(1.6); 3.270(1.6); 2.556(0.5); 2.549(0.5); 2.547(0.5); 2.541(0.5); 2.539(0.6); 2.532(0.6); 2.530(0.6); 2.515(0.5); 2.512(0.6); 2.095(0.6); 2.052(0.6); 2.044(0.6); 1.569(13.8); 0.008(0.6); 0.000(18.2); −0.008(0.5) |
| I-23 | $^1$H-NMR(400.0 MHz, CDCl3): δ = 7.519(0.6); 7.269(0.5); 7.268(0.6); 7.267(0.7); 7.266(0.9); 7.266(1.1); 7.265(1.4); 7.264(1.9); 7.263(2.5); 7.260(105.9); 7.256(1.7); 7.255(1.3); 7.254(1.0); 7.253(0.7); 7.252(0.6); 7.210(0.9); 7.200(1.1); 7.195(1.2); 7.192(0.7); 7.184(0.7); 7.181(1.3); 7.175(1.1); 6.996(0.6); 6.896(0.5); 6.890(0.9); 6.189(0.9); 6.162(1.1); 6.146(1.2); 6.119(1.2); 5.647(1.7); 5.646(1.7); 5.604(1.5); 5.603(1.5); 5.428(1.6); 5.401(1.4); 5.299(1.3); 5.217(1.1); 5.206(2.1); 5.194(1.2); 4.754(1.1); 4.742(2.3); 4.732(0.8); 4.730(0.9); 4.318(0.6); 4.301(1.9); 4.300(1.9); 4.283(2.0); 4.283(2.0); 4.265(0.7); 3.942(1.7); 3.898(1.9); 3.367(1.6); 3.324(1.4); 1.539(16.0); 1.371(3.2); 1.353(6.7); 1.335(3.1); 0.008(1.1); 0.000(41.6); −0.005(0.7); −0.006(0.6); −0.008(1.3) |
| I-24 | $^1$H-NMR(400.0 MHz, CDCl3): δ = 10.908(1.1); 7.260(57.2); 7.210(0.8); 7.194(2.0); 7.189(2.4); 7.178(1.7); 7.175(2.4); 7.169(1.8); 6.907(0.8); 6.891(1.0); 6.885(1.6); 6.879(0.8); 6.869(0.5); 6.863(0.8); 5.299(0.6); 5.222(1.3); 5.211(2.4); 5.205(2.5); 5.200(1.6); 5.194(1.3); 4.757(1.6); 4.751(2.4); 4.745(2.2); 4.741(2.3); 4.738(2.0); 4.728(1.3); 4.324(0.8); 4.319(0.8); 4.306(2.4); 4.301(2.4); 4.288(2.5); 4.283(2.4); 4.270(0.9); 4.265(0.8); 4.189(0.7); 4.171(2.0); 4.153(2.0); 4.135(0.8); 4.121(5.1); 3.852(1.4); 3.836(2.9); 3.820(1.5); 3.793(2.8); 3.756(8.4); 3.750(3.5); 3.254(3.0); 3.211(2.6); 2.655(1.4); 2.638(2.6); 2.622(1.3); 1.777(16.0); 1.554(4.9); 1.370(5.0); 1.352(10.2); 1.335(5.0); 1.285(2.5); 1.267(4.9); 1.257(1.0); 1.249(2.5); 0.008(1.3); 0.000(23.4); −0.008(1.1) |
| I-25 | $^1$H-NMR(400.0 MHz, CDCl3): δ = 7.266(0.5); 7.263(16.6); 7.200(1.2); 7.196(0.8); 7.194(1.3); 7.190(0.7); 7.183(0.7); 7.180(1.4); 7.177(0.7); 7.174(1.1); 6.907(0.5); 6.891(0.6); 6.885(1.1); 6.879(0.7); 6.863(0.5); 5.300(1.8); 5.218(0.6); 5.211(0.8); 5.207(1.1); 5.200(1.3); 5.196(0.8); 5.189(0.7); 4.753(1.0); 4.746(1.5); 4.743(1.1); 4.741(1.3); 4.736(1.2); 4.734(1.0); 4.731(0.9); 4.724(0.8); 4.120(3.7); 3.854(1.3); 3.838(2.9); 3.822(2.0); 3.818(16.0); 3.794(1.9); 3.756(6.7); 3.751(2.3); 3.706(7.2); 3.257(1.9); 3.214(1.7); 2.672(1.0); 2.656(1.9); 2.640(0.9); 1.779(10.8); 1.574(2.0); 0.000(7.0) |
| I-26 | $^1$H-NMR(400.0 MHz, CDCl3): δ = 7.520(1.9); 7.311(0.9); 7.291(0.8); 7.261(352.0); 7.255(0.8); 7.254(0.7); 7.210(2.5); 7.183(1.3); 7.177(1.5); 7.174(1.6); 7.169(1.5); 7.166(1.5); 7.163(1.5); 7.160(1.3); 7.157(1.6); 7.155(1.4); 7.149(1.1); 6.997(2.5); 6.977(0.6); 6.920(0.8); 6.915(0.8); 6.904(0.6); 6.899(1.6); 6.893(1.5); 6.887(0.6); 6.877(0.8); 6.871(0.8); 6.181(1.1); 6.174(1.0); 6.154(1.2); 6.147(1.2); 6.138(1.2); 6.131(1.3); 6.111(1.2); 6.104(1.2); 5.562(1.8); 5.561(1.7); 5.552(1.7); 5.550(1.8); 5.519(1.5); 5.517(1.6); 5.508(1.5); 5.507(1.6); 5.372(1.5); 5.360(1.6); 5.344(1.4); 5.333(1.5); 5.300(2.3); 4.729(0.6); 4.720(0.7); 4.212(1.1); 4.190(1.8); 4.167(5.4); 4.026(0.8); 4.019(0.8); 4.011(0.8); 4.002(1.1); 3.995(1.0); 3.987(1.1); 3.980(0.8); 3.943(0.9); 3.936(1.9); 3.925(2.0); 3.921(1.8); 3.905(1.6); 3.897(0.8); 3.893(2.4); 3.882(2.8); 3.739(16.0); 3.717(0.7); 3.711(1.3); 3.698(15.8); 3.687(0.7); 3.678(0.6); 3.580(1.9); 3.336(2.1); 3.294(1.8); 3.146(2.6); 3.128(2.6); 3.110(2.6); 3.091(0.8); 1.628(2.0); 1.382(2.6); 1.363(5.4); 1.345(2.5); 1.284(0.6); 1.254(0.9); 0.008(4.1); 0.000(145.8); −0.006(1.2); −0.008(4.2); −0.050(1.2) |
| I-27 | $^1$H-NMR(400.0 MHz, CDCl3): δ = 7.262(46.2); 7.212(0.8); 7.210(1.0); 7.204(1.3); 7.200(1.1); 7.194(0.9); 7.190(1.3); 7.184(1.1); 7.180(0.6); 6.909(0.9); 6.903(0.8); 5.300(3.9); 4.258(0.6); 4.236(1.0); 4.214(0.8); 4.035(0.6); |

Analytical data of Examples I-01-I-56.

| No. | NMR |
|---|---|
| | 4.026(0.8); 4.011(0.8); 3.936(0.5); 3.920(1.0); 3.901(1.2); 3.874(1.1); 3.856(1.4); 3.796(0.9); 3.788(0.6); 3.775(0.6); 3.765(0.6); 3.758(7.8); 3.744(8.3); 3.736(3.6); 3.719(3.6); 3.362(7.7); 3.356(6.1); 3.354(8.9); 3.345(1.2); 3.343(0.7); 3.337(1.2); 3.321(0.5); 3.300(1.0); 3.292(1.0); 1.558(16.0); 0.008(0.5); 0.000(18.3) |
| I-28 | $^1$H-NMR(400.0 MHz, CDCl3): δ = 7.262(57.6); 7.179(0.6); 7.174(1.0); 7.169(1.5); 7.165(1.8); 7.160(1.6); 7.154(1.3); 7.149(1.6); 7.146(1.2); 7.144(0.9); 7.140(0.8); 6.916(0.6); 6.910(0.5); 6.901(0.7); 6.895(1.2); 6.889(1.0); 6.879(0.8); 6.873(0.8); 6.867(0.5); 5.300(8.2); 4.704(0.5); 4.695(0.5); 4.202(1.1); 4.181(1.2); 4.158(0.5); 4.038(0.6); 4.023(0.6); 4.021(0.6); 4.014(1.1); 3.999(1.2); 3.990(0.7); 3.976(0.9); 3.949(0.6); 3.934(0.7); 3.926(0.6); 3.922(0.7); 3.910(0.6); 3.906(0.7); 3.899(0.5); 3.883(0.5); 3.790(1.4); 3.778(1.3); 3.773(0.8); 3.755(0.7); 3.746(12.8); 3.737(6.4); 3.730(1.3); 3.723(0.5); 3.703(0.8); 3.695(0.8); 3.691(11.2); 3.678(0.5); 3.662(0.5); 3.542(5.0); 3.211(1.9); 3.188(0.9); 3.167(1.6); 3.144(0.8); 1.722(7.6); 1.715(10.9); 1.688(4.0); 1.563(16.0); 0.008(0.7); 0.000(23.2); −0.008(0.6) |
| I-29 | $^1$H-NMR(400.0 MHz, CDCl3): δ = 7.558(1.3); 7.553(7.2); 7.549(10.9); 7.544(5.8); 7.445(1.8); 7.444(1.8); 7.440(3.4); 7.439(3.2); 7.436(2.2); 7.263(38.3); 7.005(0.6); 6.999(0.6); 6.990(0.6); 5.300(15.8); 4.798(0.6); 4.789(0.7); 4.783(0.8); 4.778(0.7); 4.774(0.7); 4.770(0.5); 4.764(0.7); 4.257(1.3); 4.235(2.0); 4.214(1.5); 4.050(0.8); 4.047(0.9); 4.035(0.9); 4.033(0.9); 4.025(1.2); 4.023(1.2); 4.011(1.2); 3.961(0.9); 3.951(1.0); 3.945(1.0); 3.938(0.9); 3.936(1.1); 3.927(1.0); 3.924(2.0); 3.912(0.9); 3.906(1.9); 3.879(2.1); 3.860(2.2); 3.806(0.8); 3.798(1.1); 3.787(1.0); 3.783(0.7); 3.774(0.9); 3.763(0.9); 3.757(15.3); 3.744(16.0); 3.736(3.1); 3.722(3.0); 3.354(14.7); 3.350(4.7); 3.347(16.0); 3.340(2.4); 3.337(0.8); 3.332(2.2); 3.294(1.9); 3.287(1.9); 3.077(0.6); 3.066(0.8); 3.061(0.6); 3.056(0.6); 3.050(0.8); 2.045(0.8); 1.575(11.7); 1.259(0.6); 0.000(15.0) |
| I-30 | $^1$H-NMR(400.0 MHz, CDCl3): δ = 7.394(0.9); 7.390(1.4); 7.388(1.2); 7.374(3.6); 7.371(2.6); 7.368(2.0); 7 366(2.7); 7.261(68.0); 7.144(0.7); 7.128(0.7); 7.121(0.7); 4.548(0.7); 4.538(0.7); 4.522(0.8); 4.512(0.8); 4.498(0.7); 4.489(0.7); 4.296(1.3); 4.293(1.3); 4.278(1.4); 4.275(1.3); 4.248(0.9); 4.230(2.8); 4.213(2.9); 4.195(1.0); 4.079(0.6); 4.065(0.6); 4.055(1.0); 4.042(0.9); 4.034(0.6); 4.021(0.6); 4.010(0.8); 3.997(0.8); 3.968(0.6); 3.963(0.6); 3.802(1.6); 3.789(1.4); 3.759(1.0); 3.746(1.6); 3.221(1.5); 3.213(1.7); 3.178(1.3); 3.170(1.5); 2.561(0.5); 2.526(0.5); 1.708(9.2); 1.684(8.0); 1.554(16.0); 1.360(2.8); 1.342(5.8); 1.325(2.7); 1.296(3.2); 1.278(6.7); 1.260(3.3); 0.008(0.7); 0.000(24.6); −0.008(0.7) |
| I-31 | $^1$H-NMR(400.0 MHz, CDCl3): δ = 7.520(1.5); 7.343(1.5); 7.322(1.6); 7.305(1.7); 7.284(1.9); 7.261(268.6); 7.179(1.2); 7.177(1.2); 7.166(5.7); 7.164(8.0); 7.161(9.1); 7.158(8.3); 7.147(8.5); 7.144(8.8); 7.141(7.4); 7.139(5.1); 7.129(1.0); 6.997(1.5); 6.906(1.3); 6.900(2.2); 6.896(1.6); 6.890(2.3); 6.884(3.3); 6.878(4.5); 6.874(3.2); 6.869(4.3); 6.863(3.1); 6.857(2.3); 6.853(1.6); 6.847(2.1); 6.841(0.9); 6.168(4.3); 6.156(4.4); 6.141(4.9); 6.130(5.1); 6.124(5.4); 6.113(5.2); 6.098(5.5); 6.086(5.4); 5.544(7.8); 5.543(6.8); 5.532(7.5); 5.531(6.8); 5.501(6.8); 5.500(6.0); 5.489(6.7); 5.355(7.2); 5.346(7.0); 5.328(6.8); 5.319(6.4); 5.299(16.0); 4.609(3.9); 4.598(7.8); 4.588(5.5); 4.585(6.1); 4.575(8.8); 4.565(5.7); 4.553(2.3); 4.546(2.1); 4.540(1.5); 4.527(1.2); 4.380(0.5); 4.150(1.0); 4.132(2.6); 4.115(2.7); 4.103(3.0); 4.097(1.2); 4.090(3.0); 4.079(7.4); 4.066(7.2); 4.056(4.9); 4.042(4.5); 4.012(3.1); 4.007(3.1); 3.988(2.1); 3.983(4.6); 3.976(3.1); 3.958(1.9); 3.952(1.8); 3.926(7.3); 3.915(7.6); 3.884(8.4); 3.872(8.6); 3.698(0.6); 3.332(7.6); 3.325(7.6); 3.289(6.6); 3.282(6.7); 2.681(1.5); 2.664(1.6); 2.657(1.6); 2.646(2.1); 2.640(3.3); 2.629(2.0); 2.623(3.4); 2.616(1.7); 2.605(3.7); 2.599(1.8); 2.588(1.8); 2.582(1.8); 2.564(1.6); 2.226(1.3); 2.219(2.1); 2.210(1.3); 2.192(1.2); 2.184(3.0); 2.176(3.1); 2.167(1.4); 2.150(1.1); 2.141(1.8); 2.133(1.1); 2.116(4.1); 2.046(10.8); 1.432(3.6); 1.304(1.2); 1.277(5.0); 1.265(5.9); 1.259(10.0); 1.242(3.6); 0.899(3.2); 0.882(11.0); 0.864(4.2); 0.008(2.5); 0.000(95.7); −0.008(2.8) |
| I-32 | $^1$H-NMR(400.0 MHz, CDCl3): δ = 7.487(0.6); 7.466(0.7); 7.434(0.6); 7.399(1.6); 7.395(1.9); 7.392(1.6); 7.388(1.8); 7.383(1.7); 7.380(1.8); 7.375(5.0); 7.372(5.4); 7.370(5.0); 7.366(5.9); 7.360(2.1); 7.357(2.4); 7.261(58.8); 7.149(0.5); 7.146(0.6); 7.139(1.0); 7.134(0.9); 7.126(1.2); 7.122(1.1); 7.119(1.2); 7.113(1.0); 7.107(0.9); 7.102(0.5); 5.144(1.2); 5.128(1.6); 5.112(1.2); 5.091(0.7); 5.075(1.3); 5.060(1.7); 5.044(1.3); 5.028(0.5); 4.602(0.6); 4.595(0.9); 4.588(1.1); 4.582(1.0); 4.577(1.1); 4.570(1.1); 4.563(0.9); 4.557(0.7); 4.550(0.5); 4.503(1.1); 4.493(1.2); 4.478(1.8); 4.468(1.9); 4.454(1.3); 4.444(1.3); 4.082(1.1); 4.068(1.1); 4.059(1.8); 4.045(1.6); 4.032(1.1); 4.018(1.1); 4.008(1.5); 3.995(1.4); 3.967(1.1); 3.961(1.1); 3.944(0.8); 3.937(0.7); 3.889(1.0); 3.882(1.1); 3.865(0.7); 3.859(0.7); 3.803(2.8); 3.791(2.5); 3.760(3.2); 3.748(2.9); 3.221(2.8); 3.212(3.1); 3.178(2.4); 3.169(2.7); 2.599(0.6); 2.581(0.6); 2.576(0.6); 2.565(0.7); 2.558(0.7); 2.555(0.7); 2.547(0.7); 2.541(0.7); 2.536(0.7); 2.531(0.7); 2.523(0.7); 2.520(0.8); 2.513(0.7); 2.502(0.7); 2.497(0.7); 2.478(0.6); 2.056(0.7); 2.022(0.6); 1.958(0.8); 1.923(0.7); 1.708(16.0); 1.685(14.4); 1.569(9.5); 1.327(7.3); 1.314(8.2); 1.311(8.4); 1.299(7.5); 1.290(8.2); 1.274(8.0); 1.262(0.6); 1.255(0.6); 1.247(0.5); 1.212(8.0); 1.196(7.9); 0.008(0.6); 0.000(19.7); −0.008(0.8) |
| I-33 | $^1$H-NMR(400.0 MHz, CDCl3): δ = 7.519(0.7); 7.387(0.5); 7.373(0.8); 7.364(1.0); 7.352(0.6); 7.260(128.7); 6.996(0.7); 3.797(0.5); 3.754(0.6); 3.743(0.5); 3.220(0.5); 3.211(0.6); 3.177(0.5); 3.168(0.5); 1.918(0.6); 1.704(3.4); 1.682(3.1); 1.540(16.0); 1.520(9.8); 1.465(10.8); 1.369(0.6); 1.335(0.6); 1.255(0.9); 1.134(0.5); 1.106(0.5); 0.008(1.6); 0.000(47.3); −0.008(1.9) |
| I-34 | $^1$H-NMR(400.0 MHz, CDCl3): δ = 7.483(0.6); 7.464(0.6); 7.448(0.6); 7.427(0.5); 7.402(1.0); 7.387(4.8); 7.384(4.6); 7.376(4.5); 7.369(7.4); 7.365(7.2); 7.352(3.1); 7.347(1.8); 7.340(1.0); 7.331(1.5); 7.328(1.1); 7.318(15.6); 7.260(69.1); 7.151(0.5); 7.142(0.8); 7.135(0.8); 7.128(1.1); 7.123(1.0); 7.120(1.4); 7.114(1.1); 7.108(0.8); 7.103(0.5); 7.097(0.7); 5.304(1.3); 5.274(3.0); 5.228(3.0); 5.197(1.4); 5.182(5.2); |

| No. | NMR |
|---|---|
| | 5.179(5.6); 4.591(0.6); 4.586(1.6); 4.576(1.8); 4.566(2.2); 4.563(2.0); 4.556(2.1); 4.553(1.8); 4.542(1.6); 4.533(1.3); 4.091(1.1); 4.077(1.1); 4.068(1.7); 4.054(1.6); 4.040(1.0); 4.026(1.0); 4.016(1.4); 4.002(1.3); 3.968(1.1); 3.961(1.1); 3.944(0.7); 3.938(0.7); 3.897(0.9); 3.890(0.9); 3.874(0.6); 3.866(0.6); 3.803(2.8); 3.785(2.4); 3.760(3.2); 3.742(2.7); 3.213(2.8); 3.210(3.3); 3.170(2.4); 3.167(2.8); 2.602(0.5); 2.584(0.6); 2.579(0.5); 2.568(0.6); 2.561(0.7); 2.556(0.6); 2.550(0.6); 2.544(0.7); 2.538(0.7); 2.533(0.7); 2.527(0.6); 2.522(0.8); 2.515(0.7); 2.503(0.7); 2.498(0.7); 2.480(0.6); 2.079(0.7); 2.045(0.6); 2.019(0.8); 1.984(0.7); 1.701(16.0); 1.647(13.2); 1.560(16.4); 0.008(0.8); 0.000(23.7); −0.008(0.7) |
| I-35 | $^1$H-NMR(400.0 MHz, CDCl3): δ = 7.519(1.7); 7.477(1.5); 7.452(2.5); 7.430(1.8); 7.260(283.4); 7.228(5.0); 7.210(0.7); 7.173(8.0); 7.158(8.0); 6.996(1.6); 6.901(2.3); 6.880(4.7); 6.858(2.4); 6.175(3.6); 6.148(4.0); 6.132(4.4); 6.105(4.5); 5.558(4.5); 5.540(5.0); 5.515(3.9); 5.497(4.4); 5.354(4.2); 5.335(4.9); 5.328(4.3); 5.309(4.5); 4.595(2.6); 4.546(2.4); 4.537(2.8); 4.530(2.5); 4.522(4.5); 4.513(2.8); 4.507(2.6); 4.498(2.3); 4.292(2.1); 4.274(7.8); 4.256(11.6); 4.238(7.8); 4.221(2.2); 4.061(1.8); 4.048(2.0); 4.038(3.5); 4.024(3.5); 4.017(3.5); 4.004(3.1); 3.947(2.4); 3.922(8.1); 3.900(6.2); 3.879(4.8); 3.857(5.2); 3.320(5.1); 3.310(4.6); 3.277(4.4); 3.267(4.1); 2.588(1.1); 2.570(1.4); 2.564(1.6); 2.554(1.7); 2.547(1.7); 2.536(2.5); 2.530(2.1); 2.520(1.4); 2.512(1.7); 2.484(1.2); 2.072(2.0); 2.031(2.4); 1.990(1.5); 1.537(40.6); 1.350(8.0); 1.332(16.0); 1.318(9.5); 1.314(9.5); 1.300(14.6); 1.282(7.4); 1.258(1.3); 0.146(0.5); 0.000(103.5) |
| I-36 | $^1$H-NMR(400.0 MHz, CDCl3): δ = 7.518(1.5); 7.460(2.0); 7.435(1.3); 7.260(234.7); 7.226(0.6); 7.211(1.0); 7.174(5.8); 7.160(5.8); 6.996(1.3); 6.900(1.5); 6.878(3.1); 6.856(1.6); 6.176(2.8); 6.150(3.1); 6.133(3.2); 6.106(3.4); 5.560(3.3); 5.544(3.5); 5.518(2.9); 5.501(3.0); 5.354(3.2); 5.329(5.3); 5.303(3.1); 5.142(0.6); 5.126(1.5); 5.110(2.1); 5.102(1.7); 5.095(1.8); 5.086(2.0); 5.071(1.6); 5.055(0.6); 4.602(2.0); 4.502(1.6); 4.493(2.0); 4.487(1.9); 4.478(3.1); 4.470(2.0); 4.464(1.9); 4.455(1.6); 4.064(1.3); 4.050(1.4); 4.040(3.4); 4.027(3.4); 4.016(2.2); 4.003(2.0); 3.946(1.4); 3.923(5.9); 3.901(4.2); 3.880(3.4); 3.858(3.5); 3.320(3.4); 3.310(3.4); 3.277(3.0); 3.267(3.0); 2.583(0.8); 2.549(1.2); 2.531(1.8); 2.501(1.2); 2.478(0.8); 2.026(1.4); 1.985(2.1); 1.949(1.2); 1.536(39.5); 1.318(10.2); 1.304(16.0); 1.298(13.5); 1.290(11.4); 1.282(11.1); 1.256(1.2); 1.240(9.5); 1.224(9.5); 0.000(88.1) |
| I-37 | $^1$H-NMR(400.0 MHz, CDCl3): δ = 7.469(0.8); 7.448(1.4); 7.428(0.8); 7.385(3.1); 7.383(3.4); 7.379(3.7); 7.372(9.3); 7.359(2.1); 7.350(2.5); 7.338(3.4); 7.332(18.3); 7.308(0.6); 7.260(75.8); 7.192(0.6); 7.186(0.7); 7.180(2.2); 7.174(4.2); 7.169(3.1); 7.164(2.5); 7.159(3.2); 7.154(4.1); 7.148(2.1); 7.142(0.7); 6.902(0.9); 6.897(0.9); 6.891(0.9); 6.886(1.3); 6.880(1.8); 6.875(1.7); 6.869(1.7); 6.864(1.2); 6.859(0.9); 6.853(0.9); 6.848(0.8); 6.168(1.6); 6.152(1.6); 6.141(1.7); 6.125(3.4); 6.109(1.9); 6.098(1.9); 6.082(1.9); 5.552(3.0); 5.537(2.9); 5.509(2.6); 5.494(2.5); 5.348(2.8); 5.321(3.0); 5.318(3.1); 5.291(2.6); 5.274(1.4); 5.252(1.5); 5.244(4.8); 5.220(7.7); 5.198(4.8); 5.189(1.5); 5.167(1.4); 4.618(0.8); 4.611(1.0); 4.604(1.0); 4.598(3.4); 4.592(1.3); 4.585(2.3); 4.576(3.4); 4.567(2.0); 4.562(1.8); 4.553(3.0); 4.544(1.4); 4.074(1.3); 4.060(1.2); 4.050(2.8); 4.036(2.5); 4.025(1.9); 4.012(1.8); 3.954(1.3); 3.947(1.3); 3.930(2.2); 3.921(4.2); 3.906(1.0); 3.898(3.7); 3.878(3.4); 3.855(3.3); 3.318(3.1); 3.306(3.1); 3.275(2.7); 3.263(2.7); 2.590(0.6); 2.573(0.7); 2.567(0.7); 2.560(0.8); 2.556(0.9); 2.549(0.8); 2.542(0.9); 2.538(1.3); 2.532(0.9); 2.526(0.9); 2.519(0.8); 2.515(0.8); 2.508(0.8); 2.502(0.8); 2.484(0.7); 2.072(0.6); 2.065(1.0); 2.058(0.6); 2.051(0.7); 2.043(1.1); 2.037(1.0); 2.022(0.6); 2.017(0.6); 2.009(0.9); 2.002(0.5); 1.554(16.0); 0.008(1.0); 0.000(27.3); −0.008(1.0) |
| I-38 | $^1$H-NMR(400.0 MHz, CDCl3): δ = 7.518(16.0); 7.454(1.7); 7.321(2.2); 7.297(3.1); 7.260(2792.7); 7.230(2.9); 7.210(9.5); 7.201(2.0); 7.177(3.3); 7.172(3.7); 7.166(4.1); 7.160(5.6); 7.146(5.5); 6.996(15.6); 6.898(1.8); 6.876(2.8); 6.175(3.9); 6.148(3.6); 6.132(4.2); 6.105(3.9); 5.559(4.5); 5.540(4.0); 5.516(4.3); 5.497(3.5); 5.349(4.3); 5.321(6.3); 5.293(3.2); 4.610(1.9); 4.432(1.7); 4.423(2.4); 4.418(2.3); 4.409(3.9); 4.399(2.0); 4.394(2.5); 4.385(2.2); 4.065(2.1); 4.052(2.5); 4.042(3.3); 4.028(3.7); 4.011(3.4); 3.944(2.3); 3.915(6.8); 3.894(5.0); 3.872(6.0); 3.852(4.5); 3.493(1.9); 3.319(4.5); 3.308(5.1); 3.276(3.8); 3.265(4.4); 2.535(1.8); 2.517(1.8); 2.501(2.1); 2.481(1.6); 1.949(5 4); 1.915(4.5); 1.713(4.1); 1.679(5.0); 1.617(2.8); 1.593(2.8); 1.574(3.2); 1.537(678.7); 1.505(87.4); 1.479(101.8); 1.398(4.2); 1.369(5.2); 1.335(5.1); 1.306(3.1); 1.254(13.8); 1.193(2.0); 1.166(3.2); 1.135(4.2); 1.105(4.8); 1.079(4.0); 0.880(1.7); 0.146(3.5); 0.008(31.6); 0.000(1031.9); −0.008(30.7); −0.050(3.7); −0.150(3.8) |
| I-39 | $^1$H-NMR(400.0 MHz, CDCl3): δ = 7.5181(3.2); 7.3998(1.1); 7.3867(2.5); 7.3811(3.4); 7.3771(3.1); 7.3707(3.0); 7.3616(1.5); 7.3073(0.9); 7.2880(0.9); 7.2592(562.4); 7.2336(0.7); 7.2088(1.0); 7.2001(0.6); 7.1603(1.1); 7.1383(0.9); 7.1308(0.7); 7.1227(0.8); 6.9953(3.6); 5.9486(1.8); 5.9409(1.8); 5.8861(1.1); 5.8789(1.1); 5.2426(0.8); 5.2314(0.6); 5.2211(0.6); 5.2124(0.5); 4.6185(0.6); 4.6035(0.8); 4.5964(0.6); 4.5766(1.0); 4.5539(0.8); 4.5293(0.6); 4.3195(0.6); 4.3024(0.6); 4.2342(1.1); 4.2240(1.1); 4.2074(1.0); 4.1973(0.9); 3.8522(13.3); 3.8423(8.0); 3.8080(1.2); 3.7891(1.8); 3.7649(1.3); 3.7458(2.1); 3.6913(0.6); 3.2485(2.1); 3.2434(1.4); 3.2052(1.8); 3.2001(1.1); 2.4632(1.1); 2.3297(1.0); 1.7155(16.0); 1.7038(0.8); 1.5291(89.5); 1.3237(0.8); 1.3064(0.7); 1.2559(0.7); 0.1460(0.9); 0.0079(6.9); −0.0002(200.7); −0.0084(6.5); −0.1498(0.9) |
| I-40 | $^1$H-NMR(599.8 MHz, CDCl3): δ = 7.4820(2.4); 7.4684(2.5); 7.4487(2.4); 7.4353(2.4); 7.4046(1.0); 7.3998(1.3); 7.3962(1.2); 7.3915(4.1); 7.3866(6.8); 7.3826(9.1); 7.3816(9.1); 7.3780(12.0); 7.3758(12.0); 7.3717(12.8); 7.3672(14.8); 7.3579(2.5); 7.3553(2.1); 7.2849(5.3); 7.1506(1.4); 7.1462(2.9); 7.1436(2.9); 7.1419(2.6); 7.1381(2.7); 7.1367(2.7); 7.1321(5.0); 7.1279(4.7); 7.1212(3.0); 7.1167(2.7); 7.1124(1.3); 7.1078(0.3); 4.6805(0.5); |

| No. | NMR |
|---|---|
| | 4.6718(1.5); 4.6672(2.4); 4.6634(3.0); 4.6594(3.4); 4.6550(3.8); 4.6512(3.5); 4.6473(2.9); 4.6429(2.4); 4.6393(1.7); 4.6298(0.6); 4.1557(3.8); 4.1474(3.9); 4.1401(4.8); 4.1318(4.5); 4.1271(3.8); 4.1185(3.8); 4.1113(4.4); 4.1027(4.1); 4.0077(0.3); 3.9767(3.9); 3.9624(3.1); 3.9614(3.1); 3.9010(3.4); 3.8990(3.6); 3.8867(50.0); 3.8552(49.2); 3.8453(0.8); 3.8328(2.0); 3.8078(0.4); 3.7963(7.8); 3.7759(7.7); 3.7675(8.7); 3.7607(0.6); 3.7471(8.3); 3.7291(0.3); 3.3491(48.2); 3.3405(48.2); 3.2449(0.4); 3.2368(8.2); 3.2253(8.6); 3.2186(0.7); 3.2163(0.6); 3.2080(7.5); 3.2021(0.6); 3.1965(7.7); 2.5589(3.2); 2.5468(3.4); 2.5351(3.9); 2.5231(3.7); 2.5024(3.4); 2.4902(3.5); 2.4785(4.0); 2.4664(3.8); 2.2319(2.9); 2.2308(3.0); 2.2264(3.0); 2.2082(2.6); 2.2071(2.6); 2.2027(2.6); 2.1546(2.9); 2.1533(3.0); 2.1493(3.1); 2.1481(2.9); 2.1307(2.6); 2.1294(2.7); 2.1255(2.8); 1.8553(1.3); 1.7169(40.5); 1.6954(39.1); 1.3373(0.8); 1.2871(1.3); 1.2573(3.3); 0.8920(0.4); 0.8808(0.9); 0.8689(0.5); 0.8424(0.3); −0.0001(4.5) |
| I-41 | $^1$H-NMR(400.0 MHz, CDCl3): δ = 7.5185(0.9); 7.3305(0.6); 7.3101(0.9); 7.2935(0.8); 7.2901(0.8); 7.2596(159.2); 7.1701(0.7); 7.1642(0.6); 7.1577(3.3); 7.1520(4.0); 7.1488(2.3); 7.1411(2.2); 7.1378(4.0); 7.1322(3.3); 7.1197(0.5); 6.9956(0.9); 6.8966(0.8); 6.8885(0.8); 6.8808(1.0); 6.8749(1.6); 6.8668(1.7); 6.8609(0.9); 6.8532(0.8); 6.8451(0.8); 5.2983(0.6); 4.6116(1.2); 4.6013(1.4); 4.5885(2.0); 4.5793(1.9); 4.5660(1.5); 4.5561(1.7); 4.5443(0.8); 4.5381(0.9); 4.5332(0.9); 4.5265(0.9); 4.5204(0.9); 4.5131(0.8); 4.5085(0.5); 4.1133(1.1); 4.1002(1.1); 4.0894(2.0); 4.0763(1.9); 4.0733(1.4); 4.0599(1.2); 4.0492(1.8); 4.0357(2.0); 4.0261(1.2); 4.0094(0.7); 4.0022(0.7); 3.9682(1.1); 3.9624(1.1); 3.9441(0.7); 3.9372(0.7); 3.7796(2.9); 3.7729(2.9); 3.7363(3.3); 3.7296(3.3); 3.1984(3.0); 3.1935(3.0); 3.1551(2.6); 3.1502(2.7); 2.6774(0.6); 2.6601(0.7); 2.6537(0.6); 2.6427(0.8); 2.6365(0.7); 2.6257(0.8); 2.6191(0.8); 2.6112(0.6); 2.6048(0.7); 2.6020(0.8); 2.5939(0.8); 2.5875(0.7); 2.5766(0.7); 2.5703(0.7); 2.5529(0.6); 2.2721(1.0); 2.2378(0.7); 2.1741(0.8); 2.1396(0.7); 2.1109(7.6); 1.7027(15.9); 1.6873(16.0); 1.4319(4.0); 1.2567(0.7); 0.8820(0.9); 0.0080(1.5); −0.0002(46.7); −0.0085(1.4) |
| I-42 | $^1$H-NMR(400.0 MHz, CDCl3): δ = 7.5186(1.0); 7.5024(0.6); 7.4829(0.6); 7.4416(0.8); 7.4215(0.8); 7.2598(167.2); 7.2093(0.6); 7.1693(2.1); 7.1639(2.6); 7.1496(3.8); 7.1370(2.2); 7.1315(1.8); 6.9958(0.9); 6.8933(1.0); 6.8888(1.0); 6.8772(1.0); 6.8718(2.0); 6.8669(2.0); 6.8554(0.6); 6.8500(1.0); 6.8454(0.9); 4.5805(1.1); 4.4363(1.2); 4.4274(1.4); 4.4131(2.3); 4.4042(2.4); 4.3899(1.1); 4.3808(1.1); 4.0768(0.9); 4.0631(0.9); 4.0533(1.5); 4.0394(1.7); 4.0231(1.2); 4.0132(1.7); 3.9994(1.6); 3.9694(1.1); 3.9633(1.2); 3.9467(0.8); 3.9395(0.7); 3.8931(1.3); 3.8869(1.4); 3.8694(0.9); 3.8631(1.1); 3.7676(2.2); 3.7564(2.7); 3.7244(2.6); 3.7133(3.1); 3.1860(2.9); 3.1770(2.6); 3.1428(2.6); 3.1338(2.3); 2.5651(0.6); 2.5472(0.7); 2.5417(0.7); 2.5311(1.0); 2.5239(0.8); 2.5127(1.1); 2.4992(0.7); 2.4910(1.0); 2.4807(0.7); 2.4756(0.7); 2.4573(0.6); 2.2528(0.6); 2.0199(1.0); 1.9855(0.9); 1.9132(0.8); 1.8784(0.7); 1.7070(13.3); 1.6833(16.0); 1.5392(24.4); 1.5194(53.5); 1.4680(43.6); 1.4445(0.7); 1.4275(0.7); 1.2552(0.7); 1.2049(0.7); 1.1885(0.8); 1.1827(2.5); 1.1713(2.3); 1.1525(1.0); 1.1368(1.0); 0.0079(2.2); −0.0002(58.9) |
| I-43 | $^1$H-NMR(400.6 MHz, CDCl3): δ = 7.5219(0.6); 7.5011(0.7); 7.4886(0.7); 7.4681(0.6); 7.2990(1.4); 7.1903(0.5); 7.1780(2.9); 7.1724(3.6); 7.1691(2.1); 7.1616(2.1); 7.1580(3.6); 7.1525(2.9); 7.1460(0.5); 7.1402(0.5); 6.9069(0.7); 6.9011(1.3); 6.8953(0.7); 6.8852(1.5); 6.8794(2.6); 6.8736(1.3); 6.8634(0.8); 6.8577(1.3); 6.8519(0.6); 4.6076(0.6); 4.6031(0.7); 4.6008(0.6); 4.5967(0.8); 4.5933(0.7); 4.5899(1.0); 4.5867(0.9); 4.5832(1.0); 4.5761(0.8); 4.5727(0.7); 4.5697(0.7); 4.5660(0.6); 4.5590(0.6); 4.5559(1.3); 4.5466(1.4); 4.5320(2.2); 4.5226(2.2); 4.5082(1.3); 4.4989(1.2); 4.3114(0.9); 4.3099(1.0); 4.2936(2.9); 4.2921(3.0); 4.2757(3.0); 4.2745(3.0); 4.2577(1.1); 4.2567(1.1); 4.2531(1.2); 4.2353(3.7); 4.2176(3.9); 4.1998(1.4); 4.0770(1.1); 4.0638(1.1); 4.0535(1.8); 4.0403(1.7); 4.0340(1.2); 4.0207(1.2); 4.0104(1.7); 3.9971(1.6); 3.9801(1.1); 3.9749(1.0); 3.9734(1.0); 3.9566(0.7); 3.9514(0.6); 3.9499(0.6); 3.9089(0.9); 3.9075(1.0); 3.9024(1.0); 3.9009(0.9); 3.8854(0.6); 3.8838(0.7); 3.8788(0.7); 3.8774(0.6); 3.8340(1.0); 3.7866(2.9); 3.7836(1.3); 3.7732(2.6); 3.7435(3.3); 3.7300(3.0); 3.2065(2.8); 3.1990(3.0); 3.1634(2.5); 3.1559(2.6); 2.6102(0.6); 2.5926(0.6); 2.5868(0.6); 2.5758(0.8); 2.5691(0.8); 2.5665(0.7); 2.5582(0.7); 2.5524(0.8); 2.5484(0.7); 2.5430(0.7); 2.5348(0.8); 2.5320(0.9); 2.5251(0.7); 2.5139(0.7); 2.5086(0.7); 2.4906(0.6); 2.1117(0.8); 2.1095(0.5); 2.0773(0.6); 2.0132(0.8); 2.0063(0.5); 1.9969(0.6); 1.9787(0.7); 1.7143(16.0); 1.6904(14.9); 1.3614(5.6); 1.3436(11.6); 1.3257(5.4); 1.3047(5.8); 1.2869(12.0); 1.2691(5.7); 1.2597(0.8); −0.0002(1.0) |
| I-44 | $^1$H-NMR(400.6 MHz, CDCl3): δ = 7.5274(0.7); 7.5067(0.8); 7.4922(0.8); 7.4716(0.7); 7.3034(1.2); 7.1783(2.8); 7.1745(3.5); 7.1728(3.3); 7.1603(3.1); 7.1586(3.6); 7.1548(2.9); 7.1532(2.4); 6.9036(0.6); 6.8991(1.0); 6.8979(1.0); 6.8935(0.6); 6.8922(0.6); 6.8832(1.1); 6.8819(1.3); 6.8774(2.0); 6.8762(2.1); 6.8718(1.1); 6.8704(1.1); 6.8614(0.6); 6.8601(0.7); 6.8558(1.0); 6.8544(1.1); 6.8501(0.5); 6.8488(0.5); 5.1433(1.3); 5.1277(1.8); 5.1120(1.3); 5.0961(0.7); 5.0947(0.7); 5.0788(1.4); 5.0631(1.8); 5.0475(1.4); 5.0318(0.5); 4.6095(0.7); 4.6023(0.9); 4.5987(0.9); 4.5952(1.0); 4.5918(1.1); 4.5889(1.0); 4.5846(1.0); 4.5820(0.9); 4.5779(0.8); 4.5748(0.7); 4.5712(0.6); 4.5124(1.2); 4.5030(1.4); 4.4888(2.5); 4.4793(2.6); 4.4651(1.4); 4.4558(1.3); 4.0796(1.1); 4.0663(1.1); 4.0561(1.9); 4.0428(1.7); 4.0321(1.2); 4.0187(1.1); 4.0085(1.7); 3.9951(1.6); 3.9824(1.2); 3.9765(1.2); 3.9589(0.8); 3.9533(0.7); 3.9036(1.1); 3.8980(1.0); 3.8800(0.7); 3.8745(0.7); 3.7882(2.9); 3.7840(0.5); 3.7769(2.7); 3.7451(3.3); 3.7337(3.1); 3.2084(2.9); 3.2001(3.1); |

| No. | NMR |
|---|---|
| | 3.1652(2.6); 3.1569(2.7); 2.6063(0.6); 2.5885(0.6); 2.5830(0.6); 2.5720(0.8); 2.5651(0.7); 2.5610(0.7); 2.5542(0.7); 2.5486(0.8); 2.5428(0.7); 2.5376(0.7); 2.5308(0.7); 2.5265(0.9); 2.5195(0.7); 2.5083(0.7); 2.5032(0.7); 2.4850(0.6); 2.0692(0.8); 2.0622(0.5); 2.0443(0.9); 2.0348(0.8); 1.9781(0.5); 1.9712(0.8); 1.9641(0.5); 1.9626(0.5); 1.9367(0.7); 1.7159(16.0); 1.6923(15.1); 1.3290(8.0); 1.3156(9.6); 1.3136(9.8); 1.3002(8.8); 1.2970(9.4); 1.2812(8.3); 1.2594(0.6); 1.2582(0.6); 1.2217(8.2); 1.2060(8.2); −0.0002(0.9) |
| I-45 | $^1$H-NMR(400.0 MHz, CDCl3): δ = 7.5182(1.0); 7.4766(0.5); 7.4574(0.6); 7.4411(0.6); 7.4206(0.6); 7.4015(0.8); 7.3897(2.3); 7.3853(4.0); 7.3813(3.4); 7.3750(1.3); 7.3723(3.1); 7.3701(3.5); 7.3646(1.0); 7.3572(1.2); 7.3547(1.7); 7.3514(1.6); 7.3487(1.4); 7.3436(1.0); 7.3313(2.3); 7.3254(13.2); 7.3128(0.7); 7.3062(0.5); 7.2935(0.6); 7.2593(174.4); 7.1696(1.9); 7.1661(2.9); 7.1637(2.9); 7.1604(3.1); 7.1528(1.5); 7.1497(3.0); 7.1463(2.9); 7.1441(2.9); 7.1405(1.8); 6.9953(1.0); 6.8960(0.8); 6.8899(0.8); 6.8839(0.8); 6.8801(1.0); 6.8743(1.6); 6.8682(1.5); 6.8622(1.5); 6.8564(0.9); 6.8526(0.8); 6.8464(0.7); 6.8405(0.8); 5.3028(1.6); 5.2723(3.6); 5.2284(4.1); 5.1973(5.2); 5.1839(4.2); 5.1533(0.8); 4.5944(0.6); 4.5894(1.9); 4.5800(2.0); 4.5765(1.3); 4.5717(2.0); 4.5659(2.1); 4.5626(2.2); 4.5565(2.0); 4.5486(1.6); 4.5391(1.5); 4.0842(1.1); 4.0709(1.1); 4.0607(1.8); 4.0473(1.6); 4.0356(1.2); 4.0222(1.2); 4.0119(1.7); 3.9985(1.5); 3.9693(1.0); 3.9637(1.0); 3.9458(0.7); 3.9399(0.7); 3.9022(1.0); 3.8967(1.0); 3.8785(0.7); 3.8731(0.7); 3.7711(2.8); 3.7541(2.8); 3.7280(3.2); 3.7110(3.2); 3.1777(3.1); 3.1733(3.1); 3.1346(2.7); 3.1302(2.7); 2.5979(0.6); 2.5800(0.6); 2.5746(0.6); 2.5634(0.8); 2.5563(1.0); 2.5456(0.7); 2.5400(0.8); 2.5373(0.8); 2.5321(0.7); 2.5212(1.1); 2.5141(0.7); 2.5027(0.7); 2.4976(0.7); 2.4795(0.6); 2.0772(0.8); 2.0428(0.7); 2.0327(0.7); 2.0231(0.8); 1.9886(0.7); 1.7099(0.6); 1.7009(16.0); 1.6443(16.0); 1.5408(30.6); 1.2557(0.5); 0.0080(1.9); −0.0002(61.3); −0.0085(1.8) |
| I-46 | $^1$H-NMR(400.0 MHz, CDCl3): δ = 7.5183(1.2); 7.4000(1.1); 7.3866(2.4); 7.3814(3.3); 7.3772(3.0); 7.3726(2.5); 7.3705(3.1); 7.3650(1.1); 7.3617(1.4); 7.2595(199.8); 7.1662(0.6); 7.1600(0.8); 7.1475(0.6); 7.1451(0.7); 7.1368(0.8); 7.1305(0.6); 7.1224(0.8); 6.9954(1.5); 5.9487(1.6); 5.9411(1.6); 5.8864(1.3); 5.8787(1.3); 5.2429(0.6); 5.2304(0.6); 5.2226(0.6); 5.2204(0.5); 5.2104(0.5); 4.6454(0.6); 4.6231(0.6); 4.6189(0.7); 4.6036(0.7); 4.5963(0.6); 4.5807(0.7); 4.5768(0.9); 4.5542(0.7); 4.3294(0.8); 4.3197(0.8); 4.3027(0.7); 4.2930(0.7); 4.2343(1.0); 4.2243(1.0); 4.2075(0.9); 4.1975(0.9); 3.8592(0.5); 3.8520(14.0); 3.8421(11.8); 3.8082(1.5); 3.7892(1.8); 3.7649(1.7); 3.7459(2.1); 3.2487(2.0); 3.2436(1.7); 3.2054(1.7); 3.2003(1.4); 2.0436(1.1); 1.7157(16.0); 1.5330(11.1); 1.2765(0.5); 1.2586(1.3); 0.8819(0.8); 0.0080(2.3); −0.0002(73.4); −0.0085(2.2) |
| I-47 | $^1$H-NMR(400.0 MHz, CDCl3): δ = 7.4477(0.6); 7.4344(0.6); 7.4155(0.7); 7.4110(0.7); 7.3960(1.4); 7.3912(1.9); 7.3889(1.7); 7.3826(2.0); 7.3779(2.5); 7.3722(3.0); 7.3673(5.3); 7.3610(3.5); 7.3520(0.6); 7.3479(0.5); 7.2625(29.8); 7.1554(0.8); 7.1497(0.8); 7.1456(0.5); 7.1421(0.5); 7.1393(0.6); 7.1352(0.9); 7.1310(1.0); 7.1277(0.8); 7.1255(0.8); 7.1172(0.6); 7.1118(0.6); 4.6657(0.6); 4.6604(0.7); 4.6525(0.8); 4.6474(0.8); 4.6402(0.7); 4.6346(0.6); 4.1581(1.0); 4.1458(1.0); 4.1345(1.4); 4.1303(1.1); 4.1222(1.2); 4.1175(1.0); 4.1066(1.2); 4.0938(1.1); 3.9763(0.8); 3.9514(0.7); 3.8892(15.7); 3.8757(0.8); 3.8727(0.8); 3.8703(0.7); 3.8592(16.0); 3.8414(0.8); 3.8008(2.1); 3.7795(2.0); 3.7576(2.3); 3.7363(2.3); 3.3514(15.6); 3.3424(15.2); 3.2389(2.2); 3.2272(2.2); 3.1956(1.9); 3.1839(1.9); 2.5668(0.8); 2.5487(0.9); 2.5311(1.1); 2.5123(1.5); 2.4932(0.9); 2.4755(1.1); 2.4573(1.0); 2.2298(0.7); 2.2275(0.7); 2.2215(0.7); 2.2192(0.7); 2.1941(0.6); 2.1917(0.6); 2.1858(0.6); 2.1834(0.6); 2.1532(0.7); 2.1506(0.7); 2.1453(0.7); 2.1428(0.7); 2.1173(0.6); 2.1148(0.6); 2.1095(0.6); 2.1069(0.6); 1.7164(11.9); 1.6946(11.4); −0.0002(10.0) |
| I-48 | $^1$H-NMR(400.0 MHz, CDCl3): δ = 7.2618(68.4); 7.1797(0.5); 7.1715(2.4); 7.1676(3.6); 7.1620(2.6); 7.1571(2.1); 7.1543(2.6); 7.1518(3.5); 7.1480(3.2); 7.1419(1.5); 7.1353(0.5); 6.9978(0.9); 6.9792(0.6); 6.9142(0.8); 6.9086(0.8); 6.9056(0.5); 6.9037(0.6); 6.8982(1.2); 6.8925(1.8); 6.8869(1.5); 6.8839(0.9); 6.8819(1.0); 6.8779(1.3); 6.8766(1.4); 6.8708(1.3); 6.8653(0.8); 6.8603(0.5); 6.8564(0.6); 6.8549(0.6); 4.6416(0.6); 4.6209(1.4); 4.6031(1.4); 4.5801(1.3); 4.5744(0.8); 4.5703(1.2); 4.5610(0.8); 4.5555(2.0); 4.5462(1.7); 4.5369(0.9); 4.5310(1.5); 4.5221(1.0); 4.1650(0.9); 4.1522(0.9); 4.1411(1.1); 4.1359(1.4); 4.1283(1.0); 4.1230(0.9); 4.1119(1.1); 4.0989(1.0); 4.0662(0.7); 4.0532(0.6); 4.0426(1.1); 4.0299(1.6); 4.0172(0.8); 4.0066(1.0); 3.9935(1.0); 3.9680(0.7); 3.9635(0.6); 3.9010(0.6); 3.8965(0.6); 3.8555(0.7); 3.8515(0.6); 3.8489(0.6); 3.8342(13.9); 3.8276(0.9); 3.8252(0.7); 3.7909(2.6); 3.7856(13.6); 3.7738(2.0); 3.7706(2.5); 3.7654(14.3); 3.7570(2.4); 3.7505(14.2); 3.7307(2.1); 3.7273(2.4); 3.7137(2.0); 3.2132(2.0); 3.2095(2.1); 3.1912(1.8); 3.1832(1.8); 3.1699(1.8); 3.1661(1.8); 3.1480(1.6); 3.1400(1.5); 2.5651(0.5); 2.5591(0.7); 2.5418(0.8); 2.5247(0.8); 2.4160(0.7); 2.3990(0.9); 2.3863(0.8); 2.3818(1.2); 2.3692(0.9); 2.3644(0.6); 2.3520(1.0); 2.3345(0.5); 1.7167(16.0); 1.7106(10.7); 1.6878(9.8); 1.5652(8.8); 0.0080(0.7); −0.0002(24.5); −0.0085(0.8) |
| I-49 | $^1$H-NMR(400.0 MHz, CDCl3): δ = 7.2603(79.2); 7.2105(0.5); 7.1993(1.7); 7.1949(2.3); 7.1797(2.3); 7.1755(1.7); 6.9331(0.8); 6.9171(0.9); 6.9113(1.6); 6.9056(0.8); 6.8897(0.8); 4.6474(0.7); 4.6423(0.7); 4.6307(0.7); 4.6268(0.7); 4.6214(0.5); 4.5982(0.8); 4.5903(0.9); 4.5751(1.2); 4.5676(1.4); 4.5526(0.9); 4.5445(0.8); 4.0667(0.7); 4.0543(0.8); 4.0430(2.0); 4.0304(1.9); |

| No. | NMR |
|---|---|
| | 4.0191(1.3); 4.0063(1.2); 3.9783(0.7); 3.9749(0.8); 3.9636(0.7); 3.9575(1.0); 3.8276(15.4); 3.8151(0.9); 3.8010(16.0); 3.7826(1.4); 3.7706(1.3); 3.6729(2.3); 3.6505(2.1); 3.6285(1.3); 3.6061(1.3); 2.5764(0.5); 2.5591(0.5); 2.5562(0.5); 2.5526(0.5); 2.5354(0.6); 2.5325(0.5); 2.5212(0.5); 2.4976(0.5); 2.1028(0.5); 2.0811(0.6); 2.0730(0.6); 2.0436(0.8); 1.8128(2.2); 1.7968(2.1); 1.7659(4.4); 1.7498(4.2); 1.7190(2.4); 1.7029(2.3); 1.5438(17.9); 0.0080(1.2); −0.0002(41.5); −0.0085(1.2) |
| I-50 | $^1$H-NMR(400.0 MHz, CDCl3): δ = 7.5191(1.2); 7.4723(1.2); 7.4535(1.2); 7.3606(0.6); 7.3094(0.5); 7.2779(0.6); 7.2771(0.6); 7.2763(0.7); 7.2755(0.7); 7.2739(0.9); 7.2731(1.0); 7.2723(1.1); 7.2715(1.2); 7.2707(1.3); 7.2699(1.4); 7.2691(1.6); 7.2683(1.8); 7.2675(2.0); 7.2602(205.8); 7.2530(1.5); 7.2521(1.2); 7.2513(0.9); 7.2505(0.8); 7.2497(0.7); 7.2489(0.6); 7.2481(0.5); 7.2095(0.6); 7.1932(0.6); 7.1876(0.6); 7.1801(2.8); 7.1761(3.4); 7.1608(3.7); 7.1568(2.5); 6.9962(1.2); 6.9293(0.9); 6.9228(1.0); 6.9138(1.0); 6.9077(2.0); 6.9011(2.0); 6.8952(0.9); 6.8862(0.9); 6.8795(1.0); 4.6357(1.2); 4.6266(1.5); 4.6216(0.8); 4.6114(3.1); 4.6023(3.8); 4.5877(2.2); 4.5785(2.0); 4.5726(0.7); 4.1498(1.2); 4.1320(3.5); 4.1195(1.2); 4.1141(3.7); 4.1069(1.1); 4.0958(2.9); 4.0884(1.2); 4.0828(1.9); 4.0755(1.0); 4.0641(1.9); 4.0511(1.8); 4.0386(1.3); 4.0335(1.3); 4.0142(1.8); 3.9952(0.6); 3.9901(0.6); 3.8220(1.4); 3.8138(1.3); 3.7775(2.8); 3.7742(3.7); 3.7681(3.2); 3.7638(2.3); 3.7574(6.6); 3.7514(2.2); 3.7471(1.5); 3.7400(3.4); 3.7221(2.1); 3.7046(0.8); 3.6642(4.8); 3.6196(2.8); 2.6928(0.6); 2.6757(0.6); 2.6688(0.6); 2.6580(0.8); 2.6518(0.7); 2.6410(0.7); 2.6342(0.9); 2.6177(1.0); 2.6123(0.7); 2.6012(0.9); 2.5951(0.7); 2.5840(0.8); 2.5775(0.7); 2.5602(0.7); 2.2473(0.5); 2.2406(0.8); 2.2307(0.7); 2.2207(0.9); 2.2137(0.9); 2.2058(0.8); 2.1948(0.6); 2.1859(0.7); 2.1136(1.6); 2.0456(16.0); 1.8760(2.4); 1.8683(2.2); 1.8594(7.1); 1.8546(1.5); 1.8505(2.2); 1.8428(2.4); 1.8042(3.1); 1.7864(2.9); 1.7572(6.5); 1.7392(5.8); 1.7104(3.5); 1.6924(3.1); 1.4320(1.1); 1.2772(4.6); 1.2655(2.4); 1.2593(9.4); 1.2480(4.5); 1.2414(4.9); 1.2391(2.8); 1.2304(2.2); 0.0079(2.0); −0.0002(64.7); −0.0068(0.9); −0.0085(2.1) |
| I-51 | $^1$H-NMR(400.0 MHz, CDCl3): δ = 7.7312(1.0); 7.7094(1.0); 7.6924(1.0); 7.6716(0.9); 7.5189(1.4); 7.2929(0.5); 7.2600(265.2); 7.2108(1.2); 7.1984(4.5); 7.1938(5.8); 7.1788(5.7); 7.1742(4.5); 7.1616(0.8); 6.9960(1.5); 6.9329(1.0); 6.9290(1.6); 6.9271(1.6); 6.9213(0.9); 6.9130(1.9); 6.9112(2.0); 6.9073(3.2); 6.9055(3.2); 6.9016(1.7); 6.8997(1.6); 6.8914(1.0); 6.8896(1.0); 6.8856(1.6); 6.8838(1.6); 6.8799(0.8); 5.1532(0.9); 5.1375(2.3); 5.1218(3.1); 5.1099(1.1); 5.1061(2.4); 5.0943(2.4); 5.0905(1.1); 5.0786(3.2); 5.0629(2.3); 5.0472(0.9); 4.6923(0.5); 4.6866(0.5); 4.6798(0.9); 4.6744(1.0); 4.6690(1.2); 4.6633(1.2); 4.6582(1.3); 4.6518(1.3); 4.6457(1.3); 4.6399(1.2); 4.6247(0.9); 4.6183(0.5); 4.6122(0.5); 4.5188(2.0); 4.5104(2.3); 4.5028(2.2); 4.4948(4.4); 4.4867(2.1); 4.4794(2.2); 4.4711(2.1); 4.0691(1.8); 4.0564(1.8); 4.0453(3.2); 4.0366(2.0); 4.0327(3.1); 4.0236(1.8); 4.0127(3.1); 3.9996(2.9); 3.9768(1.8); 3.9730(1.8); 3.9471(2.3); 3.9426(1.9); 3.9232(1.1); 3.9188(1.0); 3.8237(2.0); 3.8157(2.1); 3.7792(3.4); 3.7713(3.6); 3.6777(5.6); 3.6551(5.5); 3.6332(3.2); 3.6107(3.3); 2.6051(1.0); 2.5872(1.0); 2.5813(1.0); 2.5702(1.3); 2.5635(1.1); 2.5526(1.2); 2.5465(1.3); 2.5431(1.1); 2.5287(1.2); 2.5250(1.2); 2.5195(1.1); 2.5081(1.3); 2.5016(1.1); 2.4902(1.2); 2.4847(1.2); 2.4667(1.0); 2.0339(1.4); 2.0308(1.7); 2.0283(1.8); 2.0257(1.6); 2.0227(1.5); 1.9991(1.3); 1.9934(1.5); 1.9877(1.3); 1.8128(5.2); 1.7970(5.2); 1.7659(10.6); 1.7500(10.5); 1.7191(5.7); 1.7032(5.7); 1.5429(43.8); 1.4474(0.6); 1.3265(13.4); 1.3108(14.3); 1.3062(16.0); 1.3037(16.0); 1.2905(15.3); 1.2880(15.4); 1.2553(0.8); 1.2437(13.2); 1.2280(13.0); 0.0079(3.5); −0.0002(112.0); −0.0085(3.3) |
| I-52 | $^1$H-NMR(400.0 MHz, CDCl3): δ = 7.5190(1.4); 7.4491(1.9); 7.4333(2.6); 7.4159(1.9); 7.3658(1.7); 7.3512(1.9); 7.3461(3.2); 7.3323(3.9); 7.3263(2.8); 7.3188(2.1); 7.3122(4.5); 7.2989(2.8); 7.2938(2.8); 7.2793(2.8); 7.2731(1.4); 7.2690(2.2); 7.2683(2.4); 7.2601(236.0); 7.2109(0.6); 7.1919(0.6); 7.1861(1.2); 7.1777(1.8); 7.1738(5.6); 7.1679(7.8); 7.1653(10.5); 7.1624(8.6); 7.1597(9.8); 7.1570(6.8); 7.1541(7.7); 7.1483(8.9); 7.1456(8.8); 7.1433(6.9); 7.1400(6.9); 7.1275(1.3); 7.1177(4.0); 7.1162(4.0); 7.1138(3.4); 7.1049(2.8); 7.1009(3.7); 7.0998(3.7); 7.0972(3.3); 7.0868(1.8); 7.0815(2.4); 7.0775(1.9); 7.0581(2.8); 7.0557(2.8); 7.0524(3.4); 7.0342(4.3); 7.0303(5.4); 7.0097(3.4); 6.9961(1.7); 6.9883(1.3); 6.9818(1.0); 6.9085(1.3); 6.9027(2.3); 6.8986(1.7); 6.8929(2.5); 6.8868(3.6); 6.8810(4.6); 6.8769(3.4); 6.8754(3.0); 6.8712(4.7); 6.8653(3.4); 6.8593(2.7); 6.8552(1.7); 6.8495(2.3); 6.8436(1.0); 6.1652(4.5); 6.1552(4.5); 6.1384(5.0); 6.1284(5.0); 6.1221(5.5); 6.1120(5.2); 6.0952(5.6); 6.0852(5.4); 5.5477(7.5); 5.5463(7.7); 5.5327(7.0); 5.5311(7.3); 5.5046(6.7); 5.5032(6.7); 5.4895(6.3); 5.4880(6.3); 5.3488(6.9); 5.3476(6.7); 5.3219(6.6); 5.3207(7.2); 5.3186(7.3); 5.3171(6.7); 5.2917(5.9); 5.2903(5.9); 5.2638(2.6); 5.2385(2.7); 5.2325(8.5); 5.2069(16.0); 5.1880(8.9); 5.1749(2.6); 5.1567(2.3); 4.7085(0.8); 4.6437(0.5); 4.6373(1.0); 4.6307(1.2); 4.6238(2.0); 4.6171(2.5); 4.6101(2.4); 4.6034(3.3); 4.5998(5.6); 4.5916(8.0); 4.5832(5.6); 4.5768(5.0); 4.5683(6.3); 4.5598(3.8); 4.0771(3.3); 4.0638(3.4); 4.0532(6.5); 4.0398(5.8); 4.0283(4.9); 4.0149(4.4); 3.9575(3.0); 3.9524(2.9); 3.9328(4.4); 3.9298(4.6); 3.9257(11.9); 3.9068(2.0); 3.8998(2.3); 3.8953(8.0); 3.8827(9.2); 3.8523(8.9); 3.3196(7.7); 3.3057(7.9); 3.2766(6.7); 3.2627(6.9); 2.6071(1.7); 2.5893(1.8); 2.5837(1.8); 2.5727(2.6); 2.5660(2.0); 2.5569(2.4); 2.5549(2.6); 2.5516(2.5); 2.5494(2.5); 2.5404(2.3); 2.5337(2.3); 2.5317(2.2); 2.5226(2.1); 2.5172(2.0); 2.4993(1.8); 2.0840(1.4); 2.0772(2.3); 2.0687(2.5); 2.0602(2.5); 2.0515(2.4); 2.0427(2.1); 2.0340(2.2); 2.0256(2.1); 2.0190(1.2); 1.5534(22.4); 1.2559(0.7); 0.0079(3.2); −0.0002(99.5); −0.0068(1.2); −0.0085(3.0) |

Analytical data of Examples I-01-I-56.

| No. | NMR |
|---|---|
| I-53 | $^1$H-NMR(400.0 MHz, CDCl3):<br>δ = 7.4651(0.6); 7.4434(0.7); 7.3653(0.5); 7.3508(0.5); 7.3455(0.9); 7.3302(1.3); 7.3257(0.9); 7.3140(0.7); 7.3104(1.7); 7.2949(1.2); 7.2900(0.8); 7.2748(0.9); 7.2601(81.2); 7.1746(1.2); 7.1731(1.2); 7.1706(1.4); 7.1641(1.8); 7.1580(3.8); 7.1547(2.9); 7.1521(3.0); 7.1486(2.0); 7.1441(2.2); 7.1416(2.1); 7.1382(3.4); 7.1322(2.0); 7.1257(0.6); 7.1197(0.9); 7.1065(1.3); 7.1051(1.3); 7.0877(1.3); 7.0861(1.2); 7.0463(0.8); 7.0411(0.9); 7.0345(0.9); 7.0311(1.0); 7.0276(1.2); 7.0244(1.0); 7.0176(0.9); 7.0134(1.0); 7.0071(1.2); 6.9962(0.6); 6.8971(0.7); 6.8919(0.7); 6.8863(0.8); 6.8810(1.1); 6.8753(1.4); 6.8702(1.3); 6.8646(1.6); 6.8590(1.0); 6.8536(0.7); 6.8485(0.6); 6.8429(0.8); 5.2928(1.0); 5.2616(2.3); 5.2160(2.6); 5.1836(4.0); 5.1732(3.4); 4.6044(1.4); 4.5953(1.8); 4.5911(1.0); 4.5879(1.8); 4.5845(1.3); 4.5809(2.1); 4.5786(2.4); 4.5716(1.7); 4.5645(2.0); 4.5554(1.4); 4.0874(1.1); 4.0741(1.1); 4.0638(1.8); 4.0506(1.6); 4.0390(1.0); 4.0257(1.0); 4.0153(1.4); 4.0020(1.3); 3.9744(1.0); 3.9688(1.0); 3.9507(0.7); 3.9453(0.6); 3.9040(0.8); 3.8987(0.8); 3.8803(0.6); 3.8749(0.6); 3.7769(2.8); 3.7520(2.3); 3.7337(3.2); 3.7088(2.7); 3.1824(2.5); 3.1760(2.9); 3.1393(2.2); 3.1328(2.6); 2.5968(0.6); 2.5912(0.5); 2.5801(0.7); 2.5734(0.6); 2.5704(0.7); 2.5624(0.6); 2.5567(0.7); 2.5525(0.7); 2.5472(0.7); 2.5389(0.6); 2.5359(0.8); 2.5292(0.7); 2.5179(0.7); 2.5126(0.7); 2.4947(0.6); 2.0911(0.7); 2.0566(0.6); 2.0479(0.8); 2.0396(0.8); 2.0049(0.7); 1.7017(16.0); 1.6504(13.3); 1.5512(10.8); 1.2584(0.5); 0.0079(1.2); −0.0002(35.6); −0.0085(1.0) |
| I-54 | $^1$H-NMR(400.0 MHz, CDCl3):<br>δ = 7.4531(0.7); 7.3377(2.3); 7.3325(0.8); 7.3212(0.8); 7.3158(2.5); 7.3089(0.5); 7.2925(2.5); 7.2872(1.0); 7.2760(1.0); 7.2706(2.9); 7.2600(55.9); 7.1855(2.2); 7.1798(2.6); 7.1767(1.5); 7.1689(1.5); 7.1657(2.7); 7.1600(2.2); 6.9096(0.6); 6.9032(3.4); 6.8978(1.2); 6.8949(0.8); 6.8869(1.3); 6.8815(3.4); 6.8760(1.1); 6.8732(1.5); 6.8686(3.3); 6.8634(1.0); 6.8603(0.7); 6.8518(1.3); 6.8467(2.8); 6.1708(1.1); 6.1572(1.0); 6.1440(1.2); 6.1304(1.2); 6.1277(1.4); 6.1141(1.2); 6.1009(1.3); 6.0873(1.2); 5.5589(1.9); 5.5575(1.8); 5.5443(1.7); 5.5428(1.7); 5.5157(1.6); 5.5144(1.6); 5.5013(1.5); 5.4997(1.4); 5.3543(1.7); 5.3532(1.6); 5.3315(1.6); 5.3300(1.7); 5.3276(1.7); 5.3264(1.6); 5.3047(1.4); 5.3033(1.4); 5.2078(0.7); 5.1956(0.9); 5.1781(2.3); 5.1658(2.2); 5.1573(2.3); 5.1308(2.3); 5.1011(0.8); 4.6040(0.6); 4.5971(0.5); 4.5907(0.7); 4.5854(0.6); 4.5790(0.5); 4.5723(0.6); 4.5504(0.9); 4.5407(1.5); 4.5311(1.0); 4.5269(1.0); 4.5173(1.6); 4.5078(0.8); 4.0599(0.8); 4.0465(0.8); 4.0361(1.5); 4.0227(1.4); 4.0111(1.1); 3.9977(1.0); 3.9409(0.8); 3.9337(0.8); 3.9301(2.0); 3.9168(1.1); 3.9100(1.1); 3.8965(1.9); 3.8871(2.6); 3.8536(2.1); 3.8127(16.0); 3.7946(15.8); 3.3214(1.8); 3.3109(1.9); 3.2784(1.6); 3.2679(1.7); 2.5341(0.6); 2.5186(0.6); 2.5162(0.6); 2.5137(0.6); 2.5108(0.6); 2.5023(0.5); 2.4955(0.5); 2.0433(0.6); 2.0343(0.5); 2.0089(0.8); 2.0000(0.8); 1.5548(7.2); 1.2584(0.5); 0.0079(0.7); −0.0002(24.0); −0.0085(0.7) |
| I-55 | $^1$H-NMR(400.0 MHz, CDCl3):<br>δ = 7.2610(30.5); 7.1737(1.7); 7.1677(2.8); 7.1643(2.5); 7.1617(2.4); 7.1581(2.3); 7.1539(2.6); 7.1515(2.6); 7.1481(2.8); 7.1421(1.7); 6.9968(1.0); 6.9770(1.0); 6.9141(0.8); 6.9087(0.8); 6.8979(0.8); 6.8925(1.6); 6.8870(1.5); 6.8813(0.8); 6.8764(0.6); 6.8708(0.9); 6.8653(0.8); 4.6416(0.6); 4.6215(1.5); 4.6030(1.6); 4.5825(0.8); 4.5490(1.0); 4.5426(1.1); 4.5372(1.1); 4.5306(1.1); 4.1649(0.8); 4.1522(0.8); 4.1410(1.2); 4.1359(1.1); 4.1283(1.2); 4.1230(1.0); 4.1119(1.1); 4.0990(1.0); 3.8549(0.8); 3.8511(0.8); 3.8337(0.8); 3.8271(0.8); 3.7906(2.4); 3.7654(11.5); 3.7505(11.9); 3.7270(2.4); 3.2127(2.2); 3.2093(2.0); 3.1694(2.0); 3.1660(1.8); 2.4160(0.6); 2.3990(0.9); 2.3862(1.0); 2.3819(1.2); 2.3693(1.0); 2.3646(0.7); 2.3521(1.0); 2.3346(0.5); 2.2651(0.6); 2.1767(0.5); 1.7169(16.0); 1.5519(8.1); −0.0002(13.3) |
| I-56 | $^1$H-NMR(400.0 MHz, CDCl3):<br>δ = 7.2602(70.1); 7.1772(4.1); 7.1582(4.2); 6.9440(1.7); 6.9241(1.5); 6.9183(1.7); 6.9128(1.5); 6.8967(2.4); 6.8913(2.3); 6.8751(1.4); 6.8696(1.3); 6.1887(1.1); 6.1731(1.2); 6.1620(1.3); 6.1460(2.5); 6.1300(1.5); 6.1190(1.4); 6.1032(1.5); 5.5554(2.9); 5.5500(3.0); 5.5122(2.6); 5.5069(2.7); 5.3632(4.1); 5.3365(3.9); 4.6264(1.9); 4.6074(3.2); 4.5884(2.3); 4.5516(1.8); 4.1567(1.2); 4.1438(1.5); 4.1392(1.6); 4.1326(1.8); 4.1263(1.6); 4.1198(1.8); 4.1152(1.8); 4.1025(1.5); 3.9348(2.3); 3.9161(2.4); 3.8917(2.6); 3.8730(2.8); 3.8349(1.3); 3.8153(2.5); 3.7911(1.3); 3.7857(1.3); 3.7620(15.4); 3.7515(16.0); 3.3388(3.9); 3.2956(3.4); 2.4196(0.5); 2.4120(0.6); 2.4024(1.0); 2.3945(1.1); 2.3854(1.5); 2.3775(1.5); 2.3682(1.8); 2.3604(1.8); 2.3507(1.1); 2.3428(1.0); 2.2829(0.7); 2.2757(0.7); 2.2625(0.7); 2.2552(0.8); 2.2273(1.1); 2.2198(1.1); 2.2062(0.8); 2.1984(0.8); 2.1722(0.6); 1.5419(18.5); −0.0002(29.5) |

In analogy to the preparation examples cited above and cited at the appropriate point, and taking account of the general details relating to the preparation of substituted isoxazolinecarboxamides, the compounds cited below are obtained:

Table 2.1: Compounds 2.1-1 to 2.1-240 according to the invention of the general formula (I.1), where Z—(C=W)—O—R⁴ is as defined below.

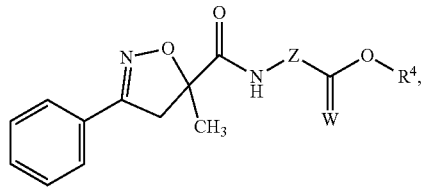

(I.1)

TABLE 2.1

| No. | ![structure] | No. | ![structure] |
|---|---|---|---|
| 2.1-1 | (Z-1)–C(=O)–O–H | 2.1-2 | (Z-1)–C(=O)–O–CH₃ |
| 2.1-3 | (Z-1)–C(=O)–O–CH₂CH₃ | 2.1-4 | (Z-1)–C(=O)–O–CH₂CH₂CH₃ |
| 2.1-5 | (Z-1)–C(=O)–O–CH(CH₃)₂ | 2.1-6 | (Z-1)–C(=O)–O–(CH₂)₃CH₃ |
| 2.1-7 | (Z-1)–C(=O)–O–CH₂CH(CH₃)₂ | 2.1-8 | (Z-1)–C(=O)–O–C(CH₃)₃ |
| 2.1-9 | (Z-1)–C(=O)–O–cyclopentyl | 2.1-10 | (Z-1)–C(=O)–O–cyclohexyl |
| 2.1-11 | (Z-1)–C(=O)–O–CH₂CH=CH₂ | 2.1-12 | (Z-1)–C(=O)–O–CH₂C≡CH |
| 2.1-13 | (Z-1)–C(=O)–O–CH₂–phenyl | 2.1-14 | (Z-1)–C(=O)–O–CH₂CH₂CN |
| 2.1-15 | (Z-1)–C(=O)–O–CH₂CH₂Cl | 2.1-16 | (Z-1)–C(=O)–O–CH₂CH₂OCH₃ |

TABLE 2.1-continued

| No. | ~Z-C(=W)-O-R⁴ | No. | ~Z-C(=W)-O-R⁴ |
|---|---|---|---|
| 2.1-17 | (Z-2), C(=O)OH | 2.1-18 | (Z-2), C(=O)OCH₃ |
| 2.1-19 | (Z-2), C(=O)OCH₂CH₃ | 2.1-20 | (Z-2), C(=O)OCH₂CH₂CH₃ |
| 2.1-21 | (Z-2), C(=O)OCH(CH₃)CH₃ | 2.1-22 | (Z-2), C(=O)OCH₂CH₂CH₂CH₃ |
| 2.1-23 | (Z-2), C(=O)OCH₂CH(CH₃)CH₃ | 2.1-24 | (Z-2), C(=O)OC(CH₃)₃ |
| 2.1-25 | (Z-2), C(=O)O-cyclopentyl | 2.1-26 | (Z-2), C(=O)O-cyclohexyl |
| 2.1-27 | (Z-2), C(=O)OCH₂CH=CH₂ | 2.1-28 | (Z-2), C(=O)OCH₂C≡CH |
| 2.1-29 | (Z-2), C(=O)OCH₂-phenyl | 2.1-30 | (Z-2), C(=O)OCH₂CH₂CN |
| 2.1-31 | (Z-2), C(=O)OCH₂CH₂Cl | 2.1-32 | (Z-2), C(=O)OCH₂CH₂OCH₃ |
| 2.1-33 | (Z-3), C(=O)OH | 2.1-34 | (Z-3), C(=O)OCH₃ |
| 2.1-35 | (Z-3), C(=O)OCH₂CH₃ | 2.1-36 | (Z-3), C(=O)OCH₂CH₂CH₃ |
| 2.1-37 | (Z-3), C(=O)OCH(CH₃)CH₃ | 2.1-38 | (Z-3), C(=O)OCH₂CH₂CH₂CH₃ |
| 2.1-39 | (Z-3), C(=O)OCH₂CH(CH₃)CH₃ | 2.1-40 | (Z-3), C(=O)OC(CH₃)₃ |

TABLE 2.1-continued
| No. | | No. | |
|---|---|---|---|
| 2.1-41 | 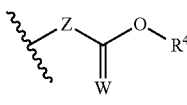 | 2.1-42 | 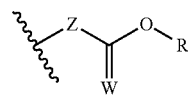 |
| 2.1-43 | 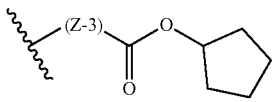 | 2.1-44 | 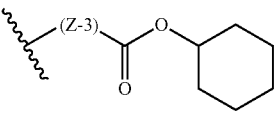 |
| 2.1-45 | 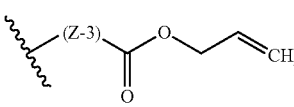 | 2.1-46 | 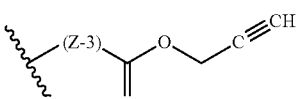 |
| 2.1-47 | 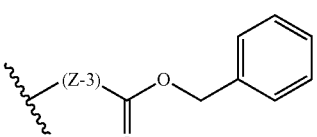 | 2.1-48 | 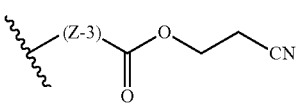 |
| 2.1-49 | 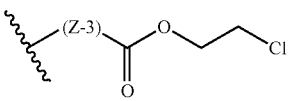 | 2.1-50 | 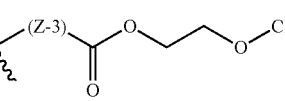 |
| 2.1-51 | 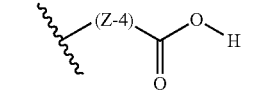 | 2.1-52 | 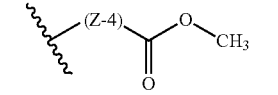 |
| 2.1-53 | 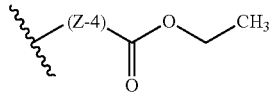 | 2.1-54 | 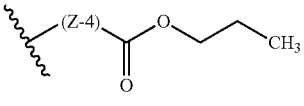 |
| 2.1-55 | 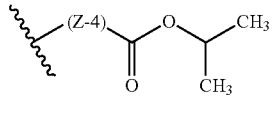 | 2.1-56 | 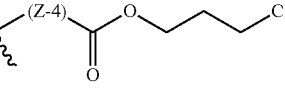 |
| 2.1-57 | 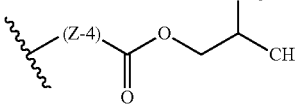 | 2.1-58 | 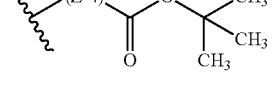 |
| 2.1-59 | 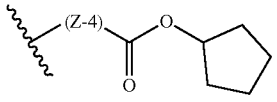 | 2.1-60 | 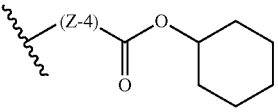 |
| 2.1-61 | 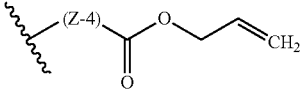 | 2.1-62 | 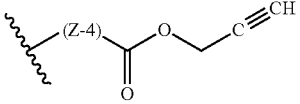 |
| 2.1-63 | 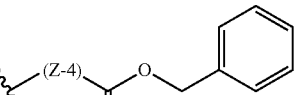 | 2.1-64 | 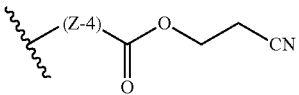 |

TABLE 2.1-continued

| No. | ![structure](Z-O-R4 with W) | No. | ![structure](Z-O-R4 with W) |
|---|---|---|---|
| 2.1-65 | (Z-5)—C(=O)—O—H | 2.1-66 | (Z-5)—C(=O)—O—CH₃ |
| 2.1-67 | (Z-5)—C(=O)—O—CH₂CH₃ | 2.1-68 | (Z-5)—C(=O)—O—CH₂CH₂CH₃ |
| 2.1-69 | (Z-5)—C(=O)—O—CH(CH₃)₂ | 2.1-70 | (Z-5)—C(=O)—O—(CH₂)₃CH₃ |
| 2.1-71 | (Z-5)—C(=O)—O—CH₂CH(CH₃)₂ | 2.1-72 | (Z-5)—C(=O)—O—C(CH₃)₃ |
| 2.1-73 | (Z-5)—C(=O)—O—cyclopentyl | 2.1-74 | (Z-5)—C(=O)—O—cyclohexyl |
| 2.1-75 | (Z-5)—C(=O)—O—CH₂CH=CH₂ | 2.1-76 | (Z-5)—C(=O)—O—CH₂C≡CH |
| 2.1-77 | (Z-5)—C(=O)—O—CH₂—Ph | 2.1-78 | (Z-5)—C(=O)—O—CH₂CH₂CN |
| 2.1-79 | (Z-5)—C(=O)—O—CH₂CH₂Cl | 2.1-80 | (Z-5)—C(=O)—O—CH₂CH₂—O—CH₃ |
| 2.1-81 | (Z-6)—C(=O)—O—H | 2.1-82 | (Z-6)—C(=O)—O—CH₃ |
| 2.1-83 | (Z-6)—C(=O)—O—CH₂CH₃ | 2.1-84 | (Z-6)—C(=O)—O—CH₂CH₂CH₃ |
| 2.1-85 | (Z-6)—C(=O)—O—CH(CH₃)₂ | 2.1-86 | (Z-6)—C(=O)—O—(CH₂)₃CH₃ |
| 2.1-87 | (Z-6)—C(=O)—O—CH₂CH(CH₃)₂ | 2.1-88 | (Z-6)—C(=O)—O—C(CH₃)₃ |

TABLE 2.1-continued

| No. | ⟨Z⟩—C(=W)—O—R⁴ | No. | ⟨Z⟩—C(=W)—O—R⁴ |
|---|---|---|---|
| 2.1-89 | 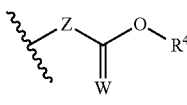 (Z-6), cyclopentyl ester | 2.1-90 | 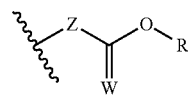 (Z-6), cyclohexyl ester |
| 2.1-91 | 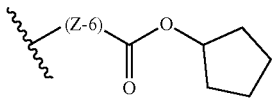 (Z-6), allyl ester | 2.1-92 | 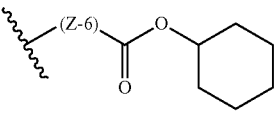 (Z-6), propargyl ester |
| 2.1-93 | 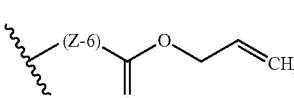 (Z-6), benzyl ester | 2.1-94 | 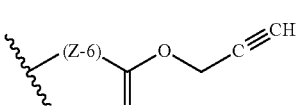 (Z-6), —O—CH₂CH₂CN |
| 2.1-95 | 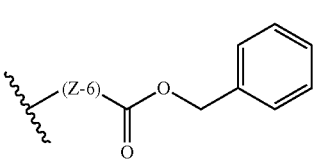 (Z-6), —O—CH₂CH₂Cl | 2.1-96 | 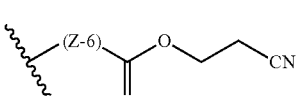 (Z-6), —O—CH₂CH₂—OCH₃ |
| 2.1-97 | 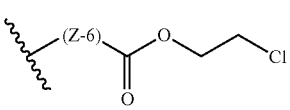 (Z-7), —OH | 2.1-98 | 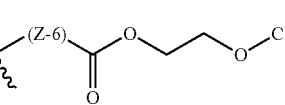 (Z-7), —O—CH₃ |
| 2.1-99 | 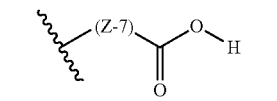 (Z-7), —O—CH₂CH₃ | 2.1-100 | 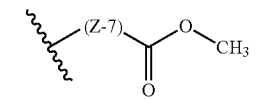 (Z-7), —O—CH₂CH₂CH₃ |
| 2.1-101 | 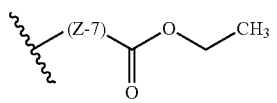 (Z-7), —O—CH(CH₃)₂ | 2.1-102 | 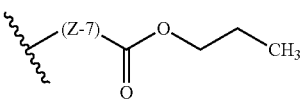 (Z-7), —O—nBu |
| 2.1-103 | 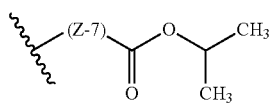 (Z-7), isobutyl ester | 2.1-104 | 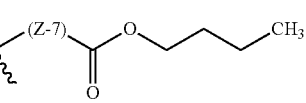 (Z-7), tert-butyl ester |
| 2.1-105 | 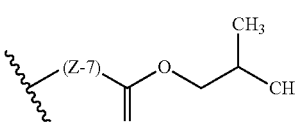 (Z-7), cyclopentyl ester | 2.1-106 | 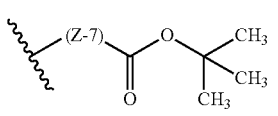 (Z-7), cyclohexyl ester |
| 2.1-107 | 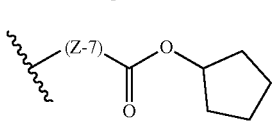 (Z-7), allyl ester | 2.1-108 | 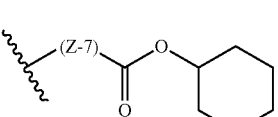 (Z-7), propargyl ester |
| 2.1-109 | 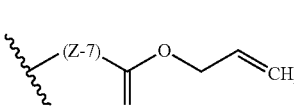 (Z-7), benzyl ester | 2.1-110 | 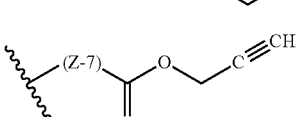 (Z-7), —O—CH₂CH₂CN |
| 2.1-111 | 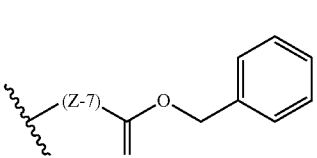 (Z-7), —O—CH₂CH₂Cl | 2.1-112 | 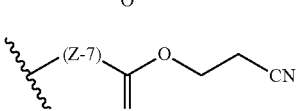 (Z-7), —O—CH₂CH₂—OCH₃ |

TABLE 2.1-continued

| No. | ![structure] | No. | ![structure] |
|---|---|---|---|
| 2.1-113 | (Z-8)-C(=O)-O-H | 2.1-114 | (Z-8)-C(=O)-O-CH₃ |
| 2.1-115 | (Z-8)-C(=O)-O-CH₂CH₃ | 2.1-116 | (Z-8)-C(=O)-O-CH₂CH₂CH₃ |
| 2.1-117 | (Z-8)-C(=O)-O-CH(CH₃)₂ | 2.1-118 | (Z-8)-C(=O)-O-CH₂CH₂CH₂CH₃ |
| 2.1-119 | (Z-8)-C(=O)-O-CH₂CH(CH₃)₂ | 2.1-120 | (Z-8)-C(=O)-O-C(CH₃)₃ |
| 2.1-121 | (Z-8)-C(=O)-O-cyclopentyl | 2.1-122 | (Z-8)-C(=O)-O-cyclohexyl |
| 2.1-123 | (Z-8)-C(=O)-O-CH₂-CH=CH₂ | 2.1-124 | (Z-8)-C(=O)-O-CH₂-C≡CH |
| 2.1-125 | (Z-8)-C(=O)-O-CH₂-phenyl | 2.1-126 | (Z-8)-C(=O)-O-CH₂CH₂-CN |
| 2.1-127 | (Z-8)-C(=O)-O-CH₂CH₂-Cl | 2.1-128 | (Z-8)-C(=O)-O-CH₂CH₂-O-CH₃ |
| 2.1-129 | (Z-9)-C(=O)-O-H | 2.1-130 | (Z-9)-C(=O)-O-CH₃ |
| 2.1-131 | (Z-9)-C(=O)-O-CH₂CH₃ | 2.1-132 | (Z-9)-C(=O)-O-CH₂CH₂CH₃ |
| 2.1-133 | (Z-9)-C(=O)-O-CH(CH₃)₂ | 2.1-134 | (Z-9)-C(=O)-O-CH₂CH₂CH₂CH₃ |
| 2.1-135 | (Z-9)-C(=O)-O-CH₂CH(CH₃)₂ | 2.1-136 | (Z-9)-C(=O)-O-C(CH₃)₃ |

TABLE 2.1-continued
| No. | | No. | |
|---|---|---|---|
| 2.1-137 | 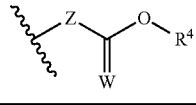 | 2.1-138 | 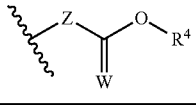 |
| 2.1-139 | 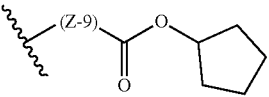 | 2.1-140 | 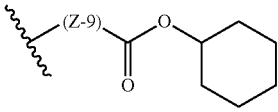 |
| 2.1-141 | 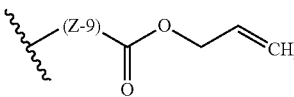 | 2.1-142 | 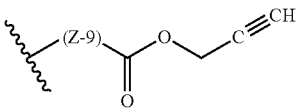 |
| 2.1-143 | 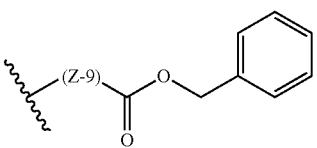 | 2.1-144 | 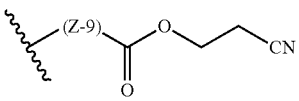 |
| 2.1-145 | 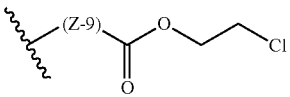 | 2.1-146 | 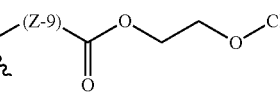 |
| 2.1-147 | 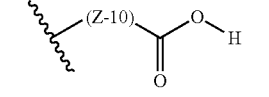 | 2.1-148 | 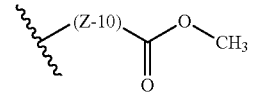 |
| 2.1-149 | 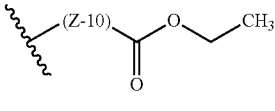 | 2.1-150 | 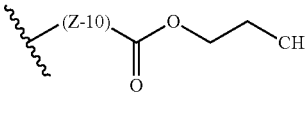 |
| 2.1-151 | 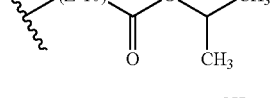 | 2.1-152 | 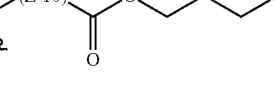 |
| 2.1-153 | 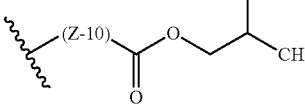 | 2.1-154 | 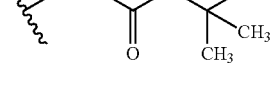 |
| 2.1-155 | 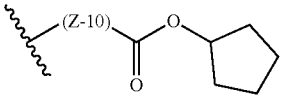 | 2.1-156 | 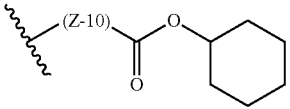 |
| 2.1-157 | 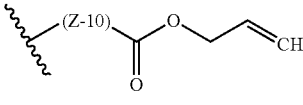 | 2.1-158 | 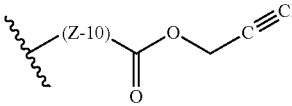 |
| 2.1-159 | 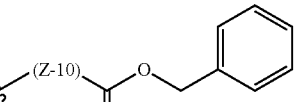 | 2.1-160 | 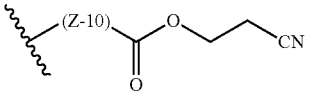 |

TABLE 2.1-continued
| No. | | No. | |
|---|---|---|---|
| 2.1-161 | 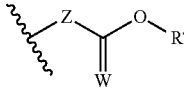 | 2.1-162 | 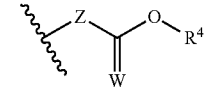 |
| 2.1-163 | 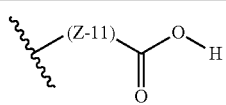 | 2.1-164 | 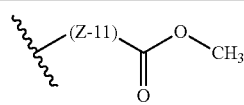 |
| 2.1-165 | 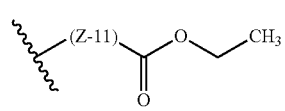 | 2.1-166 | 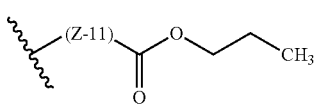 |
| 2.1-167 | 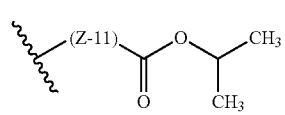 | 2.1-168 | 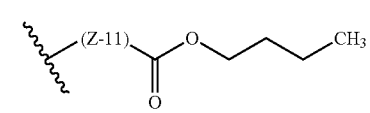 |
| 2.1-169 | 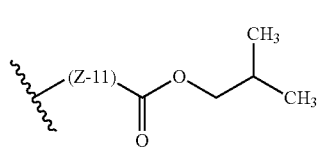 | 2.1-170 | 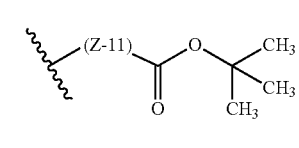 |
| 2.1-171 | 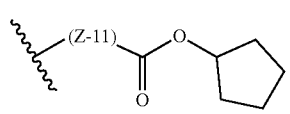 | 2.1-172 | 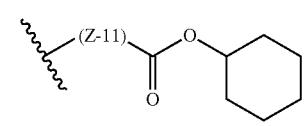 |
| 2.1-173 | 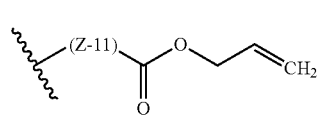 | 2.1-174 | 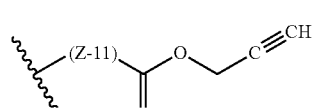 |
| 2.1-175 | 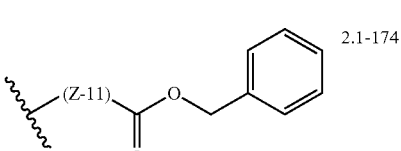 | 2.1-176 | 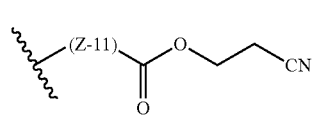 |
| 2.1-177 | 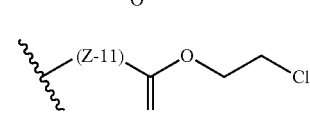 | 2.1-178 | 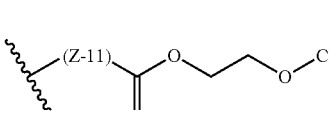 |
| 2.1-179 | 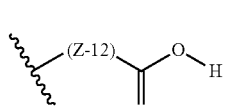 | 2.1-180 | 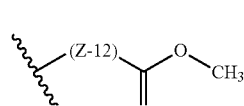 |
| 2.1-181 | 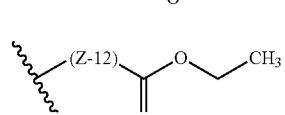 | 2.1-182 | 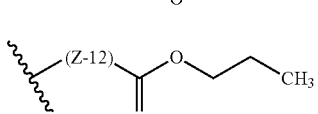 |
| 2.1-183 | 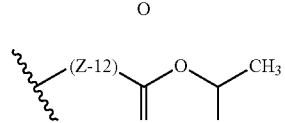 | 2.1-184 | 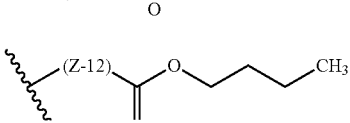 |

TABLE 2.1-continued

| No. | structure | No. | structure |
|---|---|---|---|
| 2.1-185 | (Z-12)-C(=O)-O-cyclopentyl | 2.1-186 | (Z-12)-C(=O)-O-cyclohexyl |
| 2.1-187 | (Z-12)-C(=O)-O-CH₂-CH=CH₂ | 2.1-188 | (Z-12)-C(=O)-O-CH₂-C≡CH |
| 2.1-189 | (Z-12)-C(=O)-O-CH₂-C₆H₅ | 2.1-190 | (Z-12)-C(=O)-O-CH₂CH₂-CN |
| 2.1-191 | (Z-12)-C(=O)-O-CH₂CH₂-Cl | 2.1-192 | (Z-12)-C(=O)-O-CH₂CH₂-OCH₃ |
| 2.1-193 | (Z-13)-C(=O)-O-H | 2.1-194 | (Z-13)-C(=O)-O-CH₃ |
| 2.1-195 | (Z-13)-C(=O)-O-CH₂CH₃ | 2.1-196 | (Z-13)-C(=O)-O-CH₂CH₂CH₃ |
| 2.1-197 | (Z-13)-C(=O)-O-CH(CH₃)₂ | 2.1-198 | (Z-13)-C(=O)-O-CH₂CH₂CH₂CH₃ |
| 2.1-199 | (Z-13)-C(=O)-O-CH₂CH(CH₃)₂ | 2.1-200 | (Z-13)-C(=O)-O-C(CH₃)₃ |
| 2.1-201 | (Z-13)-C(=O)-O-cyclopentyl | 2.1-202 | (Z-13)-C(=O)-O-cyclohexyl |
| 2.1-203 | (Z-13)-C(=O)-O-CH₂-CH=CH₂ | 2.1-204 | (Z-13)-C(=O)-O-CH₂-C≡CH |
| 2.1-205 | (Z-13)-C(=O)-O-CH₂-C₆H₅ | 2.1-206 | (Z-13)-C(=O)-O-CH₂CH₂-CN |
| 2.1-207 | (Z-13)-C(=O)-O-CH₂CH₂-Cl | 2.1-208 | (Z-13)-C(=O)-O-CH₂CH₂-OCH₃ |

TABLE 2.1-continued
| No. | | No. | |
|---|---|---|---|
| 2.1-209 | 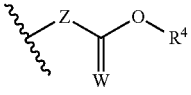 | 2.1-210 | 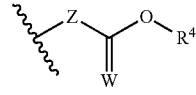 |
| 2.1-211 | 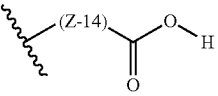 | 2.1-212 | 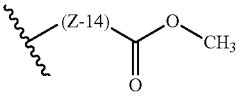 |
| 2.1-213 | 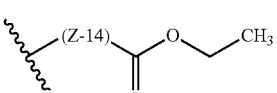 | 2.1-214 | 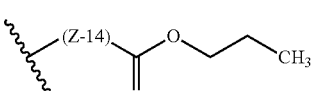 |
| 2.1-215 | 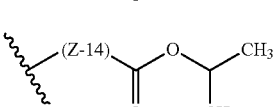 | 2.1-216 | 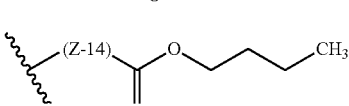 |
| 2.1-217 | 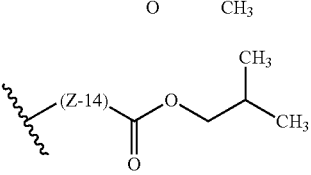 | 2.1-218 | 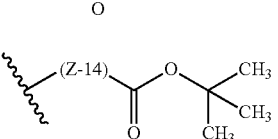 |
| 2.1-219 | 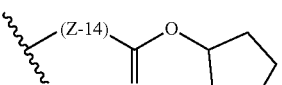 | 2.1-220 | 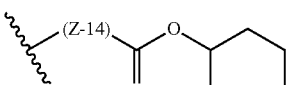 |
| 2.1-221 | 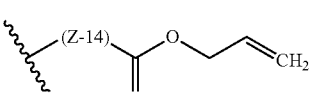 | 2.1-222 | 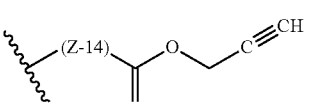 |
| 2.1-223 | 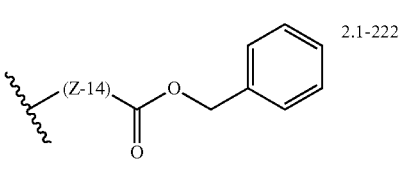 | 2.1-224 | 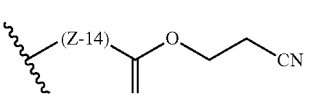 |
| 2.1-225 | 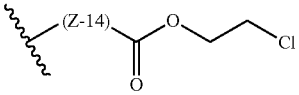 | 2.1-226 | 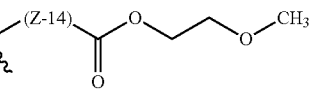 |
| 2.1-227 | 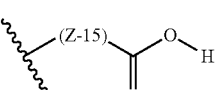 | 2.1-228 | 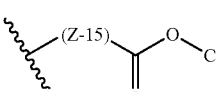 |
| 2.1-229 | 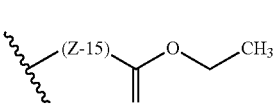 | 2.1-230 | 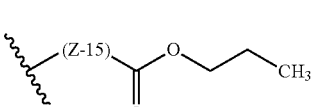 |
| 2.1-231 | 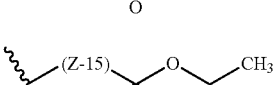 | 2.1-232 | 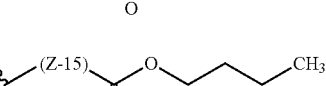 |

TABLE 2.1-continued

| No. | | No. | |
|---|---|---|---|
| 2.1-233 | 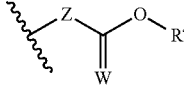 | 2.1-234 | 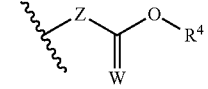 |
| 2.1-235 | 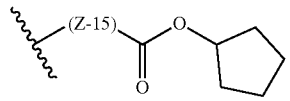 | 2.1-236 | 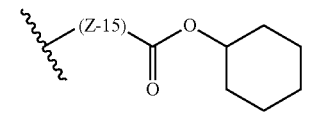 |
| 2.1-237 | 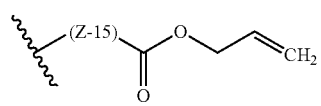 | 2.1-238 | 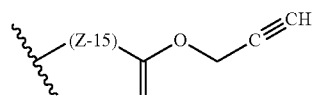 |
| 2.1-239 | 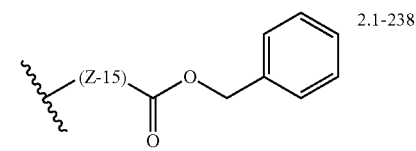 | 2.1-240 | 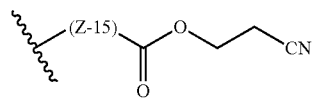 |

Table 2.2: Compounds 2.2-1 to 2.2-240 according to the invention of the general formula (I.2), where Z—(C=W)—O—$R^4$ is as defined in Table 2.1.

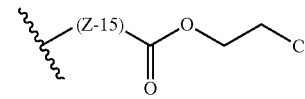
(I.2)

Table 2.3: Compounds 2.3-1 to 2.3-240 according to the invention of the general formula (I.3), where Z—(C=W)—O—$R^4$ is as defined in Table 2.1.

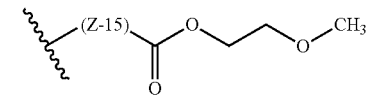
(I.3)

Table 2.4: Compounds 2.4-1 to 2.4-240 according to the invention of the general formula (I.4), where Z—(C=W)—O—$R^4$ is as defined in Table 2.1.

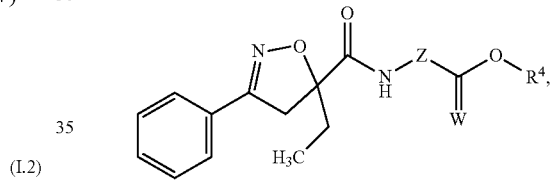
(I.4)

Table 2.5: Compounds 2.5-1 to 2.5-240 according to the invention of the general formula (I.5), where Z—(C=W)—O—$R^4$ is as defined in Table 2.1.

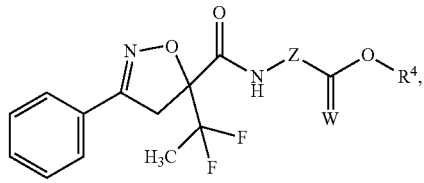
(I.5)

Table 2.6: Compounds 2.6-1 to 2.6-240 according to the invention of the general formula (I.6), where Z—(C=W)—O—$R^4$ is as defined in Table 2.1.

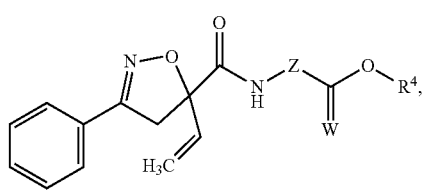
(I.6)

Table 2.7: Compounds 2.7-1 to 2.7-240 according to the invention of the general formula (I.7), where Z—(C=W)—O—R⁴ is as defined in Table 2.1.

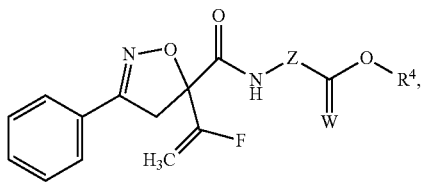
(I.7)

Table 2.8: Compounds 2.8-1 to 2.8-240 according to the invention of the general formula (I.8), where Z—(C=W)—O—R⁴ is as defined in Table 2.1.

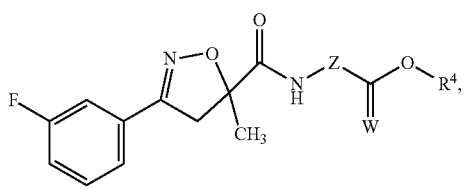
(I.8)

Table 2.9: Compounds 2.9-1 to 2.9-240 according to the invention of the general formula (I.9), where Z—(C=W)—O—R⁴ is as defined in Table 2.1.

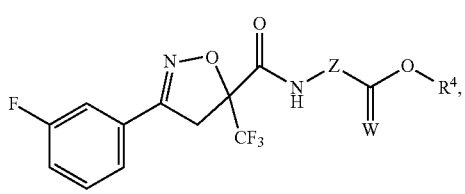
(I.9)

Table 2.10: Compounds 2.10-1 to 2.10-240 according to the invention of the general formula (I.10), where Z—(C=W)—O—R⁴ is as defined in Table 2.1.

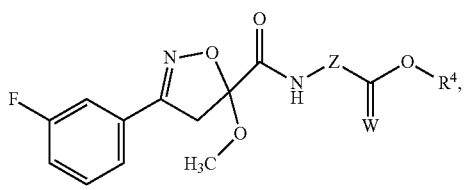
(I.10)

Table 2.11: Compounds 2.11-1 to 2.11-240 according to the invention of the general formula (I.11), where Z—(C=W)—O—R⁴ is as defined in Table 2.1.

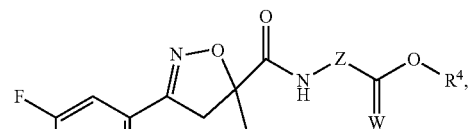
(I.11)

Table 2.12: Compounds 2.12-1 to 2.12-240 according to the invention of the general formula (I.12), where Z—(C=W)—O—R⁴ is as defined in Table 2.1.

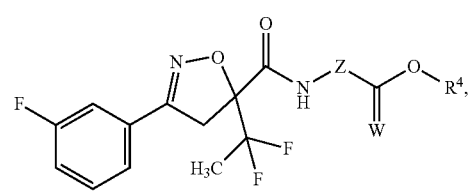
(I.12)

Table 2.13: Compounds 2.13-1 to 2.13-240 according to the invention of the general formula (I.13),

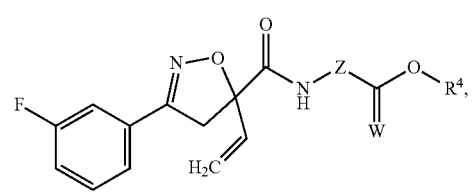
(I.13)

Table 2.14: Compounds 2.14-1 to 2.14-240 according to the invention of the general formula (I.14), where Z—(C=W)—O—R⁴ is as defined in Table 2.1.

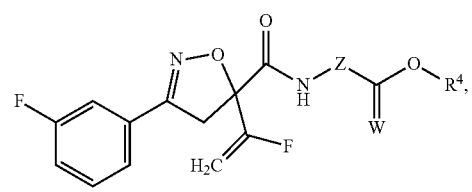
(I.14)

Table 2.15: Compounds 2.15-1 to 2.15-240 according to the invention of the general formula (I.15), where Z—(C=W)—O—R⁴ is as defined in Table 2.1.

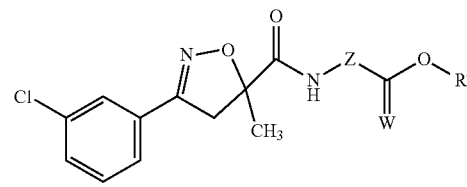
(I.15)

Table 2.16: Compounds 2.16-1 to 2.16-240 according to the invention of the general formula (I.16), where Z—(C=W)—O—R⁴ is as defined in Table 2.1.

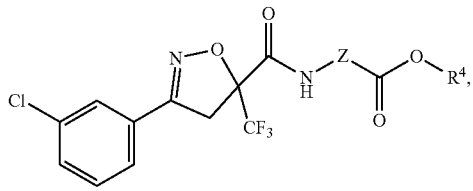
(I.16)

Table 2.17: Compounds 2.17-1 to 2.17-240 according to the invention of the general formula (I.17), where Z—(C=W)—O—R⁴ is as defined in Table 2.1.

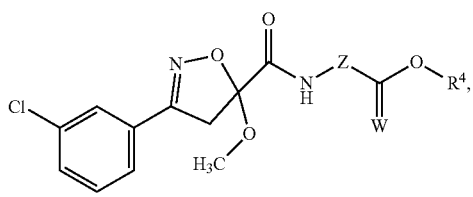
(I.17)

Table 2.18: Compounds 2.18-1 to 2.18-240 according to the invention of the general formula (I.18), where Z—(C=W)—O—R⁴ is as defined in Table 2.1.

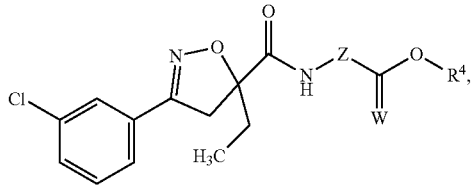
(I.18)

Table 2.19: Compounds 2.19-1 to 2.19-240 according to the invention of the general formula (I.19), where Z—(C=W)—O—R⁴ is as defined in Table 2.1.

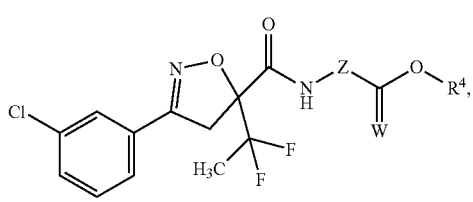
(I.19)

Table 2.20: Compounds 2.20-1 to 2.20-240 according to the invention of the general formula (I.20), where Z—(C=W)—O—R⁴ is as defined in Table 2.1.

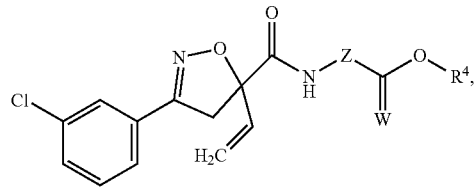
(I.20)

Table 2.21: Compounds 2.21-1 to 2.21-240 according to the invention of the general formula (I.21), where Z—(C=W)—O—R⁴ is as defined in Table 2.1.

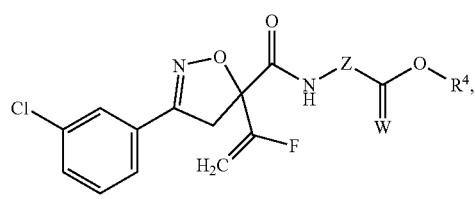
(I.21)

Table 2.22: Compounds 2.22-1 to 2.22-240 according to the invention of the general formula (I.22), where Z—(C=W)—O—R⁴ is as defined in Table 2.1.

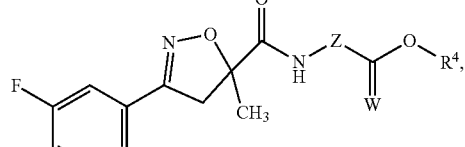
(I.22)

Table 2.23: Compounds 2.23-1 to 2.23-240 according to the invention of the general formula (I.23), where Z—(C=W)—O—R⁴ is as defined in Table 2.1.

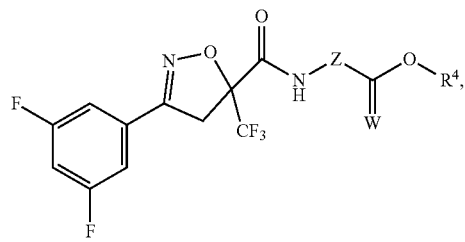
(I.23)

Table 2.24: Compounds 2.24-1 to 2.24-240 of the general formula (I.24) in which Z—(C=W)—O—R⁴ is as defined in Table 2.1.

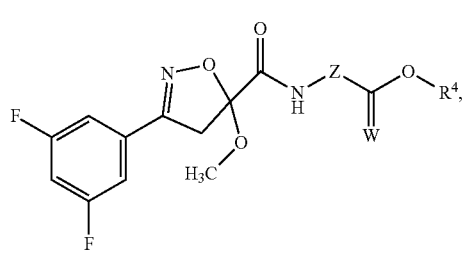
(I.24)

Table 2.25: Compounds 2.25-1 to 2.25-240 according to the invention of the general formula (I.25), where Z—(C=W)—O—R$^4$ is as defined in Table 2.1.

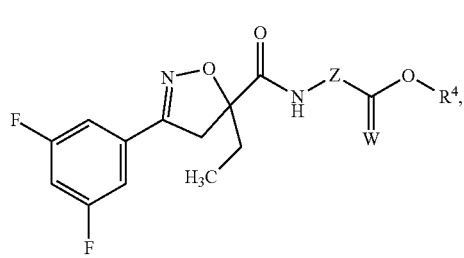
(I.25)

Table 2.26: Compounds 2.26-1 to 2.26-240 according to the invention of the general formula (I.26), where Z—(C=W)—O—R$^4$ is as defined in Table 2.1.

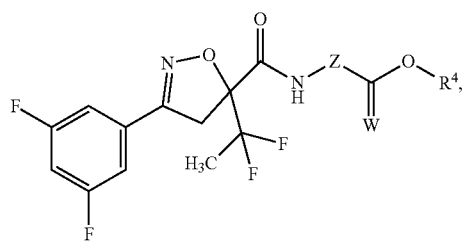
(I.26)

Table 2.27: Compounds 2.27-1 to 2.27-240 according to the invention of the general formula (I.27), where Z—(C=W)—O—R$^4$ is as defined in Table 2.1.

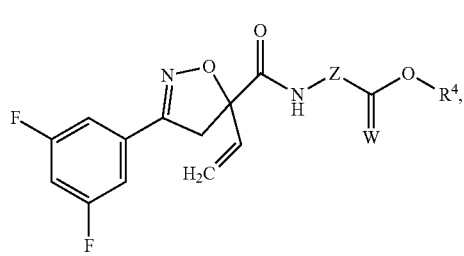
(I.27)

Table 2.28: Compounds 2.28-1 to 2.28-240 according to the invention of the general formula (I.28), where Z—(C=W)—O—R$^4$ is as defined in Table 2.1.

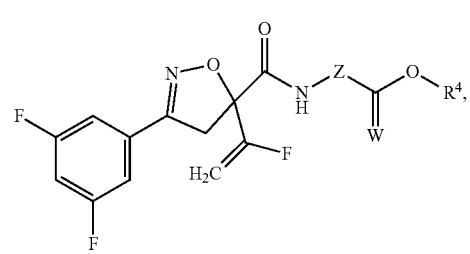
(I.28)

Table 2.29: Compounds 2.29-1 to 2.29-240 according to the invention of the general formula (I.29), where Z—(C=W)—O—R$^4$ is as defined in Table 2.1.

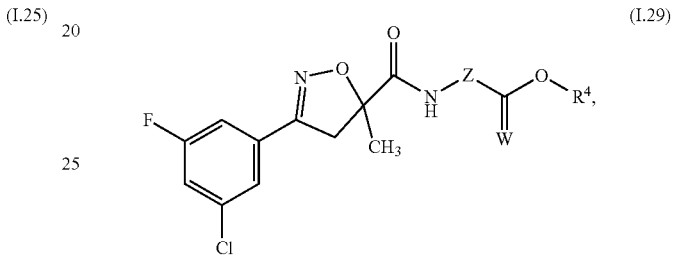
(I.29)

Table 2.30: Compounds 2.30-1 to 2.30-240 according to the invention of the general formula (I.30), where Z—(C=W)—O—R$^4$ is as defined in Table 2.1.

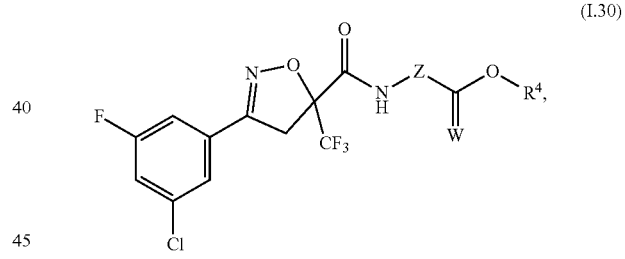
(I.30)

Table 2.31: Compounds 2.31-1 to 2.31-240 according to the invention of the general formula (I.31), where Z—(C=W)—O—R$^4$ is as defined in Table 2.1.

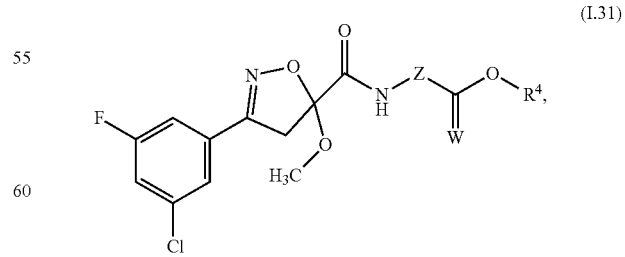
(I.31)

Table 2.32: Compounds 2.32-1 to 2.32-240 according to the invention of the general formula (I.32), where Z—(C=W)—O—R$^4$ is as defined in Table 2.1.

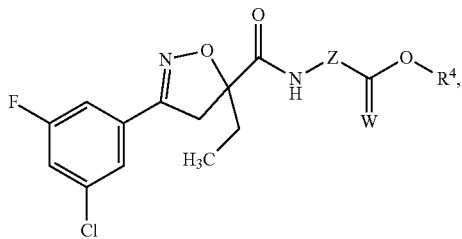
(I.32)

Table 2.33: Compounds 2.33-1 to 2.33-240 according to the invention of the general formula (I.33), where Z—(C=W)—O—R⁴ is as defined in Table 2.1.

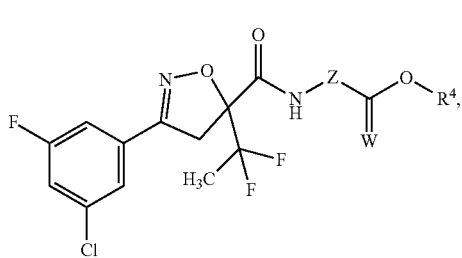
(I.33)

Table 2.34: Compounds 2.34-1 to 2.34-240 according to the invention of the general formula (I.34), where Z—(C=W)—O—R⁴ is as defined in Table 2.1.

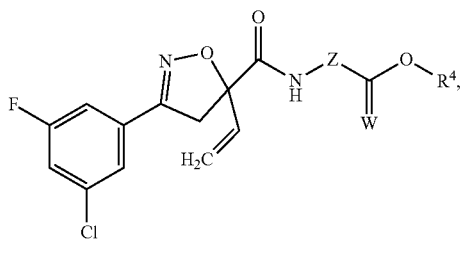
(I.34)

Table 2.35: Compounds 2.35-1 to 2.35-240 according to the invention of the general formula (I.35), where Z—(C=W)—O—R⁴ is as defined in Table 2.1.

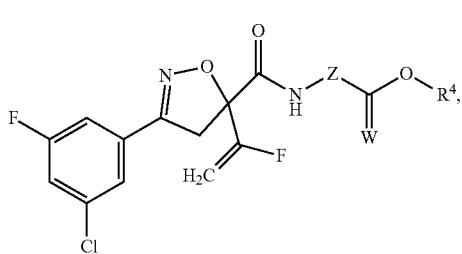
(I.35)

Table 2.36: Compounds 2.36-1 to 2.36-240 according to the invention of the general formula (I.36), where Z—(C=W)—O—R⁴ is as defined in Table 2.1.

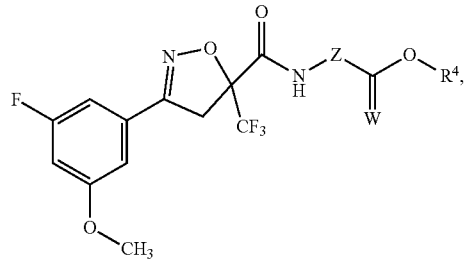
(I.36)

Table 2.37: Compounds 2.37-1 to 2.37-240 according to the invention of the general formula (I.37), where Z—(C=W)—O—R⁴ is as defined in Table 2.1.

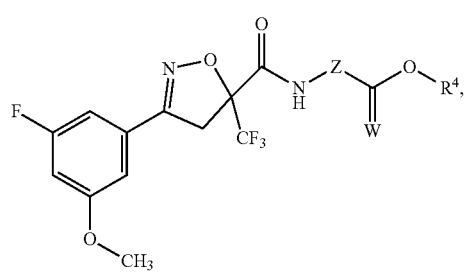
(I.37)

Table 2.38: Compounds 2.38-1 to 2.38-240 according to the invention of the general formula (I.38), where Z—(C=W)—O—R⁴ is as defined in Table 2.1.

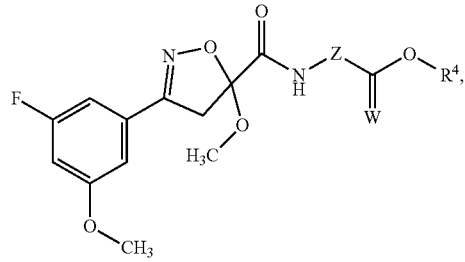
(I.38)

Table 2.39: Compounds 2.39-1 to 2.39-240 according to the invention of the general formula (I.39), where Z—(C=W)—O—R⁴ is as defined in Table 2.1.

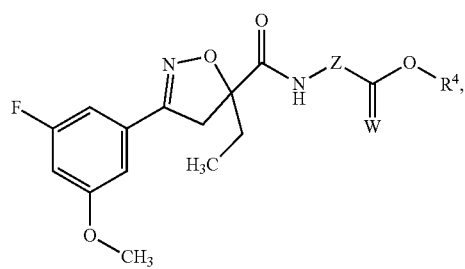
(I.39)

Table 2.40: Compounds 2.40-1 to 2.40-240 according to the invention of the general formula (I.40), where Z—(C=W)—O—R⁴ is as defined in Table 2.1.

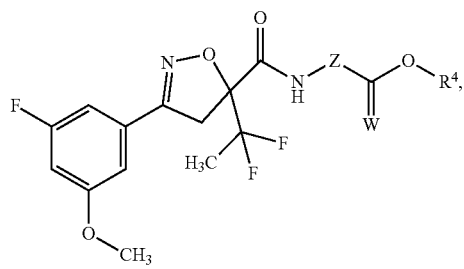

(I.40)

Table 2.41: Compounds 2.41-1 to 2.41-240 according to the invention of the general formula (I.41), where Z—(C=W)—O—R⁴ is as defined in Table 2.1.

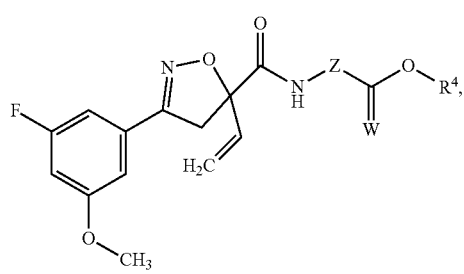

(I.41)

Table 2.42: Compounds 2.42-1 to 2.42-240 according to the invention of the general formula (I.42), where Z—(C=W)—O—R⁴ is as defined in Table 2.1.

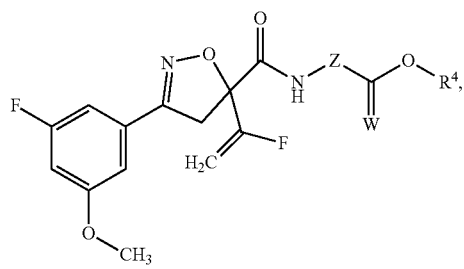

(I.42)

Table 2.43: Compounds 2.43-1 to 2.43-240 according to the invention of the general formula (I.43), where Z—(C=W)—O—R⁴ is as defined in Table 2.1.

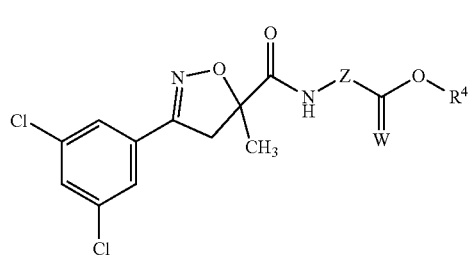

(I.43)

Table 2.44: Compounds 2.44-1 to 2.44-240 according to the invention of the general formula (I.44), where Z—(C=W)—O—R⁴ is as defined in Table 2.1.

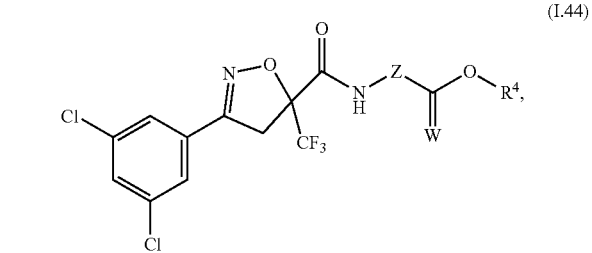

(I.44)

Table 2.45: Compounds 2.45-1 to 2.45-240 according to the invention of the general formula (I.45), where Z—(C=W)—O—R⁴ is as defined in Table 2.1.

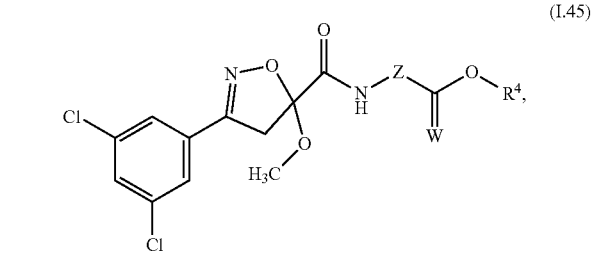

(I.45)

Table 2.46: Compounds 2.46-1 to 2.46-240 according to the invention of the general formula (I.46), where Z—(C=W)—O—R⁴ is as defined in Table 2.1.

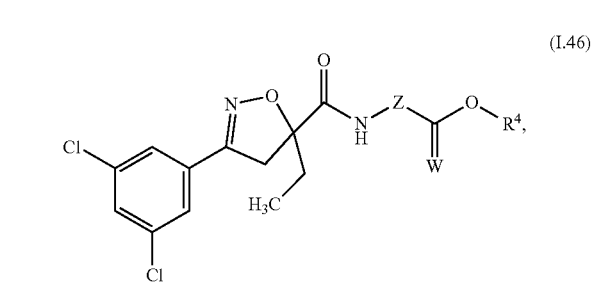

(I.46)

Table 2.47: Compounds 2.47 to 2.47-240 according to the invention of the general formula (I.47), where Z—(C=W)—O—R⁴ is as defined in Table 2.1.

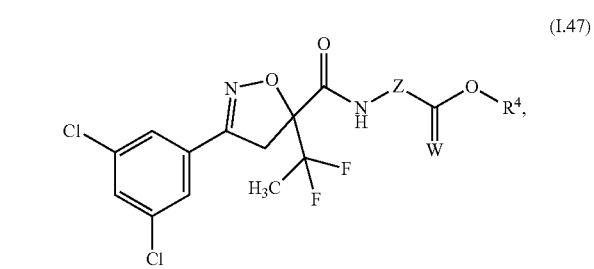

(I.47)

Table 2.48: Compounds 2.48-1 to 2.48-240 according to the invention of the general formula (I.48), where Z—(C=W)—O—R⁴ is as defined in Table 2.1.

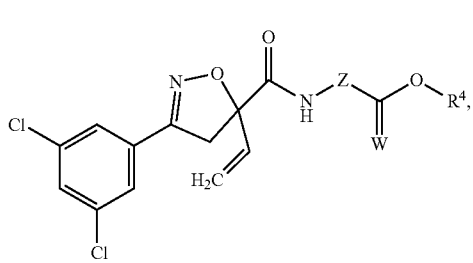

(I.48)

Table 2.49: Compounds 2.49-1 to 2.49-240 according to the invention of the general formula (I.49), where Z—(C=W)—O—R⁴ is as defined in Table 2.1.

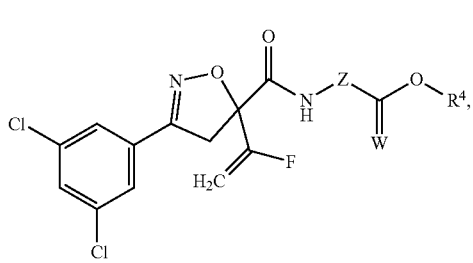

(I.49)

Table 2.50: Compounds 2.50-1 to 2.50-240 according to the invention of the general formula (I.50), where Z—(C=W)—O—R⁴ is as defined in Table 2.1.

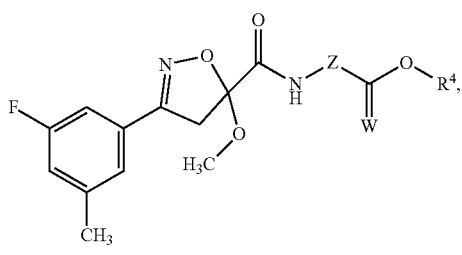

(I.50)

Table 2.51: Compounds 2.51-1 to 2.51-240 according to the invention of the general formula (I.51), where Z—(C=W)—O—R⁴ is as defined in Table 2.1.

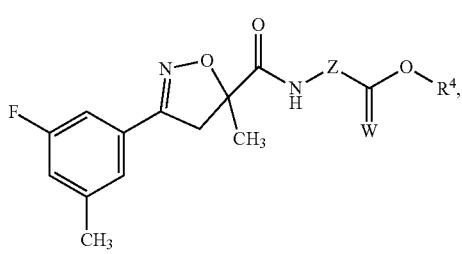

(I.51)

Table 2.52: Compounds 2.52-1 to 2.52-240 according to the invention of the general formula (I.52), where Z—(C=W)—O—R⁴ is as defined in Table 2.1.

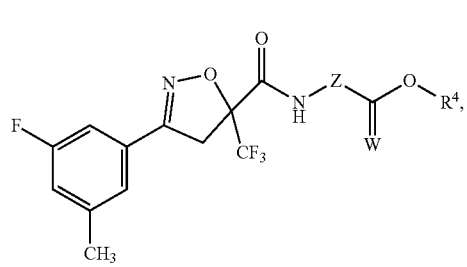

(I.52)

Table 2.53: Compounds 2.53-1 to 2.53-240 according to the invention of the general formula (I.53), where Z—(C=W)—O—R⁴ is as defined in Table 2.1.

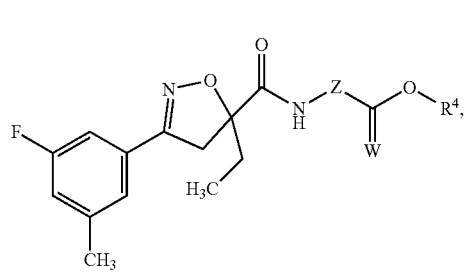

(I.53)

Table 2.54: Compounds 2.54-1 to 2.54-240 according to the invention of the general formula (I.54), where Z—(C=W)—O—R⁴ is as defined in Table 2.1.

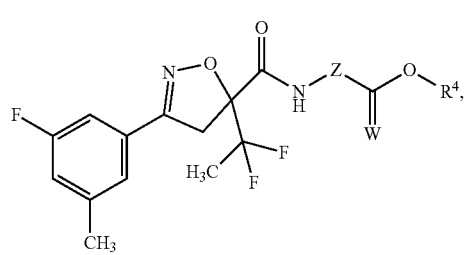

(I.54)

Table 2.55: Compounds 2.55-1 to 2.55-240 according to the invention of the general formula (I.55), where Z—(C=W)—O—R⁴ is as defined in Table 2.1.

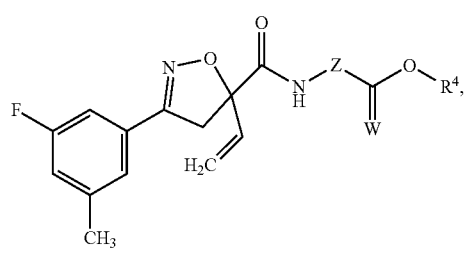

(I.55)

Table 2.56: Compounds 2.56-1 to 2.56-240 according to the invention of the general formula (I.56), where Z—(C=W)—O—R⁴ is as defined in Table 2.1.

(I.56)

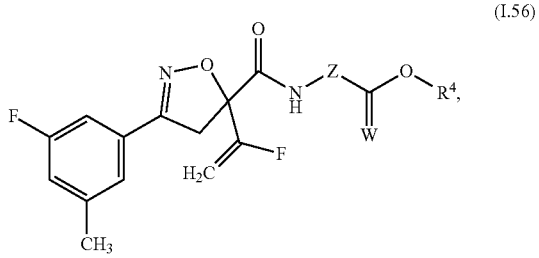

B. FORMULATION EXAMPLES

1. Dusting Products

A dusting product is obtained by mixing 10 parts by weight of a compound of the formula (I) and 90 parts by weight of talc as an inert substance and comminuting the mixture in a hammer mill.

2. Dispersible Powder

A readily water-dispersible wettable powder is obtained by mixing 25 parts by weight of a compound of the formula (I), 64 parts by weight of kaolin-containing quartz as an inert substance, 10 parts by weight of potassium lignosulfonate and 1 part by weight of sodium oleoylmethyltaurate as a wetting agent and dispersant, and grinding the mixture in a pinned-disk mill.

3. Dispersion Concentrate

A readily water-dispersible dispersion concentrate is obtained by mixing 20 parts by weight of a compound of the formula (I), 6 parts by weight of alkylphenol polyglycol ether (®Triton X 207), 3 parts by weight of isotridecanol polyglycol ether (8 EO) and 71 parts by weight of paraffinic mineral oil (boiling range for example about 255 to more than 277° C.) and grinding the mixture in a friction ball mill to a fineness of below 5 microns.

4. Emulsifiable Concentrate

An emulsifiable concentrate is obtained from 15 parts by weight of a compound of the formula (I), 75 parts by weight of cyclohexanone as a solvent and 10 parts by weight of ethoxylated nonylphenol as an emulsifier.

5. Water-Dispersible Granules

Water-dispersible granules are obtained by mixing 75 parts by weight of a compound of the formula (I), 10 parts by weight of calcium lignosulfonate, 5 parts by weight of sodium laurylsulfate, 3 parts by weight of polyvinyl alcohol and 7 parts by weight of kaolin, grinding the mixture in a pinned-disk mill, and granulating the powder in a fluidized bed by spray application of water as a granulating liquid.

Water-dispersible granules are also obtained by homogenizing and precomminuting, in a colloid mill, 25 parts by weight of a compound of the formula (I), 5 parts by weight of sodium 2,2'-dinaphthylmethane-6,6'-disulfonate, 2 parts by weight of sodium oleoylmethyltaurinate, 1 part by weight of polyvinyl alcohol, 17 parts by weight of calcium carbonate and 50 parts by weight of water, then grinding the mixture in a bead mill and atomizing and drying the suspension thus obtained in a spray tower by means of a one-phase nozzle.

C. BIOLOGICAL EXAMPLES

Test Description

1. Pre-Emergence Herbicidal Action and Crop Plant Compatibility

Seeds of monocotyledonous and dicotyledonous weed plants and crop plants are placed in plastic or wood fiber pots and covered with soil. The compounds of the invention, formulated in the form of wettable powders (WP) or as emulsion concentrates (EC), are then applied onto the surface of the covering soil as aqueous suspension or emulsion with addition of 0.5% additive at a water application rate of 600 l/ha (converted). After the treatment, the pots are placed in a greenhouse and kept under good growth conditions for the trial plants. After about 3 weeks, the effect of the preparations is scored visually in comparison with untreated controls as percentages. For example, 100% activity=the plants have died, 0% activity=like control plants.

In the tables below, the following abbreviations are used:

Undesired Plants/Weeds:

ABUTH: *Abutilon theophrasti* ALOMY: *Alopecurus myosuroides*

AMARE: *Amaranthus retroflexus* AVEFA: *Avena fatua*

ECHCG: *Echinochloa crus-galli* HORMU: *Hordeum murinum*

LOLRI: *Lolium rigidum* PHBPU: *Pharbitis purpurea*

POLCO: *Polygonum convolvulus* SETVI: *Setaria viridis*

STEME: *Stellaria media* VERPE: *Veronica persica*

VIOTR: *Viola tricolor*

TABLE C1

Pre-emergence herbicidal activity against ALOMY in %

| Example number | Dosage [g/ha] | ALOMY |
|---|---|---|
| I-49 | 80 | 100 |
| I-11 | 80 | 100 |
| I-48 | 80 | 100 |
| I-35 | 80 | 100 |
| I-36 | 80 | 100 |
| I-37 | 80 | 100 |
| I-38 | 80 | 100 |
| I-45 | 80 | 100 |
| I-42 | 80 | 100 |
| I-10 | 80 | 100 |
| I-44 | 80 | 100 |
| I-12 | 80 | 100 |
| I-43 | 80 | 100 |
| I-41 | 80 | 100 |
| I-21 | 80 | 100 |
| I-46 | 80 | 100 |
| I-09 | 80 | 100 |
| I-26 | 80 | 100 |
| I-30 | 80 | 100 |
| I-28 | 80 | 100 |
| I-29 | 80 | 90 |
| I-27 | 80 | 90 |
| I-06 | 80 | 80 |
| I-01 | 80 | 100 |
| I-34 | 80 | 100 |
| I-32 | 80 | 100 |
| I-33 | 80 | 100 |
| I-19 | 80 | 90 |
| I-23 | 80 | 90 |

TABLE C2

Pre-emergence herbicidal activity against AVEVA in %

| Example number | Dosage [g/ha] | AVEFA |
|---|---|---|
| I-49 | 80 | 100 |
| I-11 | 80 | 100 |
| I-48 | 80 | 100 |
| I-35 | 80 | 100 |
| I-36 | 80 | 100 |
| I-37 | 80 | 100 |
| I-38 | 80 | 90 |
| I-45 | 80 | 100 |
| I-42 | 80 | 90 |
| I-10 | 80 | 100 |
| I-44 | 80 | 90 |
| I-12 | 80 | 100 |
| I-43 | 80 | 100 |
| I-41 | 80 | 100 |
| I-21 | 80 | 90 |
| I-46 | 80 | 80 |
| I-09 | 80 | 90 |
| I-26 | 80 | 90 |
| I-30 | 80 | 80 |
| I-28 | 80 | 100 |
| I-29 | 80 | 80 |
| I-27 | 80 | 90 |
| I-06 | 80 | 90 |
| I-01 | 80 | 90 |
| I-34 | 80 | 80 |
| I-19 | 80 | 80 |
| I-23 | 80 | 90 |

TABLE C3

Pre-emergence herbicidal activity against ECHCG in %

| Example number | Dosage [g/ha] | ECHCG |
|---|---|---|
| I-49 | 80 | 100 |
| I-11 | 80 | 100 |
| I-48 | 80 | 90 |
| I-35 | 80 | 100 |
| I-36 | 80 | 100 |
| I-37 | 80 | 90 |
| I-38 | 80 | 100 |
| I-45 | 80 | 100 |
| I-42 | 80 | 100 |
| I-10 | 80 | 100 |
| I-44 | 80 | 90 |
| I-12 | 80 | 90 |
| I-43 | 80 | 100 |
| I-41 | 80 | 100 |
| I-21 | 80 | 100 |
| I-46 | 80 | 90 |
| I-09 | 80 | 90 |
| I-26 | 80 | 90 |
| I-28 | 80 | 90 |
| I-06 | 80 | 80 |
| I-01 | 80 | 80 |
| I-34 | 80 | 80 |

TABLE C4

Pre-emergence herbicidal activity against LOLRI in %

| Example number | Dosage [g/ha] | LOLRI |
|---|---|---|
| I-49 | 80 | 100 |
| I-11 | 80 | 100 |
| I-48 | 80 | 100 |
| I-35 | 80 | 100 |
| I-36 | 80 | 100 |
| I-37 | 80 | 100 |
| I-38 | 80 | 100 |
| I-45 | 80 | 100 |
| I-42 | 80 | 100 |
| I-10 | 80 | 100 |
| I-44 | 80 | 100 |
| I-12 | 80 | 100 |
| I-43 | 80 | 100 |
| I-41 | 80 | 100 |
| I-46 | 80 | 100 |
| I-30 | 80 | 100 |
| I-34 | 80 | 100 |
| I-32 | 80 | 100 |
| I-39 | 80 | 100 |

TABLE C5

Pre-emergence herbicidal activity against SETVI in %

| Example number | Dosage [g/ha] | SETVI |
|---|---|---|
| I-49 | 80 | 100 |
| I-11 | 80 | 100 |
| I-48 | 80 | 100 |
| I-35 | 80 | 100 |
| I-36 | 80 | 100 |
| I-37 | 80 | 100 |
| I-38 | 80 | 100 |
| I-45 | 80 | 100 |
| I-42 | 80 | 100 |
| I-10 | 80 | 100 |
| I-44 | 80 | 100 |
| I-12 | 80 | 100 |
| I-43 | 80 | 100 |
| I-41 | 80 | 100 |
| I-21 | 80 | 90 |
| I-46 | 80 | 100 |
| I-09 | 80 | 80 |
| I-26 | 80 | 100 |
| I-30 | 80 | 100 |
| I-34 | 80 | 90 |
| I-32 | 80 | 100 |
| I-33 | 80 | 100 |
| I-05 | 80 | 90 |

TABLE C6

Pre-emergence herbicidal activity against ABUTH in %

| Example number | Dosage [g/ha] | ABUTH |
|---|---|---|
| I-11 | 80 | 80 |
| I-10 | 80 | 100 |
| I-09 | 80 | 100 |
| I-06 | 80 | 100 |
| I-08 | 80 | 100 |
| I-04 | 80 | 100 |
| I-02 | 80 | 100 |
| I-14 | 80 | 100 |

TABLE C7

Pre-emergence herbicidal activity against AMARE in %

| Example number | Dosage [g/ha] | AMARE |
|---|---|---|
| I-49 | 80 | 100 |
| I-11 | 80 | 100 |
| I-48 | 80 | 100 |
| I-35 | 80 | 100 |
| I-36 | 80 | 100 |
| I-37 | 80 | 100 |
| I-38 | 80 | 100 |
| I-45 | 80 | 100 |
| I-42 | 80 | 100 |
| I-10 | 80 | 90 |
| I-44 | 80 | 90 |
| I-12 | 80 | 100 |
| I-43 | 80 | 90 |
| I-41 | 80 | 90 |
| I-21 | 80 | 100 |
| I-46 | 80 | 90 |
| I-09 | 80 | 80 |
| I-26 | 80 | 100 |
| I-30 | 80 | 80 |
| I-28 | 80 | 90 |
| I-29 | 80 | 90 |
| I-27 | 80 | 90 |
| I-32 | 80 | 90 |
| I-23 | 80 | 80 |
| I-03 | 80 | 80 |
| I-24 | 80 | 80 |
| I-07 | 80 | 90 |

TABLE C8

Pre-emergence herbicidal activity against PHBPU in %

| Example number | Dosage [g/ha] | PHBPU |
|---|---|---|
| I-49 | 80 | 90 |
| I-11 | 80 | 100 |
| I-48 | 80 | 90 |
| I-35 | 80 | 90 |
| I-36 | 80 | 90 |
| I-37 | 80 | 90 |
| I-45 | 80 | 90 |
| I-42 | 80 | 90 |
| I-10 | 80 | 80 |
| I-44 | 80 | 80 |
| I-41 | 80 | 90 |
| I-21 | 80 | 80 |
| I-26 | 80 | 90 |
| I-28 | 80 | 90 |
| I-06 | 80 | 80 |

TABLE C9

Pre-emergence herbicidal activity against POLCO in %

| Example number | Dosage [g/ha] | POLCO |
|---|---|---|
| I-49 | 80 | 100 |
| I-11 | 80 | 100 |
| I-48 | 80 | 100 |
| I-35 | 80 | 100 |
| I-36 | 80 | 100 |
| I-37 | 80 | 100 |
| I-38 | 80 | 100 |
| I-45 | 80 | 100 |
| I-42 | 80 | 100 |
| I-44 | 80 | 100 |
| I-12 | 80 | 100 |
| I-43 | 80 | 100 |

TABLE C9-continued

Pre-emergence herbicidal activity against POLCO in %

| Example number | Dosage [g/ha] | POLCO |
|---|---|---|
| I-41 | 80 | 90 |
| I-10 | 80 | 100 |
| I-21 | 80 | 90 |
| I-46 | 80 | 90 |
| I-09 | 80 | 100 |
| I-30 | 80 | 90 |
| I-29 | 80 | 100 |
| I-27 | 80 | 80 |
| I-06 | 80 | 100 |
| I-01 | 80 | 80 |
| I-34 | 80 | 90 |
| I-32 | 80 | 90 |
| I-33 | 80 | 90 |
| I-19 | 80 | 90 |
| I-39 | 80 | 80 |
| I-08 | 80 | 80 |
| I-47 | 80 | 90 |
| I-03 | 80 | 80 |
| I-04 | 80 | 90 |
| I-05 | 80 | 80 |
| I-07 | 80 | 80 |

TABLE C10

Pre-emergence herbicidal activity against STEME in %

| Example number | Dosage [g/ha] | STEME |
|---|---|---|
| I-49 | 80 | 100 |
| I-11 | 80 | 100 |
| I-48 | 80 | 100 |
| I-35 | 80 | 100 |
| I-36 | 80 | 100 |
| I-37 | 80 | 100 |
| I-38 | 80 | 100 |
| I-45 | 80 | 100 |
| I-42 | 80 | 100 |
| I-10 | 80 | 100 |
| I-44 | 80 | 90 |
| I-12 | 80 | 100 |
| I-43 | 80 | 100 |
| I-41 | 80 | 100 |
| I-21 | 80 | 100 |
| I-46 | 80 | 100 |
| I-26 | 80 | 100 |
| I-30 | 80 | 90 |
| I-28 | 80 | 100 |
| I-29 | 80 | 90 |
| I-27 | 80 | 90 |
| I-01 | 80 | 90 |
| I-34 | 80 | 90 |
| I-32 | 80 | 90 |
| I-33 | 80 | 100 |
| I-19 | 80 | 80 |
| I-25 | 80 | 100 |

TABLE C11

Pre-emergence herbicidal activity against VIOTR in %

| Example number | Dosage [g/ha] | VIOTR |
|---|---|---|
| I-49 | 80 | 100 |
| I-11 | 80 | 100 |
| I-48 | 80 | 100 |
| I-35 | 80 | 100 |
| I-36 | 80 | 100 |
| I-37 | 80 | 100 |

TABLE C11-continued

Pre-emergence herbicidal activity against VIOTR in %

| Example number | Dosage [g/ha] | VIOTR |
|---|---|---|
| I-38 | 80 | 100 |
| I-45 | 80 | 100 |
| I-42 | 80 | 100 |
| I-10 | 80 | 100 |
| I-44 | 80 | 80 |
| I-12 | 80 | 100 |
| I-43 | 80 | 90 |
| I-27 | 80 | 90 |
| I-06 | 80 | 80 |

TABLE C12

Pre-emergence herbicidal activity against VERPE in %

| Example number | Dosage [g/ha] | VERPE |
|---|---|---|
| I-49 | 80 | 100 |
| I-11 | 80 | 100 |
| I-48 | 80 | 100 |
| I-35 | 80 | 100 |
| I-36 | 80 | 100 |
| I-37 | 80 | 100 |
| I-38 | 80 | 100 |
| I-45 | 80 | 80 |
| I-42 | 80 | 90 |
| I-10 | 80 | 100 |
| I-44 | 80 | 80 |
| I-12 | 80 | 100 |
| I-43 | 80 | 90 |
| I-21 | 80 | 100 |
| I-46 | 80 | 80 |
| I-09 | 80 | 90 |
| I-26 | 80 | 100 |
| I-28 | 80 | 90 |
| I-29 | 80 | 100 |
| I-27 | 80 | 90 |
| I-01 | 80 | 80 |
| I-33 | 80 | 100 |
| I-19 | 80 | 90 |
| I-08 | 80 | 90 |
| I-25 | 80 | 100 |
| I-24 | 80 | 100 |

TABLE C13

Pre-emergence herbicidal activity against HORMU in %

| Example number | Dosage [g/ha] | HORMU |
|---|---|---|
| I-49 | 80 | 100 |
| I-11 | 80 | 100 |
| I-48 | 80 | 100 |
| I-35 | 80 | 100 |
| I-36 | 80 | 90 |
| I-37 | 80 | 100 |
| I-38 | 80 | 90 |
| I-45 | 80 | 100 |
| I-42 | 80 | 100 |
| I-10 | 80 | 100 |
| I-44 | 80 | 100 |
| I-12 | 80 | 100 |
| I-43 | 80 | 90 |
| I-41 | 80 | 100 |
| I-46 | 80 | 100 |
| I-30 | 80 | 90 |
| I-33 | 80 | 80 |

TABLE C13-continued

Pre-emergence herbicidal activity against HORMU in %

| Example number | Dosage [g/ha] | HORMU |
|---|---|---|
| I-39 | 80 | 100 |
| I-47 | 80 | 90 |

As shown by the results, compounds according to the invention such as, for example, the compounds No. I-21 and other compounds from the tables (for example I-10, I-26, I-09, I-30, I-28, I-29, I-27, I-01, I-06, I-34, I-19, I-11, I-36, I-37, I-38, I-41, I-42, I-43, I-44, I-46, I-49) have, when used for pre-emergence treatment, very good activity (80% to 100% herbicidal action) against harmful plants such as *Abutilon theophrasti, Alopecurus myosuroides, Amaranthus retroflexus, Avena fatua, Echinochloa crus-galli, Hordeum murinum, Lolium rigidum, Pharbitis purpurea, Polygonum convolvulus, Setaria viridis, Stellaria media, Veronica persica* and *Viola tricolor* at an application rate of 0.08 kg of active substance or less per hectare.

2. Post-Emergence Herbicidal Action and Crop Plant Compatibility

Seeds of monocotyledonous and dicotyledonous weeds and crop plants are placed in sandy loam in plastic or wood-fiber pots, covered with soil and cultivated in a greenhouse under controlled growth conditions. 2 to 3 weeks after sowing, the test plants are treated at the one-leaf stage. The compounds of the invention, formulated in the form of wettable powders (WP) or as emulsion concentrates (EC), are then sprayed onto the green parts of the plants as aqueous suspension or emulsion with addition of 0.5% additive at a water application rate of 600 l/ha (converted). After the test plants had been kept in the greenhouse under optimum growth conditions for about 3 weeks, the activity of the preparations is rated visually in comparison to untreated controls. For example, 100% activity=the plants have died, 0% activity=like control plants.

TABLE C14

Post-emergence herbicidal activity against ALOMY in %

| Example number | Dosage [g/ha] | ALOMY |
|---|---|---|
| I-54 | 320 | 90 |
| I-10 | 320 | 100 |
| I-56 | 320 | 90 |
| I-53 | 320 | 90 |
| I-52 | 320 | 90 |
| I-48 | 320 | 90 |
| I-55 | 320 | 90 |
| I-50 | 320 | 90 |
| I-46 | 320 | 100 |
| I-51 | 320 | 100 |
| I-42 | 320 | 100 |
| I-36 | 320 | 90 |
| I-43 | 320 | 100 |
| I-44 | 320 | 100 |
| I-45 | 320 | 100 |
| I-19 | 320 | 90 |
| I-06 | 320 | 90 |
| I-41 | 320 | 100 |
| I-28 | 320 | 90 |
| I-35 | 320 | 100 |
| I-01 | 320 | 100 |
| I-38 | 320 | 90 |
| I-39 | 320 | 100 |
| I-47 | 320 | 100 |
| I-32 | 320 | 90 |

TABLE C14-continued

Post-emergence herbicidal activity against ALOMY in %

| Example number | Dosage [g/ha] | ALOMY |
|---|---|---|
| I-11 | 320 | 90 |
| I-12 | 320 | 90 |
| I-29 | 320 | 90 |
| I-26 | 320 | 90 |
| I-33 | 320 | 100 |
| I-34 | 320 | 100 |
| I-21 | 320 | 90 |
| I-49 | 320 | 90 |
| I-09 | 320 | 90 |
| I-04 | 320 | 90 |
| I-30 | 320 | 100 |
| I-14 | 320 | 100 |
| I-05 | 320 | 90 |
| I-03 | 320 | 90 |
| I-20 | 320 | 90 |
| I-27 | 320 | 90 |
| I-40 | 320 | 90 |
| I-07 | 320 | 90 |
| I-23 | 320 | 100 |
| I-25 | 320 | 100 |
| I-13 | 320 | 90 |
| I-02 | 320 | 80 |
| I-24 | 320 | 90 |
| I-18 | 320 | 80 |

TABLE C15

Post-emergence herbicidal activity against AVEFA in %

| Example number | Dosage [g/ha] | AVEFA |
|---|---|---|
| I-54 | 320 | 90 |
| I-10 | 320 | 100 |
| I-56 | 320 | 100 |
| I-53 | 320 | 90 |
| I-52 | 320 | 90 |
| I-48 | 320 | 80 |
| I-55 | 320 | 90 |
| I-50 | 320 | 100 |
| I-46 | 320 | 100 |
| I-51 | 320 | 100 |
| I-42 | 320 | 100 |
| I-36 | 320 | 90 |
| I-43 | 320 | 100 |
| I-44 | 320 | 100 |
| I-45 | 320 | 100 |
| I-19 | 320 | 100 |
| I-06 | 320 | 90 |
| I-41 | 320 | 100 |
| I-28 | 320 | 100 |
| I-35 | 320 | 100 |
| I-01 | 320 | 100 |
| I-38 | 320 | 90 |
| I-39 | 320 | 100 |
| I-47 | 320 | 100 |
| I-32 | 320 | 100 |
| I-11 | 320 | 100 |
| I-12 | 320 | 100 |
| I-37 | 320 | 100 |
| I-29 | 320 | 90 |
| I-26 | 320 | 90 |
| I-33 | 320 | 100 |
| I-34 | 320 | 100 |
| I-21 | 320 | 90 |
| I-49 | 320 | 80 |
| I-09 | 320 | 90 |
| I-04 | 320 | 100 |
| I-30 | 320 | 100 |
| I-14 | 320 | 100 |
| I-05 | 320 | 100 |
| I-03 | 320 | 80 |

TABLE C15-continued

Post-emergence herbicidal activity against AVEFA in %

| Example number | Dosage [g/ha] | AVEFA |
|---|---|---|
| I-20 | 320 | 90 |
| I-27 | 320 | 90 |
| I-07 | 320 | 90 |
| I-23 | 320 | 100 |
| I-25 | 320 | 100 |
| I-13 | 320 | 90 |
| I-08 | 320 | 100 |
| I-24 | 320 | 90 |
| I-18 | 320 | 100 |
| I-17 | 320 | 80 |

TABLE C16

Post-emergence herbicidal activity against ECHCG in %

| Example number | Dosage [g/ha] | ECHCG |
|---|---|---|
| I-54 | 320 | 90 |
| I-10 | 320 | 100 |
| I-56 | 320 | 90 |
| I-53 | 320 | 90 |
| I-52 | 320 | 90 |
| I-48 | 320 | 90 |
| I-55 | 320 | 90 |
| I-50 | 320 | 90 |
| I-46 | 320 | 100 |
| I-51 | 320 | 90 |
| I-42 | 320 | 100 |
| I-36 | 320 | 90 |
| I-43 | 320 | 100 |
| I-44 | 320 | 100 |
| I-45 | 320 | 100 |
| I-19 | 320 | 90 |
| I-06 | 320 | 90 |
| I-41 | 320 | 100 |
| I-28 | 320 | 80 |
| I-35 | 320 | 100 |
| I-01 | 320 | 90 |
| I-38 | 320 | 90 |
| I-39 | 320 | 100 |
| I-47 | 320 | 100 |
| I-32 | 320 | 90 |
| I-11 | 320 | 90 |
| I-12 | 320 | 90 |
| I-37 | 320 | 90 |
| I-29 | 320 | 90 |
| I-26 | 320 | 90 |
| I-33 | 320 | 80 |
| I-34 | 320 | 90 |
| I-21 | 320 | 80 |
| I-49 | 320 | 80 |
| I-09 | 320 | 80 |
| I-04 | 320 | 90 |
| I-30 | 320 | 80 |
| I-14 | 320 | 80 |
| I-05 | 320 | 90 |
| I-03 | 320 | 80 |
| I-20 | 320 | 80 |
| I-40 | 320 | 80 |
| I-07 | 320 | 80 |
| I-23 | 320 | 90 |
| I-13 | 320 | 80 |
| I-02 | 320 | 90 |
| I-08 | 320 | 90 |

TABLE C17

Post-emergence herbicidal activity against LOLRI in %

| Example number | Dosage [g/ha] | LOLRI |
|---|---|---|
| I-54 | 320 | 90 |
| I-10 | 320 | 100 |
| I-56 | 320 | 90 |
| I-53 | 320 | 90 |
| I-52 | 320 | 90 |
| I-48 | 320 | 90 |
| I-55 | 320 | 90 |
| I-50 | 320 | 90 |
| I-46 | 320 | 100 |
| I-51 | 320 | 90 |
| I-42 | 320 | 100 |
| I-36 | 320 | 90 |
| I-43 | 320 | 100 |
| I-44 | 320 | 100 |
| I-45 | 320 | 100 |
| I-41 | 320 | 100 |
| I-35 | 320 | 100 |
| I-38 | 320 | 90 |
| I-39 | 320 | 100 |
| I-47 | 320 | 100 |
| I-32 | 320 | 100 |
| I-11 | 320 | 100 |
| I-12 | 320 | 100 |
| I-37 | 320 | 90 |
| I-33 | 320 | 100 |
| I-34 | 320 | 90 |
| I-49 | 320 | 90 |
| I-30 | 320 | 100 |
| I-23 | 320 | 90 |
| I-24 | 320 | 90 |

TABLE C18

Post-emergence herbicidal activity against SETVI in %

| Example number | Dosage [g/ha] | SETVI |
|---|---|---|
| I-54 | 320 | 90 |
| I-10 | 320 | 90 |
| I-56 | 320 | 90 |
| I-53 | 320 | 90 |
| I-52 | 320 | 90 |
| I-48 | 320 | 80 |
| I-55 | 320 | 90 |
| I-50 | 320 | 90 |
| I-46 | 320 | 80 |
| I-51 | 320 | 90 |
| I-42 | 320 | 90 |
| I-36 | 320 | 80 |
| I-43 | 320 | 80 |
| I-44 | 320 | 90 |
| I-45 | 320 | 90 |
| I-19 | 320 | 80 |
| I-06 | 320 | 80 |
| I-41 | 320 | 90 |
| I-28 | 320 | 80 |
| I-35 | 320 | 90 |
| I-01 | 320 | 90 |
| I-38 | 320 | 100 |
| I-39 | 320 | 90 |
| I-47 | 320 | 80 |
| I-32 | 320 | 90 |
| I-11 | 320 | 90 |
| I-12 | 320 | 90 |
| I-37 | 320 | 80 |
| I-29 | 320 | 80 |
| I-26 | 320 | 80 |
| I-33 | 320 | 90 |
| I-34 | 320 | 90 |
| I-21 | 320 | 80 |
| I-09 | 320 | 80 |
| I-04 | 320 | 80 |
| I-30 | 320 | 90 |
| I-14 | 320 | 80 |
| I-05 | 320 | 90 |
| I-03 | 320 | 80 |
| I-20 | 320 | 80 |
| I-27 | 320 | 80 |
| I-40 | 320 | 80 |
| I-07 | 320 | 80 |
| I-13 | 320 | 80 |
| I-02 | 320 | 80 |
| I-08 | 320 | 80 |

TABLE C19

Post-emergence herbicidal activity against ABUTH in %

| Example number | Dosage [g/ha] | ABUTH |
|---|---|---|
| I-54 | 320 | 90 |
| I-10 | 320 | 90 |
| I-56 | 320 | 90 |
| I-53 | 320 | 90 |
| I-52 | 320 | 90 |
| I-48 | 320 | 80 |
| I-55 | 320 | 90 |
| I-50 | 320 | 90 |
| I-46 | 320 | 80 |
| I-51 | 320 | 80 |
| I-42 | 320 | 80 |
| I-36 | 320 | 90 |
| I-43 | 320 | 80 |
| I-44 | 320 | 80 |
| I-45 | 320 | 80 |
| I-19 | 320 | 80 |
| I-41 | 320 | 80 |
| I-28 | 320 | 80 |
| I-35 | 320 | 80 |
| I-01 | 320 | 80 |
| I-38 | 320 | 80 |
| I-39 | 320 | 80 |
| I-47 | 320 | 80 |
| I-32 | 320 | 80 |
| I-11 | 320 | 90 |
| I-12 | 320 | 90 |
| I-37 | 320 | 80 |
| I-29 | 320 | 80 |
| I-34 | 320 | 80 |
| I-25 | 320 | 80 |

TABLE C20

Post-emergence herbicidal activity against AMARE in %

| Example number | Dosage [g/ha] | AMARE |
|---|---|---|
| I-54 | 320 | 80 |
| I-10 | 320 | 80 |
| I-56 | 320 | 90 |
| I-53 | 320 | 90 |
| I-52 | 320 | 90 |
| I-48 | 320 | 80 |
| I-55 | 320 | 80 |
| I-50 | 320 | 80 |
| I-46 | 320 | 80 |
| I-51 | 320 | 80 |
| I-42 | 320 | 80 |
| I-36 | 320 | 90 |

TABLE C20-continued

Post-emergence herbicidal activity against AMARE in %

| Example number | Dosage [g/ha] | AMARE |
|---|---|---|
| I-43 | 320 | 80 |
| I-44 | 320 | 80 |
| I-45 | 320 | 80 |
| I-19 | 320 | 90 |
| I-06 | 320 | 80 |
| I-41 | 320 | 100 |
| I-28 | 320 | 80 |
| I-35 | 320 | 90 |
| I-01 | 320 | 80 |
| I-38 | 320 | 100 |
| I-39 | 320 | 80 |
| I-32 | 320 | 80 |
| I-11 | 320 | 90 |
| I-12 | 320 | 90 |
| I-37 | 320 | 80 |
| I-26 | 320 | 80 |
| I-33 | 320 | 90 |
| I-34 | 320 | 80 |
| I-21 | 320 | 100 |
| I-20 | 320 | 80 |
| I-40 | 320 | 80 |
| I-23 | 320 | 80 |

TABLE C21

Post-emergence herbicidal activity against PHBPU in %

| Example number | Dosage [g/ha] | PHBPU |
|---|---|---|
| I-54 | 320 | 90 |
| I-10 | 320 | 90 |
| I-56 | 320 | 90 |
| I-53 | 320 | 90 |
| I-52 | 320 | 90 |
| I-48 | 320 | 80 |
| I-55 | 320 | 90 |
| I-50 | 320 | 90 |
| I-46 | 320 | 90 |
| I-51 | 320 | 90 |
| I-42 | 320 | 90 |
| I-36 | 320 | 80 |
| I-43 | 320 | 90 |
| I-44 | 320 | 90 |
| I-45 | 320 | 90 |
| I-19 | 320 | 80 |
| I-06 | 320 | 90 |
| I-41 | 320 | 90 |
| I-28 | 320 | 80 |
| I-35 | 320 | 90 |
| I-01 | 320 | 90 |
| I-38 | 320 | 90 |
| I-39 | 320 | 90 |
| I-47 | 320 | 90 |
| I-32 | 320 | 90 |
| I-11 | 320 | 90 |
| I-12 | 320 | 90 |
| I-37 | 320 | 90 |
| I-29 | 320 | 80 |
| I-26 | 320 | 80 |
| I-33 | 320 | 90 |
| I-34 | 320 | 90 |
| I-21 | 320 | 80 |
| I-49 | 320 | 80 |
| I-09 | 320 | 90 |
| I-04 | 320 | 90 |
| I-30 | 320 | 90 |
| I-14 | 320 | 80 |
| I-05 | 320 | 90 |
| I-03 | 320 | 90 |
| I-20 | 320 | 80 |
| I-27 | 320 | 80 |
| I-40 | 320 | 90 |
| I-07 | 320 | 90 |
| I-23 | 320 | 90 |
| I-25 | 320 | 80 |
| I-13 | 320 | 90 |
| I-02 | 320 | 90 |
| I-08 | 320 | 90 |
| I-24 | 320 | 80 |

TABLE C22

Post-emergence herbicidal activity against POLCO in %

| Example number | Dosage [g/ha] | POLCO |
|---|---|---|
| I-54 | 320 | 90 |
| I-10 | 320 | 80 |
| I-56 | 320 | 90 |
| I-53 | 320 | 90 |
| I-52 | 320 | 90 |
| I-48 | 320 | 80 |
| I-55 | 320 | 90 |
| I-50 | 320 | 90 |
| I-46 | 320 | 80 |
| I-51 | 320 | 90 |
| I-42 | 320 | 80 |
| I-36 | 320 | 80 |
| I-43 | 320 | 80 |
| I-44 | 320 | 80 |
| I-45 | 320 | 80 |
| I-19 | 320 | 80 |
| I-06 | 320 | 80 |
| I-41 | 320 | 90 |
| I-28 | 320 | 80 |
| I-01 | 320 | 80 |
| I-39 | 320 | 80 |
| I-47 | 320 | 80 |
| I-32 | 320 | 80 |
| I-11 | 320 | 90 |
| I-12 | 320 | 90 |
| I-29 | 320 | 80 |
| I-33 | 320 | 80 |
| I-49 | 320 | 80 |
| I-09 | 320 | 80 |
| I-04 | 320 | 80 |
| I-30 | 320 | 80 |
| I-14 | 320 | 90 |
| I-05 | 320 | 90 |
| I-03 | 320 | 80 |
| I-20 | 320 | 80 |
| I-27 | 320 | 80 |
| I-40 | 320 | 80 |
| I-07 | 320 | 80 |
| I-23 | 320 | 90 |
| I-25 | 320 | 80 |
| I-13 | 320 | 80 |
| I-02 | 320 | 90 |
| I-08 | 320 | 80 |
| I-24 | 320 | 90 |
| I-17 | 320 | 90 |
| I-22 | 320 | 90 |

TABLE C23

Post-emergence herbicidal activity against STEME in %

| Example number | Dosage [g/ha] | STEME |
| --- | --- | --- |
| I-54 | 320 | 90 |
| I-10 | 320 | 90 |
| I-56 | 320 | 90 |
| I-53 | 320 | 90 |
| I-52 | 320 | 90 |
| I-48 | 320 | 90 |
| I-55 | 320 | 90 |
| I-50 | 320 | 90 |
| I-46 | 320 | 90 |
| I-51 | 320 | 90 |
| I-42 | 320 | 90 |
| I-36 | 320 | 90 |
| I-43 | 320 | 100 |
| I-44 | 320 | 90 |
| I-45 | 320 | 90 |
| I-19 | 320 | 90 |
| I-06 | 320 | 80 |
| I-41 | 320 | 90 |
| I-28 | 320 | 80 |
| I-35 | 320 | 90 |
| I-01 | 320 | 90 |
| I-38 | 320 | 90 |
| I-39 | 320 | 90 |
| I-47 | 320 | 90 |
| I-32 | 320 | 90 |
| I-11 | 320 | 90 |
| I-12 | 320 | 90 |
| I-37 | 320 | 90 |
| I-29 | 320 | 80 |
| I-26 | 320 | 90 |
| I-33 | 320 | 90 |
| I-34 | 320 | 90 |
| I-21 | 320 | 80 |
| I-49 | 320 | 90 |
| I-09 | 320 | 90 |
| I-04 | 320 | 90 |
| I-30 | 320 | 90 |
| I-14 | 320 | 90 |
| I-05 | 320 | 90 |
| I-03 | 320 | 90 |
| I-20 | 320 | 80 |
| I-27 | 320 | 80 |
| I-40 | 320 | 80 |
| I-07 | 320 | 90 |
| I-23 | 320 | 90 |
| I-25 | 320 | 90 |

TABLE C24

Post-emergence herbicidal activity against VIOTR in %

| Example number | Dosage [g/ha] | VIOTR |
| --- | --- | --- |
| I-54 | 320 | 90 |
| I-56 | 320 | 90 |
| I-53 | 320 | 90 |
| I-52 | 320 | 90 |
| I-48 | 320 | 80 |
| I-55 | 320 | 90 |
| I-50 | 320 | 90 |
| I-46 | 320 | 90 |
| I-51 | 320 | 90 |
| I-42 | 320 | 90 |
| I-36 | 320 | 90 |
| I-43 | 320 | 90 |
| I-44 | 320 | 90 |
| I-45 | 320 | 90 |
| I-19 | 320 | 80 |
| I-06 | 320 | 90 |
| I-41 | 320 | 80 |
| I-28 | 320 | 80 |
| I-35 | 320 | 80 |
| I-01 | 320 | 90 |
| I-38 | 320 | 80 |
| I-39 | 320 | 80 |
| I-47 | 320 | 80 |
| I-11 | 320 | 90 |
| I-12 | 320 | 100 |
| I-37 | 320 | 80 |
| I-29 | 320 | 80 |
| I-26 | 320 | 80 |
| I-21 | 320 | 80 |
| I-49 | 320 | 80 |
| I-09 | 320 | 80 |
| I-04 | 320 | 80 |
| I-10 | 320 | 80 |
| I-27 | 320 | 80 |
| I-02 | 320 | 80 |
| I-08 | 320 | 80 |

TABLE C25

Post-emergence herbicidal activity against VERPE in %

| Example number | Dosage [g/ha] | VERPE |
| --- | --- | --- |
| I-54 | 320 | 90 |
| I-56 | 320 | 90 |
| I-53 | 320 | 90 |
| I-52 | 320 | 90 |
| I-48 | 320 | 80 |
| I-55 | 320 | 90 |
| I-50 | 320 | 90 |
| I-46 | 320 | 80 |
| I-51 | 320 | 90 |
| I-42 | 320 | 80 |
| I-36 | 320 | 90 |
| I-43 | 320 | 90 |
| I-44 | 320 | 80 |
| I-45 | 320 | 80 |
| I-19 | 320 | 80 |
| I-06 | 320 | 80 |
| I-41 | 320 | 80 |
| I-28 | 320 | 90 |
| I-35 | 320 | 80 |
| I-01 | 320 | 80 |
| I-38 | 320 | 80 |
| I-39 | 320 | 80 |
| I-47 | 320 | 80 |
| I-32 | 320 | 80 |
| I-37 | 320 | 80 |
| I-29 | 320 | 90 |
| I-26 | 320 | 90 |
| I-33 | 320 | 80 |
| I-34 | 320 | 80 |
| I-21 | 320 | 100 |
| I-49 | 320 | 80 |
| I-09 | 320 | 80 |
| I-04 | 320 | 80 |
| I-30 | 320 | 80 |
| I-14 | 320 | 80 |
| I-10 | 320 | 80 |
| I-05 | 320 | 80 |
| I-03 | 320 | 80 |
| I-20 | 320 | 90 |
| I-27 | 320 | 80 |
| I-40 | 320 | 80 |
| I-07 | 320 | 80 |
| I-25 | 320 | 80 |
| I-13 | 320 | 80 |

TABLE C25-continued

Post-emergence herbicidal activity against VERPE in %

| Example number | Dosage [g/ha] | VERPE |
|---|---|---|
| I-02 | 320 | 80 |
| I-08 | 320 | 80 |
| I-18 | 320 | 80 |

TABLE C26

Post-emergence herbicidal activity against HORMU in %

| Example number | Dosage [g/ha] | HORMU |
|---|---|---|
| I-54 | 320 | 90 |
| I-10 | 320 | 100 |
| I-56 | 320 | 90 |
| I-53 | 320 | 90 |
| I-52 | 320 | 90 |
| I-48 | 320 | 90 |
| I-55 | 320 | 100 |
| I-50 | 320 | 100 |
| I-46 | 320 | 100 |
| I-51 | 320 | 90 |
| I-42 | 320 | 100 |
| I-36 | 320 | 90 |
| I-43 | 320 | 100 |
| I-44 | 320 | 100 |
| I-45 | 320 | 100 |
| I-41 | 320 | 100 |
| I-35 | 320 | 100 |
| I-38 | 320 | 90 |
| I-39 | 320 | 100 |
| I-47 | 320 | 100 |
| I-32 | 320 | 90 |
| I-11 | 320 | 100 |
| I-12 | 320 | 90 |
| I-37 | 320 | 80 |
| I-33 | 320 | 90 |
| I-34 | 320 | 100 |
| I-30 | 320 | 100 |
| I-40 | 320 | 90 |
| I-23 | 320 | 100 |
| I-24 | 320 | 90 |

As shown by the results, compounds according to the invention such as, for example, the compounds No. I-35 and other compounds from the tables (for example I-28, I-38, I-01, I-19, I-36, I-29, I-32, I-11, I-12, I-37, I-06, I-09, I-33, I-34, I-13, I-04, I-26, I-21, I-30, I-05, I-03, I-20, I-27, I-14, I-10, I-23, I-07, I-25, I-02, I-08, I-24, I-41, I-42, I-43, I-44, I-46, I-49, I-54, I-55, I-56) have, when used for post-emergence treatment, very good herbicidal activity (80% to 100% herbicidal action) against harmful plants such as *Abutilon theophrasti, Alopecurus myosuroides, Amaranthus retroflexus, Avena fatua, Echinochloa crus-galli, Hordeum murinum, Lolium rigidum, Pharbitis purpurea, Polygonum convolvulus, Setaria viridis, Stellaria media, Veronica persica* and *Viola tricolor* at an application rate of 0.32 kg of active substance or less per hectare.

The invention claimed is:

1. A 3-phenylisoxazoline-5-carboxamide or -5-thioamide of formula (I)

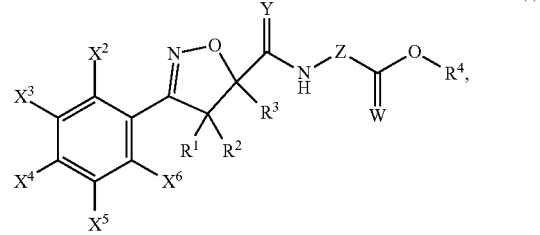

and/or an agrochemically acceptable salt thereof wherein
$R^1$ and $R^2$ independently of one another represent hydrogen, fluorine, chlorine or cyano,
or
represent $(C_1-C_3)$-alkyl or $(C_1-C_3)$-alkoxy, each of which is substituted by m radicals from the group consisting of fluorine, chlorine, bromine and cyano;
$R^3$ represents $(C_1-C_4)$-alkyl, $(C_3-C_5)$-cycloalkyl, $(C_2-C_4)$-alkenyl, $(C_2-C_4)$-alkynyl or $(C_1-C_4)$-alkoxy, each of which is substituted by m radicals from the group consisting of fluorine, chlorine, bromine, cyano, $(C_1-C_4)$-alkoxy and hydroxy;
$R^4$ represents hydrogen,
or
represents $(C_1-C_{12})$-alkyl, $(C_3-C_7)$-cycloalkyl, $(C_3-C_7)$-cycloalkyl-$(C_1-C_8)$-alkyl, $(C_2-C_6)$-alkenyl, $(C_5-C_6)$-cycloalkenyl or $(C_2-C_8)$-alkynyl, each of which is substituted by m radicals from the group consisting of halogen, cyano, $(C_1-C_6)$-alkoxy, hydroxy and aryl;
Y represents oxygen or sulfur;
W represents oxygen or sulfur;
Z represents a fully saturated or partially saturated furan ring which is substituted by k radicals from $R^5$,

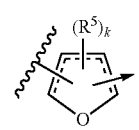

where the arrow in each case denotes a bond to the group C=W of formula (I);
$R^5$ represents fluorine, chlorine, cyano or $CO_2R^7$,
or
represents $(C_1-C_2)$-alkyl or $(C_1-C_2)$-alkoxy, each of which is substituted by m radicals from the group consisting of fluorine and chlorine;
$X^2$, $X^4$ and $X^6$ independently of one another each represent hydrogen, fluorine, chlorine, bromine or cyano,
or
represent $(C_1-C_2)$-alkyl, in each case substituted by m radicals from the group consisting of fluorine, chlorine, bromine and $(C_1-C_2)$-alkoxy;
$X^3$ and $X^5$ independently of one another represent hydrogen, fluorine, chlorine, bromine, iodine, hydroxy, cyano, nitro, $S(O)_nR^6$ or $CO_2R^7$, or represent $(C_1-C_3)$-alkyl, $(C_1-C_3)$-alkoxy, $(C_3-C_4)$-cycloalkyl, $(C_2-C_3)$-alkenyl or $(C_2-C_3)$-alkynyl, each of which is substituted by m radicals from the group consisting of fluorine, chlorine and bromine;

$R^6$ represents $(C_1-C_2)$-alkyl or $(C_3-C_4)$-cycloalkyl, each of which is substituted by m radicals from the group consisting of fluorine and chlorine;

$R^7$ represents hydrogen, or represents $(C_1-C_3)$-alkyl or $(C_3-C_5)$-cycloalkyl, each of which is substituted by m radicals from the group consisting of fluorine, chlorine and $(C_1-C_2)$-alkoxy;

k represents 0, 1 or 2;

m represents 0, 1, 2, 3, 4 or 5; and n represents 0, 1 or 2.

2. The compound as claimed in claim 1, where $R^1$ and $R^2$ independently of one another each represent hydrogen, fluorine, chlorine or cyano, or represent methyl or methoxy, each of which is substituted by m radicals from the group consisting of fluorine and chlorine.

3. The compound as claimed in claim 1, where $R^3$ represents $(C_1-C_3)$-alkyl, $(C_3-C_4)$-cycloalkyl, $(C_2-C_3)$-alkenyl, $(C_2-C_3)$-alkynyl or $(C_1-C_3)$-alkoxy, each of which is substituted by m radicals from the group consisting of fluorine, chlorine, bromine, cyano, $(C_1-C_2)$-alkoxy and hydroxy.

4. The compound as claimed in claim 1, where $R^4$ represents hydrogen, or represents $(C_1-C_6)$-alkyl, $(C_3-C_6)$-cycloalkyl, $(C_3-C_6)$-cycloalkyl-$(C_1-C_6)$-alkyl, $(C_2-C_6)$-alkenyl, $(C_5-C_6)$-cycloalkenyl or $(C_2-C_6)$-alkynyl, each of which is substituted by m radicals from the group consisting of fluorine, chlorine, bromine, cyano, $(C_1-C_4)$-alkoxy, hydroxy and aryl.

5. The compound of formula (I) as claimed in claim 1, wherein each of Y and W represents oxygen.

6. The compound as claimed in claim 1, where Z represents a group Z-1 to Z-33, where Z-1 to Z-33 have the following meaning:

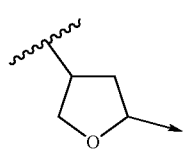

Z-1

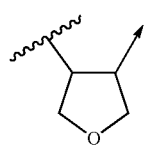

Z-2

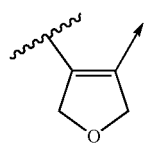

Z-3

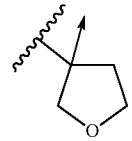

Z-4

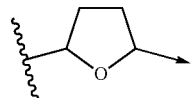

Z-5

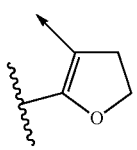

Z-6

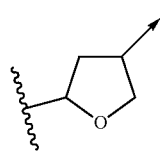

Z-7

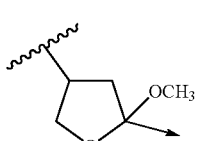

Z-8

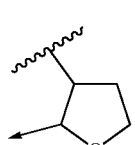

Z-9

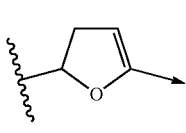

Z-10

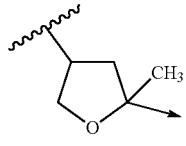

Z-11

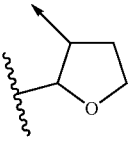

Z-12

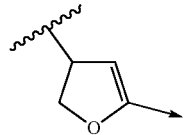

Z-13

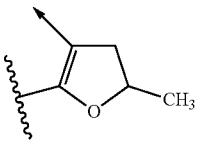

Z-14

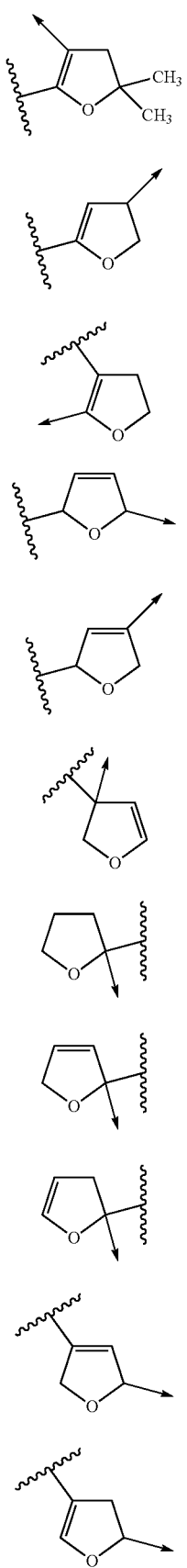
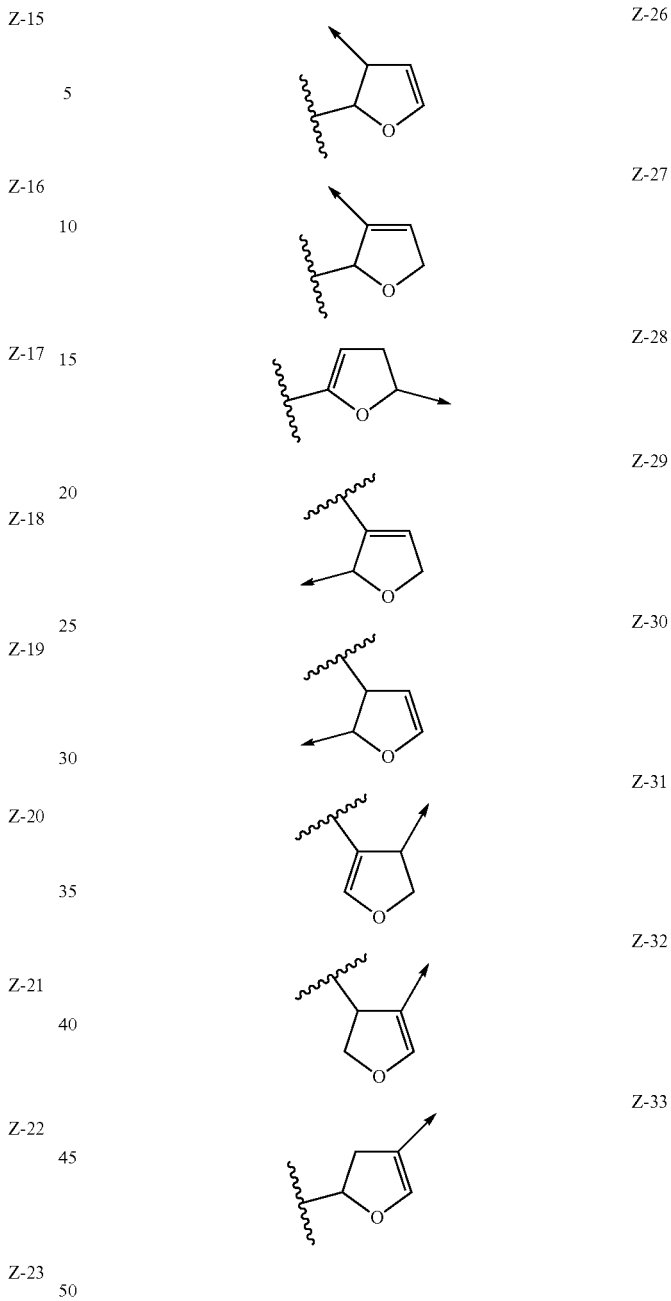

where the arrow in each case denotes a bond to the group C=W of formula (I).

7. The compound as claimed in claim 1, where $R^5$ represents fluorine, chlorine, cyano, $CO_2H$, $CO_2CH_3$ or $CO_2CH_2CH_3$, or represents $(C_1-C_2)$-alkyl or $(C_1-C_2)$-alkoxy, each of which is substituted by m radicals from the group consisting of fluorine and chlorine.

8. The compound as claimed in claim 1, where $X^2$, $X^4$ and $X^6$ independently of one another each represent hydrogen, fluorine, chlorine, bromine or cyano, or represent methyl or methoxy, each of which is substituted by m radicals from the group consisting of fluorine and chlorine.

9. The compound as claimed in claim 1, where $X^3$ and $X^5$ independently of one another each represent hydrogen, fluorine, chlorine, bromine, hydroxy or cyano, or represent $(C_1-C_3)$-alkyl, $(C_1-C_3)$-alkoxy, $(C_3-C_4)$-cycloalkyl, $(C_2-C_3)$-alkenyl or $(C_2-C_3)$-alkynyl, each of which is substituted by m radicals from the group consisting of fluorine, chlorine and bromine.

10. The compound as claimed in claim 1, where $R^7$ represents hydrogen, or represents $(C_1-C_3)$-alkyl each substituted by m radicals from the group consisting of fluorine and chlorine.

11. The compound as claimed in claim 1, where m is 0, 1, 2 or 3.

12. The compound as claimed in claim 1, wherein $R^1$ and $R^2$ each represent hydrogen;

$R^3$ represents $(C_1-C_3)$-alkyl, $(C_3-C_4)$-cycloalkyl, $(C_2-C_3)$-alkenyl, $(C_2-C_3)$-alkynyl or $(C_1-C_3)$-alkoxy, each of which is substituted by m radicals from the group consisting of fluorine, chlorine, bromine, cyano, $(C_1-C_2)$-alkoxy and hydroxy;

$R^4$ represents hydrogen, or represents $(C_1-C_6)$-alkyl, $(C_3-C_6)$-cycloalkyl, $(C_3-C_6)$-cycloalkyl-$(C_1-C_6)$-alkyl, $(C_2-C_6)$-alkenyl, $(C_5-C_6)$-cycloalkenyl or $(C_2-C_6)$-alkynyl, each of which is substituted by m radicals from the group consisting of fluorine, chlorine, bromine, cyano, $(C_1-C_4)$-alkoxy, hydroxy and aryl;

Y represents oxygen;

W represents oxygen;

Z represents a group Z-1 to Z-4, where Z-1 to Z-4 have the following meaning:

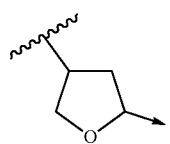
Z-1

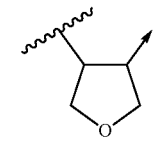
Z-2

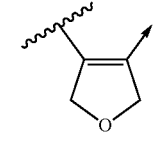
Z-3

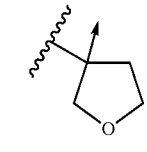
Z-4 where the arrow in each case denotes a bond to the group C=W of the formula (I):

$X^2$, $X^4$ and $X^6$ independently of one another represent hydrogen or fluorine;

$X^3$ and $X^5$ independently of one another represent hydrogen, fluorine, chlorine, bromine, hydroxy or cyano, or represent $(C_1-C_3)$-alkyl, $(C_1-C_3)$-alkoxy, $(C_3-C_4)$-cycloalkyl, $(C_2-C_3)$-alkenyl or $(C_2-C_3)$-alkynyl, each of which is substituted by m radicals from the group consisting of fluorine, chlorine and bromine; and m represents 0, 1, 2 or 3.

13. An herbicidal composition or plant growth-regulating composition, comprising one or more compounds of formula (I) or salts thereof as claimed in claim 1.

14. The herbicidal composition as claimed in claim 13, further comprising a formulation auxiliary.

15. The herbicidal composition as claimed in claim 13, further comprising at least one additional active compound from the group of insecticides, acaricides, herbicides, fungicides, safeners and/or growth regulators.

16. The herbicidal composition as claimed in claim 14, further comprising a safener.

17. The herbicidal composition as claimed in claim 16, wherein the safener is selected from the group consisting of mefenpyr-diethyl, cyprosulfamide, isoxadifen-ethyl, cloquintocet-mexyl, benoxacor and dichlormid.

18. A method of controlling one or more unwanted plants, comprising applying an effective amount of at least one compound of formula (I) as claimed in claim 1 or of an herbicidal composition thereof to the unwanted plants or to a site of the unwanted plants.

19. A product comprising a compound of formula (I) as claimed in claim 1 or a herbicidal composition thereof for controlling one or more unwanted plants.

20. The product as claimed in claim 19, comprising the compound of formula (I) or salt thereof that is capable of use for controlling said unwanted plants in one or more crops of useful plants.

21. The product as claimed in claim 20, wherein the useful plants are transgenic useful plants.

22. A compound of formula (II) and/or an agrochemically acceptable salt thereof

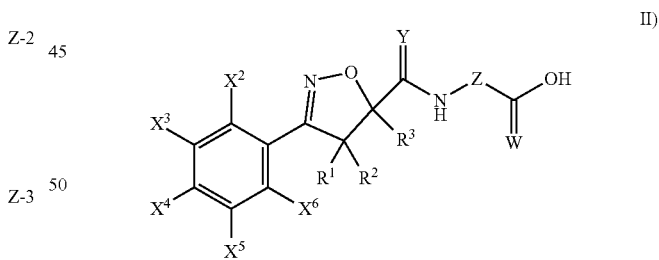
II)

wherein $R^1$ and $R^2$ independently of one another represent hydrogen, fluorine, chlorine or cyano, or represent $(C_1-C_3)$-alkyl or $(C_1-C_3)$-alkoxy, each of which is substituted by m radicals from the group consisting of fluorine, chlorine, bromine and cyano;

$R^3$ represents $(C_1-C_4)$-alkyl, $(C_3-C_5)$-cycloalkyl, $(C_2-C_4)$-alkenyl, $(C_2-C_4)$-alkynyl or $(C_1-C_4)$-alkoxy, each of which is substituted by m radicals from the group consisting of fluorine, chlorine, bromine, cyano, $(C_1-C_4)$-alkoxy and hydroxy;

$R^4$ represents hydrogen, or represents $(C_1-C_{12})$-alkyl, $(C_3-C_7)$-cycloalkyl, $(C_3-C_7)$-cycloalkyl-$(C_1-C_8)$-alkyl, $(C_2-C_6)$-alkenyl, $(C_5-C_6)$-cycloalkenyl or $(C_2-C_8)$-alkynyl, each of which is substituted by m radicals from the group consisting of halogen, cyano, $(C_1-C_6)$-alkoxy, hydroxy and aryl;

Y represents oxygen or sulfur;

W represents oxygen or sulfur;

Z represents a fully saturated or partially saturated furan ring which is substituted by k radicals from $R^5$,

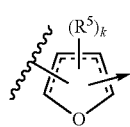

where the arrow in each case denotes a bond to the group C=W of formula (I);

$R^5$ represents fluorine, chlorine, cyano or $CO_2R^7$, or represents $(C_1-C_2)$-alkyl or $(C_1-C_2)$-alkoxy, each of which is substituted by m radicals from the group consisting of fluorine and chlorine;

$X^2$, $X^4$ and $X^6$ independently of one another each represent hydrogen, fluorine, chlorine, bromine or cyano, or represent $(C_1-C_2)$-alkyl, in each case substituted by m radicals from the group consisting of fluorine, chlorine, bromine and $(C_1-C_2)$-alkoxy;

$X^3$ and $X^5$ independently of one another represent hydrogen, fluorine, chlorine, bromine, iodine, hydroxy, cyano, nitro, $S(O)_nR^6$ or $CO_2R^7$, or represent $(C_1-C_3)$-alkyl, $(C_1-C_3)$-alkoxy, $(C_3-C_4)$-cycloalkyl, $(C_2-C_3)$-alkenyl or $(C_2-C_3)$-alkynyl, each of which is substituted by m radicals from the group consisting of fluorine, chlorine and bromine;

$R^6$ represents $(C_1-C_2)$-alkyl or $(C_3-C_4)$-cycloalkyl, each of which is substituted by m radicals from the group consisting of fluorine and chlorine;

$R^7$ represents hydrogen, or represents $(C_1-C_3)$-alkyl or $(C_3-C_5)$-cycloalkyl, each of which is substituted by m radicals from the group consisting of fluorine, chlorine and $(C_1-C_2)$-alkoxy;

k represents 0, 1 or 2;

m represents 0, 1, 2, 3, 4 or 5; and n represents 0, 1 or 2.

* * * * *